US010029963B2

(12) United States Patent
Bonnet et al.

(10) Patent No.: US 10,029,963 B2
(45) Date of Patent: *Jul. 24, 2018

(54) COMPOSITION COMPRISING HF AND 1,3,3,3-TETRAFLUOROPROPENE

(71) Applicant: ARKEMA FRANCE, Colombes (FR)

(72) Inventors: Philippe Bonnet, Lyons (FR); Bertrand Collier, Saint-Genis-Laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 218 days.

This patent is subject to a terminal disclaimer.

(21) Appl. No.: 14/773,961

(22) PCT Filed: Feb. 24, 2014

(86) PCT No.: PCT/FR2014/050369
§ 371 (c)(1),
(2) Date: Sep. 9, 2015

(87) PCT Pub. No.: WO2014/147313
PCT Pub. Date: Sep. 25, 2014

(65) Prior Publication Data
US 2016/0031773 A1    Feb. 4, 2016

(30) Foreign Application Priority Data
Mar. 20, 2013  (FR) ..................... 13 52485

(51) Int. Cl.
*C01B 7/19* (2006.01)
*C07C 21/18* (2006.01)
*C09K 3/30* (2006.01)
*C09K 5/04* (2006.01)

(52) U.S. Cl.
CPC .............. *C07C 21/18* (2013.01); *C01B 7/191* (2013.01); *C01B 7/195* (2013.01); *C09K 3/30* (2013.01); *C09K 5/045* (2013.01)

(58) Field of Classification Search
None
See application file for complete search history.

(56) References Cited

U.S. PATENT DOCUMENTS

| | | | | |
|---|---|---|---|---|
| 6,013,846 A * | 1/2000 | Wismer | ................... | C07C 17/00 570/164 |
| 8,450,537 B2 * | 5/2013 | Rao | ........................ | C07C 17/10 570/156 |
| 8,951,432 B2 | 2/2015 | Boutier et al. | | |
| 9,005,468 B2 | 4/2015 | Rached | | |
| 9,315,706 B2 | 4/2016 | Boussand | | |
| 9,512,343 B2 | 12/2016 | Rached et al. | | |
| 2007/0100173 A1 * | 5/2007 | Miller | ..................... | C01B 7/191 570/178 |
| 2007/0100175 A1 * | 5/2007 | Miller | ..................... | C01B 7/196 570/178 |
| 2008/0051612 A1 * | 2/2008 | Knapp | ..................... | C07C 17/25 570/178 |
| 2009/0127496 A1 * | 5/2009 | Rao | ........................ | B01J 27/125 252/67 |
| 2010/0072415 A1 * | 3/2010 | Rao | ........................ | B01J 23/26 252/67 |
| 2010/0187088 A1 * | 7/2010 | Merkel | ................... | B01D 3/36 203/50 |
| 2010/0237279 A1 * | 9/2010 | Hulse | .................... | C07C 17/206 252/182.12 |
| 2011/0112340 A1 * | 5/2011 | Smith | .................... | C07C 17/04 570/169 |
| 2011/0218369 A1 * | 9/2011 | Elsheikh | ............... | C07C 17/206 570/151 |
| 2012/0041239 A1 * | 2/2012 | Suzuki | .................. | C07C 17/206 570/160 |
| 2012/0053369 A1 * | 3/2012 | Hulse | .................... | C07C 17/206 570/135 |
| 2012/0056122 A1 * | 3/2012 | Hulse | .................... | C01B 7/191 252/67 |
| 2012/0068104 A1 | 3/2012 | Rached et al. | | |
| 2012/0068105 A1 | 3/2012 | Rached et al. | | |
| 2012/0138841 A1 * | 6/2012 | Hulse | .................. | A62D 1/0057 252/2 |
| 2012/0222448 A1 * | 9/2012 | Chaki | ................... | C07C 17/383 62/617 |
| 2013/0055733 A1 | 3/2013 | Rached | | |
| 2013/0055739 A1 | 3/2013 | Rached | | |
| 2013/0061613 A1 | 3/2013 | Rached | | |
| 2013/0105296 A1 * | 5/2013 | Chaki | .................... | C01B 7/196 203/60 |
| 2013/0299733 A1 | 11/2013 | Boussand | | |
| 2014/0012052 A1 * | 1/2014 | Pham | ..................... | C07C 17/38 570/160 |

(Continued)

FOREIGN PATENT DOCUMENTS

EP  2 527 313 A1  11/2012
WO  WO 2009/105521 A1  8/2009

OTHER PUBLICATIONS

Boussand, Béatrice, U.S. Appl. No. 14/880,605 entitled "3,3,3-Trifluoropropene Composition," filed Oct. 12, 2015.
Rached, Wissam, et al., U.S. Appl. No. 15/297,569 entitled "Composition Based on 2,3,3,3-Tetrafluoropropene," filed Oct. 19, 2016.
Rached, Wissam, U.S. Appl. No. 15/343,664 entitled "Heat Transfer Fluid for a Centrifugal Compressor," filed Nov. 4, 2016.
International Search Report (PCT/ISA/210) dated Jun. 4, 2014, by the French Patent Office as the International Searching Authority for International Application No. PCT/FR2014/050369.

(Continued)

*Primary Examiner* — Joseph D Anthony
(74) *Attorney, Agent, or Firm* — Buchanan Ingersoll & Rooney P.C.

(57) ABSTRACT

An azeotropic or quasi-azeotropic composition including hydrogen fluoride, 1,3,3,3-tetrafluoropropene and one or more (hydro)halogen-carbon compounds including between 1 and 3 carbon atoms. Also, a preferred azeotropic or quasi-azeotropic composition comprising hydrogen fluoride, 1,3,3,3-tetrafluoropropene, and one or more compounds selected from among 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,3,3-pentafluoropropene, 1,1,1,3,3-pentafluoropropene, 1,1,1,2,3-pentafluoropropene and 2-chloro, 1,1,1,2-tetrafluoropropane.

17 Claims, No Drawings

(56) References Cited

U.S. PATENT DOCUMENTS

| | | |
|---|---|---|
| 2014/0110623 A1 | 4/2014 | Boutier et al. |
| 2015/0184051 A1 | 7/2015 | Rached |
| 2016/0009555 A1* | 1/2016 | Bonnet .................. C07C 21/18 252/182.12 |
| 2016/0023176 A1* | 1/2016 | Bonnet .................. C01B 7/191 51/307 |
| 2016/0023974 A1* | 1/2016 | Bonnet .................. C07C 21/18 252/182.12 |
| 2016/0031773 A1* | 2/2016 | Bonnet .................. C01B 7/195 252/182.12 |
| 2016/0032165 A1 | 2/2016 | Boussand |
| 2016/0046548 A1* | 2/2016 | Bonnet .................... C01B 7/19 252/182.12 |

* cited by examiner

COMPOSITION COMPRISING HF AND 1,3,3,3-TETRAFLUOROPROPENE

The present invention relates to azeotropic or quasi-azeotropic compositions comprising 1,3,3,3-tetrafluoropropene and hydrogen fluoride. These compositions may originate from intermediate compositions in the production of 1,3,3,3-tetrafluoropropene and are generally useful in processes for recycling hydrogen fluoride.

The manufacture of 1,3,3,3-tetrafluoropropene accompanied by a multitude of by-products, having a boiling point close to HFO-1234ze, leads to relatively complex and expensive purification steps. The difficulty encountered during the purification of HFO-1234ze generally implies an appreciable loss of desired product. Furthermore, these by-products may form azeotropic compositions with 1,3,3,3-tetrafluoropropene, making separation by distillation simple, very difficult, or even impossible.

Fluids based on 1,3,3,3-tetrafluoropropene have found numerous applications in varied industrial fields, especially as heat-transfer fluid, propellants, foaming agents, swelling agents, gaseous dielectrics, polymerization medium or monomer, support fluids, abrasive agents, drying agents and fluids for power production units.

Particular importance is given to fluids that have a low impact on the environment.

The subject of the present invention is an azeotropic or quasi-azeotropic composition comprising hydrogen fluoride, 1,3,3,3-tetrafluoropropene and one or more (hydro)halocarbon compounds comprising between 1 and 3 carbon atoms.

According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation. This property is a considerable advantage for the recovery of HF.

The term "quasi-azeotropic" or "quasi-heteroazeotropic" has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

Compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2=CF-CF_3$
HFC-245cb: 1,1,1,2,2-pentafluoropropane or $CF_3-CF_2-CH_3$
HFO-1234zeE: E-1,3,3,3-tetrafluoropropene or E-$CF_3-CH=CHF$
HFO-1234zeZ: Z-1,3,3,3-tetrafluoropropene or Z-$CF_3-CH=CHF$
HFO-1243zf: 3,3,3-trifluoropropene or $CF_3-CH=CH_2$
HCFO-1233xf: 3,3,3-trifluoro-2-chloropropene or $CF_3-CCl=CH_2$
HCFO-1233zdE: E-3,3,3-trifluoro-1-chloropropene or E-$CF_3-CH=CHCl$
HCFO-1233zdZ: Z-3,3,3-trifluoro-1-chloropropene or Z-$CF_3-CH=CHCl$
HFO-1225yeZ: Z-1,1,1,2,3-pentafluoropropene or Z-$CHF=CF-CF_3$
HFO-1225yeE: E-1,1,1,2,3-pentafluoropropene or E-$CHF=CF-CF_3$
HFO-1225zc: 1,1,3,3,3-pentafluoropropene or $CF_2=CH-CF_3$
HFO-1225yc: 1,1,2,3,3-pentafluoropropene or $CF_2=CF-CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F-CCl=CF_2$
HCFO-1233xe: 1,3,3-trifluoro-2-chloropropene or $CHF_2-CCl=CHF$
HCFO-1233yb: 1,2,3-trifluoro-1-chloropropene or $CH_2F-CF=CFCl$
HCFO-1233yc: 1,1,2-trifluoro-3-chloropropene or $CH_2Cl-CF=CF_2$
HCFO-1233yd: 2,3,3-trifluoro-1-chloropropene or $CHF_2-CF=CHCl$
HCFO-1233ye: 1,2,3-trifluoro-3-chloropropene or $CHClF-CF=CHF$
HCFO-1233yf: 2,3,3-trifluoro-3-chloropropene or $CClF_2-CF=CH_2$
HCFO-1233zb: 1,3,3-trifluoro-1-chloropropene or $CHF_2-CH=CFCl$
HCFO-1233zc: 1,1,3-trifluoro-3-chloropropene or $CHClF-CH=CF_2$
HCFO-1233ze: 1,3,3-trifluoro-3-chloropropene or $CClF_2-CH=CHF$
HFO-1234yc: 1,1,2,3-tetrafluoropropene or $CF_2=CF-CH_2F$
HFO-1234ye: 2,3,3-tetrafluoropropene or $CHF=CF-CHF_2$
HFO-1234zc: 1,1,3,3-tetrafluoropropene or $CF_2=CH-CHF_2$
HCFO-1242: chlorodifluoropropene, or $C_3H_3F_2Cl$
HFO-1243yc: 1,1,2-trifluoropropene or $CH_3-CF=CF_2$
HFO-1243ye: 1,2,3-trifluoropropene or $CH_2F-CF=CHF$
HFO-1243yf: 2,3,3-trifluoropropene or $CHF_2-CF=CH_2$
HFO-1243zc: 1,1,3-trifluoropropene or $CH_2F-CH=CF_2$ HFO-1243ze: 1,3,3-trifluoropropene or CHF$_2$—CH=CHF
HCFO-1251: chlorofluoropropene, or C$_3$H$_4$FCl
HFO-1252: difluoropropene, or C$_3$H$_4$F$_2$
HFO-216: hexafluoropropene, or C$_3$F$_6$Cl$_2$
HCFO-217: chloroheptafluoropropane, or C$_3$F$_7$Cl
HFC-218: octafluoropropane, or C$_3$F$_8$
HCFC-225: dichloropentafluoropropane, or C$_3$HF$_5$Cl$_2$
HCFC-226: chlorohexafluoropropane, or C$_3$HF$_6$Cl
HFC-227: heptafluoropropane, or C$_3$HF$_7$
HCFC-234: dichlorotetrafluoropropane, or C$_3$H$_2$F$_4$Cl$_2$
HCFC-235: chloropentafluoropropane, or C$_3$H$_2$F$_5$Cl
HFC-236: hexafluoropropane, or C$_3$H$_2$F$_6$
HCFC-243: dichlorotrifluoropropane, or C$_3$H$_3$F$_3$Cl$_2$
HCFC-244: chlorotetrafluoropropane, or C$_3$H$_3$F$_4$Cl
HCFC-244bb: 2-chloro-1,1,1,2-tetrafluoropropane or CF$_3$—CFCl—CH$_3$
HFC-245fa: 1,1,1,3,3-pentafluoropropane or CF$_3$—CH$_2$—CHF$_2$
HFC-245ea: 1,1,2,3,3-pentafluoropropane or CHF$_2$—CHF—CHF$_2$
HFC-245eb: 1,1,1,2,3-pentafluoropropane or CF$_3$—CHF—CH$_2$F
HFC-245ca: 1,1,2,2,3-pentafluoropropane or CHF$_2$—CF$_2$—CH$_2$F
HCFC-253: chlorotrifluoropropane, or C$_3$H$_4$F$_3$Cl
HFC-254: tetrafluoropropane, or C$_3$H$_4$F$_4$
HCFC-262: chlorodifluoropropane, or C$_3$H$_5$F$_2$Cl
HFC-263: trifluoropropane, or C$_3$H$_5$F$_3$
trifluoropropyne: CF$_3$—C≡CH The composition according to the invention may optionally be a mixture of one or more azeotropes and/or heteroazeotropes of ternary, quaternary, penternary systems, systems with six compounds, systems with seven compounds, systems with eight or more compounds.

The compound 1,3,3,3-tetrafluoropropene comprises either the compound E-1,3,3,3-tetrafluoropropene or the compound Z-1,3,3,3-tetrafluoropropene or a mixture of the compounds E-1,3,3,3-tetrafluoropropene and Z-1,3,3,3-tetrafluoropropene.

According to one embodiment of the invention, the 1,3,3,3-tetrafluoropropene is E-1,3,3,3-tetrafluoropropene.

According to one embodiment of the invention, the 1,3,3,3-tetrafluoropropene is Z-1,3,3,3-tetrafluoropropene.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, 1-chlorohexafluoropropane, 2-chloro-1,1,1,2,3,3-hexafluoropropane, 3-chloro-1,1,1,2,2,3-hexafluoropropane, 1-chloro-1,1,2,2,3,3-hexafluoropropane, 2-chloro-1,1,1,3,3,3-hexafluoropropane, 1-chloro-1,2,3,3,3-hexafluoropropane, 1,1,2,2,3,3,3-heptafluoropropane, 1,1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,1,2,3-tetrafluoropropane, 1,1-dichloro-1,2,3,3-tetrafluoropropane, chloropentafluoro-propane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,1,3,3-pentafluoropropane, 1-chloro-1,1,3,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,2,3-tetrafluoropropane, 3-chloro-1,1,1,2-tetrafluoropropane, 1-chloro-1,2,3-tetrafluoropropane, 3-chloro-1,1,1,3-tetrafluoropropane, 1-chloro-1,1,3,3-tetrafluoropropane, pentafluoropropane, 1,1,1,3,3-pentafluoropropane, 1,1,2,2,3-pentafluoropropane, 1,1,2,3,3-pentafluoropropane, 1,1,1,2,3-pentafluoropropane, chlorotrifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,2-trifluoropropane, 3-chloro-1,3,3-trifluoropropane, 3-chloro-1,1,1-trifluoropropane, 1-chloro-1,1,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3-tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 1,1,2,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-1,3-difluoropropene, 2-chloro-3,3-difluoropropene, 1-chloro-1,2-difluoropropene, 1-chloro-2,3-difluoropropene, 3-chloro-1,2-difluoropropene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, 1,1,1,2,2-pentafluoropropane, 2,3,3,3-tetrafluoropropene, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne.

Preferably, the ternary compositions consisting essentially of HF—HFO-1234ze-HFC-245fa and HF—HFO-1234zeE-HFO-1234zeZ are excluded from the present invention.

A subject of the present invention is also an azeotropic or quasi-azeotropic composition comprising hydrogen fluoride, 1,3,3,3-tetrafluoropropene, and one or more compounds chosen from 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

A subject of the present invention is also an azeotropic or quasi-azeotropic composition comprising hydrogen fluoride, 1,3,3,3-tetrafluoropropene and at least one or more organic compounds chosen from 3,3,3-trifluoro-2-chloropropene, E-3,3,3-trifluoro-1-chloropropene, 3,3,3-trifluoropropene, 1,1,1,2,2-pentafluoropropane and 2,3,3,3-tetrafluoropropene.

According to one embodiment, the composition according to the invention comprises hydrogen fluoride, 1,3,3,3-tetrafluoropropene, 1,1,1,2,2-pentafluoropropane and optionally one or more compounds chosen from 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 2,3,3,3-tetrafluoropropene and optionally one or more compounds chosen from 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 1,3,3,3-tetrafluoropropene, 3,3,3-trifluoropropene and optionally one or more compounds chosen from 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 3,3,3-trifluoro-2-chloropropene and optionally one or more compounds chosen from E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 1,3,3,3-tetrafluoropropene, E-3,3,3-trifluoro-1-chloropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, trifluoropropyne and optionally one or more compounds chosen from 1,1,1,3,3-pentafluoropropene, 1,1,1,3,3-pentafluoropropane, 1,1,1,2,3-pentafluoropropene and 2-chloro-1,1,1,2-tetrafluoropropane.

According to one embodiment, the composition according to the invention comprises hydrogen fluoride, 1,3,3,3-tetrafluoropropene, 1,1,1,3,3-pentafluoropropene and optionally one or more compounds chosen from 1,1,1,3,3-pentafluoropropane, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 1,1,1,2,3-pentafluoropropene and optionally one or more compounds chosen from 1,1,1,3,3-pentafluoropropane, 2-chloro-1,1,1,2-tetrafluoropropane.

According to another embodiment, the composition according to the invention comprises hydrogen fluoride, 1,3,3,3-tetrafluoropropene, 3,3,3-trifluoro-2-chloropropene and optionally one or more compounds chosen from E-3,3,3-trifluoro-1-chloropropene, 3,3,3-trifluoropropene, 1,1,1,2,2-pentafluoropropane, 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment according to the invention, the composition comprises hydrogen fluoride, 1,3,3,3-tetrafluoropropene, E-3,3,3-trifluoro-1-chloropropene and optionally one or more compounds chosen from 3,3,3-trifluoropropene, 1,1,1,2,2-pentafluoropropane 2,3,3,3-tetrafluoropropene, trifluoropropyne, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 3,3,3-trifluoropropene and optionally one or more compounds chosen from 1,1,1,2,2-pentafluoropropane, 2,3,3,3-tetrafluoropropene, trifluoropropyne, 1,1,1,3,3-pentafluoropropene, 1,1,1,3,3-pentafluoropropane, 1,1,1,2,3-pentafluoropropene and 2-chloro-1,1,1,2-tetrafluoropropane.

According to one embodiment of the invention, the composition comprises hydrogen fluoride, 1,3,3,3-tetrafluoropropene, 1,1,1,2,2-pentafluoropropane and optionally one or more compounds chosen from 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

Irrespective of the embodiment, the composition preferably comprises from 1% to 95% and advantageously from 5% to 80% by weight of hydrogen fluoride and from 99% to 5% and advantageously from 20% to 95% by weight of the sum of the organic compounds; more particularly, the composition comprises from 1% to 85% by weight of hydrogen fluoride and from 99% to 15% by weight of the sum of the organic compounds (HFO-1234ze and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, 1,3,3,3-tetrafluoropropene and a compound chosen from 1,1,1,2,2-pentafluoropropane, 2,3,3,3-tetrafluoropropene, 3,3,3-trifluoropropene, 3,3,3-trifluoro-2-chloropropene and E-3,3,3-trifluoro-1-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, 1,3,3,3-tetrafluoropropene and a compound chosen from trifluoropropyne, 1,1,1,3,3-pentafluoropropane, 1,1,1,3,3-pentafluoropropene, Z-1,1,1,2,3-pentafluoropropene and 2-chloro-1,1,1,2-tetrafluoropropane are characterized by a phase depleted in HF and a phase enriched in HF for at least isotherms at 0° C., 25° C. and 40° C.

The Applicant has observed the same phenomenon for compositions of hydrogen fluoride, 1,3,3,3-tetrafluoropropene comprising several compounds chosen from 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

An azeotropic or quasi-azeotropic composition that is preferred according to the invention comprises from 1% to 80% by weight of hydrogen fluoride, and from 99% to 20% by weight of the sum of HFO-1234zeE and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFC-1234zeE, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HFO-1243zf and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HFO-1243zf and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233zdE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233zdE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf, HCFO-1233zdE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233zdE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HCFO-1233zdE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HCFO-1233zdE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf, HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233xf, HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 1% to 85% by weight of hydrogen fluoride, and from 99% to 15% by weight of the sum of HFO-1234zeE, HFC-245cb, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233zdE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233zdE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HFO-1243zf, HCFO-1233zdE and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1243zf, HCFO-1233zdE and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HFO-1234zeZ, and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HFO-1234zeZ, and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HFO-1234zeZ, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HFO-1234zeZ, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf, HFO-1234zeZ, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1234zeZ, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233zdE, HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233zdE, HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HFO-1234zeZ, HCFO-1233zdE and HFO1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HFO-1234zeZ, and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HCFC-244bb and HFO-1234zeE, the boiling point of this preferred composition is between 0 and 40° C. at a pressure of between 0.7 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HCFC-244bb and HFO-1234zeE, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, trifluoropropyne and HFO-1234zeE, the boiling point of this preferred composition is between 0 and 40° C. at a pressure of between 0.9 and 18 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, trifluoropropyne and HFO-1234zeE, the boiling point of this preferred composition is between 0 and 40° C. at a pressure of between 0.9 and 18 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFC-245fa and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFC-245fa and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFO-1225yeZ and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFO-1225yeZ and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFO-1225zc and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFO-1225zc and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFO-1225zc, trifluoropropyne, HCFC-244bb, HFC-245fa, HFO-1225yeZ, HFO-1243zf and HFO-1234zeE, the boiling point of this preferred composition is between 0 and 40° C. at a pressure of between 0.7 and 18.0 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFO-1225zc, trifluoropropyne, HCFC-244bb, HFC-245fa, HFO-1225yeZ, HFO-1243zf and HFO-1234zeE, the boiling point of this preferred composition is between 0 and 40° C. at a pressure of between 0.7 and 18.0 bar absolute.

The pressure characteristics of the mixtures of Examples 1, 4, 7, 10, 13, 16 and 19 were calculated for an isotherm at 25° C.

Examples 2, 5, 8, 11, 14, 17 and 20 represent the boiling points and pressure ranges of the mixtures and Examples 3, 6, 9, 12, 15, 18 and 21 represent the decantation ranges of the mixtures of Examples 1, 4, 7, 10, 13, 16 and 19 as a function of the mass percentage of HF characterized for isotherms at 0° C., 25° C. and 40° C. The decantation ranges of Examples 3, 6, 9, 12, 15, 18 and 21 are calculated for mixtures of organic compounds having equal-mass contents. By way of example, for a ternary mixture, a mixture containing 50% by weight of each of the two organic compounds is considered; for a penternary mixture, a mixture containing 25% by weight of each of the four organic compounds is considered, the mass fraction of HF ranging from 0 to 1. These calculations are performed at the liquid-vapor equilibrium, under azeotropic conditions.

EXAMPLE 1

Ternary Mixtures, Isotherm at 25° C.

| HF - HFO-1234zeE - HCFO-1233xf | | | | | |
|---|---|---|---|---|---|
| Organics 0.95 F1234zeE + 0.05 F1233xf | | Organics 0.5 F1234zeE + 0.5 F1233xf | | Organics 0.05 F1234zeE + 0.95 F1233xf | |
| MASSFRAC HF | TOTAL PRESSURE bar | MASSFRAC HF | TOTAL PRESSURE bar | MASSFRAC HF | TOTAL PRESSURE bar |
| 0 | 4.7 | 0 | 3.3 | 0 | 1.7 |
| 0.05 | 5.7 | 0.05 | 4.3 | 0.05 | 2.8 |
| 0.1 | 5.7 | 0.1 | 4.3 | 0.1 | 2.8 |
| 0.15 | 5.7 | 0.15 | 4.3 | 0.15 | 2.8 |
| 0.2 | 5.7 | 0.2 | 4.3 | 0.2 | 2.8 |
| 0.25 | 5.7 | 0.25 | 4.3 | 0.25 | 2.8 |
| 0.3 | 5.7 | 0.3 | 4.3 | 0.3 | 2.8 |
| 0.35 | 5.7 | 0.35 | 4.3 | 0.35 | 2.8 |
| 0.4 | 5.7 | 0.4 | 4.3 | 0.4 | 2.8 |
| 0.45 | 5.7 | 0.45 | 4.3 | 0.45 | 2.8 |
| 0.5 | 5.6 | 0.5 | 4.3 | 0.5 | 2.8 |
| 0.55 | 5.6 | 0.55 | 4.2 | 0.55 | 2.8 |
| 0.6 | 5.5 | 0.6 | 4.2 | 0.6 | 2.8 |
| 0.65 | 5.4 | 0.65 | 4.2 | 0.65 | 2.8 |
| 0.7 | 5.2 | 0.7 | 4.1 | 0.7 | 2.8 |
| 0.75 | 5.0 | 0.75 | 3.9 | 0.75 | 2.8 |
| 0.8 | 4.7 | 0.8 | 3.7 | 0.8 | 2.6 |
| 0.85 | 4.2 | 0.85 | 3.3 | 0.85 | 2.4 |
| 0.9 | 3.5 | 0.9 | 2.8 | 0.9 | 2.2 |
| 0.95 | 2.5 | 0.95 | 2.1 | 0.95 | 1.7 |
| 1 | 1.2 | 1 | 1.2 | 1 | 1.2 |

| HF - HFO-1234zeZ - HCFO-1233xf | | | | | |
|---|---|---|---|---|---|
| Organics 0.95 F1234zeZ + 0.05 F1233xf | | Organics 0.5 F1234zeZ + 0.5 F1233xf | | Organics 0.05 F1234zeZ + 0.95 F1233xf | |
| MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.7 | 0 | 1.6 |
| 0.05 | 2.9 | 0.05 | 2.8 | 0.05 | 2.7 |
| 0.1 | 2.9 | 0.1 | 2.8 | 0.1 | 2.7 |
| 0.15 | 2.9 | 0.15 | 2.8 | 0.15 | 2.7 |
| 0.2 | 2.9 | 0.2 | 2.8 | 0.2 | 2.7 |
| 0.25 | 2.9 | 0.25 | 2.8 | 0.25 | 2.7 |
| 0.3 | 2.9 | 0.3 | 2.8 | 0.3 | 2.7 |
| 0.35 | 2.9 | 0.35 | 2.8 | 0.35 | 2.7 |
| 0.4 | 2.9 | 0.4 | 2.8 | 0.4 | 2.7 |
| 0.45 | 2.9 | 0.45 | 2.8 | 0.45 | 2.7 |
| 0.5 | 2.9 | 0.5 | 2.8 | 0.5 | 2.7 |
| 0.55 | 2.9 | 0.55 | 2.8 | 0.55 | 2.7 |
| 0.6 | 2.9 | 0.6 | 2.8 | 0.6 | 2.7 |
| 0.65 | 2.9 | 0.65 | 2.8 | 0.65 | 2.7 |
| 0.7 | 2.9 | 0.7 | 2.8 | 0.7 | 2.7 |
| 0.75 | 2.9 | 0.75 | 2.8 | 0.75 | 2.7 |
| 0.8 | 2.8 | 0.8 | 2.7 | 0.8 | 2.5 |
| 0.85 | 2.6 | 0.85 | 2.5 | 0.85 | 2.4 |
| 0.9 | 2.3 | 0.9 | 2.2 | 0.9 | 2.1 |
| 0.95 | 1.8 | 0.95 | 1.8 | 0.95 | 1.7 |
| 1 | 1.2 | 1 | 1.2 | 1 | 1.2 |

HF - HFO-1234zeE - HCFO-1233zdE

| Organics 0.95 F1233zdE + 0.05 F1234zeE | | Organics 0.5 F1233zdE + 0.5 F1234zeE | | Organics 0.05 F1233zdE + 0.95 F1234zeE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.5 | 0 | 3.2 | 0 | 4.7 |
| 0.05 | 2.6 | 0.05 | 4.2 | 0.05 | 5.7 |
| 0.1 | 2.6 | 0.1 | 4.2 | 0.1 | 5.7 |
| 0.15 | 2.6 | 0.15 | 4.2 | 0.15 | 5.7 |
| 0.2 | 2.6 | 0.2 | 4.2 | 0.2 | 5.7 |
| 0.25 | 2.6 | 0.25 | 4.2 | 0.25 | 5.7 |
| 0.3 | 2.6 | 0.3 | 4.2 | 0.3 | 5.7 |
| 0.35 | 2.6 | 0.35 | 4.2 | 0.35 | 5.7 |
| 0.4 | 2.6 | 0.4 | 4.2 | 0.4 | 5.7 |
| 0.45 | 2.6 | 0.45 | 4.2 | 0.45 | 5.7 |
| 0.5 | 2.6 | 0.5 | 4.1 | 0.5 | 5.6 |
| 0.55 | 2.6 | 0.55 | 4.1 | 0.55 | 5.6 |
| 0.6 | 2.6 | 0.6 | 4.1 | 0.6 | 5.5 |
| 0.65 | 2.6 | 0.65 | 4.1 | 0.65 | 5.4 |
| 0.7 | 2.6 | 0.7 | 4.0 | 0.7 | 5.2 |
| 0.75 | 2.6 | 0.75 | 3.8 | 0.75 | 5.0 |
| 0.8 | 2.4 | 0.8 | 3.6 | 0.8 | 4.7 |
| 0.85 | 2.3 | 0.85 | 3.2 | 0.85 | 4.2 |
| 0.9 | 2.0 | 0.9 | 2.8 | 0.9 | 3.5 |
| 0.95 | 1.7 | 0.95 | 2.1 | 0.95 | 2.5 |
| 1 | 1.2 | 1 | 1.2 | 1 | 1.2 |

HF - HFO-1234zeZ - HCFO-1233zdE

| Organics 0.95 F1233zdE + 0.05 F1234zeZ | | Organics 0.5 F1233zdE + 0.5 F1234zeZ | | Organics 0.05 F1233zdE + 0.95 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.3 | 0 | 1.6 | 0 | 1.8 |
| 0.05 | 2.4 | 0.05 | 2.7 | 0.05 | 2.9 |
| 0.1 | 2.4 | 0.1 | 2.7 | 0.1 | 2.9 |
| 0.15 | 2.4 | 0.15 | 2.7 | 0.15 | 2.9 |
| 0.2 | 2.4 | 0.2 | 2.7 | 0.2 | 2.9 |
| 0.25 | 2.4 | 0.25 | 2.7 | 0.25 | 2.9 |
| 0.3 | 2.4 | 0.3 | 2.7 | 0.3 | 2.9 |
| 0.35 | 2.4 | 0.35 | 2.7 | 0.35 | 2.9 |
| 0.4 | 2.4 | 0.4 | 2.7 | 0.4 | 2.9 |
| 0.45 | 2.4 | 0.45 | 2.7 | 0.45 | 2.9 |
| 0.5 | 2.4 | 0.5 | 2.7 | 0.5 | 2.9 |
| 0.55 | 2.4 | 0.55 | 2.7 | 0.55 | 2.9 |
| 0.6 | 2.4 | 0.6 | 2.7 | 0.6 | 2.9 |
| 0.65 | 2.4 | 0.65 | 2.7 | 0.65 | 2.9 |
| 0.7 | 2.4 | 0.7 | 2.7 | 0.7 | 2.9 |
| 0.75 | 2.4 | 0.75 | 2.7 | 0.75 | 2.9 |
| 0.8 | 2.3 | 0.8 | 2.6 | 0.8 | 2.8 |
| 0.85 | 2.2 | 0.85 | 2.4 | 0.85 | 2.6 |
| 0.9 | 2.0 | 0.9 | 2.1 | 0.9 | 2.3 |
| 0.95 | 1.6 | 0.95 | 1.7 | 0.95 | 1.8 |
| 1 | 1.2 | 1 | 1.2 | 1 | 1.2 |

HF - HFO-1234zeE - HFO-1234yf

| Organics 0.95 F1234zeE + 0.05 F1234yf | | Organics 0.5 F1234zeE + 0.5 F1234yf | | Organics 0.05 F1234zeE + 0.95 F1234yf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.0 | 0 | 5.9 | 0 | 6.7 |
| 0.05 | 5.9 | 0.05 | 6.8 | 0.05 | 7.7 |
| 0.1 | 5.9 | 0.1 | 6.8 | 0.1 | 7.7 |
| 0.15 | 5.9 | 0.15 | 6.8 | 0.15 | 7.7 |
| 0.2 | 5.9 | 0.2 | 6.8 | 0.2 | 7.7 |
| 0.25 | 5.9 | 0.25 | 6.8 | 0.25 | 7.6 |
| 0.3 | 5.9 | 0.3 | 6.8 | 0.3 | 7.7 |
| 0.35 | 5.9 | 0.35 | 6.8 | 0.35 | 7.7 |
| 0.4 | 5.9 | 0.4 | 6.8 | 0.4 | 7.7 |
| 0.45 | 5.9 | 0.45 | 6.8 | 0.45 | 7.7 |
| 0.5 | 5.9 | 0.5 | 6.8 | 0.5 | 7.7 |
| 0.55 | 5.8 | 0.55 | 6.8 | 0.55 | 7.7 |
| 0.6 | 5.8 | 0.6 | 6.8 | 0.6 | 7.7 |
| 0.65 | 5.7 | 0.65 | 6.7 | 0.65 | 7.7 |
| 0.7 | 5.5 | 0.7 | 6.6 | 0.7 | 7.6 |
| 0.75 | 5.3 | 0.75 | 6.4 | 0.75 | 7.5 |
| 0.8 | 4.9 | 0.8 | 6.1 | 0.8 | 7.1 |
| 0.85 | 4.4 | 0.85 | 5.5 | 0.85 | 6.5 |
| 0.9 | 3.7 | 0.9 | 4.6 | 0.9 | 5.5 |
| 0.95 | 2.6 | 0.95 | 3.2 | 0.95 | 3.8 |
| 1 | 1.2 | 1 | 1.2 | 1 | 1.2 |

HF - HFO-1234zeZ - HFO-1234yf

| Organics 0.95 F1234zeZ + 0.05 F1234yf | | Organics 0.5 F1234zeZ + 0.5 F1234yf | | Organics 0.05 F1234zeZ + 0.95 F1234yf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 2.1 | 0 | 4.3 | 0 | 6.5 |
| 0.05 | 3.2 | 0.05 | 5.4 | 0.05 | 7.5 |
| 0.1 | 3.2 | 0.1 | 5.4 | 0.1 | 7.5 |
| 0.15 | 3.2 | 0.15 | 5.4 | 0.15 | 7.5 |
| 0.2 | 3.2 | 0.2 | 5.4 | 0.2 | 7.5 |
| 0.25 | 3.2 | 0.25 | 5.4 | 0.25 | 7.5 |
| 0.3 | 3.2 | 0.3 | 5.4 | 0.3 | 7.5 |
| 0.35 | 3.2 | 0.35 | 5.4 | 0.35 | 7.5 |
| 0.4 | 3.2 | 0.4 | 5.4 | 0.4 | 7.5 |
| 0.45 | 3.2 | 0.45 | 5.4 | 0.45 | 7.5 |
| 0.5 | 3.2 | 0.5 | 5.4 | 0.5 | 7.5 |
| 0.55 | 3.2 | 0.55 | 5.4 | 0.55 | 7.5 |
| 0.6 | 3.2 | 0.6 | 5.4 | 0.6 | 7.5 |
| 0.65 | 3.2 | 0.65 | 5.4 | 0.65 | 7.5 |
| 0.7 | 3.2 | 0.7 | 5.4 | 0.7 | 7.5 |
| 0.75 | 3.2 | 0.75 | 5.3 | 0.75 | 7.3 |
| 0.8 | 3.0 | 0.8 | 5.0 | 0.8 | 7.0 |
| 0.85 | 2.8 | 0.85 | 4.6 | 0.85 | 6.5 |
| 0.9 | 2.5 | 0.9 | 3.9 | 0.9 | 5.4 |
| 0.95 | 1.9 | 0.95 | 2.8 | 0.95 | 3.8 |
| 1 | 1.2 | 1 | 1.2 | 1 | 1.2 |

HF - HFO-1234zeE - HFC-245cb

| Organics 0.95 F1234zeE + 0.05 F245cb | | Organics 0.5 F1234zeE + 0.5 F245cb | | Organics 0.05 F1234zeE + 0.95 F245cb | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.9 | 0 | 4.8 | 0 | 4.7 |
| 0.05 | 5.8 | 0.05 | 5.9 | 0.05 | 5.8 |
| 0.1 | 5.9 | 0.1 | 5.9 | 0.1 | 5.8 |
| 0.15 | 5.9 | 0.15 | 5.9 | 0.15 | 5.8 |
| 0.2 | 5.9 | 0.2 | 5.9 | 0.2 | 5.8 |
| 0.25 | 5.9 | 0.25 | 5.9 | 0.25 | 5.8 |
| 0.3 | 5.9 | 0.3 | 5.9 | 0.3 | 5.8 |
| 0.35 | 5.9 | 0.35 | 5.9 | 0.35 | 5.8 |
| 0.4 | 5.8 | 0.4 | 5.9 | 0.4 | 5.8 |
| 0.45 | 5.8 | 0.45 | 5.9 | 0.45 | 5.8 |
| 0.5 | 5.8 | 0.5 | 5.9 | 0.5 | 5.8 |

| HF - HFO-1234zeZ - HFC-245cb ||||||
| Organics 0.95 F1234zeZ + 0.05 F245cb || Organics 0.5 F1234zeZ + 0.5 F245cb || Organics 0.05 F1234zeZ + 0.95 F245cb ||
| MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- |
| 0 | 1.9 | 0 | 3.2 | 0 | 4.5 |
| 0.05 | 3.1 | 0.05 | 4.3 | 0.05 | 5.7 |
| 0.1 | 3.1 | 0.1 | 4.3 | 0.1 | 5.7 |
| 0.15 | 3.1 | 0.15 | 4.3 | 0.15 | 5.7 |
| 0.2 | 3.1 | 0.2 | 4.3 | 0.2 | 5.7 |
| 0.25 | 3.1 | 0.25 | 4.3 | 0.25 | 5.7 |
| 0.3 | 3.1 | 0.3 | 4.3 | 0.3 | 5.7 |
| 0.35 | 3.1 | 0.35 | 4.3 | 0.35 | 5.7 |
| 0.4 | 3.1 | 0.4 | 4.3 | 0.4 | 5.7 |
| 0.45 | 3.1 | 0.45 | 4.4 | 0.45 | 5.7 |
| 0.5 | 3.1 | 0.5 | 4.4 | 0.5 | 5.7 |
| 0.55 | 3.1 | 0.55 | 4.4 | 0.55 | 5.7 |
| 0.6 | 3.1 | 0.6 | 4.4 | 0.6 | 5.7 |
| 0.65 | 3.1 | 0.65 | 4.4 | 0.65 | 5.7 |
| 0.7 | 3.1 | 0.7 | 4.5 | 0.7 | 5.7 |
| 0.75 | 3.1 | 0.75 | 4.5 | 0.75 | 5.7 |
| 0.8 | 3.0 | 0.8 | 4.5 | 0.8 | 5.7 |
| 0.85 | 2.8 | 0.85 | 4.2 | 0.85 | 5.7 |
| 0.9 | 2.4 | 0.9 | 3.6 | 0.9 | 4.9 |
| 0.95 | 1.9 | 0.95 | 2.7 | 0.95 | 3.5 |
| 1 | 1.2 | 1 | 1.2 | 1 | 1.2 |

(continued from previous page)

| | | | | | |
| --- | --- | --- | --- | --- | --- |
| 0.55 | 5.8 | 0.55 | 5.9 | 0.55 | 5.8 |
| 0.6 | 5.7 | 0.6 | 5.9 | 0.6 | 5.8 |
| 0.65 | 5.6 | 0.65 | 5.9 | 0.65 | 5.8 |
| 0.7 | 5.4 | 0.7 | 5.9 | 0.7 | 5.8 |
| 0.75 | 5.2 | 0.75 | 5.8 | 0.75 | 5.8 |
| 0.8 | 4.9 | 0.8 | 5.6 | 0.8 | 5.8 |
| 0.85 | 4.4 | 0.85 | 5.1 | 0.85 | 5.8 |
| 0.9 | 3.7 | 0.9 | 4.3 | 0.9 | 5.0 |
| 0.95 | 2.6 | 0.95 | 3.1 | 0.95 | 3.5 |
| 1 | 1.2 | 1 | 1.2 | 1 | 1.2 |

| HF - HFO-1234zeE - HFO-1243zf ||||||
| Organics 0.95 F1243zf + 0.05 F1234zeE || Organics 0.5 F1243zf + 0.5 F1234zeE || Organics 0.05 F1243zf + 0.95 F1234zeE ||
| MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- |
| 0 | 5.8 | 0 | 5.4 | 0 | 4.9 |
| 0.05 | 6.7 | 0.05 | 6.3 | 0.05 | 5.9 |
| 0.1 | 6.8 | 0.1 | 6.4 | 0.1 | 5.9 |
| 0.15 | 6.8 | 0.15 | 6.4 | 0.15 | 5.9 |
| 0.2 | 6.8 | 0.2 | 6.4 | 0.2 | 5.9 |
| 0.25 | 6.8 | 0.25 | 6.4 | 0.25 | 5.9 |
| 0.3 | 6.8 | 0.3 | 6.4 | 0.3 | 5.9 |
| 0.35 | 6.8 | 0.35 | 6.4 | 0.35 | 5.9 |
| 0.4 | 6.7 | 0.4 | 6.4 | 0.4 | 5.9 |
| 0.45 | 6.7 | 0.45 | 6.4 | 0.45 | 5.9 |
| 0.5 | 6.7 | 0.5 | 6.3 | 0.5 | 5.8 |
| 0.55 | 6.7 | 0.55 | 6.3 | 0.55 | 5.8 |
| 0.6 | 6.7 | 0.6 | 6.3 | 0.6 | 5.7 |
| 0.65 | 6.6 | 0.65 | 6.2 | 0.65 | 5.6 |
| 0.7 | 6.5 | 0.7 | 6.1 | 0.7 | 5.5 |
| 0.75 | 6.4 | 0.75 | 5.8 | 0.75 | 5.2 |
| 0.8 | 6.1 | 0.8 | 5.5 | 0.8 | 4.9 |
| 0.85 | 5.6 | 0.85 | 5.0 | 0.85 | 4.4 |
| 0.9 | 4.7 | 0.9 | 4.2 | 0.9 | 3.6 |
| 0.95 | 3.4 | 0.95 | 3.0 | 0.95 | 2.6 |
| 1 | 1.2 | 1 | 1.2 | 1 | 1.2 |

| HF - HFO-1234zeZ - HFO-1243zf ||||||
| Organics 0.95 F1243zf + 0.05 F1234zeZ || Organics 0.5 F1243zf + 0.5 F1234zeZ || Organics 0.05 F1243zf + 0.95 F1234zeZ ||
| MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- |
| 0 | 5.7 | 0 | 4.0 | 0 | 2.0 |
| 0.05 | 6.6 | 0.05 | 5.0 | 0.05 | 3.1 |
| 0.1 | 6.6 | 0.1 | 5.0 | 0.1 | 3.1 |
| 0.15 | 6.6 | 0.15 | 5.0 | 0.15 | 3.1 |
| 0.2 | 6.6 | 0.2 | 5.0 | 0.2 | 3.1 |
| 0.25 | 6.6 | 0.25 | 5.0 | 0.25 | 3.1 |
| 0.3 | 6.6 | 0.3 | 5.0 | 0.3 | 3.1 |
| 0.35 | 6.6 | 0.35 | 5.0 | 0.35 | 3.1 |
| 0.4 | 6.6 | 0.4 | 5.0 | 0.4 | 3.1 |
| 0.45 | 6.6 | 0.45 | 5.0 | 0.45 | 3.1 |
| 0.5 | 6.6 | 0.5 | 5.0 | 0.5 | 3.1 |
| 0.55 | 6.6 | 0.55 | 5.0 | 0.55 | 3.1 |
| 0.6 | 6.6 | 0.6 | 5.0 | 0.6 | 3.1 |
| 0.65 | 6.5 | 0.65 | 5.0 | 0.65 | 3.1 |
| 0.7 | 6.4 | 0.7 | 4.9 | 0.7 | 3.1 |
| 0.75 | 6.3 | 0.75 | 4.8 | 0.75 | 3.1 |
| 0.8 | 6.0 | 0.8 | 4.5 | 0.8 | 3.0 |
| 0.85 | 5.5 | 0.85 | 4.2 | 0.85 | 2.8 |
| 0.9 | 4.7 | 0.9 | 3.6 | 0.9 | 2.4 |
| 0.95 | 3.3 | 0.95 | 2.6 | 0.95 | 1.9 |
| 1 | 1.2 | 1 | 1.2 | 1 | 1.2 |

EXAMPLE 2

Temperature and Pressure Range of Ternary Mixtures

| | Boiling point range ||
| Ternary | Temperature ° C. | Pressure bar abs |
| --- | --- | --- |
| HF-HFO-1234zeE-HFC-245cb | 0 to 40 | ~2.5 to ~9.1 |
| HF-HFO-1234zeZ-HFC-245cb | 0 to 40 | ~1.2 to ~8.9 |
| HF-HFO-1234yf-HFO-1234zeE | 0 to 40 | ~2.6 to ~11.6 |
| HF-HFO-1234yf-HFO-1234zeZ | 0 to 40 | ~1.3 to ~11.4 |
| HF-HCFO-1233xf-HFO-1234zeE | 0 to 40 | ~1.1 to ~8.8 |
| HF-HCFO-1233xf-HFO-1234zeZ | 0 to 40 | ~1.0 to ~4.8 |
| HF-HFO-1234zeE-HCFO-1233zdE | 0 to 40 | ~1.0 to ~8.8 |
| HF-HFO-1234zeE-HFO-1243zf | 0 to 40 | ~2.5 to ~10.4 |
| HF-HFO-1234zeZ-HCFO-1233zdE | 0 to 40 | ~0.9 to ~4.8 |
| HF-HFO-1234zeZ-HFO-1243zf | 0 to 40 | ~1.2 to ~10.2 |

EXAMPLE 3

Decantation Range of Ternary Mixtures

| | Decantation ranges Mass percentage of HF |||
| Ternary | Isotherm 0° C. | Isotherm 25° C. | Isotherm 40° C. |
| --- | --- | --- | --- |
| HF-HFO-1234zeE-HFC-245cb | 5-75 | 10-70 | 40-65 |
| HF-HFO-1234zeZ-HFC-245cb | 5-80 | 5-75 | 10-75 |

| Ternary | Decantation ranges Mass percentage of HF | | |
|---|---|---|---|
| | Isotherm 0° C. | Isotherm 25° C. | Isotherm 40° C. |
| HF-HFO-1234yf-HFO-1234zeE | 5-65 | * | * |
| HF-HFO-1234yf-HFO-1234zeZ | 5-75 | 10-70 | 15-30 |
| HF-HCFO-1233xf-HFO-1234zeE | 5-70 | 5-60 | 10-45 |
| HF-HCFO-1233xf-HFO-1234zeZ | 5-80 | 5-70 | 5-65 |
| HF-HFO-1234zeE-HCFO-1233zdE | 5-70 | 5-65 | 10-50 |
| HF-HFO-1234zeE-HFO-1243zf | 5-65 | * | * |
| HF-HFO-1234zeZ-HCFO-1233zdE | 5-80 | 5-75 | 5-65 |
| HF-HFO-1234zeZ-HFO-1243zf | 5-75 | 10-65 | * |

EXAMPLE 4

Quaternary Mixtures, Isotherm at 25° C.

| HF-HCFO-1233xf-HFO-1234zeE-HFC-245cb | | | | | | | |
|---|---|---|---|---|---|---|---|
| Organics 0.9 F1233xf + 0.05 F1234zeE + 0.05 F245cb | | Organics 0.4 F1233xf + 0.3 F1234zeE + 0.3 F245cb | | Organics 0.05 F1233xf + 0.9 F1234zeE + 0.05 F245cb | | Organics 0.05 F1233xf + 0.05 F1234zeE + 0.9 F245cb | |
| MASSFRAC HF | TOTAL PRES bar | MASSFRAC HF | TOTAL PRES bar | MASSFRAC HF | TOTAL PRES bar | MASSFRAC HF | TOTAL PRES bar |
| 0 | 3.2 | 0 | 3.5 | 0 | 4.7 | 0 | 4.5 |
| 0.05 | 4.3 | 0.05 | 4.6 | 0.05 | 5.7 | 0.05 | 5.7 |
| 0.1 | 4.3 | 0.1 | 4.6 | 0.1 | 5.7 | 0.1 | 5.7 |
| 0.15 | 4.3 | 0.15 | 4.6 | 0.15 | 5.7 | 0.15 | 5.7 |
| 0.2 | 4.3 | 0.2 | 4.6 | 0.2 | 5.7 | 0.2 | 5.7 |
| 0.25 | 4.3 | 0.25 | 4.6 | 0.25 | 5.7 | 0.25 | 5.7 |
| 0.3 | 4.3 | 0.3 | 4.6 | 0.3 | 5.7 | 0.3 | 5.7 |
| 0.35 | 4.3 | 0.35 | 4.6 | 0.35 | 5.7 | 0.35 | 5.7 |
| 0.4 | 4.4 | 0.4 | 4.6 | 0.4 | 5.7 | 0.4 | 5.7 |
| 0.45 | 4.4 | 0.45 | 4.6 | 0.45 | 5.7 | 0.45 | 5.7 |
| 0.5 | 4.4 | 0.5 | 4.6 | 0.5 | 5.7 | 0.5 | 5.7 |
| 0.55 | 4.4 | 0.55 | 4.6 | 0.55 | 5.6 | 0.55 | 5.7 |
| 0.6 | 4.4 | 0.6 | 4.6 | 0.6 | 5.6 | 0.6 | 5.7 |
| 0.65 | 4.4 | 0.65 | 4.7 | 0.65 | 5.5 | 0.65 | 5.7 |
| 0.7 | 4.5 | 0.7 | 4.7 | 0.7 | 5.3 | 0.7 | 5.7 |
| 0.75 | 4.5 | 0.75 | 4.6 | 0.75 | 5.1 | 0.75 | 5.7 |
| 0.8 | 4.5 | 0.8 | 4.4 | 0.8 | 4.8 | 0.8 | 5.7 |
| 0.85 | 4.2 | 0.85 | 4.0 | 0.85 | 4.3 | 0.85 | 5.6 |
| 0.9 | 3.6 | 0.9 | 3.4 | 0.9 | 3.6 | 0.9 | 4.8 |
| 0.95 | 2.6 | 0.95 | 2.5 | 0.95 | 2.6 | 0.95 | 3.4 |
| 1 | 1.2 | 1 | 1.2 | 1 | 1.2 | 1 | 1.2 |

| HF-HCFO-1233xf-HFO-1234zeZ-HFC-245cb | | | | | | | |
|---|---|---|---|---|---|---|---|
| Organics 0.9 F1233xf + 0.05 F1234zeZ + 0.05 F245cb | | Organics 0.4 F1233xf + 0.3 F1234zeZ + 0.3 F245cb | | Organics 0.05 F1233xf + 0.9 F1234zeZ + 0.05 F245cb | | Organics 0.05 F1233xf + 0.05 F1234zeZ + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 2.6 | 0 | 1.9 | 0 | 4.3 |
| 0.05 | 2.8 | 0.05 | 3.7 | 0.05 | 3.0 | 0.05 | 5.5 |
| 0.1 | 2.8 | 0.1 | 3.7 | 0.1 | 3.0 | 0.1 | 5.5 |
| 0.15 | 2.8 | 0.15 | 3.7 | 0.15 | 3.0 | 0.15 | 5.5 |
| 0.2 | 2.8 | 0.2 | 3.7 | 0.2 | 3.0 | 0.2 | 5.5 |
| 0.25 | 2.8 | 0.25 | 3.7 | 0.25 | 3.0 | 0.25 | 5.5 |
| 0.3 | 2.8 | 0.3 | 3.7 | 0.3 | 3.0 | 0.3 | 5.5 |
| 0.35 | 2.8 | 0.35 | 3.7 | 0.35 | 3.0 | 0.35 | 5.5 |
| 0.4 | 2.8 | 0.4 | 3.7 | 0.4 | 3.0 | 0.4 | 5.5 |
| 0.45 | 2.8 | 0.45 | 3.7 | 0.45 | 3.1 | 0.45 | 5.5 |
| 0.5 | 2.8 | 0.5 | 3.7 | 0.5 | 3.1 | 0.5 | 5.5 |
| 0.55 | 2.9 | 0.55 | 3.7 | 0.55 | 3.1 | 0.55 | 5.5 |
| 0.6 | 2.9 | 0.6 | 3.8 | 0.6 | 3.1 | 0.6 | 5.5 |
| 0.65 | 2.9 | 0.65 | 3.8 | 0.65 | 3.1 | 0.65 | 5.6 |
| 0.7 | 2.9 | 0.7 | 3.8 | 0.7 | 3.1 | 0.7 | 5.6 |
| 0.75 | 2.9 | 0.75 | 3.8 | 0.75 | 3.1 | 0.75 | 5.6 |
| 0.8 | 2.7 | 0.8 | 3.8 | 0.8 | 2.9 | 0.8 | 5.6 |
| 0.85 | 2.5 | 0.85 | 3.5 | 0.85 | 2.7 | 0.85 | 5.5 |
| 0.9 | 2.2 | 0.9 | 3.0 | 0.9 | 2.4 | 0.9 | 4.8 |

-continued

| | | | | | | | |
|---|---|---|---|---|---|---|---|
| 0.95 | 1.8 | 0.95 | 2.3 | 0.95 | 1.9 | 0.95 | 3.4 |
| 1 | 1.2 | 1 | 1.2 | 1 | 1.2 | 1 | 1.2 |

HF-HCFO-1233xf-HCFO-1233zdE-HFO-1234zeE

| Organics<br>0.9 F1233xf + 0.05<br>F1233zdE + 0.05 F1234zeE | | Organics<br>0.05 F1233xf + 0.9<br>F1233zdE + 0.05 F1234zeE | | Organics<br>0.05 F1233xf + 0.05<br>F1233zdE + 0.9 F1234zeE | | Organics<br>0.4 F1233xf + 0.3<br>F1233zdE + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.6 | 0 | 2.5 |
| 0.05 | 2.8 | 0.05 | 2.6 | 0.05 | 5.5 | 0.05 | 3.6 |
| 0.1 | 2.8 | 0.1 | 2.6 | 0.1 | 5.5 | 0.1 | 3.6 |
| 0.15 | 2.8 | 0.15 | 2.6 | 0.15 | 5.5 | 0.15 | 3.6 |
| 0.2 | 2.8 | 0.2 | 2.6 | 0.2 | 5.5 | 0.2 | 3.6 |
| 0.25 | 2.8 | 0.25 | 2.6 | 0.25 | 5.5 | 0.25 | 3.6 |
| 0.3 | 2.8 | 0.3 | 2.6 | 0.3 | 5.5 | 0.3 | 3.6 |
| 0.35 | 2.8 | 0.35 | 2.6 | 0.35 | 5.5 | 0.35 | 3.6 |
| 0.4 | 2.8 | 0.4 | 2.6 | 0.4 | 5.5 | 0.4 | 3.6 |
| 0.45 | 2.8 | 0.45 | 2.6 | 0.45 | 5.5 | 0.45 | 3.6 |
| 0.5 | 2.8 | 0.5 | 2.6 | 0.5 | 5.5 | 0.5 | 3.6 |
| 0.55 | 2.8 | 0.55 | 2.6 | 0.55 | 5.4 | 0.55 | 3.5 |
| 0.6 | 2.8 | 0.6 | 2.6 | 0.6 | 5.4 | 0.6 | 3.5 |
| 0.65 | 2.8 | 0.65 | 2.6 | 0.65 | 5.3 | 0.65 | 3.5 |
| 0.7 | 2.8 | 0.7 | 2.6 | 0.7 | 5.1 | 0.7 | 3.5 |
| 0.75 | 2.8 | 0.75 | 2.6 | 0.75 | 4.9 | 0.75 | 3.3 |
| 0.8 | 2.6 | 0.8 | 2.5 | 0.8 | 4.6 | 0.8 | 3.2 |
| 0.85 | 2.4 | 0.85 | 2.3 | 0.85 | 4.1 | 0.85 | 2.9 |
| 0.9 | 2.2 | 0.9 | 2.0 | 0.9 | 3.4 | 0.9 | 2.5 |
| 0.95 | 1.7 | 0.95 | 1.7 | 0.95 | 2.5 | 0.95 | 1.9 |
| 1 | 1.2 | 1 | 1.2 | 1 | 1.2 | 1 | 1.2 |

HF-HCFO-1233xf-HCFO-1233zdE-HFO-1234zeZ

| Organics<br>0.9 F1233xf + 0.05<br>F1233zdE + 0.05 F1234zeZ | | Organics<br>0.05 F1233xf + 0.9<br>F1233zdE + 0.05 F1234zeZ | | Organics<br>0.05 F1233xf + 0.05<br>F1233zdE + 0.9 F1234zeZ | | Organics<br>0.4 F1233xf + 0.3<br>F1233zdE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 1.4 | 0 | 1.8 | 0 | 1.6 |
| 0.05 | 2.7 | 0.05 | 2.5 | 0.05 | 2.9 | 0.05 | 2.7 |
| 0.1 | 2.7 | 0.1 | 2.5 | 0.1 | 2.9 | 0.1 | 2.7 |
| 0.15 | 2.7 | 0.15 | 2.5 | 0.15 | 2.9 | 0.15 | 2.7 |
| 0.2 | 2.7 | 0.2 | 2.5 | 0.2 | 2.9 | 0.2 | 2.7 |
| 0.25 | 2.7 | 0.25 | 2.5 | 0.25 | 2.9 | 0.25 | 2.7 |
| 0.3 | 2.7 | 0.3 | 2.5 | 0.3 | 2.9 | 0.3 | 2.7 |
| 0.35 | 2.7 | 0.35 | 2.5 | 0.35 | 2.9 | 0.35 | 2.7 |
| 0.4 | 2.7 | 0.4 | 2.5 | 0.4 | 2.9 | 0.4 | 2.7 |
| 0.45 | 2.7 | 0.45 | 2.5 | 0.45 | 2.9 | 0.45 | 2.7 |
| 0.5 | 2.7 | 0.5 | 2.5 | 0.5 | 2.9 | 0.5 | 2.7 |
| 0.55 | 2.7 | 0.55 | 2.5 | 0.55 | 2.9 | 0.55 | 2.7 |
| 0.6 | 2.7 | 0.6 | 2.5 | 0.6 | 2.9 | 0.6 | 2.7 |
| 0.65 | 2.7 | 0.65 | 2.5 | 0.65 | 2.9 | 0.65 | 2.7 |
| 0.7 | 2.7 | 0.7 | 2.5 | 0.7 | 2.9 | 0.7 | 2.7 |
| 0.75 | 2.7 | 0.75 | 2.5 | 0.75 | 2.9 | 0.75 | 2.7 |
| 0.8 | 2.5 | 0.8 | 2.4 | 0.8 | 2.8 | 0.8 | 2.6 |
| 0.85 | 2.4 | 0.85 | 2.2 | 0.85 | 2.6 | 0.85 | 2.4 |
| 0.9 | 2.1 | 0.9 | 2.0 | 0.9 | 2.3 | 0.9 | 2.1 |
| 0.95 | 1.7 | 0.95 | 1.6 | 0.95 | 1.8 | 0.95 | 1.7 |
| 1 | 1.2 | 1 | 1.2 | 1 | 1.2 | 1 | 1.2 |

HF-HCFO-1233xf-HFO-1234zeE-HFO-1234zeZ

| Organics<br>0.9 F1233xf + 0.05<br>F1234zeE + 0.05 F1234zeZ | | Organics<br>0.05 F1233xf + 0.9<br>F1234zeE + 0.05 F1234zeZ | | Organics<br>0.05 F1233xf + 0.05<br>F1234zeE + 0.9 F1234zeZ | | Organics<br>0.4 F1233xf + 0.3<br>F1234zeE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.9 | 0 | 2.7 |
| 0.05 | 2.8 | 0.05 | 5.5 | 0.05 | 3.1 | 0.05 | 3.7 |

-continued

| MASSFRAC | TOTAL PRESSURE bar | MASSFRAC | TOTAL PRESSURE bar | MASSFRAC | TOTAL PRESSURE bar | MASSFRAC | TOTAL PRESSURE bar |
|---|---|---|---|---|---|---|---|
| 0.1 | 2.8 | 0.1 | 5.5 | 0.1 | 3.0 | 0.1 | 3.7 |
| 0.15 | 2.8 | 0.15 | 5.5 | 0.15 | 3.0 | 0.15 | 3.7 |
| 0.2 | 2.8 | 0.2 | 5.5 | 0.2 | 3.0 | 0.2 | 3.7 |
| 0.25 | 2.8 | 0.25 | 5.5 | 0.25 | 3.0 | 0.25 | 3.7 |
| 0.3 | 2.8 | 0.3 | 5.5 | 0.3 | 3.0 | 0.3 | 3.7 |
| 0.35 | 2.8 | 0.35 | 5.5 | 0.35 | 3.0 | 0.35 | 3.7 |
| 0.4 | 2.8 | 0.4 | 5.5 | 0.4 | 3.0 | 0.4 | 3.7 |
| 0.45 | 2.8 | 0.45 | 5.5 | 0.45 | 3.0 | 0.45 | 3.7 |
| 0.5 | 2.8 | 0.5 | 5.5 | 0.5 | 3.0 | 0.5 | 3.7 |
| 0.55 | 2.8 | 0.55 | 5.4 | 0.55 | 3.0 | 0.55 | 3.7 |
| 0.6 | 2.8 | 0.6 | 5.4 | 0.6 | 3.0 | 0.6 | 3.6 |
| 0.65 | 2.8 | 0.65 | 5.3 | 0.65 | 3.0 | 0.65 | 3.6 |
| 0.7 | 2.8 | 0.7 | 5.1 | 0.7 | 3.0 | 0.7 | 3.6 |
| 0.75 | 2.8 | 0.75 | 4.9 | 0.75 | 3.0 | 0.75 | 3.5 |
| 0.8 | 2.7 | 0.8 | 4.6 | 0.8 | 2.9 | 0.8 | 3.3 |
| 0.85 | 2.5 | 0.85 | 4.1 | 0.85 | 2.7 | 0.85 | 3.0 |
| 0.9 | 2.2 | 0.9 | 3.4 | 0.9 | 2.3 | 0.9 | 2.6 |
| 0.95 | 1.8 | 0.95 | 2.5 | 0.95 | 1.9 | 0.95 | 2.0 |
| 1 | 1.2 | 1 | 1.2 | 1 | 1.2 | 1 | 1.2 |

HF-HCFO-1233xf-HFO-1234zeE-HFO-1243zf

| Organics 0.9 F1233xf + 0.05 F1234zeE + 0.05 F1243zf | | Organics 0.05 F1233xf + 0.9 F1234zeE + 0.05 F1243zf | | Organics 0.05 F1233xf + 0.05 F1234zeE + 0.9 F1243zf | | Organics 0.4 F1233xf + 0.3 F1234zeE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 5.6 | 0 | 4.0 |
| 0.05 | 3.1 | 0.05 | 5.7 | 0.05 | 6.6 | 0.05 | 5.1 |
| 0.1 | 3.1 | 0.1 | 5.8 | 0.1 | 6.6 | 0.1 | 5.1 |
| 0.15 | 3.1 | 0.15 | 5.8 | 0.15 | 6.6 | 0.15 | 5.1 |
| 0.2 | 3.1 | 0.2 | 5.8 | 0.2 | 6.6 | 0.2 | 5.1 |
| 0.25 | 3.1 | 0.25 | 5.8 | 0.25 | 6.6 | 0.25 | 5.1 |
| 0.3 | 3.1 | 0.3 | 5.8 | 0.3 | 6.6 | 0.3 | 5.0 |
| 0.35 | 3.1 | 0.35 | 5.7 | 0.35 | 6.6 | 0.35 | 5.0 |
| 0.4 | 3.1 | 0.4 | 5.7 | 0.4 | 6.6 | 0.4 | 5.0 |
| 0.45 | 3.1 | 0.45 | 5.7 | 0.45 | 6.6 | 0.45 | 5.0 |
| 0.5 | 3.1 | 0.5 | 5.7 | 0.5 | 6.6 | 0.5 | 5.0 |
| 0.55 | 3.1 | 0.55 | 5.7 | 0.55 | 6.6 | 0.55 | 5.0 |
| 0.6 | 3.1 | 0.6 | 5.6 | 0.6 | 6.5 | 0.6 | 5.0 |
| 0.65 | 3.1 | 0.65 | 5.5 | 0.65 | 6.5 | 0.65 | 4.9 |
| 0.7 | 3.0 | 0.7 | 5.3 | 0.7 | 6.4 | 0.7 | 4.8 |
| 0.75 | 3.0 | 0.75 | 5.1 | 0.75 | 6.2 | 0.75 | 4.7 |
| 0.8 | 2.9 | 0.8 | 4.8 | 0.8 | 5.9 | 0.8 | 4.4 |
| 0.85 | 2.6 | 0.85 | 4.3 | 0.85 | 5.4 | 0.85 | 4.0 |
| 0.9 | 2.3 | 0.9 | 3.6 | 0.9 | 4.6 | 0.9 | 3.4 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF-HCFO-1233xf-HFO-1234zeZ-HFO-1243zf

| Organics 0.9 F1233xf + 0.05 F1234zeZ + 0.05 F1243zf | | Organics 0.05 F1233xf + 0.9 F1234zeZ + 0.05 F1243zf | | Organics 0.05 F1233xf + 0.05 F1234zeZ + 0.9 F1243zf | | Organics 0.4 F1233xf + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 5.5 | 0 | 3.1 |
| 0.05 | 2.9 | 0.05 | 3.1 | 0.05 | 6.4 | 0.05 | 4.2 |
| 0.1 | 2.9 | 0.1 | 3.1 | 0.1 | 6.5 | 0.1 | 4.2 |
| 0.15 | 2.9 | 0.15 | 3.1 | 0.15 | 6.5 | 0.15 | 4.2 |
| 0.2 | 2.9 | 0.2 | 3.1 | 0.2 | 6.5 | 0.2 | 4.2 |
| 0.25 | 2.9 | 0.25 | 3.1 | 0.25 | 6.5 | 0.25 | 4.2 |
| 0.3 | 2.9 | 0.3 | 3.1 | 0.3 | 6.5 | 0.3 | 4.2 |
| 0.35 | 2.9 | 0.35 | 3.1 | 0.35 | 6.5 | 0.35 | 4.2 |
| 0.4 | 2.9 | 0.4 | 3.1 | 0.4 | 6.5 | 0.4 | 4.2 |
| 0.45 | 2.9 | 0.45 | 3.1 | 0.45 | 6.5 | 0.45 | 4.2 |
| 0.5 | 2.9 | 0.5 | 3.1 | 0.5 | 6.4 | 0.5 | 4.2 |
| 0.55 | 2.9 | 0.55 | 3.1 | 0.55 | 6.4 | 0.55 | 4.2 |
| 0.6 | 2.9 | 0.6 | 3.1 | 0.6 | 6.4 | 0.6 | 4.1 |
| 0.65 | 2.9 | 0.65 | 3.1 | 0.65 | 6.4 | 0.65 | 4.1 |

-continued

| MASSFRAC | TOTAL PRESSURE bar | MASSFRAC | TOTAL PRESSURE bar | MASSFRAC | TOTAL PRESSURE bar | MASSFRAC | TOTAL PRESSURE bar |
|---|---|---|---|---|---|---|---|
| 0.7 | 2.9 | 0.7 | 3.1 | 0.7 | 6.3 | 0.7 | 4.1 |
| 0.75 | 2.9 | 0.75 | 3.1 | 0.75 | 6.1 | 0.75 | 4.0 |
| 0.8 | 2.8 | 0.8 | 3.0 | 0.8 | 5.8 | 0.8 | 3.8 |
| 0.85 | 2.5 | 0.85 | 2.7 | 0.85 | 5.3 | 0.85 | 3.5 |
| 0.9 | 2.2 | 0.9 | 2.4 | 0.9 | 4.5 | 0.9 | 3.0 |
| 0.95 | 1.8 | 0.95 | 1.9 | 0.95 | 3.2 | 0.95 | 2.3 |
| 1 | 1.2 | 1 | 1.2 | 1 | 1.2 | 1 | 1.2 |

HF-HCFO-1233xf-HFO-1234yf-HFO-1234zeE

| Organics 0.9 F1233xf + 0.05 F1234yf + 0.05 F1234zeE | | Organics 0.05 F1233xf + 0.9 F1234yf + 0.05 F1234zeE | | Organics 0.05 F1233xf + 0.05 F1234yf + 0.9 F1234zeE | | Organics 0.4 F1233xf + 0.3 F1234yf + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 6.5 | 0 | 4.8 | 0 | 4.2 |
| 0.05 | 3.1 | 0.05 | 7.4 | 0.05 | 5.8 | 0.05 | 5.3 |
| 0.1 | 3.1 | 0.1 | 7.4 | 0.1 | 5.8 | 0.1 | 5.3 |
| 0.15 | 3.1 | 0.15 | 7.4 | 0.15 | 5.8 | 0.15 | 5.3 |
| 0.2 | 3.1 | 0.2 | 7.4 | 0.2 | 5.8 | 0.2 | 5.3 |
| 0.25 | 3.1 | 0.25 | 7.4 | 0.25 | 5.8 | 0.25 | 5.3 |
| 0.3 | 3.1 | 0.3 | 7.4 | 0.3 | 5.8 | 0.3 | 5.3 |
| 0.35 | 3.1 | 0.35 | 7.4 | 0.35 | 5.8 | 0.35 | 5.3 |
| 0.4 | 3.1 | 0.4 | 7.4 | 0.4 | 5.8 | 0.4 | 5.3 |
| 0.45 | 3.1 | 0.45 | 7.4 | 0.45 | 5.8 | 0.45 | 5.3 |
| 0.5 | 3.1 | 0.5 | 7.4 | 0.5 | 5.8 | 0.5 | 5.3 |
| 0.55 | 3.1 | 0.55 | 7.4 | 0.55 | 5.7 | 0.55 | 5.3 |
| 0.6 | 3.1 | 0.6 | 7.4 | 0.6 | 5.6 | 0.6 | 5.3 |
| 0.65 | 3.1 | 0.65 | 7.5 | 0.65 | 5.5 | 0.65 | 5.3 |
| 0.7 | 3.1 | 0.7 | 7.4 | 0.7 | 5.4 | 0.7 | 5.2 |
| 0.75 | 3.1 | 0.75 | 7.2 | 0.75 | 5.2 | 0.75 | 5.0 |
| 0.8 | 2.9 | 0.8 | 6.9 | 0.8 | 4.8 | 0.8 | 4.7 |
| 0.85 | 2.7 | 0.85 | 6.3 | 0.85 | 4.3 | 0.85 | 4.3 |
| 0.9 | 2.3 | 0.9 | 5.3 | 0.9 | 3.6 | 0.9 | 3.6 |
| 0.95 | 1.9 | 0.95 | 3.7 | 0.95 | 2.6 | 0.95 | 2.6 |
| 1 | 1.2 | 1 | 1.2 | 1 | 1.2 | 1 | 1.2 |

HF-HCFO-1233xf-HFO-1234yf-HFO-1234zeZ

| Organics 0.9 F1233xf + 0.05 F1234yf + 0.05 F1234zeZ | | Organics 0.05 F1233xf + 0.9 F1234yf + 0.05 F1234zeZ | | Organics 0.05 F1233xf + 0.05 F1234yf + 0.9 F1234zeZ | | Organics 0.4 F1233xf + 0.3 F1234yf + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 6.3 | 0 | 2.1 | 0 | 3.3 |
| 0.05 | 3.0 | 0.05 | 7.3 | 0.05 | 3.2 | 0.05 | 4.4 |
| 0.1 | 3.0 | 0.1 | 7.3 | 0.1 | 3.2 | 0.1 | 4.4 |
| 0.15 | 3.0 | 0.15 | 7.3 | 0.15 | 3.2 | 0.15 | 4.4 |
| 0.2 | 3.0 | 0.2 | 7.3 | 0.2 | 3.2 | 0.2 | 4.4 |
| 0.25 | 3.0 | 0.25 | 7.3 | 0.25 | 3.2 | 0.25 | 4.4 |
| 0.3 | 3.0 | 0.3 | 7.3 | 0.3 | 3.2 | 0.3 | 4.4 |
| 0.35 | 3.0 | 0.35 | 7.3 | 0.35 | 3.2 | 0.35 | 4.4 |
| 0.4 | 3.0 | 0.4 | 7.3 | 0.4 | 3.2 | 0.4 | 4.4 |
| 0.45 | 3.0 | 0.45 | 7.3 | 0.45 | 3.2 | 0.45 | 4.4 |
| 0.5 | 3.0 | 0.5 | 7.3 | 0.5 | 3.2 | 0.5 | 4.4 |
| 0.55 | 3.0 | 0.55 | 7.3 | 0.55 | 3.2 | 0.55 | 4.4 |
| 0.6 | 3.0 | 0.6 | 7.3 | 0.6 | 3.2 | 0.6 | 4.4 |
| 0.65 | 3.0 | 0.65 | 7.3 | 0.65 | 3.2 | 0.65 | 4.4 |
| 0.7 | 3.0 | 0.7 | 7.3 | 0.7 | 3.2 | 0.7 | 4.4 |
| 0.75 | 2.9 | 0.75 | 7.1 | 0.75 | 3.1 | 0.75 | 4.3 |
| 0.8 | 2.8 | 0.8 | 6.8 | 0.8 | 3.0 | 0.8 | 4.1 |
| 0.85 | 2.6 | 0.85 | 6.3 | 0.85 | 2.8 | 0.85 | 3.7 |
| 0.9 | 2.3 | 0.9 | 5.3 | 0.9 | 2.4 | 0.9 | 3.2 |
| 0.95 | 1.8 | 0.95 | 3.7 | 0.95 | 1.9 | 0.95 | 2.4 |
| 1 | 1.2 | 1 | 1.2 | 1 | 1.2 | 1 | 1.2 |

-continued

| HF-HFO-1234yf-HFO-1234zeE-HFC-245cb ||||||||
| Organics 0.9 F1234yf + 0.05 F1234zeE + 0.05 F245cb || Organics 0.4 F1234yf + 0.3 F1234zeE + 0.3 F245cb || Organics 0.05 F1234yf + 0.9 F1234zeE + 0.05 F245cb || Organics 0.05 F1234yf + 0.05 F1234zeE + 0.9 F245cb ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0 | 6.6 | 0 | 5.6 | 0 | 5.0 | 0 | 4.8 |
| 0.05 | 7.6 | 0.05 | 6.7 | 0.05 | 5.9 | 0.05 | 6.0 |
| 0.1 | 7.6 | 0.1 | 6.7 | 0.1 | 6.0 | 0.1 | 6.0 |
| 0.15 | 7.6 | 0.15 | 6.7 | 0.15 | 6.0 | 0.15 | 6.0 |
| 0.2 | 7.6 | 0.2 | 6.7 | 0.2 | 6.0 | 0.2 | 6.0 |
| 0.25 | 7.6 | 0.25 | 6.7 | 0.25 | 6.0 | 0.25 | 6.0 |
| 0.3 | 7.6 | 0.3 | 6.7 | 0.3 | 6.0 | 0.3 | 6.0 |
| 0.35 | 7.6 | 0.35 | 6.7 | 0.35 | 6.0 | 0.35 | 6.0 |
| 0.4 | 7.6 | 0.4 | 6.7 | 0.4 | 6.0 | 0.4 | 6.0 |
| 0.45 | 7.6 | 0.45 | 6.7 | 0.45 | 5.9 | 0.45 | 6.0 |
| 0.5 | 7.6 | 0.5 | 6.7 | 0.5 | 5.9 | 0.5 | 6.0 |
| 0.55 | 7.6 | 0.55 | 6.7 | 0.55 | 5.9 | 0.55 | 5.9 |
| 0.6 | 7.6 | 0.6 | 6.7 | 0.6 | 5.8 | 0.6 | 5.9 |
| 0.65 | 7.6 | 0.65 | 6.7 | 0.65 | 5.7 | 0.65 | 5.9 |
| 0.7 | 7.6 | 0.7 | 6.7 | 0.7 | 5.6 | 0.7 | 5.9 |
| 0.75 | 7.4 | 0.75 | 6.6 | 0.75 | 5.3 | 0.75 | 5.9 |
| 0.8 | 7.1 | 0.8 | 6.3 | 0.8 | 5.0 | 0.8 | 5.9 |
| 0.85 | 6.5 | 0.85 | 5.7 | 0.85 | 4.5 | 0.85 | 5.8 |
| 0.9 | 5.5 | 0.9 | 4.8 | 0.9 | 3.8 | 0.9 | 5.0 |
| 0.95 | 3.8 | 0.95 | 3.4 | 0.95 | 2.7 | 0.95 | 3.5 |
| 1 | 1.2 | 1 | 1.2 | 1 | 1.2 | 1 | 1.2 |

| HF-HFO-1234yf-HFO-1234zeZ-HFC-245cb ||||||||
| Organics 0.9 F1234yf + 0.05 F1234zeZ + 0.05 F245cb || Organics 0.4 F1234yf + 0.3 F1234zeZ + 0.3 F245cb || Organics 0.05 F1234yf + 0.9 F1234zeZ + 0.05 F245cb || Organics 0.05 F1234yf + 0.05 F1234zeZ + 0.9 F245cb ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0 | 6.4 | 0 | 4.6 | 0 | 2.2 | 0 | 4.6 |
| 0.05 | 7.4 | 0.05 | 5.7 | 0.05 | 3.3 | 0.05 | 5.8 |
| 0.1 | 7.4 | 0.1 | 5.7 | 0.1 | 3.3 | 0.1 | 5.8 |
| 0.15 | 7.4 | 0.15 | 5.7 | 0.15 | 3.3 | 0.15 | 5.8 |
| 0.2 | 7.4 | 0.2 | 5.7 | 0.2 | 3.3 | 0.2 | 5.8 |
| 0.25 | 7.4 | 0.25 | 5.7 | 0.25 | 3.3 | 0.25 | 5.8 |
| 0.3 | 7.4 | 0.3 | 5.7 | 0.3 | 3.3 | 0.3 | 5.8 |
| 0.35 | 7.4 | 0.35 | 5.7 | 0.35 | 3.3 | 0.35 | 5.8 |
| 0.4 | 7.4 | 0.4 | 5.8 | 0.4 | 3.3 | 0.4 | 5.8 |
| 0.45 | 7.4 | 0.45 | 5.8 | 0.45 | 3.3 | 0.45 | 5.8 |
| 0.5 | 7.4 | 0.5 | 5.8 | 0.5 | 3.3 | 0.5 | 5.8 |
| 0.55 | 7.4 | 0.55 | 5.8 | 0.55 | 3.3 | 0.55 | 5.8 |
| 0.6 | 7.4 | 0.6 | 5.8 | 0.6 | 3.3 | 0.6 | 5.8 |
| 0.65 | 7.4 | 0.65 | 5.8 | 0.65 | 3.3 | 0.65 | 5.8 |
| 0.7 | 7.4 | 0.7 | 5.8 | 0.7 | 3.3 | 0.7 | 5.8 |
| 0.75 | 7.3 | 0.75 | 5.8 | 0.75 | 3.3 | 0.75 | 5.8 |
| 0.8 | 7.0 | 0.8 | 5.6 | 0.8 | 3.2 | 0.8 | 5.8 |
| 0.85 | 6.4 | 0.85 | 5.2 | 0.85 | 3.0 | 0.85 | 5.7 |
| 0.9 | 5.4 | 0.9 | 4.4 | 0.9 | 2.6 | 0.9 | 4.9 |
| 0.95 | 3.8 | 0.95 | 3.2 | 0.95 | 2.0 | 0.95 | 3.5 |
| 1 | 1.2 | 1 | 1.2 | 1 | 1.2 | 1 | 1.2 |

| HF-HFO-1234yf-HFO-1234zeE-HFO-1234zeZ ||||||||
| Organics 0.9 F1234yf + 0.05 F1234zeE + 0.05 F1234zeZ || Organics 0.05 F1234yf + 0.9 F1234zeE + 0.05 F1234zeZ || Organics 0.05 F1234yf + 0.05 F1234zeE + 0.9 F1234zeZ || Organics 0.4 F1234yf + 0.3 F1234zeE + 0.3 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0 | 6.4 | 0 | 4.8 | 0 | 2.2 | 0 | 4.7 |
| 0.05 | 7.4 | 0.05 | 5.8 | 0.05 | 3.3 | 0.05 | 5.7 |
| 0.1 | 7.4 | 0.1 | 5.8 | 0.1 | 3.3 | 0.1 | 5.7 |
| 0.15 | 7.4 | 0.15 | 5.8 | 0.15 | 3.3 | 0.15 | 5.7 |
| 0.2 | 7.4 | 0.2 | 5.8 | 0.2 | 3.3 | 0.2 | 5.7 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0.25 | 7.4 | 0.25 | 5.8 | 0.25 | 3.3 | 0.25 | 5.8 |
| 0.3 | 7.4 | 0.3 | 5.8 | 0.3 | 3.3 | 0.3 | 5.8 |
| 0.35 | 7.4 | 0.35 | 5.8 | 0.35 | 3.3 | 0.35 | 5.8 |
| 0.4 | 7.4 | 0.4 | 5.8 | 0.4 | 3.3 | 0.4 | 5.8 |
| 0.45 | 7.4 | 0.45 | 5.8 | 0.45 | 3.3 | 0.45 | 5.8 |
| 0.5 | 7.4 | 0.5 | 5.7 | 0.5 | 3.3 | 0.5 | 5.8 |
| 0.55 | 7.4 | 0.55 | 5.7 | 0.55 | 3.3 | 0.55 | 5.8 |
| 0.6 | 7.4 | 0.6 | 5.6 | 0.6 | 3.3 | 0.6 | 5.8 |
| 0.65 | 7.4 | 0.65 | 5.5 | 0.65 | 3.3 | 0.65 | 5.7 |
| 0.7 | 7.4 | 0.7 | 5.4 | 0.7 | 3.3 | 0.7 | 5.6 |
| 0.75 | 7.2 | 0.75 | 5.2 | 0.75 | 3.3 | 0.75 | 5.5 |
| 0.8 | 6.9 | 0.8 | 4.8 | 0.8 | 3.1 | 0.8 | 5.2 |
| 0.85 | 6.3 | 0.85 | 4.3 | 0.85 | 2.9 | 0.85 | 4.7 |
| 0.9 | 5.3 | 0.9 | 3.6 | 0.9 | 2.5 | 0.9 | 4.0 |
| 0.95 | 3.7 | 0.95 | 2.6 | 0.95 | 2.0 | 0.95 | 2.9 |
| 1 | 1.2 | 1 | 1.2 | 1 | 1.2 | 1 | 1.2 |

HF-HFO-1234yf-HFO-1234zeE-HCFO-1233zdE

| Organics 0.9 F1234yf + 0.05 F1234zeE + 0.05 F1233zdE | | Organics 0.05 F1234yf + 0.9 F1234zeE + 0.05 F1233zdE | | Organics 0.05 F1234yf + 0.05 F1234zeE + 0.9 F1233zdE | | Organics 0.4 F1234yf + 0.3 F1234zeE + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 1.8 | 0 | 4.7 |
| 0.05 | 7.4 | 0.05 | 5.8 | 0.05 | 2.9 | 0.05 | 5.7 |
| 0.1 | 7.4 | 0.1 | 5.8 | 0.1 | 2.9 | 0.1 | 5.7 |
| 0.15 | 7.4 | 0.15 | 5.8 | 0.15 | 2.9 | 0.15 | 5.7 |
| 0.2 | 7.4 | 0.2 | 5.8 | 0.2 | 2.9 | 0.2 | 5.7 |
| 0.25 | 7.4 | 0.25 | 5.8 | 0.25 | 2.9 | 0.25 | 5.7 |
| 0.3 | 7.4 | 0.3 | 5.8 | 0.3 | 2.9 | 0.3 | 5.7 |
| 0.35 | 7.4 | 0.35 | 5.8 | 0.35 | 2.9 | 0.35 | 5.7 |
| 0.4 | 7.4 | 0.4 | 5.8 | 0.4 | 2.9 | 0.4 | 5.7 |
| 0.45 | 7.4 | 0.45 | 5.8 | 0.45 | 2.9 | 0.45 | 5.7 |
| 0.5 | 7.4 | 0.5 | 5.7 | 0.5 | 2.9 | 0.5 | 5.7 |
| 0.55 | 7.4 | 0.55 | 5.7 | 0.55 | 2.9 | 0.55 | 5.7 |
| 0.6 | 7.4 | 0.6 | 5.6 | 0.6 | 2.9 | 0.6 | 5.7 |
| 0.65 | 7.4 | 0.65 | 5.5 | 0.65 | 2.9 | 0.65 | 5.7 |
| 0.7 | 7.4 | 0.7 | 5.4 | 0.7 | 2.9 | 0.7 | 5.6 |
| 0.75 | 7.2 | 0.75 | 5.1 | 0.75 | 2.9 | 0.75 | 5.4 |
| 0.8 | 6.9 | 0.8 | 4.8 | 0.8 | 2.7 | 0.8 | 5.1 |
| 0.85 | 6.3 | 0.85 | 4.3 | 0.85 | 2.5 | 0.85 | 4.7 |
| 0.9 | 5.3 | 0.9 | 3.6 | 0.9 | 2.2 | 0.9 | 3.9 |
| 0.95 | 3.7 | 0.95 | 2.6 | 0.95 | 1.8 | 0.95 | 2.8 |
| 1 | 1.2 | 1 | 1.2 | 1 | 1.2 | 1 | 1.2 |

HF-HFO-1234yf-HFO-1234zeE-HFO-1243zf

| Organics 0.9 F1234yf + 0.05 F1234zeE + 0.05 F1243zf | | Organics 0.05 F1234yf + 0.9 F1234zeE + 0.05 F1243zf | | Organics 0.05 F1234yf + 0.05 F1234zeE + 0.9 F1243zf | | Organics 0.4 F1234yf + 0.3 F1234zeE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.7 | 0 | 5.0 | 0 | 5.8 | 0 | 5.9 |
| 0.05 | 7.6 | 0.05 | 6.0 | 0.05 | 6.8 | 0.05 | 6.9 |
| 0.1 | 7.6 | 0.1 | 6.0 | 0.1 | 6.8 | 0.1 | 6.9 |
| 0.15 | 7.6 | 0.15 | 6.0 | 0.15 | 6.8 | 0.15 | 6.9 |
| 0.2 | 7.6 | 0.2 | 6.0 | 0.2 | 6.8 | 0.2 | 6.9 |
| 0.25 | 7.6 | 0.25 | 6.0 | 0.25 | 6.8 | 0.25 | 6.9 |
| 0.3 | 7.6 | 0.3 | 6.0 | 0.3 | 6.8 | 0.3 | 6.9 |
| 0.35 | 7.6 | 0.35 | 6.0 | 0.35 | 6.8 | 0.35 | 6.9 |
| 0.4 | 7.6 | 0.4 | 6.0 | 0.4 | 6.8 | 0.4 | 6.9 |
| 0.45 | 7.6 | 0.45 | 6.0 | 0.45 | 6.8 | 0.45 | 6.9 |
| 0.5 | 7.6 | 0.5 | 6.0 | 0.5 | 6.8 | 0.5 | 6.9 |
| 0.55 | 7.6 | 0.55 | 5.9 | 0.55 | 6.8 | 0.55 | 6.9 |
| 0.6 | 7.6 | 0.6 | 5.8 | 0.6 | 6.7 | 0.6 | 6.9 |
| 0.65 | 7.6 | 0.65 | 5.7 | 0.65 | 6.7 | 0.65 | 6.8 |
| 0.7 | 7.6 | 0.7 | 5.6 | 0.7 | 6.6 | 0.7 | 6.7 |
| 0.75 | 7.4 | 0.75 | 5.4 | 0.75 | 6.4 | 0.75 | 6.5 |
| 0.8 | 7.1 | 0.8 | 5.0 | 0.8 | 6.1 | 0.8 | 6.2 |
| 0.85 | 6.5 | 0.85 | 4.5 | 0.85 | 5.6 | 0.85 | 5.7 |
| 0.9 | 5.5 | 0.9 | 3.8 | 0.9 | 4.8 | 0.9 | 4.8 |

| | | | | | | | |
|---|---|---|---|---|---|---|---|
| 0.95 | 3.8 | 0.95 | 2.7 | 0.95 | 3.4 | 0.95 | 3.3 |
| 1 | 1.2 | 1 | 1.2 | 1 | 1.2 | 1 | 1.2 |

HF-HFO-1234yf-HFO-1234zeZ-HCFO-1233zdE

| Organics 0.9 F1234yf + 0.05 F1234zeZ + 0.05 F1233zdE | | Organics 0.05 F1234yf + 0.9 F1234zeZ + 0.05 F1233zdE | | Organics 0.05 F1234yf + 0.05 F1234zeZ + 0.9 F1233zdE | | Organics 0.4 F1234yf + 0.3 F1234zeZ + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.3 | 0 | 2.0 | 0 | 1.7 | 0 | 3.8 |
| 0.05 | 7.3 | 0.05 | 3.2 | 0.05 | 2.8 | 0.05 | 4.8 |
| 0.1 | 7.3 | 0.1 | 3.2 | 0.1 | 2.8 | 0.1 | 4.8 |
| 0.15 | 7.3 | 0.15 | 3.2 | 0.15 | 2.8 | 0.15 | 4.8 |
| 0.2 | 7.3 | 0.2 | 3.2 | 0.2 | 2.8 | 0.2 | 4.8 |
| 0.25 | 7.3 | 0.25 | 3.2 | 0.25 | 2.8 | 0.25 | 4.8 |
| 0.3 | 7.3 | 0.3 | 3.2 | 0.3 | 2.8 | 0.3 | 4.8 |
| 0.35 | 7.3 | 0.35 | 3.1 | 0.35 | 2.8 | 0.35 | 4.8 |
| 0.4 | 7.3 | 0.4 | 3.1 | 0.4 | 2.8 | 0.4 | 4.8 |
| 0.45 | 7.3 | 0.45 | 3.1 | 0.45 | 2.8 | 0.45 | 4.8 |
| 0.5 | 7.3 | 0.5 | 3.1 | 0.5 | 2.8 | 0.5 | 4.8 |
| 0.55 | 7.3 | 0.55 | 3.1 | 0.55 | 2.8 | 0.55 | 4.8 |
| 0.6 | 7.3 | 0.6 | 3.1 | 0.6 | 2.8 | 0.6 | 4.8 |
| 0.65 | 7.3 | 0.65 | 3.1 | 0.65 | 2.8 | 0.65 | 4.8 |
| 0.7 | 7.3 | 0.7 | 3.1 | 0.7 | 2.7 | 0.7 | 4.8 |
| 0.75 | 7.1 | 0.75 | 3.1 | 0.75 | 2.7 | 0.75 | 4.7 |
| 0.8 | 6.8 | 0.8 | 3.0 | 0.8 | 2.6 | 0.8 | 4.5 |
| 0.85 | 6.2 | 0.85 | 2.8 | 0.85 | 2.4 | 0.85 | 4.1 |
| 0.9 | 5.3 | 0.9 | 2.4 | 0.9 | 2.2 | 0.9 | 3.5 |
| 0.95 | 3.7 | 0.95 | 1.9 | 0.95 | 1.7 | 0.95 | 2.6 |
| 1 | 1.2 | 1 | 1.2 | 1 | 1.2 | 1 | 1.2 |

HF-HFO-1234yf-HFO-1234zeZ-HFO-1243zf

| Organics 0.9 F1234yf + 0.05 F1234zeZ + 0.05 F1243zf | | Organics 0.05 F1234yf + 0.9 F1234zeZ + 0.05 F1243zf | | Organics 0.05 F1234yf + 0.05 F1234zeZ + 0.9 F1243zf | | Organics 0.4 F1234yf + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.3 | 0 | 5.7 | 0 | 5.0 |
| 0.05 | 7.5 | 0.05 | 3.4 | 0.05 | 6.7 | 0.05 | 6.0 |
| 0.1 | 7.5 | 0.1 | 3.4 | 0.1 | 6.7 | 0.1 | 6.1 |
| 0.15 | 7.5 | 0.15 | 3.4 | 0.15 | 6.7 | 0.15 | 6.1 |
| 0.2 | 7.4 | 0.2 | 3.4 | 0.2 | 6.7 | 0.2 | 6.1 |
| 0.25 | 7.4 | 0.25 | 3.4 | 0.25 | 6.7 | 0.25 | 6.1 |
| 0.3 | 7.4 | 0.3 | 3.4 | 0.3 | 6.7 | 0.3 | 6.1 |
| 0.35 | 7.5 | 0.35 | 3.4 | 0.35 | 6.7 | 0.35 | 6.1 |
| 0.4 | 7.5 | 0.4 | 3.4 | 0.4 | 6.7 | 0.4 | 6.1 |
| 0.45 | 7.5 | 0.45 | 3.4 | 0.45 | 6.7 | 0.45 | 6.1 |
| 0.5 | 7.5 | 0.5 | 3.4 | 0.5 | 6.7 | 0.5 | 6.1 |
| 0.55 | 7.5 | 0.55 | 3.4 | 0.55 | 6.6 | 0.55 | 6.1 |
| 0.6 | 7.5 | 0.6 | 3.4 | 0.6 | 6.6 | 0.6 | 6.1 |
| 0.65 | 7.5 | 0.65 | 3.4 | 0.65 | 6.6 | 0.65 | 6.1 |
| 0.7 | 7.4 | 0.7 | 3.4 | 0.7 | 6.5 | 0.7 | 6.0 |
| 0.75 | 7.3 | 0.75 | 3.3 | 0.75 | 6.3 | 0.75 | 5.9 |
| 0.8 | 7.0 | 0.8 | 3.2 | 0.8 | 6.0 | 0.8 | 5.6 |
| 0.85 | 6.4 | 0.85 | 3.0 | 0.85 | 5.5 | 0.85 | 5.1 |
| 0.9 | 5.4 | 0.9 | 2.6 | 0.9 | 4.7 | 0.9 | 4.4 |
| 0.95 | 3.7 | 0.95 | 2.0 | 0.95 | 3.3 | 0.95 | 3.1 |
| 1 | 1.2 | 1 | 1.2 | 1 | 1.2 | 1 | 1.2 |

HF-HFC-245cb-HCFO-1233zdE-HFO-1234zeE

| Organics 0.9 F245cb + 0.05 F1233zdE + 0.05 F1234zeE | | Organics 0.05 F245cb + 0.9 F1233zdE + 0.05 F1234zeE | | Organics 0.05 F245cb + 0.05 F1233zdE + 0.9 F1234zeE | | Organics 0.4 F245cb + 0.3 F1233zdE + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 1.7 | 0 | 4.7 | 0 | 3.8 |
| 0.05 | 5.7 | 0.05 | 2.8 | 0.05 | 5.7 | 0.05 | 4.9 |

-continued

| MASSFRAC | TOTAL PRESSURE bar | MASSFRAC | TOTAL PRESSURE bar | MASSFRAC | TOTAL PRESSURE bar | MASSFRAC | TOTAL PRESSURE bar |
|---|---|---|---|---|---|---|---|
| 0.1 | 5.7 | 0.1 | 2.8 | 0.1 | 5.7 | 0.1 | 4.9 |
| 0.15 | 5.7 | 0.15 | 2.8 | 0.15 | 5.7 | 0.15 | 4.9 |
| 0.2 | 5.7 | 0.2 | 2.8 | 0.2 | 5.7 | 0.2 | 4.9 |
| 0.25 | 5.7 | 0.25 | 2.8 | 0.25 | 5.7 | 0.25 | 4.9 |
| 0.3 | 5.7 | 0.3 | 2.8 | 0.3 | 5.7 | 0.3 | 4.9 |
| 0.35 | 5.7 | 0.35 | 2.8 | 0.35 | 5.7 | 0.35 | 4.9 |
| 0.4 | 5.7 | 0.4 | 2.8 | 0.4 | 5.7 | 0.4 | 4.9 |
| 0.45 | 5.7 | 0.45 | 2.8 | 0.45 | 5.7 | 0.45 | 4.9 |
| 0.5 | 5.7 | 0.5 | 2.8 | 0.5 | 5.7 | 0.5 | 4.9 |
| 0.55 | 5.7 | 0.55 | 2.8 | 0.55 | 5.6 | 0.55 | 4.9 |
| 0.6 | 5.7 | 0.6 | 2.8 | 0.6 | 5.5 | 0.6 | 4.9 |
| 0.65 | 5.7 | 0.65 | 2.8 | 0.65 | 5.5 | 0.65 | 4.9 |
| 0.7 | 5.7 | 0.7 | 2.8 | 0.7 | 5.3 | 0.7 | 4.9 |
| 0.75 | 5.7 | 0.75 | 2.8 | 0.75 | 5.1 | 0.75 | 4.9 |
| 0.8 | 5.7 | 0.8 | 2.7 | 0.8 | 4.8 | 0.8 | 4.7 |
| 0.85 | 5.6 | 0.85 | 2.5 | 0.85 | 4.3 | 0.85 | 4.3 |
| 0.9 | 4.8 | 0.9 | 2.2 | 0.9 | 3.6 | 0.9 | 3.7 |
| 0.95 | 3.4 | 0.95 | 1.8 | 0.95 | 2.6 | 0.95 | 2.7 |
| 1 | 1.2 | 1 | 1.2 | 1 | 1.2 | 1 | 1.2 |

HF-HFC-245cb-HCFO-1233zdE-HFO-1234zeZ

| Organics 0.9 F245cb + 0.05 F1233zdE + 0.05 F1234zeZ | | Organics 0.05 F245cb + 0.9 F1233zdE + 0.05 F1234zeZ | | Organics 0.05 F245cb + 0.05 F1233zdE + 0.9 F1234zeZ | | Organics 0.4 F245cb + 0.3 F1233zdE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.5 | 0 | 1.9 | 0 | 2.8 |
| 0.05 | 5.5 | 0.05 | 2.6 | 0.05 | 3.0 | 0.05 | 3.9 |
| 0.1 | 5.5 | 0.1 | 2.6 | 0.1 | 3.0 | 0.1 | 3.9 |
| 0.15 | 5.5 | 0.15 | 2.6 | 0.15 | 3.0 | 0.15 | 3.9 |
| 0.2 | 5.5 | 0.2 | 2.6 | 0.2 | 3.0 | 0.2 | 3.9 |
| 0.25 | 5.5 | 0.25 | 2.6 | 0.25 | 3.0 | 0.25 | 3.9 |
| 0.3 | 5.5 | 0.3 | 2.6 | 0.3 | 3.0 | 0.3 | 4.0 |
| 0.35 | 5.5 | 0.35 | 2.6 | 0.35 | 3.0 | 0.35 | 4.0 |
| 0.4 | 5.5 | 0.4 | 2.6 | 0.4 | 3.0 | 0.4 | 4.0 |
| 0.45 | 5.5 | 0.45 | 2.6 | 0.45 | 3.0 | 0.45 | 4.0 |
| 0.5 | 5.5 | 0.5 | 2.6 | 0.5 | 3.0 | 0.5 | 4.0 |
| 0.55 | 5.5 | 0.55 | 2.6 | 0.55 | 3.0 | 0.55 | 4.0 |
| 0.6 | 5.5 | 0.6 | 2.6 | 0.6 | 3.0 | 0.6 | 4.0 |
| 0.65 | 5.5 | 0.65 | 2.7 | 0.65 | 3.1 | 0.65 | 4.0 |
| 0.7 | 5.6 | 0.7 | 2.7 | 0.7 | 3.1 | 0.7 | 4.1 |
| 0.75 | 5.6 | 0.75 | 2.7 | 0.75 | 3.1 | 0.75 | 4.1 |
| 0.8 | 5.6 | 0.8 | 2.6 | 0.8 | 2.9 | 0.8 | 4.1 |
| 0.85 | 5.5 | 0.85 | 2.4 | 0.85 | 2.7 | 0.85 | 3.8 |
| 0.9 | 4.8 | 0.9 | 2.1 | 0.9 | 2.4 | 0.9 | 3.3 |
| 0.95 | 3.4 | 0.95 | 1.7 | 0.95 | 1.9 | 0.95 | 2.5 |
| 1 | 1.2 | 1 | 1.2 | 1 | 1.2 | 1 | 1.2 |

HF-HCFO-1233zdE-HFO-1234zeE-HFO-1234zeZ

| Organics 0.9 1233zdE + 0.05 1234zeE + 0.05 1234zeZ | | Organics 0.05 1233zdE + 0.9 1234zeE + 0.05 1234zeZ | | Organics 0.05 1233zdE + 0.05 1234zeE + 0.9 1234zeZ | | Organics 0.4 1233zdE + 0.3 1234zeE + 0.3 1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 4.5 | 0 | 1.9 | 0 | 2.6 |
| 0.05 | 2.6 | 0.05 | 5.5 | 0.05 | 3.0 | 0.05 | 3.7 |
| 0.1 | 2.6 | 0.1 | 5.5 | 0.1 | 3.0 | 0.1 | 3.6 |
| 0.15 | 2.6 | 0.15 | 5.5 | 0.15 | 3.0 | 0.15 | 3.6 |
| 0.2 | 2.6 | 0.2 | 5.5 | 0.2 | 3.0 | 0.2 | 3.6 |
| 0.25 | 2.6 | 0.25 | 5.5 | 0.25 | 3.0 | 0.25 | 3.6 |
| 0.3 | 2.6 | 0.3 | 5.5 | 0.3 | 3.0 | 0.3 | 3.6 |
| 0.35 | 2.6 | 0.35 | 5.5 | 0.35 | 3.0 | 0.35 | 3.6 |
| 0.4 | 2.6 | 0.4 | 5.5 | 0.4 | 3.0 | 0.4 | 3.6 |
| 0.45 | 2.6 | 0.45 | 5.5 | 0.45 | 3.0 | 0.45 | 3.6 |
| 0.5 | 2.6 | 0.5 | 5.5 | 0.5 | 3.0 | 0.5 | 3.6 |
| 0.55 | 2.6 | 0.55 | 5.4 | 0.55 | 3.0 | 0.55 | 3.6 |

-continued

| | | | | | | | |
|---|---|---|---|---|---|---|---|
| 0.6 | 2.6 | 0.6 | 5.4 | 0.6 | 3.0 | 0.6 | 3.6 |
| 0.65 | 2.6 | 0.65 | 5.3 | 0.65 | 3.0 | 0.65 | 3.5 |
| 0.7 | 2.6 | 0.7 | 5.1 | 0.7 | 3.0 | 0.7 | 3.5 |
| 0.75 | 2.6 | 0.75 | 4.9 | 0.75 | 3.0 | 0.75 | 3.4 |
| 0.8 | 2.5 | 0.8 | 4.6 | 0.8 | 2.9 | 0.8 | 3.2 |
| 0.85 | 2.3 | 0.85 | 4.1 | 0.85 | 2.7 | 0.85 | 2.9 |
| 0.9 | 2.0 | 0.9 | 3.4 | 0.9 | 2.3 | 0.9 | 2.5 |
| 0.95 | 1.7 | 0.95 | 2.5 | 0.95 | 1.9 | 0.95 | 2.0 |
| 1 | 1.2 | 1 | 1.2 | 1 | 1.2 | 1 | 1.2 |

HF-HCFO-1233zdE-HFO-1234zeE-HFO-1243zf

| Organics 0.9 F1233zdE + 0.05 F1234zeE + 0.05 F1243zf | | Organics 0.05 F1233zdE + 0.9 F1234zeE + 0.05 F1243zf | | Organics 0.05 F1233zdE + 0.05 F1234zeE + 0.9 F1243zf | | Organics 0.4 F1233zdE + 0.3 F1234zeE + 0.3 F1243zf | |
|---|---|---|---|---|---|---|---|
| HF HF | PRESSURE PRES bar | HF HF | PRESSURE PRES bar | HF HF | PRESSURE PRES bar | HF HF | PRESSURE PRES bar |
| 0 | 1.8 | 0 | 4.8 | 0 | 5.6 | 0 | 3.9 |
| 0.05 | 2.9 | 0.05 | 5.7 | 0.05 | 6.6 | 0.05 | 5.0 |
| 0.1 | 2.9 | 0.1 | 5.7 | 0.1 | 6.6 | 0.1 | 5.0 |
| 0.15 | 2.9 | 0.15 | 5.7 | 0.15 | 6.6 | 0.15 | 5.0 |
| 0.2 | 2.9 | 0.2 | 5.7 | 0.2 | 6.6 | 0.2 | 5.0 |
| 0.25 | 2.9 | 0.25 | 5.7 | 0.25 | 6.6 | 0.25 | 5.0 |
| 0.3 | 2.9 | 0.3 | 5.7 | 0.3 | 6.6 | 0.3 | 5.0 |
| 0.35 | 2.9 | 0.35 | 5.7 | 0.35 | 6.6 | 0.35 | 5.0 |
| 0.4 | 2.9 | 0.4 | 5.7 | 0.4 | 6.6 | 0.4 | 4.9 |
| 0.45 | 2.9 | 0.45 | 5.7 | 0.45 | 6.6 | 0.45 | 4.9 |
| 0.5 | 2.9 | 0.5 | 5.7 | 0.5 | 6.6 | 0.5 | 4.9 |
| 0.55 | 2.9 | 0.55 | 5.6 | 0.55 | 6.5 | 0.55 | 4.9 |
| 0.6 | 2.9 | 0.6 | 5.6 | 0.6 | 6.5 | 0.6 | 4.9 |
| 0.65 | 2.9 | 0.65 | 5.5 | 0.65 | 6.5 | 0.65 | 4.9 |
| 0.7 | 2.8 | 0.7 | 5.3 | 0.7 | 6.4 | 0.7 | 4.8 |
| 0.75 | 2.8 | 0.75 | 5.1 | 0.75 | 6.2 | 0.75 | 4.6 |
| 0.8 | 2.7 | 0.8 | 4.8 | 0.8 | 5.9 | 0.8 | 4.3 |
| 0.85 | 2.5 | 0.85 | 4.3 | 0.85 | 5.4 | 0.85 | 3.9 |
| 0.9 | 2.2 | 0.9 | 3.6 | 0.9 | 4.6 | 0.9 | 3.3 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF-HCFO-1233zdE-HFO-1234zeZ-HFO-1243zf

| Organics 0.9 F1233zdE + 0.05 F1234zeZ + 0.05 F1243zf | | Organics 0.05 F1233zdE + 0.9 F1234zeZ + 0.05 F1243zf | | Organics 0.05 F1233zdE + 0.05 F1234zeZ + 0.9 F1243zf | | Organics 0.4 F1233zdE + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.6 | 0 | 2.0 | 0 | 5.5 | 0 | 3.0 |
| 0.05 | 2.7 | 0.05 | 3.1 | 0.05 | 6.4 | 0.05 | 4.1 |
| 0.1 | 2.7 | 0.1 | 3.1 | 0.1 | 6.5 | 0.1 | 4.1 |
| 0.15 | 2.7 | 0.15 | 3.1 | 0.15 | 6.5 | 0.15 | 4.1 |
| 0.2 | 2.7 | 0.2 | 3.1 | 0.2 | 6.5 | 0.2 | 4.1 |
| 0.25 | 2.7 | 0.25 | 3.1 | 0.25 | 6.5 | 0.25 | 4.1 |
| 0.3 | 2.7 | 0.3 | 3.1 | 0.3 | 6.4 | 0.3 | 4.1 |
| 0.35 | 2.7 | 0.35 | 3.1 | 0.35 | 6.4 | 0.35 | 4.1 |
| 0.4 | 2.7 | 0.4 | 3.1 | 0.4 | 6.4 | 0.4 | 4.1 |
| 0.45 | 2.7 | 0.45 | 3.1 | 0.45 | 6.4 | 0.45 | 4.1 |
| 0.5 | 2.7 | 0.5 | 3.1 | 0.5 | 6.4 | 0.5 | 4.1 |
| 0.55 | 2.7 | 0.55 | 3.1 | 0.55 | 6.4 | 0.55 | 4.1 |
| 0.6 | 2.7 | 0.6 | 3.1 | 0.6 | 6.4 | 0.6 | 4.1 |
| 0.65 | 2.7 | 0.65 | 3.1 | 0.65 | 6.3 | 0.65 | 4.0 |
| 0.7 | 2.7 | 0.7 | 3.1 | 0.7 | 6.3 | 0.7 | 4.0 |
| 0.75 | 2.7 | 0.75 | 3.1 | 0.75 | 6.1 | 0.75 | 3.9 |
| 0.8 | 2.6 | 0.8 | 3.0 | 0.8 | 5.8 | 0.8 | 3.7 |
| 0.85 | 2.4 | 0.85 | 2.7 | 0.85 | 5.3 | 0.85 | 3.4 |
| 0.9 | 2.1 | 0.9 | 2.4 | 0.9 | 4.5 | 0.9 | 2.9 |
| 0.95 | 1.7 | 0.95 | 1.9 | 0.95 | 3.2 | 0.95 | 2.2 |
| 1 | 1.2 | 1 | 1.2 | 1 | 1.2 | 1 | 1.2 |

-continued

| HF-HFC-245cb-HFO-1234zeE-HFO-1234zeZ | | | | | | | |
|---|---|---|---|---|---|---|---|
| Organics 0.9 F245cb + 0.05 F1234zeE + 0.05 F1234zeZ | | Organics 0.05 F245cb + 0.9 F1234zeE + 0.05 F1234zeZ | | Organics 0.05 F245cb + 0.05 F1234zeE + 0.9 F1234zeZ | | Organics 0.4 F245cb + 0.3 F1234zeE + 0.3 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 4.7 | 0 | 2.1 | 0 | 3.8 |
| 0.05 | 5.7 | 0.05 | 5.7 | 0.05 | 3.2 | 0.05 | 4.9 |
| 0.1 | 5.7 | 0.1 | 5.7 | 0.1 | 3.2 | 0.1 | 4.9 |
| 0.15 | 5.7 | 0.15 | 5.7 | 0.15 | 3.2 | 0.15 | 4.9 |
| 0.2 | 5.7 | 0.2 | 5.7 | 0.2 | 3.2 | 0.2 | 4.9 |
| 0.25 | 5.7 | 0.25 | 5.7 | 0.25 | 3.2 | 0.25 | 4.9 |
| 0.3 | 5.7 | 0.3 | 5.7 | 0.3 | 3.2 | 0.3 | 4.9 |
| 0.35 | 5.7 | 0.35 | 5.7 | 0.35 | 3.2 | 0.35 | 5.0 |
| 0.4 | 5.7 | 0.4 | 5.7 | 0.4 | 3.2 | 0.4 | 5.0 |
| 0.45 | 5.7 | 0.45 | 5.7 | 0.45 | 3.2 | 0.45 | 5.0 |
| 0.5 | 5.7 | 0.5 | 5.7 | 0.5 | 3.2 | 0.5 | 5.0 |
| 0.55 | 5.7 | 0.55 | 5.6 | 0.55 | 3.2 | 0.55 | 5.0 |
| 0.6 | 5.7 | 0.6 | 5.6 | 0.6 | 3.2 | 0.6 | 5.0 |
| 0.65 | 5.7 | 0.65 | 5.5 | 0.65 | 3.2 | 0.65 | 5.0 |
| 0.7 | 5.7 | 0.7 | 5.3 | 0.7 | 3.2 | 0.7 | 5.0 |
| 0.75 | 5.7 | 0.75 | 5.1 | 0.75 | 3.2 | 0.75 | 5.0 |
| 0.8 | 5.7 | 0.8 | 4.8 | 0.8 | 3.1 | 0.8 | 4.8 |
| 0.85 | 5.6 | 0.85 | 4.3 | 0.85 | 2.8 | 0.85 | 4.4 |
| 0.9 | 4.8 | 0.9 | 3.6 | 0.9 | 2.5 | 0.9 | 3.8 |
| 0.95 | 3.4 | 0.95 | 2.6 | 0.95 | 2.0 | 0.95 | 2.7 |
| 1 | 1.2 | 1 | 1.2 | 1 | 1.2 | 1 | 1.2 |

| HF-HFC-245cb-HFO-1234zeE-HFO-1243zf | | | | | | | |
|---|---|---|---|---|---|---|---|
| Organics 0.9 F245cb + 0.05 F1234zeE + 0.05 F1243zf | | Organics 0.05 F245cb + 0.9 F1234zeE + 0.05 F1243zf | | Organics 0.05 F245cb + 0.05 F1234zeE + 0.9 F1243zf | | Organics 0.4 F245cb + 0.3 F1234zeE + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 4.9 | 0 | 5.8 | 0 | 5.2 |
| 0.05 | 5.9 | 0.05 | 5.9 | 0.05 | 6.7 | 0.05 | 6.2 |
| 0.1 | 5.9 | 0.1 | 5.9 | 0.1 | 6.7 | 0.1 | 6.2 |
| 0.15 | 5.9 | 0.15 | 5.9 | 0.15 | 6.7 | 0.15 | 6.2 |
| 0.2 | 5.9 | 0.2 | 5.9 | 0.2 | 6.7 | 0.2 | 6.2 |
| 0.25 | 5.9 | 0.25 | 5.9 | 0.25 | 6.7 | 0.25 | 6.2 |
| 0.3 | 5.9 | 0.3 | 5.9 | 0.3 | 6.7 | 0.3 | 6.2 |
| 0.35 | 5.9 | 0.35 | 5.9 | 0.35 | 6.7 | 0.35 | 6.2 |
| 0.4 | 5.9 | 0.4 | 5.9 | 0.4 | 6.7 | 0.4 | 6.2 |
| 0.45 | 5.9 | 0.45 | 5.9 | 0.45 | 6.7 | 0.45 | 6.2 |
| 0.5 | 5.9 | 0.5 | 5.9 | 0.5 | 6.7 | 0.5 | 6.2 |
| 0.55 | 5.9 | 0.55 | 5.8 | 0.55 | 6.7 | 0.55 | 6.2 |
| 0.6 | 5.9 | 0.6 | 5.8 | 0.6 | 6.7 | 0.6 | 6.2 |
| 0.65 | 5.9 | 0.65 | 5.7 | 0.65 | 6.6 | 0.65 | 6.2 |
| 0.7 | 5.9 | 0.7 | 5.5 | 0.7 | 6.5 | 0.7 | 6.2 |
| 0.75 | 5.9 | 0.75 | 5.3 | 0.75 | 6.4 | 0.75 | 6.1 |
| 0.8 | 5.9 | 0.8 | 5.0 | 0.8 | 6.1 | 0.8 | 5.8 |
| 0.85 | 5.8 | 0.85 | 4.5 | 0.85 | 5.6 | 0.85 | 5.3 |
| 0.9 | 5.0 | 0.9 | 3.7 | 0.9 | 4.7 | 0.9 | 4.5 |
| 0.95 | 3.5 | 0.95 | 2.7 | 0.95 | 3.4 | 0.95 | 3.2 |
| 1 | 1.2 | 1 | 1.2 | 1 | 1.2 | 1 | 1.2 |

| HF-HFC-245cb-HFO-1234zeZ-HFO-1243zf | | | | | | | |
|---|---|---|---|---|---|---|---|
| Organics 0.9 F245cb + 0.05 F1234zeZ + 0.05 F1243zf | | Organics 0.05 F245cb + 0.9 F1234zeZ + 0.05 F1243zf | | Organics 0.05 F245cb + 0.05 F1234zeZ + 0.9 F1243zf | | Organics 0.4 F245cb + 0.3 F1234zeZ + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 2.2 | 0 | 5.6 | 0 | 4.2 |
| 0.05 | 5.7 | 0.05 | 3.3 | 0.05 | 6.6 | 0.05 | 5.3 |
| 0.1 | 5.7 | 0.1 | 3.3 | 0.1 | 6.6 | 0.1 | 5.3 |
| 0.15 | 5.7 | 0.15 | 3.3 | 0.15 | 6.6 | 0.15 | 5.3 |
| 0.2 | 5.7 | 0.2 | 3.3 | 0.2 | 6.6 | 0.2 | 5.3 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0.25 | 5.7 | 0.25 | 3.3 | 0.25 | 6.6 | 0.25 | 5.3 |
| 0.3 | 5.7 | 0.3 | 3.3 | 0.3 | 6.6 | 0.3 | 5.3 |
| 0.35 | 5.7 | 0.35 | 3.3 | 0.35 | 6.6 | 0.35 | 5.3 |
| 0.4 | 5.7 | 0.4 | 3.3 | 0.4 | 6.6 | 0.4 | 5.3 |
| 0.45 | 5.7 | 0.45 | 3.3 | 0.45 | 6.6 | 0.45 | 5.3 |
| 0.5 | 5.7 | 0.5 | 3.3 | 0.5 | 6.6 | 0.5 | 5.3 |
| 0.55 | 5.8 | 0.55 | 3.3 | 0.55 | 6.6 | 0.55 | 5.3 |
| 0.6 | 5.8 | 0.6 | 3.3 | 0.6 | 6.5 | 0.6 | 5.3 |
| 0.65 | 5.8 | 0.65 | 3.3 | 0.65 | 6.5 | 0.65 | 5.3 |
| 0.7 | 5.8 | 0.7 | 3.3 | 0.7 | 6.4 | 0.7 | 5.4 |
| 0.75 | 5.8 | 0.75 | 3.3 | 0.75 | 6.3 | 0.75 | 5.4 |
| 0.8 | 5.8 | 0.8 | 3.1 | 0.8 | 6.0 | 0.8 | 5.2 |
| 0.85 | 5.7 | 0.85 | 2.9 | 0.85 | 5.5 | 0.85 | 4.8 |
| 0.9 | 4.9 | 0.9 | 2.6 | 0.9 | 4.7 | 0.9 | 4.1 |
| 0.95 | 3.5 | 0.95 | 2.0 | 0.95 | 3.3 | 0.95 | 3.0 |
| 1 | 1.2 | 1 | 1.2 | 1 | 1.2 | 1 | 1.2 |

HF-HFO-1234zeE-HFO-1234zeZ-HFO-1243zf

| Organics 0.9 F1234zeE + 0.05 F1234zeZ + 0.05 F1243zf | | Organics 0.05 F1234zeE + 0.9 F1234zeZ + 0.05 F1243zf | | Organics 0.05 F1234zeE + 0.05 F1234zeZ + 0.9 F1243zf | | Organics 0.4 F1234zeE + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 2.2 | 0 | 5.6 | 0 | 4.3 |
| 0.05 | 5.7 | 0.05 | 3.3 | 0.05 | 6.6 | 0.05 | 5.3 |
| 0.1 | 5.8 | 0.1 | 3.3 | 0.1 | 6.6 | 0.1 | 5.3 |
| 0.15 | 5.8 | 0.15 | 3.3 | 0.15 | 6.6 | 0.15 | 5.3 |
| 0.2 | 5.7 | 0.2 | 3.3 | 0.2 | 6.6 | 0.2 | 5.3 |
| 0.25 | 5.7 | 0.25 | 3.3 | 0.25 | 6.6 | 0.25 | 5.3 |
| 0.3 | 5.7 | 0.3 | 3.3 | 0.3 | 6.6 | 0.3 | 5.3 |
| 0.35 | 5.7 | 0.35 | 3.3 | 0.35 | 6.6 | 0.35 | 5.3 |
| 0.4 | 5.7 | 0.4 | 3.3 | 0.4 | 6.6 | 0.4 | 5.3 |
| 0.45 | 5.7 | 0.45 | 3.3 | 0.45 | 6.6 | 0.45 | 5.3 |
| 0.5 | 5.7 | 0.5 | 3.3 | 0.5 | 6.6 | 0.5 | 5.3 |
| 0.55 | 5.7 | 0.55 | 3.3 | 0.55 | 6.5 | 0.55 | 5.3 |
| 0.6 | 5.6 | 0.6 | 3.3 | 0.6 | 6.5 | 0.6 | 5.3 |
| 0.65 | 5.5 | 0.65 | 3.3 | 0.65 | 6.5 | 0.65 | 5.2 |
| 0.7 | 5.3 | 0.7 | 3.3 | 0.7 | 6.4 | 0.7 | 5.1 |
| 0.75 | 5.1 | 0.75 | 3.2 | 0.75 | 6.2 | 0.75 | 4.9 |
| 0.8 | 4.8 | 0.8 | 3.1 | 0.8 | 5.9 | 0.8 | 4.6 |
| 0.85 | 4.3 | 0.85 | 2.8 | 0.85 | 5.4 | 0.85 | 4.2 |
| 0.9 | 3.6 | 0.9 | 2.5 | 0.9 | 4.6 | 0.9 | 3.6 |
| 0.95 | 2.6 | 0.95 | 2.0 | 0.95 | 3.3 | 0.95 | 2.6 |
| 1 | 1.2 | 1 | 1.2 | 1 | 1.2 | 1 | 1.2 |

HF-HFO-1234yf-HFO-1234zeE-Trifluoropropyne

| Organics 0.34 F1234yf + 0.33 F1234zeE + 0.33 TFP | | Organics 0.99 F1234yf + 0.005 F1234zeE + 0.005 TFP | | Organics 0.005 F1234yf + 0.99 F1234zeE + 0.005 TFP | | Organics 0.005 F1234yf + 0.005 F1234zeE + 0.99 TFP | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 8.0 | 0 | 6.8 | 0 | 4.9 | 0 | 11.6 |
| 0.05 | 8.8 | 0.05 | 7.8 | 0.05 | 5.9 | 0.05 | 12.4 |
| 0.1 | 8.8 | 0.1 | 7.8 | 0.1 | 5.9 | 0.1 | 12.3 |
| 0.15 | 8.8 | 0.15 | 7.8 | 0.15 | 5.9 | 0.15 | 12.2 |
| 0.2 | 8.8 | 0.2 | 7.8 | 0.2 | 5.9 | 0.2 | 12.1 |
| 0.25 | 8.7 | 0.25 | 7.8 | 0.25 | 5.9 | 0.25 | 12.0 |
| 0.3 | 8.7 | 0.3 | 7.7 | 0.3 | 5.9 | 0.3 | 11.9 |
| 0.35 | 8.7 | 0.35 | 7.8 | 0.35 | 5.9 | 0.35 | 11.8 |
| 0.4 | 8.7 | 0.4 | 7.8 | 0.4 | 5.9 | 0.4 | 11.8 |
| 0.45 | 8.7 | 0.45 | 7.8 | 0.45 | 5.9 | 0.45 | 11.8 |
| 0.5 | 8.7 | 0.5 | 7.8 | 0.5 | 5.8 | 0.5 | 11.8 |
| 0.55 | 8.7 | 0.55 | 7.8 | 0.55 | 5.8 | 0.55 | 11.8 |
| 0.6 | 8.7 | 0.6 | 7.8 | 0.6 | 5.7 | 0.6 | 11.8 |
| 0.65 | 8.7 | 0.65 | 7.8 | 0.65 | 5.6 | 0.65 | 11.8 |
| 0.7 | 8.6 | 0.7 | 7.7 | 0.7 | 5.4 | 0.7 | 11.8 |
| 0.75 | 8.5 | 0.75 | 7.6 | 0.75 | 5.2 | 0.75 | 11.8 |
| 0.8 | 8.1 | 0.8 | 7.3 | 0.8 | 4.8 | 0.8 | 11.6 |
| 0.85 | 7.4 | 0.85 | 6.7 | 0.85 | 4.3 | 0.85 | 10.8 |
| 0.9 | 6.2 | 0.9 | 5.6 | 0.9 | 3.6 | 0.9 | 9.1 |

-continued

| MASSFRAC | TOTAL PRESSURE bar | MASSFRAC | TOTAL PRESSURE bar | MASSFRAC | TOTAL PRESSURE bar | MASSFRAC | TOTAL PRESSURE bar |
|---|---|---|---|---|---|---|---|
| 0.95 | 4.2 | 0.95 | 3.9 | 0.95 | 2.6 | 0.95 | 6.1 |
| 1 | 1.2 | 1 | 1.2 | 1 | 1.2 | 1 | 1.2 |

HF-HFO-1234yf-HFO-1234zeE-HCFC-244bb

| Organics 0.34 F1234yf + 0.33 F1234zeE + 0.33 F244bb | | Organics 0.99 F1234yf + 0.005 F1234zeE + 0.005 F244bb | | Organics 0.005 F1234yf + 0.99 F1234zeE + 0.005 F244bb | | Organics 0.005 F1234yf + 0.005 F1234zeE + 0.99 F244bb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.8 | 0 | 4.9 | 0 | 0.7 |
| 0.05 | 5.4 | 0.05 | 7.7 | 0.05 | 5.8 | 0.05 | 1.8 |
| 0.1 | 5.4 | 0.1 | 7.7 | 0.1 | 5.8 | 0.1 | 1.8 |
| 0.15 | 5.4 | 0.15 | 7.7 | 0.15 | 5.8 | 0.15 | 1.8 |
| 0.2 | 5.4 | 0.2 | 7.7 | 0.2 | 5.8 | 0.2 | 1.8 |
| 0.25 | 5.4 | 0.25 | 7.7 | 0.25 | 5.8 | 0.25 | 1.8 |
| 0.3 | 5.4 | 0.3 | 7.7 | 0.3 | 5.8 | 0.3 | 1.8 |
| 0.35 | 5.4 | 0.35 | 7.7 | 0.35 | 5.8 | 0.35 | 1.8 |
| 0.4 | 5.4 | 0.4 | 7.7 | 0.4 | 5.8 | 0.4 | 1.8 |
| 0.45 | 5.3 | 0.45 | 7.7 | 0.45 | 5.8 | 0.45 | 1.8 |
| 0.5 | 5.3 | 0.5 | 7.7 | 0.5 | 5.8 | 0.5 | 1.8 |
| 0.55 | 5.3 | 0.55 | 7.7 | 0.55 | 5.7 | 0.55 | 1.8 |
| 0.6 | 5.2 | 0.6 | 7.7 | 0.6 | 5.6 | 0.6 | 1.8 |
| 0.65 | 5.2 | 0.65 | 7.7 | 0.65 | 5.5 | 0.65 | 1.8 |
| 0.7 | 5.1 | 0.7 | 7.7 | 0.7 | 5.4 | 0.7 | 1.8 |
| 0.75 | 5.0 | 0.75 | 7.5 | 0.75 | 5.1 | 0.75 | 1.8 |
| 0.8 | 4.8 | 0.8 | 7.2 | 0.8 | 4.8 | 0.8 | 1.8 |
| 0.85 | 4.3 | 0.85 | 6.6 | 0.85 | 4.3 | 0.85 | 1.8 |
| 0.9 | 3.7 | 0.9 | 5.6 | 0.9 | 3.6 | 0.9 | 1.7 |
| 0.95 | 2.7 | 0.95 | 3.8 | 0.95 | 2.6 | 0.95 | 1.5 |
| 1 | 1.2 | 1 | 1.2 | 1 | 1.2 | 1 | 1.2 |

HF-HFO-1234yf-HFO-1234zeE-HFC-245fa

| Organics 0.34 F1234yf + 0.33 F1234zeE + 0.33 F245fa | | Organics 0.99 F1234yf + 0.005 F1234zeE + 0.005 F245fa | | Organics 0.005 F1234yf + 0.99 F1234zeE + 0.005 F245fa | | Organics 0.005 F1234yf + 0.005 F1234zeE + 0.99 F245fa | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 6.8 | 0 | 4.9 | 0 | 1.6 |
| 0.05 | 5.6 | 0.05 | 7.7 | 0.05 | 5.8 | 0.05 | 2.7 |
| 0.1 | 5.6 | 0.1 | 7.7 | 0.1 | 5.8 | 0.1 | 2.7 |
| 0.15 | 5.6 | 0.15 | 7.7 | 0.15 | 5.8 | 0.15 | 2.7 |
| 0.2 | 5.6 | 0.2 | 7.7 | 0.2 | 5.8 | 0.2 | 2.7 |
| 0.25 | 5.6 | 0.25 | 7.7 | 0.25 | 5.8 | 0.25 | 2.7 |
| 0.3 | 5.6 | 0.3 | 7.7 | 0.3 | 5.8 | 0.3 | 2.7 |
| 0.35 | 5.6 | 0.35 | 7.7 | 0.35 | 5.8 | 0.35 | 2.7 |
| 0.4 | 5.6 | 0.4 | 7.7 | 0.4 | 5.8 | 0.4 | 2.7 |
| 0.45 | 5.6 | 0.45 | 7.7 | 0.45 | 5.8 | 0.45 | 2.7 |
| 0.5 | 5.6 | 0.5 | 7.7 | 0.5 | 5.8 | 0.5 | 2.7 |
| 0.55 | 5.5 | 0.55 | 7.7 | 0.55 | 5.7 | 0.55 | 2.7 |
| 0.6 | 5.5 | 0.6 | 7.7 | 0.6 | 5.6 | 0.6 | 2.7 |
| 0.65 | 5.5 | 0.65 | 7.7 | 0.65 | 5.5 | 0.65 | 2.7 |
| 0.7 | 5.4 | 0.7 | 7.7 | 0.7 | 5.4 | 0.7 | 2.7 |
| 0.75 | 5.3 | 0.75 | 7.5 | 0.75 | 5.1 | 0.75 | 2.7 |
| 0.8 | 5.0 | 0.8 | 7.2 | 0.8 | 4.8 | 0.8 | 2.6 |
| 0.85 | 4.5 | 0.85 | 6.6 | 0.85 | 4.3 | 0.85 | 2.4 |
| 0.9 | 3.8 | 0.9 | 5.6 | 0.9 | 3.6 | 0.9 | 2.1 |
| 0.95 | 2.7 | 0.95 | 3.9 | 0.95 | 2.6 | 0.95 | 1.7 |
| 1 | 1.2 | 1 | 1.2 | 1 | 1.2 | 1 | 1.2 |

HF-HFO-1234yf-HFO-1234zeE-HFO-1225yeZ

| Organics 0.34 F1234yf + 0.33 F1234zeE + 0.33 | | Organics 0.99 F1234yf + 0.005 F1234zeE + 0.005 | | Organics 0.005 F1234yf + 0.99 F1234zeE + 0.005 | | Organics 0.005 F1234yf + 0.005 F1234zeE + 0.99 | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.9 | 0 | 5.2 |
| 0.05 | 6.6 | 0.05 | 7.7 | 0.05 | 5.8 | 0.05 | 6.2 |

-continued

| | | | | | | | |
|---|---|---|---|---|---|---|---|
| 0.1 | 6.7 | 0.1 | 7.8 | 0.1 | 5.9 | 0.1 | 6.2 |
| 0.15 | 6.7 | 0.15 | 7.7 | 0.15 | 5.9 | 0.15 | 6.2 |
| 0.2 | 6.7 | 0.2 | 7.7 | 0.2 | 5.9 | 0.2 | 6.2 |
| 0.25 | 6.7 | 0.25 | 7.7 | 0.25 | 5.9 | 0.25 | 6.2 |
| 0.3 | 6.7 | 0.3 | 7.7 | 0.3 | 5.9 | 0.3 | 6.2 |
| 0.35 | 6.7 | 0.35 | 7.7 | 0.35 | 5.9 | 0.35 | 6.2 |
| 0.4 | 6.7 | 0.4 | 7.7 | 0.4 | 5.8 | 0.4 | 6.2 |
| 0.45 | 6.7 | 0.45 | 7.7 | 0.45 | 5.8 | 0.45 | 6.2 |
| 0.5 | 6.7 | 0.5 | 7.7 | 0.5 | 5.8 | 0.5 | 6.2 |
| 0.55 | 6.7 | 0.55 | 7.7 | 0.55 | 5.7 | 0.55 | 6.2 |
| 0.6 | 6.6 | 0.6 | 7.7 | 0.6 | 5.7 | 0.6 | 6.2 |
| 0.65 | 6.6 | 0.65 | 7.7 | 0.65 | 5.6 | 0.65 | 6.2 |
| 0.7 | 6.5 | 0.7 | 7.7 | 0.7 | 5.4 | 0.7 | 6.1 |
| 0.75 | 6.3 | 0.75 | 7.6 | 0.75 | 5.2 | 0.75 | 5.9 |
| 0.8 | 5.9 | 0.8 | 7.2 | 0.8 | 4.8 | 0.8 | 5.6 |
| 0.85 | 5.4 | 0.85 | 6.6 | 0.85 | 4.3 | 0.85 | 5.1 |
| 0.9 | 4.5 | 0.9 | 5.6 | 0.9 | 3.6 | 0.9 | 4.2 |
| 0.95 | 3.1 | 0.95 | 3.9 | 0.95 | 2.6 | 0.95 | 3.0 |
| 1 | 1.2 | 1 | 1.2 | 1 | 1.2 | 1 | 1.2 |

HF-HFO-1234yf-HFO-1234zeE-HFO-1225zc

| Organics 0.34 F1234yf + 0.33 F1234zeE + 0.33 F1225zc | | Organics 0.99 F1234yf + 0.005 F1234zeE + 0.005 F1225zc | | Organics 0.005 F1234yf + 0.99 F1234zeE + 0.005 F1225zc | | Organics 0.005 F1234yf + 0.005 F1234zeE + 0.99 F1225zc | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.9 | 0 | 5.3 |
| 0.05 | 6.7 | 0.05 | 7.7 | 0.05 | 5.8 | 0.05 | 6.3 |
| 0.1 | 6.7 | 0.1 | 7.8 | 0.1 | 5.9 | 0.1 | 6.3 |
| 0.15 | 6.7 | 0.15 | 7.7 | 0.15 | 5.9 | 0.15 | 6.3 |
| 0.2 | 6.7 | 0.2 | 7.7 | 0.2 | 5.9 | 0.2 | 6.3 |
| 0.25 | 6.7 | 0.25 | 7.7 | 0.25 | 5.9 | 0.25 | 6.3 |
| 0.3 | 6.7 | 0.3 | 7.7 | 0.3 | 5.9 | 0.3 | 6.3 |
| 0.35 | 6.7 | 0.35 | 7.7 | 0.35 | 5.9 | 0.35 | 6.3 |
| 0.4 | 6.7 | 0.4 | 7.7 | 0.4 | 5.8 | 0.4 | 6.3 |
| 0.45 | 6.7 | 0.45 | 7.7 | 0.45 | 5.8 | 0.45 | 6.3 |
| 0.5 | 6.7 | 0.5 | 7.7 | 0.5 | 5.8 | 0.5 | 6.2 |
| 0.55 | 6.7 | 0.55 | 7.7 | 0.55 | 5.7 | 0.55 | 6.2 |
| 0.6 | 6.6 | 0.6 | 7.7 | 0.6 | 5.7 | 0.6 | 6.1 |
| 0.65 | 6.5 | 0.65 | 7.7 | 0.65 | 5.6 | 0.65 | 6.0 |
| 0.7 | 6.4 | 0.7 | 7.7 | 0.7 | 5.4 | 0.7 | 5.9 |
| 0.75 | 6.2 | 0.75 | 7.6 | 0.75 | 5.2 | 0.75 | 5.6 |
| 0.8 | 5.8 | 0.8 | 7.2 | 0.8 | 4.8 | 0.8 | 5.2 |
| 0.85 | 5.3 | 0.85 | 6.6 | 0.85 | 4.3 | 0.85 | 4.6 |
| 0.9 | 4.4 | 0.9 | 5.6 | 0.9 | 3.6 | 0.9 | 3.8 |
| 0.95 | 3.1 | 0.95 | 3.9 | 0.95 | 2.6 | 0.95 | 2.7 |
| 1 | 1.2 | 1 | 1.2 | 1 | 1.2 | 1 | 1.2 |

EXAMPLE 5

Temperature and Pressure Range of Quaternary Mixtures

| | Boiling point range | |
|---|---|---|
| Quaternary | Temperature ° C. | Pressure bar abs |
| HF-HCFO-1233xf-HFC-245cb-HFO-1234zeE | 0 to 40 | ~1.1 to ~8.8 |
| HF-HCFO-1233xf-HFC-245cb-HFO-1234zeZ | 0 to 40 | ~1.1 to ~8.8 |
| HF-HFO-1234yf-HFC-245cb-HFO-1234zeE | 0 to 40 | ~2.5 to ~11.5 |
| HF-HFO-1234yf-HFC-245cb-HFO-1234zeZ | 0 to 40 | ~1.3 to ~11.3 |
| HF-HCFO-1233xf-HFO-1234yf-HFO-1234zeE | 0 to 40 | ~1.2 to ~11.3 |
| HF-HCFO-1233xf-HFO-1234yf-HFO-1234zeZ | 0 to 40 | ~1.0 to ~11.0 |
| HF-HCFO-1233xf-HCFO-1233zdE-HFO-1234zeE | 0 to 40 | ~1.0 to ~8.6 |
| HF-HCFO-1233xf-HCFO-1233zdE-HFO-1234zeZ | 0 to 40 | ~0.9 to ~4.8 |
| HF-HCFO-1233xf-HFO-1234zeE-HFO-1234zeZ | 0 to 40 | ~1.1 to ~8.6 |

| Quaternary | Boiling point range Temperature ° C. | Pressure bar abs |
|---|---|---|
| HF-HCFO-1233xf-HFO-1234zeE-HFO-1243zf | 0 to 40 | ~1.2 to ~10.1 |
| HF-HCFO-1233xf-HFO-1234zeZ-HFO-1243zf | 0 to 40 | ~1.1 to ~9.9 |
| HF-HFO-1234yf-HFO-1234zeE-HFO-1234zeZ | 0 to 40 | ~1.3 to ~11.3 |
| HF-HFO-1234yf-HFO-1234zeE-HCFO-1233zdE | 0 to 40 | ~1.1 to ~11.3 |
| HF-HFO-1234yf-HFO-1234zeE-HFO-1243zf | 0 to 40 | ~3.0 to ~11.6 |
| HF-HFO-1234yf-HFO-1234zeZ-HCFO-1233zdE | 0 to 40 | ~1.0 to ~11.0 |
| HF-HFO-1234yf-HFO-1234zeZ-HFO-1243zf | 0 to 40 | ~1.3 to ~11.3 |
| HF-HFC-245cb-HCFO-1233zdE-HFO-1234zeE | 0 to 40 | ~1.0 to ~8.9 |
| HF-HFC-245cb-HCFO-1233zdE-HFO-1234zeZ | 0 to 40 | ~1.0 to ~8.9 |
| HF-HFC-245cb-HFO-1234zeE-HFO-1234zeZ | 0 to 40 | ~1.2 to ~9.0 |
| HF-HFC-245cb-HFO-1234zeE-HFO-1243zf | 0 to 40 | ~2.5 to ~10.3 |
| HF-HFC-245cb-HFO-1234zeZ-HFO-1243zf | 0 to 40 | ~1.3 to ~10.1 |
| HF-HCFO-1233zdE-F 1234zeE-HFO-1234zeZ | 0 to 40 | ~1.0 to ~8.6 |
| HF-HCFO-1233zdE-F 1234zeE-HFO-1243zf | 0 to 40 | ~1.1 to ~10.1 |
| HF-HCFO-1233zdE-F 1234zeZ-HFO-1243zf | 0 to 40 | ~1.0 to ~9.9 |
| HF-HFO-1234zeE-HFO-1234zeZ-HFO-1243zf | 0 to 40 | ~1.3 to ~10.1 |
| HF-HFO-1234yf-HFO-1234zeE-Trifluoropropyne | 0 to 40 | ~5.9 to ~12.4 |
| HF-HFO-1234yf-HFO-1234zeE-HCFC-244bb | 0 to 40 | ~1.8 to ~7.7 |
| HF-HFO-1234yf-HFO-1234zeE-HFC-245fa | 0 to 40 | ~2.7 to ~7.7 |
| HF-HFO-1234yf-HFO-1234zeE-HFO-1225yeZ | 0 to 40 | ~5.2 to ~7.7 |
| HF-HFO-1234yf-HFO-1234zeE-HFO-1225zc | 0 to 40 | ~5.2 to ~7.7 |

EXAMPLE 6

Decantation Range of Quaternary Mixtures

| Quaternary HF-Orga1 Orga2 Orga3 | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HFO-1234zeE | 5-75 | 5-70 | 15-60 |
| HF-HCFO-1233xf-HFC-245cb-HFO-1234zeZ | 5-80 | 5-75 | 5-70 |
| HF-HFO-1234yf-HFC-245cb-HFO-1234zeE | 5-75 | 10-70 | * |
| HF-HFO-1234yf-HFC-245cb-HFO-1234zeZ | 5-75 | 10-75 | 20-70 |
| HF-HCFO-1233xf-HFO-1234yf-HFO-1234zeE | 5-70 | 10-60 | * |
| HF-HCFO-1233xf-HFO-1234yf-HFO-1234zeZ | 5-75 | 5-70 | 10-60 |
| HF-HCFO-1233xf-HCFO-1233zdE-HFO-1234zeE | 5-75 | 5-65 | 5-55 |
| HF-HCFO-1233xf-HCFO-1233zdE-HFO-1234zeZ | 5-80 | 5-75 | 5-65 |
| HF-HCFO-1233xf-HFO-1234zeE-HFO-1234zeZ | 5-75 | 5-65 | 10-55 |
| HF-HCFO-1233xf-HFO-1234zeE-HFO-1243zf | 5-70 | 10-60 | * |
| HF-HCFO-1233xf-HFO-1234zeZ-HFO-1243zf | 5-75 | 5-70 | 10-55 |
| HF-HFO-1234yf-HFO-1234zeE-HFO-1234zeZ | 5-70 | 10-60 | * |
| HF-HFO-1234yf-HFO-1234zeE-HCFO-1233zdE | 5-70 | 10-60 | * |
| HF-HFO-1234yf-HFO-1234zeE-HFO-1243zf | 5-65 | * | * |
| HF-HFO-1234yf-HFO-1234zeZ-HCFO-1233zdE | 5-75 | 5-70 | 10-60 |
| HF-HFO-1234yf-HFO-1234zeZ-HFO-1243zf | 5-75 | 10-65 | * |
| HF-HFC-245cb-HCFO-1233zdE-HFO-1234zeE | 5-75 | 5-70 | 10-65 |
| HF-HFC-245cb-HCFO-1233zdE-HFO-1234zeZ | 5-80 | 5-75 | 5-70 |
| HF-HFC-245cb-HFO-1234zeE-HFO-1234zeZ | 5-75 | 5-70 | 15-55 |
| HF-HFC-245cb-HFO-1234zeE-HFO-1243zf | 5-75 | 15-65 | * |
| HF-HFC-245cb-HFO-1234zeZ-HFO-1243zf | 5-75 | 10-70 | 20-60 |
| HF-HCFO-1233zdE-F 1234zeE-HFO-1234zeZ | 5-75 | 5-65 | 10-55 |
| HF-HCFO-1233zdE-F 1234zeE-HFO-1243zf | 5-70 | 10-60 | * |
| HF-HCFO-1233zdE-F 1234zeZ-HFO-1243zf | 5-75 | 5-70 | 10-55 |
| HF-HFO-1234zeE-HFO-1234zeZ-HFO-1243zf | 5-70 | 10-60 | * |
| HF-HFO-1234yf-HFO-1234zeE-Trifluoropropyne | 10-65 | * | * |
| HF-HFO-1234yf-HFO-1234zeE-HCFC-244bb | 5-80 | 5-75 | 10-65 |
| HF-HFO-1234yf-HFO-1234zeE-HFC-245fa | 5-70 | 10-65 | * |
| HF-HFO-1234yf-HFO-1234zeE-HFO-1225yeZ | 5-70 | 20-45 | * |
| HF-HFO-1234yf-HFO-1234zeE-HFO-1225zc | 5-65 | * | * |

EXAMPLE 7

Penternary Mixtures, Isotherm at 25° C.

| HF-HCFO-1233xf-HFC-245cb-HCFO-1233zdE-HFO-1234zeE ||||||||||
|---|---|---|---|---|---|---|---|---|---|
| Organics 0.9 F1233xf + 0.033 F1233zdE + 0.033 F245cb + 0.034 F1234zeE || Organics 0.033 F1233xf + 0.9 F1233zdE + 0.033 F245cb + 0.034 F1234zeE || Organics 0.033 F1233xf + 0.033 F1233zdE + 0.9 245cb + 0.034 F1234zeE || Organics 0.034 F1233xf + 0.033 F1233zdE + 0.033 F245cb + 0.9 F1234zeE || Organics 0.25 F1233xf + 0.25 F1233zdE + 0.25 F245cb + 0.25 F1234zeE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.4 | 0 | 4.7 | 0 | 3.2 |
| 0.05 | 2.9 | 0.05 | 2.7 | 0.05 | 5.6 | 0.05 | 5.6 | 0.05 | 4.3 |
| 0.1 | 2.9 | 0.1 | 2.7 | 0.1 | 5.6 | 0.1 | 5.6 | 0.1 | 4.3 |
| 0.15 | 2.9 | 0.15 | 2.7 | 0.15 | 5.6 | 0.15 | 5.6 | 0.15 | 4.3 |
| 0.2 | 2.9 | 0.2 | 2.7 | 0.2 | 5.6 | 0.2 | 5.6 | 0.2 | 4.3 |
| 0.25 | 2.9 | 0.25 | 2.7 | 0.25 | 5.6 | 0.25 | 5.6 | 0.25 | 4.3 |
| 0.3 | 2.9 | 0.3 | 2.7 | 0.3 | 5.6 | 0.3 | 5.6 | 0.3 | 4.3 |
| 0.35 | 2.9 | 0.35 | 2.7 | 0.35 | 5.6 | 0.35 | 5.6 | 0.35 | 4.3 |
| 0.4 | 2.9 | 0.4 | 2.7 | 0.4 | 5.6 | 0.4 | 5.6 | 0.4 | 4.3 |
| 0.45 | 2.9 | 0.45 | 2.7 | 0.45 | 5.6 | 0.45 | 5.6 | 0.45 | 4.3 |
| 0.5 | 2.9 | 0.5 | 2.7 | 0.5 | 5.6 | 0.5 | 5.6 | 0.5 | 4.3 |
| 0.55 | 2.9 | 0.55 | 2.7 | 0.55 | 5.6 | 0.55 | 5.6 | 0.55 | 4.3 |
| 0.6 | 2.9 | 0.6 | 2.7 | 0.6 | 5.6 | 0.6 | 5.5 | 0.6 | 4.3 |
| 0.65 | 2.9 | 0.65 | 2.7 | 0.65 | 5.6 | 0.65 | 5.4 | 0.65 | 4.3 |
| 0.7 | 2.9 | 0.7 | 2.7 | 0.7 | 5.7 | 0.7 | 5.2 | 0.7 | 4.3 |
| 0.75 | 2.9 | 0.75 | 2.7 | 0.75 | 5.7 | 0.75 | 5.0 | 0.75 | 4.2 |
| 0.8 | 2.7 | 0.8 | 2.6 | 0.8 | 5.7 | 0.8 | 4.7 | 0.8 | 4.0 |
| 0.85 | 2.5 | 0.85 | 2.4 | 0.85 | 5.6 | 0.85 | 4.2 | 0.85 | 3.7 |
| 0.9 | 2.2 | 0.9 | 2.1 | 0.9 | 4.8 | 0.9 | 3.5 | 0.9 | 3.2 |
| 0.95 | 1.8 | 0.95 | 1.7 | 0.95 | 3.4 | 0.95 | 2.5 | 0.95 | 2.4 |
| 1 | 1.2 | 1 | 1.2 | 1 | 1.2 | 1 | 1.2 | 1 | 1.2 |

| HF-HCFO-1233xf-HFC-245cb-HCFO-1233zdE-HFO-1234zeZ ||||||||||
|---|---|---|---|---|---|---|---|---|---|
| Organics 0.9 F1233xf + 0.033 F1233zdE + 0.033 F245cb + 0.034 F1234zeZ || Organics 0.033 F1233xf + 0.9 F1233zdE + 0.033 F245cb + 0.034 F1234zeZ || Organics 0.033 F1233xf + 0.033 F1233zdE + 0.9 F245cb + 0.034 F1234zeZ || Organics 0.034 F1233xf + 0.033 F1233zdE + 0.033 F245cb + 0.9 F1234zeZ || Organics 0.25 F1233xf + 0.25 F1233zdE + 0.25 F245cb + 0.25 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.3 | 0 | 1.9 | 0 | 2.3 |
| 0.05 | 2.8 | 0.05 | 2.6 | 0.05 | 5.5 | 0.05 | 3.0 | 0.05 | 3.5 |
| 0.1 | 2.8 | 0.1 | 2.6 | 0.1 | 5.5 | 0.1 | 3.0 | 0.1 | 3.5 |
| 0.15 | 2.8 | 0.15 | 2.6 | 0.15 | 5.5 | 0.15 | 3.0 | 0.15 | 3.5 |
| 0.2 | 2.8 | 0.2 | 2.6 | 0.2 | 5.5 | 0.2 | 3.0 | 0.2 | 3.5 |
| 0.25 | 2.8 | 0.25 | 2.6 | 0.25 | 5.5 | 0.25 | 3.0 | 0.25 | 3.5 |
| 0.3 | 2.8 | 0.3 | 2.6 | 0.3 | 5.5 | 0.3 | 3.0 | 0.3 | 3.5 |
| 0.35 | 2.8 | 0.35 | 2.6 | 0.35 | 5.5 | 0.35 | 3.0 | 0.35 | 3.5 |
| 0.4 | 2.8 | 0.4 | 2.6 | 0.4 | 5.5 | 0.4 | 3.0 | 0.4 | 3.5 |
| 0.45 | 2.8 | 0.45 | 2.6 | 0.45 | 5.5 | 0.45 | 3.0 | 0.45 | 3.5 |
| 0.5 | 2.8 | 0.5 | 2.6 | 0.5 | 5.5 | 0.5 | 3.0 | 0.5 | 3.5 |
| 0.55 | 2.8 | 0.55 | 2.6 | 0.55 | 5.5 | 0.55 | 3.0 | 0.55 | 3.5 |
| 0.6 | 2.8 | 0.6 | 2.6 | 0.6 | 5.5 | 0.6 | 3.0 | 0.6 | 3.5 |
| 0.65 | 2.8 | 0.65 | 2.6 | 0.65 | 5.5 | 0.65 | 3.0 | 0.65 | 3.6 |
| 0.7 | 2.8 | 0.7 | 2.6 | 0.7 | 5.6 | 0.7 | 3.0 | 0.7 | 3.6 |
| 0.75 | 2.8 | 0.75 | 2.6 | 0.75 | 5.6 | 0.75 | 3.0 | 0.75 | 3.6 |
| 0.8 | 2.7 | 0.8 | 2.5 | 0.8 | 5.6 | 0.8 | 2.9 | 0.8 | 3.5 |
| 0.85 | 2.5 | 0.85 | 2.3 | 0.85 | 5.5 | 0.85 | 2.7 | 0.85 | 3.3 |
| 0.9 | 2.2 | 0.9 | 2.1 | 0.9 | 4.8 | 0.9 | 2.4 | 0.9 | 2.8 |
| 0.95 | 1.8 | 0.95 | 1.7 | 0.95 | 3.4 | 0.95 | 1.9 | 0.95 | 2.2 |
| 1 | 1.2 | 1 | 1.2 | 1 | 1.2 | 1 | 1.2 | 1 | 1.2 |

HF-HCFO-1233xf-HFC-245cb-HFO-1233zeE-HFO-1234zeZ

| Organics 0.9 F1233xf + 0.033 F1234zeE + 0.033 F245cb + 0.034 F1234zeZ | | Organics 0.033 F1233xf + 0.9 F1234zeE + 0.033 F245cb + 0.034 F1234zeZ | | Organics 0.033 F1233xf + 0.033 F1234zeE + 0.9 F245cb + 0.034 F1234zeZ | | Organics 0.034 F1233xf + 0.033 F1234zeE + 0.033 F245cb + 0.9 F1234zeZ | | Organics 0.25 F1233xf + 0.25 F1234zeE + 0.25 F245cb + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 4.7 | 0 | 4.5 | 0 | 2.0 | 0 | 3.2 |
| 0.05 | 2.9 | 0.05 | 5.6 | 0.05 | 5.6 | 0.05 | 3.1 | 0.05 | 4.3 |
| 0.1 | 2.9 | 0.1 | 5.7 | 0.1 | 5.6 | 0.1 | 3.1 | 0.1 | 4.3 |
| 0.15 | 2.9 | 0.15 | 5.6 | 0.15 | 5.6 | 0.15 | 3.1 | 0.15 | 4.3 |
| 0.2 | 2.9 | 0.2 | 5.6 | 0.2 | 5.6 | 0.2 | 3.1 | 0.2 | 4.3 |
| 0.25 | 2.9 | 0.25 | 5.6 | 0.25 | 5.6 | 0.25 | 3.1 | 0.25 | 4.3 |
| 0.3 | 2.9 | 0.3 | 5.6 | 0.3 | 5.6 | 0.3 | 3.1 | 0.3 | 4.3 |
| 0.35 | 2.9 | 0.35 | 5.6 | 0.35 | 5.6 | 0.35 | 3.1 | 0.35 | 4.3 |
| 0.4 | 2.9 | 0.4 | 5.6 | 0.4 | 5.6 | 0.4 | 3.1 | 0.4 | 4.3 |
| 0.45 | 2.9 | 0.45 | 5.6 | 0.45 | 5.6 | 0.45 | 3.1 | 0.45 | 4.3 |
| 0.5 | 2.9 | 0.5 | 5.6 | 0.5 | 5.6 | 0.5 | 3.1 | 0.5 | 4.3 |
| 0.55 | 2.9 | 0.55 | 5.6 | 0.55 | 5.6 | 0.55 | 3.1 | 0.55 | 4.3 |
| 0.6 | 2.9 | 0.6 | 5.5 | 0.6 | 5.6 | 0.6 | 3.1 | 0.6 | 4.3 |
| 0.65 | 2.9 | 0.65 | 5.4 | 0.65 | 5.7 | 0.65 | 3.1 | 0.65 | 4.4 |
| 0.7 | 2.9 | 0.7 | 5.2 | 0.7 | 5.7 | 0.7 | 3.1 | 0.7 | 4.4 |
| 0.75 | 2.9 | 0.75 | 5.0 | 0.75 | 5.7 | 0.75 | 3.1 | 0.75 | 4.3 |
| 0.8 | 2.7 | 0.8 | 4.7 | 0.8 | 5.7 | 0.8 | 3.0 | 0.8 | 4.1 |
| 0.85 | 2.5 | 0.85 | 4.2 | 0.85 | 5.6 | 0.85 | 2.7 | 0.85 | 3.8 |
| 0.9 | 2.2 | 0.9 | 3.5 | 0.9 | 4.8 | 0.9 | 2.4 | 0.9 | 3.3 |
| 0.95 | 1.8 | 0.95 | 2.6 | 0.95 | 3.4 | 0.95 | 1.9 | 0.95 | 2.4 |
| 1 | 1.2 | 1 | 1.2 | 1 | 1.2 | 1 | 1.2 | 1 | 1.2 |

HF-HCFO-1233xf-HFC-245cb-HFO-1234zeE-HFO-1243zf

| Organics 0.9 F1233xf + 0.033 F1234zeE + 0.033 F245cb + 0.034 F1243zf | | Organics 0.033 F1233xf + 0.9 F1234zeE + 0.033 F245cb + 0.034 F1243zf | | Organics 0.033 F1233xf + 0.033 F1234zeE + 0.9 F245cb + 0.034 F1243zf | | Organics 0.034 F1233xf + 0.033 F1234zeE + 0.033 F245cb + 0.9 F1243zf | | Organics 0.25 F1233xf + 0.25 F1234zeE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 5.7 | 0 | 4.4 |
| 0.05 | 3.1 | 0.05 | 5.8 | 0.05 | 5.8 | 0.05 | 6.6 | 0.05 | 5.4 |
| 0.1 | 3.1 | 0.1 | 5.8 | 0.1 | 5.8 | 0.1 | 6.7 | 0.1 | 5.4 |
| 0.15 | 3.1 | 0.15 | 5.8 | 0.15 | 5.8 | 0.15 | 6.6 | 0.15 | 5.4 |
| 0.2 | 3.1 | 0.2 | 5.8 | 0.2 | 5.8 | 0.2 | 6.6 | 0.2 | 5.4 |
| 0.25 | 3.1 | 0.25 | 5.8 | 0.25 | 5.8 | 0.25 | 6.6 | 0.25 | 5.4 |
| 0.3 | 3.1 | 0.3 | 5.8 | 0.3 | 5.8 | 0.3 | 6.6 | 0.3 | 5.4 |
| 0.35 | 3.1 | 0.35 | 5.8 | 0.35 | 5.8 | 0.35 | 6.6 | 0.35 | 5.4 |
| 0.4 | 3.1 | 0.4 | 5.8 | 0.4 | 5.8 | 0.4 | 6.6 | 0.4 | 5.4 |
| 0.45 | 3.1 | 0.45 | 5.8 | 0.45 | 5.8 | 0.45 | 6.6 | 0.45 | 5.4 |
| 0.5 | 3.1 | 0.5 | 5.7 | 0.5 | 5.8 | 0.5 | 6.6 | 0.5 | 5.4 |
| 0.55 | 3.1 | 0.55 | 5.7 | 0.55 | 5.8 | 0.55 | 6.6 | 0.55 | 5.4 |
| 0.6 | 3.1 | 0.6 | 5.6 | 0.6 | 5.8 | 0.6 | 6.6 | 0.6 | 5.4 |
| 0.65 | 3.1 | 0.65 | 5.5 | 0.65 | 5.8 | 0.65 | 6.5 | 0.65 | 5.4 |
| 0.7 | 3.1 | 0.7 | 5.4 | 0.7 | 5.8 | 0.7 | 6.4 | 0.7 | 5.4 |
| 0.75 | 3.0 | 0.75 | 5.2 | 0.75 | 5.8 | 0.75 | 6.3 | 0.75 | 5.3 |
| 0.8 | 2.9 | 0.8 | 4.8 | 0.8 | 5.8 | 0.8 | 6.0 | 0.8 | 5.0 |
| 0.85 | 2.7 | 0.85 | 4.3 | 0.85 | 5.7 | 0.85 | 5.5 | 0.85 | 4.6 |
| 0.9 | 2.3 | 0.9 | 3.6 | 0.9 | 4.9 | 0.9 | 4.7 | 0.9 | 3.9 |
| 0.95 | 1.9 | 0.95 | 2.6 | 0.95 | 3.5 | 0.95 | 3.3 | 0.95 | 2.8 |
| 1 | 1.2 | 1 | 1.2 | 1 | 1.2 | 1 | 1.2 | 1 | 1.2 |

HF-HCFO-1233xf-HFC-245cb-HFO-1234zeE-HFO-1234yf

| Organics 0.9 F1233xf + 0.033 F1234zeE + 0.033 F245cb + 0.034 F1234yf | | Organics 0.033 F1233xf + 0.9 F1234zeE + 0.033 F245cb + 0.034 F1234yf | | Organics 0.033 F1233xf + 0.033 F1234zeE + 0.9 F245cb + 0.034 F1234yf | | Organics 0.034 F1233xf + 0.033 F1234zeE + 0.033 F245cb + 0.9 F1234yf | | Organics 0.25 F1233xf + 0.25 F1234zeE + 0.25 F245cb + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 6.5 | 0 | 4.6 |
| 0.05 | 3.1 | 0.05 | 5.8 | 0.05 | 5.8 | 0.05 | 7.5 | 0.05 | 5.6 |
| 0.1 | 3.1 | 0.1 | 5.8 | 0.1 | 5.8 | 0.1 | 7.5 | 0.1 | 5.6 |
| 0.15 | 3.1 | 0.15 | 5.8 | 0.15 | 5.8 | 0.15 | 7.5 | 0.15 | 5.6 |
| 0.2 | 3.1 | 0.2 | 5.8 | 0.2 | 5.8 | 0.2 | 7.5 | 0.2 | 5.6 |
| 0.25 | 3.1 | 0.25 | 5.8 | 0.25 | 5.8 | 0.25 | 7.5 | 0.25 | 5.6 |
| 0.3 | 3.1 | 0.3 | 5.8 | 0.3 | 5.8 | 0.3 | 7.5 | 0.3 | 5.6 |
| 0.35 | 3.1 | 0.35 | 5.8 | 0.35 | 5.8 | 0.35 | 7.5 | 0.35 | 5.6 |
| 0.4 | 3.1 | 0.4 | 5.8 | 0.4 | 5.8 | 0.4 | 7.5 | 0.4 | 5.6 |
| 0.45 | 3.1 | 0.45 | 5.8 | 0.45 | 5.8 | 0.45 | 7.5 | 0.45 | 5.6 |
| 0.5 | 3.1 | 0.5 | 5.8 | 0.5 | 5.8 | 0.5 | 7.5 | 0.5 | 5.6 |
| 0.55 | 3.1 | 0.55 | 5.7 | 0.55 | 5.8 | 0.55 | 7.5 | 0.55 | 5.6 |
| 0.6 | 3.1 | 0.6 | 5.7 | 0.6 | 5.8 | 0.6 | 7.5 | 0.6 | 5.6 |
| 0.65 | 3.1 | 0.65 | 5.6 | 0.65 | 5.8 | 0.65 | 7.5 | 0.65 | 5.7 |
| 0.7 | 3.1 | 0.7 | 5.4 | 0.7 | 5.8 | 0.7 | 7.5 | 0.7 | 5.7 |
| 0.75 | 3.1 | 0.75 | 5.2 | 0.75 | 5.8 | 0.75 | 7.3 | 0.75 | 5.5 |
| 0.8 | 2.9 | 0.8 | 4.9 | 0.8 | 5.8 | 0.8 | 7.0 | 0.8 | 5.3 |
| 0.85 | 2.7 | 0.85 | 4.4 | 0.85 | 5.7 | 0.85 | 6.4 | 0.85 | 4.8 |
| 0.9 | 2.4 | 0.9 | 3.7 | 0.9 | 4.9 | 0.9 | 5.4 | 0.9 | 4.1 |
| 0.95 | 1.9 | 0.95 | 2.6 | 0.95 | 3.5 | 0.95 | 3.7 | 0.95 | 2.9 |
| 1 | 1.2 | 1 | 1.2 | 1 | 1.2 | 1 | 1.2 | 1 | 1.2 |

HF-HCFO-1233xf-HFC-245cb-HFO-1234zeZ-HFO-1243zf

| Organics 0.9 F1233xf + 0.033 F1234zeZ + 0.033 F245cb + 0.034 F1243zf | | Organics 0.033 F1233xf + 0.9 F1234zeZ + 0.033 F245cb + 0.034 F1243zf | | Organics 0.033 F1233xf + 0.033 F1234zeZ + 0.9 F245cb + 0.034 F1243zf | | Organics 0.034 F1233xf + 0.033 F1234zeZ + 0.033 F245cb + 0.9 F1243zf | | Organics 0.25 F1233xf + 0.25 F1234zeZ + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 5.6 | 0 | 3.6 |
| 0.05 | 3.0 | 0.05 | 3.2 | 0.05 | 5.7 | 0.05 | 6.5 | 0.05 | 4.7 |
| 0.1 | 3.0 | 0.1 | 3.2 | 0.1 | 5.7 | 0.1 | 6.6 | 0.1 | 4.7 |
| 0.15 | 3.0 | 0.15 | 3.2 | 0.15 | 5.7 | 0.15 | 6.6 | 0.15 | 4.7 |
| 0.2 | 3.0 | 0.2 | 3.2 | 0.2 | 5.7 | 0.2 | 6.6 | 0.2 | 4.7 |
| 0.25 | 3.0 | 0.25 | 3.2 | 0.25 | 5.7 | 0.25 | 6.5 | 0.25 | 4.7 |
| 0.3 | 3.0 | 0.3 | 3.2 | 0.3 | 5.7 | 0.3 | 6.5 | 0.3 | 4.7 |
| 0.35 | 3.0 | 0.35 | 3.2 | 0.35 | 5.7 | 0.35 | 6.5 | 0.35 | 4.7 |
| 0.4 | 3.0 | 0.4 | 3.2 | 0.4 | 5.7 | 0.4 | 6.5 | 0.4 | 4.7 |
| 0.45 | 3.0 | 0.45 | 3.2 | 0.45 | 5.7 | 0.45 | 6.5 | 0.45 | 4.7 |
| 0.5 | 3.0 | 0.5 | 3.2 | 0.5 | 5.7 | 0.5 | 6.5 | 0.5 | 4.7 |
| 0.55 | 3.0 | 0.55 | 3.2 | 0.55 | 5.7 | 0.55 | 6.5 | 0.55 | 4.7 |
| 0.6 | 3.0 | 0.6 | 3.2 | 0.6 | 5.7 | 0.6 | 6.5 | 0.6 | 4.7 |
| 0.65 | 3.0 | 0.65 | 3.2 | 0.65 | 5.7 | 0.65 | 6.5 | 0.65 | 4.7 |
| 0.7 | 3.0 | 0.7 | 3.2 | 0.7 | 5.7 | 0.7 | 6.4 | 0.7 | 4.7 |
| 0.75 | 3.0 | 0.75 | 3.2 | 0.75 | 5.7 | 0.75 | 6.2 | 0.75 | 4.7 |
| 0.8 | 2.8 | 0.8 | 3.0 | 0.8 | 5.7 | 0.8 | 5.9 | 0.8 | 4.5 |
| 0.85 | 2.6 | 0.85 | 2.8 | 0.85 | 5.6 | 0.85 | 5.4 | 0.85 | 4.2 |
| 0.9 | 2.3 | 0.9 | 2.5 | 0.9 | 4.8 | 0.9 | 4.6 | 0.9 | 3.6 |
| 0.95 | 1.8 | 0.95 | 1.9 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

HF-HCFO-1233xf-HFC-245cb-HFO-1234zeZ-HFO-1234yf

| Organics 0.9 F1233xf + 0.033 F1234zeZ + 0.033 F245cb + 0.034 F1234yf | | Organics 0.033 F1233xf + 0.9 F1234zeZ + 0.033 F245cb + 0.034 F1234yf | | Organics 0.033 F1233xf + 0.033 F1234zeZ + 0.9 F245cb + 0.034 F1234yf | | Organics 0.034 F1233xf + 0.033 F1234zeZ + 0.033 F245cb + 0.9 F1234yf | | Organics 0.25 F1233xf + 0.25 F1234zeZ + 0.25 F245cb + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 6.4 | 0 | 3.7 |
| 0.05 | 3.0 | 0.05 | 3.2 | 0.05 | 5.7 | 0.05 | 7.4 | 0.05 | 4.9 |
| 0.1 | 3.0 | 0.1 | 3.2 | 0.1 | 5.7 | 0.1 | 7.4 | 0.1 | 4.9 |
| 0.15 | 3.0 | 0.15 | 3.2 | 0.15 | 5.7 | 0.15 | 7.4 | 0.15 | 4.9 |
| 0.2 | 3.0 | 0.2 | 3.2 | 0.2 | 5.7 | 0.2 | 7.4 | 0.2 | 4.9 |
| 0.25 | 3.0 | 0.25 | 3.2 | 0.25 | 5.7 | 0.25 | 7.4 | 0.25 | 4.9 |
| 0.3 | 3.0 | 0.3 | 3.2 | 0.3 | 5.7 | 0.3 | 7.4 | 0.3 | 4.9 |
| 0.35 | 3.0 | 0.35 | 3.2 | 0.35 | 5.7 | 0.35 | 7.4 | 0.35 | 4.9 |
| 0.4 | 3.0 | 0.4 | 3.2 | 0.4 | 5.7 | 0.4 | 7.4 | 0.4 | 4.9 |
| 0.45 | 3.0 | 0.45 | 3.2 | 0.45 | 5.7 | 0.45 | 7.4 | 0.45 | 4.9 |
| 0.5 | 3.0 | 0.5 | 3.2 | 0.5 | 5.7 | 0.5 | 7.4 | 0.5 | 4.9 |
| 0.55 | 3.0 | 0.55 | 3.2 | 0.55 | 5.7 | 0.55 | 7.4 | 0.55 | 4.9 |
| 0.6 | 3.0 | 0.6 | 3.2 | 0.6 | 5.7 | 0.6 | 7.4 | 0.6 | 4.9 |
| 0.65 | 3.0 | 0.65 | 3.2 | 0.65 | 5.7 | 0.65 | 7.4 | 0.65 | 4.9 |
| 0.7 | 3.0 | 0.7 | 3.2 | 0.7 | 5.7 | 0.7 | 7.4 | 0.7 | 4.9 |
| 0.75 | 3.0 | 0.75 | 3.2 | 0.75 | 5.7 | 0.75 | 7.2 | 0.75 | 5.0 |
| 0.8 | 2.8 | 0.8 | 3.0 | 0.8 | 5.7 | 0.8 | 6.9 | 0.8 | 4.8 |
| 0.85 | 2.6 | 0.85 | 2.8 | 0.85 | 5.7 | 0.85 | 6.4 | 0.85 | 4.4 |
| 0.9 | 2.3 | 0.9 | 2.5 | 0.9 | 4.9 | 0.9 | 5.4 | 0.9 | 3.8 |
| 0.95 | 1.8 | 0.95 | 2.0 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

HF-HCFO-1233xf-HCFO-1233zdE-HFO-1234zeE-HFO-1234zeZ

| Organics 0.9 F1233xf + 0.033 F1234zeE + 0.033 F1233zdE + 0.034 F1234zeZ | | Organics 0.033 F1233xf + 0.9 F1234zeE + 0.033 F1233zdE + 0.034 F1234zeZ | | Organics 0.033 F1233xf + 0.033 F1234zeE + 0.9 F1233zdE + 0.034 F1234zeZ | | Organics 0.034 F1233xf + 0.033 F1234zeE + 0.033 F1233zdE + 0.9 F1234zeZ | | Organics 0.25 F1233xf + 0.25 F1234zeE + 0.25 F1233zdE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.5 | 0 | 1.9 | 0 | 2.4 |
| 0.05 | 2.8 | 0.05 | 5.5 | 0.05 | 2.6 | 0.05 | 3.0 | 0.05 | 3.5 |
| 0.1 | 2.8 | 0.1 | 5.5 | 0.1 | 2.6 | 0.1 | 3.0 | 0.1 | 3.5 |
| 0.15 | 2.8 | 0.15 | 5.5 | 0.15 | 2.6 | 0.15 | 3.0 | 0.15 | 3.5 |
| 0.2 | 2.8 | 0.2 | 5.5 | 0.2 | 2.6 | 0.2 | 3.0 | 0.2 | 3.5 |
| 0.25 | 2.8 | 0.25 | 5.5 | 0.25 | 2.6 | 0.25 | 3.0 | 0.25 | 3.5 |
| 0.3 | 2.8 | 0.3 | 5.5 | 0.3 | 2.6 | 0.3 | 3.0 | 0.3 | 3.5 |
| 0.35 | 2.8 | 0.35 | 5.5 | 0.35 | 2.6 | 0.35 | 3.0 | 0.35 | 3.5 |
| 0.4 | 2.8 | 0.4 | 5.5 | 0.4 | 2.6 | 0.4 | 3.0 | 0.4 | 3.5 |
| 0.45 | 2.8 | 0.45 | 5.5 | 0.45 | 2.6 | 0.45 | 3.0 | 0.45 | 3.5 |
| 0.5 | 2.8 | 0.5 | 5.5 | 0.5 | 2.6 | 0.5 | 3.0 | 0.5 | 3.5 |
| 0.55 | 2.8 | 0.55 | 5.4 | 0.55 | 2.6 | 0.55 | 3.0 | 0.55 | 3.4 |
| 0.6 | 2.8 | 0.6 | 5.4 | 0.6 | 2.6 | 0.6 | 3.0 | 0.6 | 3.4 |
| 0.65 | 2.8 | 0.65 | 5.3 | 0.65 | 2.6 | 0.65 | 3.0 | 0.65 | 3.4 |
| 0.7 | 2.8 | 0.7 | 5.1 | 0.7 | 2.5 | 0.7 | 3.0 | 0.7 | 3.4 |
| 0.75 | 2.7 | 0.75 | 4.9 | 0.75 | 2.5 | 0.75 | 3.0 | 0.75 | 3.3 |
| 0.8 | 2.6 | 0.8 | 4.6 | 0.8 | 2.4 | 0.8 | 2.8 | 0.8 | 3.1 |
| 0.85 | 2.4 | 0.85 | 4.1 | 0.85 | 2.3 | 0.85 | 2.6 | 0.85 | 2.9 |
| 0.9 | 2.1 | 0.9 | 3.4 | 0.9 | 2.0 | 0.9 | 2.3 | 0.9 | 2.5 |
| 0.95 | 1.7 | 0.95 | 2.5 | 0.95 | 1.7 | 0.95 | 1.9 | 0.95 | 1.9 |
| 1 | 1.2 | 1 | 1.2 | 1 | 1.2 | 1 | 1.2 | 1 | 1.2 |

-continued

| HF-HCFO-1233xf-HCFO-1233zdE-HFO-1234zeE-HFO-1243zf ||||||||||
|---|---|---|---|---|---|---|---|---|---|
| Organics 0.9 F1233xf + 0.033 F1234zeE + 0.033 F1233zdE + 0.034 F1243zf || Organics 0.033 F1233xf + 0.9 F1234zeE + 0.033 F1233zdE + 0.034 F1243zf || Organics 0.033 F1233xf + 0.033 F1234zeE + 0.9 F1233zdE + 0.034 F1243zf || Organics 0.034 F1233xf + 0.033 F1234zeE + 0.033 F1233zdE + 0.9 F1243zf || Organics 0.25 F1233xf + 0.25 1234zeE + 0.25 F1233zdE + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 5.6 | 0 | 3.6 |
| 0.05 | 3.0 | 0.05 | 5.7 | 0.05 | 2.8 | 0.05 | 6.5 | 0.05 | 4.7 |
| 0.1 | 3.0 | 0.1 | 5.7 | 0.1 | 2.8 | 0.1 | 6.6 | 0.1 | 4.7 |
| 0.15 | 3.0 | 0.15 | 5.7 | 0.15 | 2.8 | 0.15 | 6.6 | 0.15 | 4.7 |
| 0.2 | 3.0 | 0.2 | 5.7 | 0.2 | 2.8 | 0.2 | 6.5 | 0.2 | 4.7 |
| 0.25 | 3.0 | 0.25 | 5.7 | 0.25 | 2.8 | 0.25 | 6.5 | 0.25 | 4.6 |
| 0.3 | 2.9 | 0.3 | 5.7 | 0.3 | 2.7 | 0.3 | 6.5 | 0.3 | 4.6 |
| 0.35 | 2.9 | 0.35 | 5.7 | 0.35 | 2.7 | 0.35 | 6.5 | 0.35 | 4.6 |
| 0.4 | 2.9 | 0.4 | 5.7 | 0.4 | 2.7 | 0.4 | 6.5 | 0.4 | 4.6 |
| 0.45 | 2.9 | 0.45 | 5.7 | 0.45 | 2.7 | 0.45 | 6.5 | 0.45 | 4.6 |
| 0.5 | 2.9 | 0.5 | 5.6 | 0.5 | 2.7 | 0.5 | 6.5 | 0.5 | 4.6 |
| 0.55 | 2.9 | 0.55 | 5.6 | 0.55 | 2.7 | 0.55 | 6.5 | 0.55 | 4.6 |
| 0.6 | 2.9 | 0.6 | 5.5 | 0.6 | 2.7 | 0.6 | 6.5 | 0.6 | 4.6 |
| 0.65 | 2.9 | 0.65 | 5.4 | 0.65 | 2.7 | 0.65 | 6.4 | 0.65 | 4.5 |
| 0.7 | 2.9 | 0.7 | 5.3 | 0.7 | 2.7 | 0.7 | 6.3 | 0.7 | 4.5 |
| 0.75 | 2.9 | 0.75 | 5.0 | 0.75 | 2.7 | 0.75 | 6.2 | 0.75 | 4.3 |
| 0.8 | 2.7 | 0.8 | 4.7 | 0.8 | 2.6 | 0.8 | 5.9 | 0.8 | 4.1 |
| 0.85 | 2.5 | 0.85 | 4.2 | 0.85 | 2.4 | 0.85 | 5.4 | 0.85 | 3.7 |
| 0.9 | 2.2 | 0.9 | 3.5 | 0.9 | 2.1 | 0.9 | 4.6 | 0.9 | 3.1 |
| 0.95 | 1.8 | 0.95 | 2.5 | 0.95 | 1.7 | 0.95 | 3.3 | 0.95 | 2.3 |
| 1 | 1.2 | 1 | 1.2 | 1 | 1.2 | 1 | 1.2 | 1 | 1.2 |
| HF-HCFO-1233xf-HCFO-1233zdE-HFO-1234zeZ-HFO-1243zf ||||||||||
| Organics 0.9 F1233xf + 0.033 F1234zeZ + 0.033 F1233zdE + 0.034 F1243zf || Organics 0.033 F1233xf + 0.9 F1234zeZ + 0.033 F1233zdE + 0.034 F1243zf || Organics 0.033 F1233xf + 0.033 F1234zeZ + 0.9 F1233zdE + 0.034 F1243zf || Organics 0.034 F1233xf + 0.033 F1234zeZ + 0.033 F1233zdE + 0.9 F1243zf || Organics 0.25 F1233xf + 0.25 F1234zeZ + 0.25 F1233zdE + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.4 | 0.45 | 3.9 |
| 0.5 | 2.8 | 0.5 | 3.0 | 0.5 | 2.6 | 0.5 | 6.4 | 0.5 | 3.9 |
| 0.55 | 2.8 | 0.55 | 3.0 | 0.55 | 2.6 | 0.55 | 6.4 | 0.55 | 3.9 |
| 0.6 | 2.8 | 0.6 | 3.0 | 0.6 | 2.6 | 0.6 | 6.4 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

HF-HCFO-1233xf-HFO-1234zeE-HFO-1234zeZ-HFO-1243zf

| Organics 0.9 F1233xf + 0.033 F1234zeE + 0.033 F1234zeZ + 0.034 F1243zf | | Organics 0.033 F1233xf + 0.9 F1234zeE + 0.033 F1234zeZ + 0.034 F1243zf | | Organics 0.033 F1233xf + 0.033 F1234zeE + 0.9 F1234zeZ + 0.034 F1243zf | | Organics 0.034 F1233xf + 0.033 F1234zeE + 0.033 F1234zeZ + 0.9 F1243zf | | Organics 0.25 F1233xf + 0.25 F1234zeE + 0.25 F1234zeZ + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 2.1 | 0 | 5.6 | 0 | 3.7 |
| 0.05 | 3.0 | 0.05 | 5.7 | 0.05 | 3.2 | 0.05 | 6.5 | 0.05 | 4.7 |
| 0.1 | 3.0 | 0.1 | 5.7 | 0.1 | 3.2 | 0.1 | 6.6 | 0.1 | 4.7 |
| 0.15 | 3.0 | 0.15 | 5.7 | 0.15 | 3.2 | 0.15 | 6.6 | 0.15 | 4.7 |
| 0.2 | 3.0 | 0.2 | 5.7 | 0.2 | 3.2 | 0.2 | 6.5 | 0.2 | 4.7 |
| 0.25 | 3.0 | 0.25 | 5.7 | 0.25 | 3.2 | 0.25 | 6.5 | 0.25 | 4.7 |
| 0.3 | 3.0 | 0.3 | 5.7 | 0.3 | 3.2 | 0.3 | 6.5 | 0.3 | 4.7 |
| 0.35 | 3.0 | 0.35 | 5.7 | 0.35 | 3.2 | 0.35 | 6.5 | 0.35 | 4.7 |
| 0.4 | 3.0 | 0.4 | 5.7 | 0.4 | 3.2 | 0.4 | 6.5 | 0.4 | 4.7 |
| 0.45 | 3.0 | 0.45 | 5.7 | 0.45 | 3.2 | 0.45 | 6.5 | 0.45 | 4.7 |
| 0.5 | 3.0 | 0.5 | 5.6 | 0.5 | 3.2 | 0.5 | 6.5 | 0.5 | 4.7 |
| 0.55 | 2.9 | 0.55 | 5.6 | 0.55 | 3.1 | 0.55 | 6.5 | 0.55 | 4.6 |
| 0.6 | 2.9 | 0.6 | 5.5 | 0.6 | 3.1 | 0.6 | 6.5 | 0.6 | 4.6 |
| 0.65 | 2.9 | 0.65 | 5.4 | 0.65 | 3.1 | 0.65 | 6.4 | 0.65 | 4.6 |
| 0.7 | 2.9 | 0.7 | 5.3 | 0.7 | 3.1 | 0.7 | 6.3 | 0.7 | 4.5 |
| 0.75 | 2.9 | 0.75 | 5.0 | 0.75 | 3.1 | 0.75 | 6.2 | 0.75 | 4.4 |
| 0.8 | 2.8 | 0.8 | 4.7 | 0.8 | 3.0 | 0.8 | 5.9 | 0.8 | 4.1 |
| 0.85 | 2.6 | 0.85 | 4.2 | 0.85 | 2.7 | 0.85 | 5.4 | 0.85 | 3.8 |
| 0.9 | 2.2 | 0.9 | 3.5 | 0.9 | 2.4 | 0.9 | 4.6 | 0.9 | 3.2 |
| 0.95 | 1.8 | 0.95 | 2.5 | 0.95 | 1.9 | 0.95 | 3.3 | 0.95 | 2.4 |
| 1 | 1.2 | 1 | 1.2 | 1 | 1.2 | 1 | 1.2 | 1 | 1.2 |

HF-HCFO-1233xf-HFO-1234yf-HFO-1234zeE-HFO-1234zeZ

| Organics 0.9 F1233xf + 0.033 F1234zeE + 0.033 F1234zeZ + 0.034 F1234yf | | Organics 0.033 F1233xf + 0.9 F1234zeE + 0.033 F1234zeZ + 0.034 F1234yf | | Organics 0.033 F1233xf + 0.033 F1234zeE + 0.9 F1234zeZ + 0.034 F1234yf | | Organics 0.034 F1233xf + 0.033 F1234zeE + 0.033 F1234zeZ + 0.9 F1234yf | | Organics 0.25 F1233xf + 0.25 F1234zeE + 0.25 F1234zeZ + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 2.1 | 0 | 6.4 | 0 | 3.8 |
| 0.05 | 3.0 | 0.05 | 5.7 | 0.05 | 3.2 | 0.05 | 7.4 | 0.05 | 4.9 |
| 0.1 | 3.0 | 0.1 | 5.7 | 0.1 | 3.2 | 0.1 | 7.4 | 0.1 | 4.9 |
| 0.15 | 3.0 | 0.15 | 5.7 | 0.15 | 3.2 | 0.15 | 7.4 | 0.15 | 4.9 |
| 0.2 | 3.0 | 0.2 | 5.7 | 0.2 | 3.2 | 0.2 | 7.4 | 0.2 | 4.9 |
| 0.25 | 3.0 | 0.25 | 5.7 | 0.25 | 3.2 | 0.25 | 7.4 | 0.25 | 4.9 |
| 0.3 | 3.0 | 0.3 | 5.7 | 0.3 | 3.2 | 0.3 | 7.4 | 0.3 | 4.9 |
| 0.35 | 3.0 | 0.35 | 5.7 | 0.35 | 3.2 | 0.35 | 7.4 | 0.35 | 4.9 |
| 0.4 | 3.0 | 0.4 | 5.7 | 0.4 | 3.2 | 0.4 | 7.4 | 0.4 | 4.9 |
| 0.45 | 3.0 | 0.45 | 5.7 | 0.45 | 3.2 | 0.45 | 7.4 | 0.45 | 4.9 |
| 0.5 | 3.0 | 0.5 | 5.7 | 0.5 | 3.2 | 0.5 | 7.4 | 0.5 | 4.9 |
| 0.55 | 3.0 | 0.55 | 5.6 | 0.55 | 3.2 | 0.55 | 7.4 | 0.55 | 4.9 |
| 0.6 | 3.0 | 0.6 | 5.6 | 0.6 | 3.2 | 0.6 | 7.4 | 0.6 | 4.8 |
| 0.65 | 3.0 | 0.65 | 5.5 | 0.65 | 3.2 | 0.65 | 7.4 | 0.65 | 4.8 |
| 0.7 | 3.0 | 0.7 | 5.3 | 0.7 | 3.2 | 0.7 | 7.4 | 0.7 | 4.8 |
| 0.75 | 2.9 | 0.75 | 5.1 | 0.75 | 3.1 | 0.75 | 7.2 | 0.75 | 4.6 |
| 0.8 | 2.8 | 0.8 | 4.7 | 0.8 | 3.0 | 0.8 | 6.9 | 0.8 | 4.4 |
| 0.85 | 2.6 | 0.85 | 4.3 | 0.85 | 2.8 | 0.85 | 6.3 | 0.85 | 4.0 |
| 0.9 | 2.3 | 0.9 | 3.6 | 0.9 | 2.4 | 0.9 | 5.3 | 0.9 | 3.4 |
| 0.95 | 1.8 | 0.95 | 2.6 | 0.95 | 1.9 | 0.95 | 3.7 | 0.95 | 2.5 |
| 1 | 1.2 | 1 | 1.2 | 1 | 1.2 | 1 | 1.2 | 1 | 1.2 |

HF-HCFO-1233xf-HFO-1234yf-HFO-1234zeE-HFO-1243zf

| Organics 0.9 F1233xf + 0.033 F1234zeE + 0.033 F1243zf + 0.034 F1234yf | | Organics 0.033 F1233xf + 0.9 F1234zeE + 0.033 F1243zf + 0.034 F1234yf | | Organics 0.033 F1233xf + 0.033 F1234zeE + 0.9 F1243zf + 0.034 F1234yf | | Organics 0.034 F1233xf + 0.033 F1234zeE + 0.033 F1243zf + 0.9 F1234yf | | Organics 0.25 F1233xf + 0.25 F1234zeE + 0.25 F1243zf + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.1 | 0 | 4.9 | 0 | 5.7 | 0 | 6.5 | 0 | 4.9 |
| 0.05 | 3.2 | 0.05 | 5.8 | 0.05 | 6.7 | 0.05 | 7.5 | 0.05 | 5.9 |
| 0.1 | 3.2 | 0.1 | 5.9 | 0.1 | 6.7 | 0.1 | 7.5 | 0.1 | 5.9 |
| 0.15 | 3.2 | 0.15 | 5.9 | 0.15 | 6.7 | 0.15 | 7.5 | 0.15 | 5.9 |
| 0.2 | 3.2 | 0.2 | 5.9 | 0.2 | 6.7 | 0.2 | 7.5 | 0.2 | 5.9 |
| 0.25 | 3.2 | 0.25 | 5.9 | 0.25 | 6.7 | 0.25 | 7.5 | 0.25 | 5.9 |
| 0.3 | 3.2 | 0.3 | 5.9 | 0.3 | 6.7 | 0.3 | 7.5 | 0.3 | 5.9 |
| 0.35 | 3.2 | 0.35 | 5.9 | 0.35 | 6.7 | 0.35 | 7.5 | 0.35 | 5.9 |
| 0.4 | 3.1 | 0.4 | 5.8 | 0.4 | 6.7 | 0.4 | 7.5 | 0.4 | 5.9 |
| 0.45 | 3.1 | 0.45 | 5.8 | 0.45 | 6.7 | 0.45 | 7.5 | 0.45 | 5.9 |
| 0.5 | 3.1 | 0.5 | 5.8 | 0.5 | 6.7 | 0.5 | 7.5 | 0.5 | 5.9 |
| 0.55 | 3.1 | 0.55 | 5.8 | 0.55 | 6.7 | 0.55 | 7.5 | 0.55 | 5.9 |
| 0.6 | 3.1 | 0.6 | 5.7 | 0.6 | 6.6 | 0.6 | 7.5 | 0.6 | 5.9 |
| 0.65 | 3.1 | 0.65 | 5.6 | 0.65 | 6.6 | 0.65 | 7.5 | 0.65 | 5.8 |
| 0.7 | 3.1 | 0.7 | 5.4 | 0.7 | 6.5 | 0.7 | 7.5 | 0.7 | 5.7 |
| 0.75 | 3.1 | 0.75 | 5.2 | 0.75 | 6.3 | 0.75 | 7.3 | 0.75 | 5.6 |
| 0.8 | 2.9 | 0.8 | 4.9 | 0.8 | 6.0 | 0.8 | 7.0 | 0.8 | 5.3 |
| 0.85 | 2.7 | 0.85 | 4.4 | 0.85 | 5.5 | 0.85 | 6.4 | 0.85 | 4.8 |
| 0.9 | 2.4 | 0.9 | 3.6 | 0.9 | 4.7 | 0.9 | 5.4 | 0.9 | 4.0 |
| 0.95 | 1.9 | 0.95 | 2.6 | 0.95 | 3.3 | 0.95 | 3.7 | 0.95 | 2.9 |
| 1 | 1.2 | 1 | 1.2 | 1 | 1.2 | 1 | 1.2 | 1 | 1.2 |

HF-HCFO-1233xf-HFO-1234yf-HFO-1234zeE-HCFO-1233zdE

| Organics 0.9 F1233xf + 0.033 F1234zeE + 0.033 F1233zdE + 0.034 F1234yf | | Organics 0.033 F1233xf + 0.9 F1234zeE + 0.033 F1233zdE + 0.034 F1234yf | | Organics 0.033 F1233xf + 0.033 F1234zeE + 0.9 F1233zdE + 0.034 F1234yf | | Organics 0.034 F1233xf + 0.033 F1234zeE + 0.033 F1233zdE + 0.9 F1234yf | | Organics 0.25 F1233xf + 0.25 F1234zeE + 0.25 F1233zdE + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 6.4 | 0 | 3.8 |
| 0.05 | 3.0 | 0.05 | 5.7 | 0.05 | 2.8 | 0.05 | 7.4 | 0.05 | 4.8 |
| 0.1 | 3.0 | 0.1 | 5.7 | 0.1 | 2.8 | 0.1 | 7.4 | 0.1 | 4.8 |
| 0.15 | 3.0 | 0.15 | 5.7 | 0.15 | 2.8 | 0.15 | 7.4 | 0.15 | 4.8 |
| 0.2 | 3.0 | 0.2 | 5.7 | 0.2 | 2.8 | 0.2 | 7.4 | 0.2 | 4.8 |
| 0.25 | 3.0 | 0.25 | 5.7 | 0.25 | 2.8 | 0.25 | 7.4 | 0.25 | 4.8 |
| 0.3 | 3.0 | 0.3 | 5.7 | 0.3 | 2.8 | 0.3 | 7.4 | 0.3 | 4.8 |
| 0.35 | 3.0 | 0.35 | 5.7 | 0.35 | 2.8 | 0.35 | 7.4 | 0.35 | 4.8 |
| 0.4 | 3.0 | 0.4 | 5.7 | 0.4 | 2.8 | 0.4 | 7.4 | 0.4 | 4.8 |
| 0.45 | 3.0 | 0.45 | 5.7 | 0.45 | 2.8 | 0.45 | 7.4 | 0.45 | 4.8 |
| 0.5 | 3.0 | 0.5 | 5.7 | 0.5 | 2.8 | 0.5 | 7.4 | 0.5 | 4.8 |
| 0.55 | 3.0 | 0.55 | 5.6 | 0.55 | 2.8 | 0.55 | 7.4 | 0.55 | 4.8 |
| 0.6 | 3.0 | 0.6 | 5.5 | 0.6 | 2.8 | 0.6 | 7.4 | 0.6 | 4.8 |
| 0.65 | 2.9 | 0.65 | 5.4 | 0.65 | 2.7 | 0.65 | 7.4 | 0.65 | 4.8 |
| 0.7 | 2.9 | 0.7 | 5.3 | 0.7 | 2.7 | 0.7 | 7.4 | 0.7 | 4.7 |
| 0.75 | 2.9 | 0.75 | 5.1 | 0.75 | 2.7 | 0.75 | 7.2 | 0.75 | 4.6 |
| 0.8 | 2.8 | 0.8 | 4.7 | 0.8 | 2.6 | 0.8 | 6.9 | 0.8 | 4.3 |
| 0.85 | 2.6 | 0.85 | 4.2 | 0.85 | 2.4 | 0.85 | 6.3 | 0.85 | 3.9 |
| 0.9 | 2.3 | 0.9 | 3.6 | 0.9 | 2.1 | 0.9 | 5.3 | 0.9 | 3.3 |
| 0.95 | 1.8 | 0.95 | 2.6 | 0.95 | 1.7 | 0.95 | 3.7 | 0.95 | 2.4 |
| 1 | 1.2 | 1 | 1.2 | 1 | 1.2 | 1 | 1.2 | 1 | 1.2 |

-continued

HF-HCFO-1233xf-HFO-1234yf-HFO-1234zeZ-HFO-1243zf

| Organics 0.9 F1233xf + 0.033 F1234zeZ + 0.033 F1243zf + 0.034 F1234yf | | Organics 0.033 F1233xf + 0.9 F1234zeZ + 0.033 F1243zf + 0.034 F1234yf | | Organics 0.033 F1233xf + 0.033 F1234zeZ + 0.9 F1243zf + 0.034 F1234yf | | Organics 0.034 F1233xf + 0.033 F1234zeZ + 0.033 F1243zf + 0.9 F1234yf | | Organics 0.25 F1233xf + 0.25 F1234zeZ + 0.25 F1243zf + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 5.6 | 0 | 6.4 | 0 | 4.1 |
| 0.05 | 3.1 | 0.05 | 3.2 | 0.05 | 6.6 | 0.05 | 7.4 | 0.05 | 5.2 |
| 0.1 | 3.1 | 0.1 | 3.2 | 0.1 | 6.6 | 0.1 | 7.4 | 0.1 | 5.2 |
| 0.15 | 3.1 | 0.15 | 3.2 | 0.15 | 6.6 | 0.15 | 7.4 | 0.15 | 5.2 |
| 0.2 | 3.1 | 0.2 | 3.2 | 0.2 | 6.6 | 0.2 | 7.4 | 0.2 | 5.2 |
| 0.25 | 3.1 | 0.25 | 3.2 | 0.25 | 6.6 | 0.25 | 7.4 | 0.25 | 5.2 |
| 0.3 | 3.1 | 0.3 | 3.2 | 0.3 | 6.6 | 0.3 | 7.4 | 0.3 | 5.2 |
| 0.35 | 3.0 | 0.35 | 3.2 | 0.35 | 6.6 | 0.35 | 7.4 | 0.35 | 5.2 |
| 0.4 | 3.0 | 0.4 | 3.2 | 0.4 | 6.6 | 0.4 | 7.4 | 0.4 | 5.2 |
| 0.45 | 3.0 | 0.45 | 3.2 | 0.45 | 6.6 | 0.45 | 7.4 | 0.45 | 5.2 |
| 0.5 | 3.0 | 0.5 | 3.2 | 0.5 | 6.6 | 0.5 | 7.4 | 0.5 | 5.2 |
| 0.55 | 3.0 | 0.55 | 3.2 | 0.55 | 6.6 | 0.55 | 7.4 | 0.55 | 5.2 |
| 0.6 | 3.0 | 0.6 | 3.2 | 0.6 | 6.5 | 0.6 | 7.4 | 0.6 | 5.2 |
| 0.65 | 3.0 | 0.65 | 3.2 | 0.65 | 6.5 | 0.65 | 7.4 | 0.65 | 5.2 |
| 0.7 | 3.0 | 0.7 | 3.2 | 0.7 | 6.4 | 0.7 | 7.4 | 0.7 | 5.1 |
| 0.75 | 3.0 | 0.75 | 3.2 | 0.75 | 6.2 | 0.75 | 7.2 | 0.75 | 5.0 |
| 0.8 | 2.9 | 0.8 | 3.1 | 0.8 | 6.0 | 0.8 | 6.9 | 0.8 | 4.8 |
| 0.85 | 2.6 | 0.85 | 2.8 | 0.85 | 5.5 | 0.85 | 6.3 | 0.85 | 4.4 |
| 0.9 | 2.3 | 0.9 | 2.5 | 0.9 | 4.6 | 0.9 | 5.3 | 0.9 | 3.7 |
| 0.95 | 1.8 | 0.95 | 2.0 | 0.95 | 3.3 | 0.95 | 3.7 | 0.95 | 2.7 |
| 1 | 1.2 | 1 | 1.2 | 1 | 1.2 | 1 | 1.2 | 1 | 1.2 |

HF-HCFO-1233xf-HFO-1234yf-HFO-1234zeZ-HCFO-1233zdE

| Organics 0.9 F1233xf + 0.033 F1234zeZ + 0.033 F1233zdE + 0.034 F1234yf | | Organics 0.033 F1233xf + 0.9 F1234zeZ + 0.033 F1233zdE + 0.034 F1234yf | | Organics 0.033 F1233xf + 0.033 F1234zeZ + 0.9 F1233zdE + 0.034 F1234yf | | Organics 0.034 F1233xf + 0.033 F1234zeZ + 0.033 F1233zdE + 0.9 F1234yf | | Organics 0.25 F1233xf + 0.25 F1234zeZ + 0.25 F1233zdE + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 1.6 | 0 | 6.3 | 0 | 3.0 |
| 0.05 | 2.9 | 0.05 | 3.1 | 0.05 | 2.7 | 0.05 | 7.3 | 0.05 | 4.1 |
| 0.1 | 2.9 | 0.1 | 3.1 | 0.1 | 2.7 | 0.1 | 7.3 | 0.1 | 4.1 |
| 0.15 | 2.9 | 0.15 | 3.1 | 0.15 | 2.7 | 0.15 | 7.3 | 0.15 | 4.1 |
| 0.2 | 2.9 | 0.2 | 3.1 | 0.2 | 2.7 | 0.2 | 7.3 | 0.2 | 4.1 |
| 0.25 | 2.9 | 0.25 | 3.1 | 0.25 | 2.7 | 0.25 | 7.3 | 0.25 | 4.1 |
| 0.3 | 2.9 | 0.3 | 3.1 | 0.3 | 2.7 | 0.3 | 7.3 | 0.3 | 4.1 |
| 0.35 | 2.9 | 0.35 | 3.1 | 0.35 | 2.7 | 0.35 | 7.3 | 0.35 | 4.1 |
| 0.4 | 2.9 | 0.4 | 3.1 | 0.4 | 2.7 | 0.4 | 7.3 | 0.4 | 4.1 |
| 0.45 | 2.9 | 0.45 | 3.1 | 0.45 | 2.7 | 0.45 | 7.3 | 0.45 | 4.1 |
| 0.5 | 2.9 | 0.5 | 3.1 | 0.5 | 2.7 | 0.5 | 7.3 | 0.5 | 4.1 |
| 0.55 | 2.9 | 0.55 | 3.1 | 0.55 | 2.7 | 0.55 | 7.3 | 0.55 | 4.1 |
| 0.6 | 2.9 | 0.6 | 3.1 | 0.6 | 2.7 | 0.6 | 7.3 | 0.6 | 4.1 |
| 0.65 | 2.9 | 0.65 | 3.1 | 0.65 | 2.7 | 0.65 | 7.3 | 0.65 | 4.1 |
| 0.7 | 2.9 | 0.7 | 3.1 | 0.7 | 2.7 | 0.7 | 7.3 | 0.7 | 4.0 |
| 0.75 | 2.8 | 0.75 | 3.1 | 0.75 | 2.6 | 0.75 | 7.1 | 0.75 | 4.0 |
| 0.8 | 2.7 | 0.8 | 2.9 | 0.8 | 2.5 | 0.8 | 6.8 | 0.8 | 3.8 |
| 0.85 | 2.5 | 0.85 | 2.7 | 0.85 | 2.4 | 0.85 | 6.2 | 0.85 | 3.5 |
| 0.9 | 2.2 | 0.9 | 2.4 | 0.9 | 2.1 | 0.9 | 5.3 | 0.9 | 3.0 |
| 0.95 | 1.8 | 0.95 | 1.9 | 0.95 | 1.7 | 0.95 | 3.7 | 0.95 | 2.3 |
| 1 | 1.2 | 1 | 1.2 | 1 | 1.2 | 1 | 1.2 | 1 | 1.2 |

HF-HFO-1234yf-HFO-1234zeE-HFO-1234zeZ-HCFO-1233zdE

| Organics 0.9 F1234yf + 0.033 F1233zdE + 0.033 F1234zeE + 0.034 F1234zeZ | | Organics 0.033 F1234yf + 0.9 F1233zdE + 0.033 F1234zeE + 0.034 F1234zeZ | | Organics 0.033 F1234yf + 0.033 F1233zdE + 0.9 F1234zeE + 0.034 F1234zeZ | | Organics 0.034 F1234yf + 0.033 F1233zdE + 0.033 F1234zeE + 0.9 F1234zeZ | | Organics 0.25 F1234yf + 0.25 F1233zdE + 0.25 F1234zeE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 4.7 | 0 | 2.1 | 0 | 3.8 |
| 0.05 | 7.4 | 0.05 | 2.8 | 0.05 | 5.7 | 0.05 | 3.2 | 0.05 | 4.8 |
| 0.1 | 7.4 | 0.1 | 2.8 | 0.1 | 5.7 | 0.1 | 3.2 | 0.1 | 4.8 |
| 0.15 | 7.4 | 0.15 | 2.8 | 0.15 | 5.7 | 0.15 | 3.2 | 0.15 | 4.8 |
| 0.2 | 7.4 | 0.2 | 2.8 | 0.2 | 5.7 | 0.2 | 3.2 | 0.2 | 4.8 |
| 0.25 | 7.4 | 0.25 | 2.8 | 0.25 | 5.7 | 0.25 | 3.2 | 0.25 | 4.8 |
| 0.3 | 7.4 | 0.3 | 2.8 | 0.3 | 5.7 | 0.3 | 3.2 | 0.3 | 4.8 |
| 0.35 | 7.4 | 0.35 | 2.8 | 0.35 | 5.7 | 0.35 | 3.2 | 0.35 | 4.8 |
| 0.4 | 7.4 | 0.4 | 2.8 | 0.4 | 5.7 | 0.4 | 3.2 | 0.4 | 4.8 |
| 0.45 | 7.4 | 0.45 | 2.8 | 0.45 | 5.7 | 0.45 | 3.2 | 0.45 | 4.8 |
| 0.5 | 7.4 | 0.5 | 2.8 | 0.5 | 5.7 | 0.5 | 3.2 | 0.5 | 4.8 |
| 0.55 | 7.4 | 0.55 | 2.8 | 0.55 | 5.6 | 0.55 | 3.2 | 0.55 | 4.8 |
| 0.6 | 7.4 | 0.6 | 2.8 | 0.6 | 5.5 | 0.6 | 3.2 | 0.6 | 4.8 |
| 0.65 | 7.4 | 0.65 | 2.7 | 0.65 | 5.4 | 0.65 | 3.2 | 0.65 | 4.8 |
| 0.7 | 7.4 | 0.7 | 2.7 | 0.7 | 5.3 | 0.7 | 3.2 | 0.7 | 4.7 |
| 0.75 | 7.2 | 0.75 | 2.7 | 0.75 | 5.1 | 0.75 | 3.1 | 0.75 | 4.6 |
| 0.8 | 6.9 | 0.8 | 2.6 | 0.8 | 4.7 | 0.8 | 3.0 | 0.8 | 4.3 |
| 0.85 | 6.3 | 0.85 | 2.4 | 0.85 | 4.2 | 0.85 | 2.8 | 0.85 | 4.0 |
| 0.9 | 5.3 | 0.9 | 2.1 | 0.9 | 3.6 | 0.9 | 2.4 | 0.9 | 3.4 |
| 0.95 | 3.7 | 0.95 | 1.7 | 0.95 | 2.6 | 0.95 | 1.9 | 0.95 | 2.5 |
| 1 | 1.2 | 1 | 1.2 | 1 | 1.2 | 1 | 1.2 | 1 | 1.2 |

HF-HFO-1234yf-HFO-1234zeE-HFO-1234zeZ-HFO-1243zf

| Organics 0.9 F1234yf + 0.033 F1234zeZ + 0.033 F1234zeE + 0.034 F1243zf | | Organics 0.033 F1234yf + 0.9 F1234zeZ + 0.033 F1234zeE + 0.034 F1243zf | | Organics 0.033 F1234yf + 0.033 F1234zeZ + 0.9 F1234zeE + 0.034 F1243zf | | Organics 0.034 F1234yf + 0.033 F1234zeZ + 0.033 F1234zeE + 0.9 F1243zf | | Organics 0.25 F1234yf + 0.25 F1234zeZ + 0.25 F1234zeE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.2 | 0 | 4.9 | 0 | 5.7 | 0 | 4.9 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.9 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.7 | 0.6 | 6.6 | 0.6 | 5.9 |
| 0.65 | 7.5 | 0.65 | 3.3 | 0.65 | 5.6 | 0.65 | 6.6 | 0.65 | 5.8 |
| 0.7 | 7.5 | 0.7 | 3.3 | 0.7 | 5.4 | 0.7 | 6.5 | 0.7 | 5.7 |
| 0.75 | 7.3 | 0.75 | 3.3 | 0.75 | 5.2 | 0.75 | 6.3 | 0.75 | 5.6 |
| 0.8 | 7.0 | 0.8 | 3.1 | 0.8 | 4.9 | 0.8 | 6.0 | 0.8 | 5.3 |
| 0.85 | 6.4 | 0.85 | 2.9 | 0.85 | 4.4 | 0.85 | 5.5 | 0.85 | 4.8 |
| 0.9 | 5.4 | 0.9 | 2.5 | 0.9 | 3.7 | 0.9 | 4.7 | 0.9 | 4.1 |
| 0.95 | 3.7 | 0.95 | 2.0 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

HF-HFO-1234yf-HFO-1234zeE-HCFO-1233zdE-HFO-1243zf

| Organics 0.9 F1234yf + 0.033 F1233zdE + 0.033 F1234zeE + 0.034 F1243zf | | Organics 0.033 F1234yf + 0.9 F1233zdE + 0.033 F1234zeE + 0.034 F1243zf | | Organics 0.033 F1234yf + 0.033 F1233zdE + 0.9 F1234zeE + 0.034 F1243zf | | Organics 0.034 F1234yf + 0.033 F1233zdE + 0.033 F1234zeE + 0.9 F1243zf | | Organics 0.25 F1234yf + 0.25 F1233zdE + 0.25 F1234zeE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 4.9 | 0 | 5.7 | 0 | 4.8 |
| 0.05 | 7.5 | 0.05 | 3.0 | 0.05 | 5.8 | 0.05 | 6.7 | 0.05 | 5.8 |
| 0.1 | 7.5 | 0.1 | 3.0 | 0.1 | 5.9 | 0.1 | 6.7 | 0.1 | 5.9 |
| 0.15 | 7.5 | 0.15 | 3.0 | 0.15 | 5.8 | 0.15 | 6.7 | 0.15 | 5.9 |
| 0.2 | 7.5 | 0.2 | 3.0 | 0.2 | 5.8 | 0.2 | 6.7 | 0.2 | 5.9 |
| 0.25 | 7.5 | 0.25 | 3.0 | 0.25 | 5.8 | 0.25 | 6.7 | 0.25 | 5.9 |
| 0.3 | 7.5 | 0.3 | 3.0 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.8 |
| 0.55 | 7.5 | 0.55 | 2.9 | 0.55 | 5.8 | 0.55 | 6.6 | 0.55 | 5.8 |
| 0.6 | 7.5 | 0.6 | 2.9 | 0.6 | 5.7 | 0.6 | 6.6 | 0.6 | 5.8 |
| 0.65 | 7.5 | 0.65 | 2.9 | 0.65 | 5.6 | 0.65 | 6.6 | 0.65 | 5.8 |
| 0.7 | 7.5 | 0.7 | 2.9 | 0.7 | 5.4 | 0.7 | 6.5 | 0.7 | 5.7 |
| 0.75 | 7.3 | 0.75 | 2.9 | 0.75 | 5.2 | 0.75 | 6.3 | 0.75 | 5.5 |
| 0.8 | 7.0 | 0.8 | 2.7 | 0.8 | 4.9 | 0.8 | 6.0 | 0.8 | 5.2 |
| 0.85 | 6.4 | 0.85 | 2.5 | 0.85 | 4.4 | 0.85 | 5.5 | 0.85 | 4.8 |
| 0.9 | 5.4 | 0.9 | 2.2 | 0.9 | 3.6 | 0.9 | 4.7 | 0.9 | 4.0 |
| 0.95 | 3.7 | 0.95 | 1.8 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

HF-HFO-1234yf-HFO-1234zeZ-HCFO-1233zdE-HFO-1243zf

| Organics 0.9 F1234yf + 0.033 F1233zdE + 0.033 F1234zeZ + 0.034 F1243zf | | Organics 0.033 F1234yf + 0.9 F1233zdE + 0.033 F1234zeZ + 0.034 F1243zf | | Organics 0.033 F1234yf + 0.033 F1233zdE + 0.9 F1234zeZ + 0.034 F1243zf | | Organics 0.034 F1234yf + 0.033 F1233zdE + 0.033 F1234zeZ + 0.9 F1243zf | | Organics 0.25 F1234yf + 0.25 F1233zdE + 0.25 F1234zeZ + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 2.1 | 0 | 5.6 | 0 | 4.1 |
| 0.05 | 7.4 | 0.05 | 2.9 | 0.05 | 3.2 | 0.05 | 6.6 | 0.05 | 5.2 |
| 0.1 | 7.4 | 0.1 | 2.9 | 0.1 | 3.2 | 0.1 | 6.6 | 0.1 | 5.2 |
| 0.15 | 7.4 | 0.15 | 2.9 | 0.15 | 3.2 | 0.15 | 6.6 | 0.15 | 5.2 |
| 0.2 | 7.4 | 0.2 | 2.9 | 0.2 | 3.2 | 0.2 | 6.6 | 0.2 | 5.2 |
| 0.25 | 7.4 | 0.25 | 2.8 | 0.25 | 3.2 | 0.25 | 6.6 | 0.25 | 5.2 |
| 0.3 | 7.4 | 0.3 | 2.8 | 0.3 | 3.2 | 0.3 | 6.6 | 0.3 | 5.2 |
| 0.35 | 7.4 | 0.35 | 2.8 | 0.35 | 3.2 | 0.35 | 6.6 | 0.35 | 5.1 |
| 0.4 | 7.4 | 0.4 | 2.8 | 0.4 | 3.2 | 0.4 | 6.6 | 0.4 | 5.1 |
| 0.45 | 7.4 | 0.45 | 2.8 | 0.45 | 3.2 | 0.45 | 6.6 | 0.45 | 5.1 |
| 0.5 | 7.4 | 0.5 | 2.8 | 0.5 | 3.2 | 0.5 | 6.6 | 0.5 | 5.1 |
| 0.55 | 7.4 | 0.55 | 2.8 | 0.55 | 3.2 | 0.55 | 6.6 | 0.55 | 5.1 |
| 0.6 | 7.4 | 0.6 | 2.8 | 0.6 | 3.2 | 0.6 | 6.5 | 0.6 | 5.1 |
| 0.65 | 7.4 | 0.65 | 2.8 | 0.65 | 3.2 | 0.65 | 6.5 | 0.65 | 5.1 |
| 0.7 | 7.4 | 0.7 | 2.8 | 0.7 | 3.2 | 0.7 | 6.4 | 0.7 | 5.1 |
| 0.75 | 7.2 | 0.75 | 2.8 | 0.75 | 3.2 | 0.75 | 6.2 | 0.75 | 5.0 |
| 0.8 | 6.9 | 0.8 | 2.7 | 0.8 | 3.0 | 0.8 | 5.9 | 0.8 | 4.7 |
| 0.85 | 6.3 | 0.85 | 2.5 | 0.85 | 2.8 | 0.85 | 5.5 | 0.85 | 4.3 |
| 0.9 | 5.3 | 0.9 | 2.2 | 0.9 | 2.5 | 0.9 | 4.6 | 0.9 | 3.7 |
| 0.95 | 3.7 | 0.95 | 1.8 | 0.95 | 2.0 | 0.95 | 3.3 | 0.95 | 2.7 |
| 1 | 1.2 | 1 | 1.2 | 1 | 1.2 | 1 | 1.2 | 1 | 1.2 |

-continued

HF-HFO-1234yf-HFC-245cb-HFO-1234zeE-HCFO-1233zdE

| Organics 0.9 F1234yf + 0.033 F1234zeE + 0.033 F245cb + 0.034 F1233zdE | | Organics 0.033 F1234yf + 0.9 F1234zeE + 0.033 F245cb + 0.034 F1233zdE | | Organics 0.033 F1234yf + 0.033 F1234zeE + 0.9 F245cb + 0.034 F1233zdE | | Organics 0.034 F1234yf + 0.033 F1234zeE + 0.033 F245cb + 0.9 F1233zdE | | Organics 0.25 F1234yf + 0.25 F1234zeE + 0.25 F245cb + 0.25 F1233zdE | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 1.8 | 0 | 4.5 |
| 0.05 | 7.5 | 0.05 | 5.8 | 0.05 | 5.8 | 0.05 | 2.9 | 0.05 | 5.6 |
| 0.1 | 7.5 | 0.1 | 5.8 | 0.1 | 5.8 | 0.1 | 2.9 | 0.1 | 5.6 |
| 0.15 | 7.5 | 0.15 | 5.8 | 0.15 | 5.8 | 0.15 | 2.9 | 0.15 | 5.6 |
| 0.2 | 7.5 | 0.2 | 5.8 | 0.2 | 5.8 | 0.2 | 2.9 | 0.2 | 5.6 |
| 0.25 | 7.5 | 0.25 | 5.8 | 0.25 | 5.8 | 0.25 | 2.9 | 0.25 | 5.6 |
| 0.3 | 7.5 | 0.3 | 5.8 | 0.3 | 5.8 | 0.3 | 2.9 | 0.3 | 5.6 |
| 0.35 | 7.5 | 0.35 | 5.8 | 0.35 | 5.8 | 0.35 | 2.9 | 0.35 | 5.6 |
| 0.4 | 7.5 | 0.4 | 5.8 | 0.4 | 5.8 | 0.4 | 2.9 | 0.4 | 5.6 |
| 0.45 | 7.5 | 0.45 | 5.8 | 0.45 | 5.8 | 0.45 | 2.9 | 0.45 | 5.6 |
| 0.5 | 7.5 | 0.5 | 5.8 | 0.5 | 5.8 | 0.5 | 2.9 | 0.5 | 5.6 |
| 0.55 | 7.5 | 0.55 | 5.7 | 0.55 | 5.8 | 0.55 | 2.9 | 0.55 | 5.6 |
| 0.6 | 7.5 | 0.6 | 5.7 | 0.6 | 5.8 | 0.6 | 2.9 | 0.6 | 5.6 |
| 0.65 | 7.5 | 0.65 | 5.6 | 0.65 | 5.8 | 0.65 | 2.9 | 0.65 | 5.6 |
| 0.7 | 7.5 | 0.7 | 5.4 | 0.7 | 5.8 | 0.7 | 2.9 | 0.7 | 5.6 |
| 0.75 | 7.3 | 0.75 | 5.2 | 0.75 | 5.8 | 0.75 | 2.9 | 0.75 | 5.5 |
| 0.8 | 7.0 | 0.8 | 4.9 | 0.8 | 5.8 | 0.8 | 2.7 | 0.8 | 5.2 |
| 0.85 | 6.4 | 0.85 | 4.4 | 0.85 | 5.7 | 0.85 | 2.5 | 0.85 | 4.8 |
| 0.9 | 5.4 | 0.9 | 3.6 | 0.9 | 4.9 | 0.9 | 2.2 | 0.9 | 4.1 |
| 0.95 | 3.7 | 0.95 | 2.6 | 0.95 | 3.5 | 0.95 | 1.8 | 0.95 | 2.9 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1234zeZ

| Organics 0.9 F1234yf + 0.033 F1234zeE + 0.033 F245cb + 0.034 F1234zeZ | | Organics 0.033 F1234yf + 0.9 F1234zeE + 0.033 F245cb + 0.034 F1234zeZ | | Organics 0.033 F1234yf + 0.033 F1234zeE + 0.9 F245cb + 0.034 F1234zeZ | | Organics 0.034 F1234yf + 0.033 F1234zeE + 0.033 F245cb + 0.9 F1234zeZ | | Organics 0.25 F1234yf + 0.25 F1234zeE + 0.25 F245cb + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 2.2 | 0 | 4.5 |
| 0.05 | 7.5 | 0.05 | 5.8 | 0.05 | 5.8 | 0.05 | 3.3 | 0.05 | 5.6 |
| 0.1 | 7.5 | 0.1 | 5.8 | 0.1 | 5.8 | 0.1 | 3.3 | 0.1 | 5.6 |
| 0.15 | 7.5 | 0.15 | 5.8 | 0.15 | 5.8 | 0.15 | 3.3 | 0.15 | 5.6 |
| 0.2 | 7.5 | 0.2 | 5.8 | 0.2 | 5.8 | 0.2 | 3.3 | 0.2 | 5.6 |
| 0.25 | 7.5 | 0.25 | 5.8 | 0.25 | 5.8 | 0.25 | 3.3 | 0.25 | 5.6 |
| 0.3 | 7.5 | 0.3 | 5.8 | 0.3 | 5.8 | 0.3 | 3.3 | 0.3 | 5.6 |
| 0.35 | 7.5 | 0.35 | 5.8 | 0.35 | 5.8 | 0.35 | 3.3 | 0.35 | 5.6 |
| 0.4 | 7.5 | 0.4 | 5.8 | 0.4 | 5.8 | 0.4 | 3.3 | 0.4 | 5.6 |
| 0.45 | 7.5 | 0.45 | 5.8 | 0.45 | 5.8 | 0.45 | 3.3 | 0.45 | 5.6 |
| 0.5 | 7.5 | 0.5 | 5.8 | 0.5 | 5.8 | 0.5 | 3.3 | 0.5 | 5.6 |
| 0.55 | 7.5 | 0.55 | 5.7 | 0.55 | 5.8 | 0.55 | 3.3 | 0.55 | 5.6 |
| 0.6 | 7.5 | 0.6 | 5.7 | 0.6 | 5.8 | 0.6 | 3.3 | 0.6 | 5.6 |
| 0.65 | 7.5 | 0.65 | 5.6 | 0.65 | 5.8 | 0.65 | 3.3 | 0.65 | 5.6 |
| 0.7 | 7.5 | 0.7 | 5.4 | 0.7 | 5.8 | 0.7 | 3.3 | 0.7 | 5.6 |
| 0.75 | 7.3 | 0.75 | 5.2 | 0.75 | 5.8 | 0.75 | 3.3 | 0.75 | 5.5 |
| 0.8 | 7.0 | 0.8 | 4.9 | 0.8 | 5.8 | 0.8 | 3.1 | 0.8 | 5.3 |
| 0.85 | 6.4 | 0.85 | 4.4 | 0.85 | 5.7 | 0.85 | 2.9 | 0.85 | 4.9 |
| 0.9 | 5.4 | 0.9 | 3.7 | 0.9 | 4.9 | 0.9 | 2.5 | 0.9 | 4.1 |
| 0.95 | 3.7 | 0.95 | 2.6 | 0.95 | 3.5 | 0.95 | 2.0 | 0.95 | 3.0 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1243zf

| Organics 0.9 F1234yf + 0.033 F1234zeE + 0.033 F245cb + 0.034 F1243zf | | Organics 0.033 F1234yf + 0.9 F1234zeE + 0.033 F245cb + 0.034 F1243zf | | Organics 0.033 F1234yf + 0.033 F1234zeE + 0.9 F245cb + 0.034 F1243zf | | Organics 0.034 F1234yf + 0.033 F1234zeE + 0.033 F245cb + 0.9 F1243zf | | Organics 0.25 F1234yf + 0.25 F1234zeE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 5.0 | 0 | 4.8 | 0 | 5.8 | 0 | 5.6 |
| 0.05 | 7.6 | 0.05 | 5.9 | 0.05 | 6.0 | 0.05 | 6.8 | 0.05 | 6.6 |
| 0.1 | 7.6 | 0.1 | 6.0 | 0.1 | 6.0 | 0.1 | 6.8 | 0.1 | 6.6 |
| 0.15 | 7.6 | 0.15 | 6.0 | 0.15 | 6.0 | 0.15 | 6.8 | 0.15 | 6.6 |
| 0.2 | 7.6 | 0.2 | 6.0 | 0.2 | 6.0 | 0.2 | 6.8 | 0.2 | 6.6 |
| 0.25 | 7.6 | 0.25 | 6.0 | 0.25 | 6.0 | 0.25 | 6.8 | 0.25 | 6.6 |
| 0.3 | 7.6 | 0.3 | 6.0 | 0.3 | 6.0 | 0.3 | 6.8 | 0.3 | 6.6 |
| 0.35 | 7.6 | 0.35 | 6.0 | 0.35 | 6.0 | 0.35 | 6.8 | 0.35 | 6.6 |
| 0.4 | 7.6 | 0.4 | 6.0 | 0.4 | 6.0 | 0.4 | 6.8 | 0.4 | 6.6 |
| 0.45 | 7.6 | 0.45 | 5.9 | 0.45 | 6.0 | 0.45 | 6.8 | 0.45 | 6.6 |
| 0.5 | 7.6 | 0.5 | 5.9 | 0.5 | 6.0 | 0.5 | 6.8 | 0.5 | 6.6 |
| 0.55 | 7.6 | 0.55 | 5.9 | 0.55 | 6.0 | 0.55 | 6.7 | 0.55 | 6.6 |
| 0.6 | 7.6 | 0.6 | 5.8 | 0.6 | 6.0 | 0.6 | 6.7 | 0.6 | 6.6 |
| 0.65 | 7.6 | 0.65 | 5.7 | 0.65 | 5.9 | 0.65 | 6.7 | 0.65 | 6.6 |
| 0.7 | 7.6 | 0.7 | 5.6 | 0.7 | 5.9 | 0.7 | 6.6 | 0.7 | 6.6 |
| 0.75 | 7.4 | 0.75 | 5.3 | 0.75 | 5.9 | 0.75 | 6.4 | 0.75 | 6.4 |
| 0.8 | 7.1 | 0.8 | 5.0 | 0.8 | 5.9 | 0.8 | 6.1 | 0.8 | 6.1 |
| 0.85 | 6.5 | 0.85 | 4.5 | 0.85 | 5.8 | 0.85 | 5.6 | 0.85 | 5.6 |
| 0.9 | 5.5 | 0.9 | 3.7 | 0.9 | 5.0 | 0.9 | 4.8 | 0.9 | 4.8 |
| 0.95 | 3.8 | 0.95 | 2.7 | 0.95 | 3.5 | 0.95 | 3.4 | 0.95 | 3.4 |
| 1 | 1.2 | 1 | 1.2 | 1 | 1.2 | 1 | 1.2 | 1 | 1.2 |

HF-HFO-1234yf-HFC-245cb-HFO-1234zeZ-HCFO-1233zdE

| Organics 0.9 F1234yf + 0.033 F1234zeZ + 0.033 F245cb + 0.034 F1233zdE | | Organics 0.033 F1234yf + 0.9 F1234zeZ + 0.033 F245cb + 0.034 F1233zdE | | Organics 0.033 F1234yf + 0.033 F1234zeZ + 0.9 F245cb + 0.034 F1233zdE | | Organics 0.034 F1234yf + 0.033 F1234zeZ + 0.033 F245cb + 0.9 F1233zdE | | Organics 0.25 F1234yf + 0.25 F1234zeZ + 0.25 F245cb + 0.25 F1233zdE | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 2.1 | 0 | 4.5 | 0 | 1.7 | 0 | 3.7 |
| 0.05 | 7.4 | 0.05 | 3.2 | 0.05 | 5.7 | 0.05 | 2.8 | 0.05 | 4.8 |
| 0.1 | 7.4 | 0.1 | 3.2 | 0.1 | 5.7 | 0.1 | 2.8 | 0.1 | 4.8 |
| 0.15 | 7.4 | 0.15 | 3.2 | 0.15 | 5.7 | 0.15 | 2.8 | 0.15 | 4.8 |
| 0.2 | 7.4 | 0.2 | 3.2 | 0.2 | 5.7 | 0.2 | 2.8 | 0.2 | 4.8 |
| 0.25 | 7.4 | 0.25 | 3.2 | 0.25 | 5.7 | 0.25 | 2.8 | 0.25 | 4.8 |
| 0.3 | 7.4 | 0.3 | 3.2 | 0.3 | 5.7 | 0.3 | 2.8 | 0.3 | 4.8 |
| 0.35 | 7.4 | 0.35 | 3.2 | 0.35 | 5.7 | 0.35 | 2.8 | 0.35 | 4.8 |
| 0.4 | 7.4 | 0.4 | 3.2 | 0.4 | 5.7 | 0.4 | 2.8 | 0.4 | 4.8 |
| 0.45 | 7.4 | 0.45 | 3.2 | 0.45 | 5.7 | 0.45 | 2.8 | 0.45 | 4.8 |
| 0.5 | 7.4 | 0.5 | 3.2 | 0.5 | 5.7 | 0.5 | 2.8 | 0.5 | 4.8 |
| 0.55 | 7.4 | 0.55 | 3.2 | 0.55 | 5.7 | 0.55 | 2.8 | 0.55 | 4.8 |
| 0.6 | 7.4 | 0.6 | 3.2 | 0.6 | 5.7 | 0.6 | 2.8 | 0.6 | 4.9 |
| 0.65 | 7.4 | 0.65 | 3.2 | 0.65 | 5.7 | 0.65 | 2.8 | 0.65 | 4.9 |
| 0.7 | 7.4 | 0.7 | 3.2 | 0.7 | 5.7 | 0.7 | 2.8 | 0.7 | 4.9 |
| 0.75 | 7.2 | 0.75 | 3.2 | 0.75 | 5.7 | 0.75 | 2.8 | 0.75 | 4.9 |
| 0.8 | 6.9 | 0.8 | 3.0 | 0.8 | 5.7 | 0.8 | 2.7 | 0.8 | 4.7 |
| 0.85 | 6.4 | 0.85 | 2.8 | 0.85 | 5.7 | 0.85 | 2.5 | 0.85 | 4.3 |
| 0.9 | 5.4 | 0.9 | 2.5 | 0.9 | 4.9 | 0.9 | 2.2 | 0.9 | 3.7 |
| 0.95 | 3.7 | 0.95 | 2.0 | 0.95 | 3.5 | 0.95 | 1.8 | 0.95 | 2.7 |
| 1 | 1.2 | 1 | 1.2 | 1 | 1.2 | 1 | 1.2 | 1 | 1.2 |

HF-HFO-1234yf-HFC-245cb-HFO-1234zeZ-HFO-1243zf

| Organics 0.9 F1234yf + 0.033 F1234zeZ + 0.033 F245cb + 0.034 F1243zf | | Organics 0.033 F1234yf + 0.9 F1234zeZ + 0.033 F245cb + 0.034 F1243zf | | Organics 0.033 F1234yf + 0.033 F1234zeZ + 0.9 F245cb + 0.034 F1243zf | | Organics 0.034 F1234yf + 0.033 F1234zeZ + 0.033 F245cb + 0.9 F1243zf | | Organics 0.25 F1234yf + 0.25 F1234zeZ + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.2 | 0 | 4.7 | 0 | 5.7 | 0 | 4.8 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.8 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.8 | 0.6 | 6.6 | 0.6 | 5.9 |
| 0.65 | 7.5 | 0.65 | 3.3 | 0.65 | 5.8 | 0.65 | 6.6 | 0.65 | 5.9 |
| 0.7 | 7.5 | 0.7 | 3.3 | 0.7 | 5.9 | 0.7 | 6.5 | 0.7 | 5.9 |
| 0.75 | 7.3 | 0.75 | 3.3 | 0.75 | 5.9 | 0.75 | 6.3 | 0.75 | 5.9 |
| 0.8 | 7.0 | 0.8 | 3.2 | 0.8 | 5.9 | 0.8 | 6.1 | 0.8 | 5.6 |
| 0.85 | 6.5 | 0.85 | 2.9 | 0.85 | 5.8 | 0.85 | 5.6 | 0.85 | 5.2 |
| 0.9 | 5.4 | 0.9 | 2.6 | 0.9 | 5.0 | 0.9 | 4.7 | 0.9 | 4.4 |
| 0.95 | 3.8 | 0.95 | 2.0 | 0.95 | 3.5 | 0.95 | 3.4 | 0.95 | 3.2 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1234zeZ

| Organics 0.9 F245cb + 0.033 F1234zeE + 0.033 F1233zdE + 0.034 F1234zeZ | | Organics 0.033 F245cb + 0.9 F1234zeE + 0.033 F1233zdE + 0.034 F1234zeZ | | Organics 0.033 F245cb + 0.033 F1234zeE + 0.9 F1233zdE + 0.034 F1234zeZ | | Organics 0.034 F245cb + 0.033 F1234zeE + 0.033 F1233zdE + 0.9 F1234zeZ | | Organics 0.25 F245cb + 0.25 F1234zeE + 0.25 F1233zdE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 4.7 | 0 | 1.6 | 0 | 2.0 | 0 | 3.2 |
| 0.05 | 5.6 | 0.05 | 5.6 | 0.05 | 2.7 | 0.05 | 3.1 | 0.05 | 4.3 |
| 0.1 | 5.6 | 0.1 | 5.6 | 0.1 | 2.7 | 0.1 | 3.1 | 0.1 | 4.3 |
| 0.15 | 5.6 | 0.15 | 5.6 | 0.15 | 2.7 | 0.15 | 3.1 | 0.15 | 4.3 |
| 0.2 | 5.6 | 0.2 | 5.6 | 0.2 | 2.7 | 0.2 | 3.1 | 0.2 | 4.3 |
| 0.25 | 5.6 | 0.25 | 5.6 | 0.25 | 2.7 | 0.25 | 3.1 | 0.25 | 4.3 |
| 0.3 | 5.6 | 0.3 | 5.6 | 0.3 | 2.7 | 0.3 | 3.1 | 0.3 | 4.3 |
| 0.35 | 5.6 | 0.35 | 5.6 | 0.35 | 2.7 | 0.35 | 3.1 | 0.35 | 4.3 |
| 0.4 | 5.6 | 0.4 | 5.6 | 0.4 | 2.7 | 0.4 | 3.1 | 0.4 | 4.3 |
| 0.45 | 5.6 | 0.45 | 5.6 | 0.45 | 2.7 | 0.45 | 3.1 | 0.45 | 4.3 |
| 0.5 | 5.6 | 0.5 | 5.6 | 0.5 | 2.7 | 0.5 | 3.1 | 0.5 | 4.3 |
| 0.55 | 5.6 | 0.55 | 5.6 | 0.55 | 2.7 | 0.55 | 3.1 | 0.55 | 4.3 |
| 0.6 | 5.6 | 0.6 | 5.5 | 0.6 | 2.7 | 0.6 | 3.1 | 0.6 | 4.3 |
| 0.65 | 5.6 | 0.65 | 5.4 | 0.65 | 2.7 | 0.65 | 3.1 | 0.65 | 4.3 |
| 0.7 | 5.7 | 0.7 | 5.2 | 0.7 | 2.7 | 0.7 | 3.1 | 0.7 | 4.3 |
| 0.75 | 5.7 | 0.75 | 5.0 | 0.75 | 2.7 | 0.75 | 3.1 | 0.75 | 4.3 |
| 0.8 | 5.7 | 0.8 | 4.7 | 0.8 | 2.6 | 0.8 | 3.0 | 0.8 | 4.1 |
| 0.85 | 5.6 | 0.85 | 4.2 | 0.85 | 2.4 | 0.85 | 2.7 | 0.85 | 3.7 |
| 0.9 | 4.8 | 0.9 | 3.5 | 0.9 | 2.1 | 0.9 | 2.4 | 0.9 | 3.2 |
| 0.95 | 3.4 | 0.95 | 2.5 | 0.95 | 1.7 | 0.95 | 1.9 | 0.95 | 2.4 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1243zf

| Organics 0.9 F245cb + 0.033 F1234zeE + 0.033 F1233zdE + 0.034 F1243zf | | Organics 0.033 F245cb + 0.9 F1234zeE + 0.033 F1233zdE + 0.034 F1243zf | | Organics 0.033 F245cb + 0.033 F1234zeE + 0.9 F1233zdE + 0.034 F1243zf | | Organics 0.034 F245cb + 0.033 F1234zeE + 0.033 F1233zdE + 0.9 F1243zf | | Organics 0.25 F245cb + 0.25 F1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.8 | 0 | 5.7 | 0 | 4.3 |
| 0.05 | 5.8 | 0.05 | 5.8 | 0.05 | 2.9 | 0.05 | 6.6 | 0.05 | 5.4 |
| 0.1 | 5.8 | 0.1 | 5.8 | 0.1 | 2.9 | 0.1 | 6.6 | 0.1 | 5.4 |
| 0.15 | 5.8 | 0.15 | 5.8 | 0.15 | 2.9 | 0.15 | 6.6 | 0.15 | 5.4 |
| 0.2 | 5.8 | 0.2 | 5.8 | 0.2 | 2.9 | 0.2 | 6.6 | 0.2 | 5.4 |
| 0.25 | 5.8 | 0.25 | 5.8 | 0.25 | 2.9 | 0.25 | 6.6 | 0.25 | 5.4 |
| 0.3 | 5.8 | 0.3 | 5.8 | 0.3 | 2.9 | 0.3 | 6.6 | 0.3 | 5.4 |
| 0.35 | 5.8 | 0.35 | 5.8 | 0.35 | 2.9 | 0.35 | 6.6 | 0.35 | 5.4 |
| 0.4 | 5.8 | 0.4 | 5.8 | 0.4 | 2.9 | 0.4 | 6.6 | 0.4 | 5.4 |
| 0.45 | 5.8 | 0.45 | 5.8 | 0.45 | 2.9 | 0.45 | 6.6 | 0.45 | 5.4 |
| 0.5 | 5.8 | 0.5 | 5.7 | 0.5 | 2.9 | 0.5 | 6.6 | 0.5 | 5.4 |
| 0.55 | 5.8 | 0.55 | 5.7 | 0.55 | 2.9 | 0.55 | 6.6 | 0.55 | 5.4 |
| 0.6 | 5.8 | 0.6 | 5.6 | 0.6 | 2.9 | 0.6 | 6.6 | 0.6 | 5.4 |
| 0.65 | 5.8 | 0.65 | 5.5 | 0.65 | 2.8 | 0.65 | 6.5 | 0.65 | 5.4 |
| 0.7 | 5.8 | 0.7 | 5.4 | 0.7 | 2.8 | 0.7 | 6.4 | 0.7 | 5.4 |
| 0.75 | 5.8 | 0.75 | 5.2 | 0.75 | 2.8 | 0.75 | 6.3 | 0.75 | 5.2 |
| 0.8 | 5.8 | 0.8 | 4.8 | 0.8 | 2.7 | 0.8 | 6.0 | 0.8 | 5.0 |
| 0.85 | 5.7 | 0.85 | 4.3 | 0.85 | 2.5 | 0.85 | 5.5 | 0.85 | 4.5 |
| 0.9 | 4.9 | 0.9 | 3.6 | 0.9 | 2.2 | 0.9 | 4.7 | 0.9 | 3.9 |
| 0.95 | 3.5 | 0.95 | 2.6 | 0.95 | 1.8 | 0.95 | 3.3 | 0.95 | 2.8 |
| 1 | 1.2 | 1 | 1.2 | 1 | 1.2 | 1 | 1.2 | 1 | 1.2 |

HF-HFC-245cb-HCFO-1233zdE-HFO-1234zeZ-HFO-1243zf

| Organics 0.9 F245cb + 0.033 F1234zeZ + 0.033 F1233zdE + 0.034 F1243zf | | Organics 0.033 F245cb + 0.9 F1234zeZ + 0.033 F1233zdE + 0.034 F1243zf | | Organics 0.033 F245cb + 0.033 F1234zeZ + 0.9 F1233zdE + 0.034 F1243zf | | Organics 0.034 F245cb + 0.033 F1234zeZ + 0.033 F1233zdE + 0.9 F1243zf | | Organics 0.25 F245cb + 0.25 F1234zeZ + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 2.0 | 0 | 1.7 | 0 | 5.6 | 0 | 3.5 |
| 0.05 | 5.7 | 0.05 | 3.2 | 0.05 | 2.8 | 0.05 | 6.5 | 0.05 | 4.6 |
| 0.1 | 5.7 | 0.1 | 3.2 | 0.1 | 2.8 | 0.1 | 6.6 | 0.1 | 4.6 |
| 0.15 | 5.7 | 0.15 | 3.2 | 0.15 | 2.8 | 0.15 | 6.6 | 0.15 | 4.6 |
| 0.2 | 5.7 | 0.2 | 3.2 | 0.2 | 2.8 | 0.2 | 6.5 | 0.2 | 4.6 |
| 0.25 | 5.7 | 0.25 | 3.2 | 0.25 | 2.8 | 0.25 | 6.5 | 0.25 | 4.6 |
| 0.3 | 5.7 | 0.3 | 3.2 | 0.3 | 2.8 | 0.3 | 6.5 | 0.3 | 4.6 |
| 0.35 | 5.7 | 0.35 | 3.2 | 0.35 | 2.8 | 0.35 | 6.5 | 0.35 | 4.6 |
| 0.4 | 5.7 | 0.4 | 3.2 | 0.4 | 2.8 | 0.4 | 6.5 | 0.4 | 4.6 |
| 0.45 | 5.7 | 0.45 | 3.2 | 0.45 | 2.8 | 0.45 | 6.5 | 0.45 | 4.6 |
| 0.5 | 5.7 | 0.5 | 3.2 | 0.5 | 2.8 | 0.5 | 6.5 | 0.5 | 4.7 |
| 0.55 | 5.7 | 0.55 | 3.2 | 0.55 | 2.8 | 0.55 | 6.5 | 0.55 | 4.7 |
| 0.6 | 5.7 | 0.6 | 3.2 | 0.6 | 2.8 | 0.6 | 6.5 | 0.6 | 4.7 |
| 0.65 | 5.7 | 0.65 | 3.2 | 0.65 | 2.8 | 0.65 | 6.4 | 0.65 | 4.7 |
| 0.7 | 5.7 | 0.7 | 3.2 | 0.7 | 2.8 | 0.7 | 6.4 | 0.7 | 4.7 |
| 0.75 | 5.7 | 0.75 | 3.1 | 0.75 | 2.8 | 0.75 | 6.2 | 0.75 | 4.7 |
| 0.8 | 5.7 | 0.8 | 3.0 | 0.8 | 2.6 | 0.8 | 5.9 | 0.8 | 4.5 |
| 0.85 | 5.6 | 0.85 | 2.8 | 0.85 | 2.4 | 0.85 | 5.4 | 0.85 | 4.1 |
| 0.9 | 4.8 | 0.9 | 2.5 | 0.9 | 2.2 | 0.9 | 4.6 | 0.9 | 3.5 |
| 0.95 | 3.4 | 0.95 | 1.9 | 0.95 | 1.8 | 0.95 | 3.3 | 0.95 | 2.6 |
| 1 | 1.2 | 1 | 1.2 | 1 | 1.2 | 1 | 1.2 | 1 | 1.2 |

HF-HCFO-1233zdE-HFO-1234zeE-HFO-1234zeZ-HFO-1243zf

| Organics 0.9 F1234zeE + 0.033 F1234zeZ + 0.033 F1233zdE + 0.034 F1243zf | | Organics 0.033 F1234zeE + 0.9 F1234zeZ + 0.033 F1233zdE + 0.034 F1243zf | | Organics 0.033 F1234zeE + 0.033 F1234zeZ + 0.9 F1233zdE + 0.034 F1243zf | | Organics 0.034 F1234zeE + 0.033 F1234zeZ + 0.033 F1233zdE + 0.9 F1243zf | | Organics 0.25 F1234zeE + 0.25 F1234zeZ + 0.25 F1233zdE + 0.25 F1243zf | |
|---|---|---|---|---|---|---|---|---|---|
| MASSFRAC HF | TOTAL PRES bar | MASSFRAC HF | TOTAL PRES bar | MASSFRAC HF | TOTAL PRES bar | MASSFRAC HF | TOTAL PRES bar | MASSFRAC HF | TOTAL PRES bar |
| 0 | 4.7 | 0 | 2.1 | 0 | 1.7 | 0 | 5.6 | 0 | 3.6 |
| 0.05 | 5.7 | 0.05 | 3.2 | 0.05 | 2.8 | 0.05 | 6.5 | 0.05 | 4.7 |
| 0.1 | 5.7 | 0.1 | 3.2 | 0.1 | 2.8 | 0.1 | 6.6 | 0.1 | 4.7 |
| 0.15 | 5.7 | 0.15 | 3.2 | 0.15 | 2.8 | 0.15 | 6.5 | 0.15 | 4.7 |
| 0.2 | 5.7 | 0.2 | 3.2 | 0.2 | 2.8 | 0.2 | 6.5 | 0.2 | 4.7 |
| 0.25 | 5.7 | 0.25 | 3.2 | 0.25 | 2.8 | 0.25 | 6.5 | 0.25 | 4.7 |
| 0.3 | 5.7 | 0.3 | 3.2 | 0.3 | 2.8 | 0.3 | 6.5 | 0.3 | 4.6 |
| 0.35 | 5.7 | 0.35 | 3.1 | 0.35 | 2.8 | 0.35 | 6.5 | 0.35 | 4.6 |
| 0.4 | 5.7 | 0.4 | 3.1 | 0.4 | 2.8 | 0.4 | 6.5 | 0.4 | 4.6 |
| 0.45 | 5.7 | 0.45 | 3.1 | 0.45 | 2.7 | 0.45 | 6.5 | 0.45 | 4.6 |
| 0.5 | 5.6 | 0.5 | 3.1 | 0.5 | 2.7 | 0.5 | 6.5 | 0.5 | 4.6 |
| 0.55 | 5.6 | 0.55 | 3.1 | 0.55 | 2.7 | 0.55 | 6.5 | 0.55 | 4.6 |
| 0.6 | 5.5 | 0.6 | 3.1 | 0.6 | 2.7 | 0.6 | 6.5 | 0.6 | 4.6 |
| 0.65 | 5.4 | 0.65 | 3.1 | 0.65 | 2.7 | 0.65 | 6.4 | 0.65 | 4.6 |
| 0.7 | 5.3 | 0.7 | 3.1 | 0.7 | 2.7 | 0.7 | 6.3 | 0.7 | 4.5 |
| 0.75 | 5.0 | 0.75 | 3.1 | 0.75 | 2.7 | 0.75 | 6.2 | 0.75 | 4.3 |
| 0.8 | 4.7 | 0.8 | 3.0 | 0.8 | 2.6 | 0.8 | 5.9 | 0.8 | 4.1 |
| 0.85 | 4.2 | 0.85 | 2.7 | 0.85 | 2.4 | 0.85 | 5.4 | 0.85 | 3.7 |
| 0.9 | 3.5 | 0.9 | 2.4 | 0.9 | 2.1 | 0.9 | 4.6 | 0.9 | 3.2 |
| 0.95 | 2.5 | 0.95 | 1.9 | 0.95 | 1.7 | 0.95 | 3.3 | 0.95 | 2.4 |
| 1 | 1.2 | 1 | 1.2 | 1 | 1.2 | 1 | 1.2 | 1 | 1.2 |

HF-HFC-245cb-HFO-1234zeE-HFO-1234zeZ-HFO-1243zf

| Organics 0.9 F245cb + 0.033 F1234zeE + 0.033 F1234zeZ + 0.034 F1243zf | | Organics 0.033 F245cb + 0.9 F1234zeE + 0.033 F1234zeZ + 0.034 F1243zf | | Organics 0.033 F245cb + 0.033 F1234zeE + 0.9 F1234zeZ + 0.034 F1243zf | | Organics 0.034 F245cb + 0.033 F1234zeE + 0.033 F1234zeZ + 0.9 F1243zf | | Organics 0.25 F245cb + 0.25 F1234zeE + 0.25 F1234zeZ + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 2.2 | 0 | 5.7 | 0 | 4.4 |
| 0.05 | 5.8 | 0.05 | 5.8 | 0.05 | 3.3 | 0.05 | 6.6 | 0.05 | 5.4 |
| 0.1 | 5.8 | 0.1 | 5.8 | 0.1 | 3.3 | 0.1 | 6.7 | 0.1 | 5.4 |
| 0.15 | 5.8 | 0.15 | 5.8 | 0.15 | 3.3 | 0.15 | 6.6 | 0.15 | 5.4 |
| 0.2 | 5.8 | 0.2 | 5.8 | 0.2 | 3.3 | 0.2 | 6.6 | 0.2 | 5.4 |
| 0.25 | 5.8 | 0.25 | 5.8 | 0.25 | 3.3 | 0.25 | 6.6 | 0.25 | 5.4 |
| 0.3 | 5.8 | 0.3 | 5.8 | 0.3 | 3.3 | 0.3 | 6.6 | 0.3 | 5.4 |
| 0.35 | 5.8 | 0.35 | 5.8 | 0.35 | 3.3 | 0.35 | 6.6 | 0.35 | 5.4 |
| 0.4 | 5.8 | 0.4 | 5.8 | 0.4 | 3.3 | 0.4 | 6.6 | 0.4 | 5.4 |
| 0.45 | 5.8 | 0.45 | 5.8 | 0.45 | 3.3 | 0.45 | 6.6 | 0.45 | 5.4 |
| 0.5 | 5.8 | 0.5 | 5.7 | 0.5 | 3.3 | 0.5 | 6.6 | 0.5 | 5.4 |
| 0.55 | 5.8 | 0.55 | 5.7 | 0.55 | 3.3 | 0.55 | 6.6 | 0.55 | 5.4 |
| 0.6 | 5.8 | 0.6 | 5.6 | 0.6 | 3.3 | 0.6 | 6.6 | 0.6 | 5.4 |
| 0.65 | 5.8 | 0.65 | 5.5 | 0.65 | 3.3 | 0.65 | 6.5 | 0.65 | 5.4 |
| 0.7 | 5.8 | 0.7 | 5.4 | 0.7 | 3.2 | 0.7 | 6.4 | 0.7 | 5.4 |
| 0.75 | 5.8 | 0.75 | 5.2 | 0.75 | 3.2 | 0.75 | 6.3 | 0.75 | 5.3 |
| 0.8 | 5.8 | 0.8 | 4.8 | 0.8 | 3.1 | 0.8 | 6.0 | 0.8 | 5.0 |
| 0.85 | 5.7 | 0.85 | 4.3 | 0.85 | 2.9 | 0.85 | 5.5 | 0.85 | 4.6 |
| 0.9 | 4.9 | 0.9 | 3.6 | 0.9 | 2.5 | 0.9 | 4.7 | 0.9 | 3.9 |
| 0.95 | 3.5 | 0.95 | 2.6 | 0.95 | 2.0 | 0.95 | 3.3 | 0.95 | 2.8 |
| 1 | 1.2 | 1 | 1.2 | 1 | 1.2 | 1 | 1.2 | 1 | 1.2 |

EXAMPLE 8

Temperature and Pressure Range of Penternary Mixtures

| System with 5 compounds | Boiling point range | |
|---|---|---|
| | Temperature ° C. | Pressure bar abs |
| HF-HCFO-1233xf-HFC-245cb-HCFO-1233zdE-HFO-1234zeE | 0 to 40 | ~1.0 ~ 8.9 |
| HF-HCFO-1233xf-HFC-245cb-HCFO-1233zdE-HFO-1234zeZ | 0 to 40 | ~1.0 to ~8.8 |
| HF-HCFO-1233xf-HFC-245cb-HFO-1234zeE-HFO-1234zeZ | 0 to 40 | ~1.1 to ~8.8 |
| HF-HCFO-1233xf-HFC-245cb-HFO-1234zeE-HFO-1243zf | 0 to 40 | ~1.0 to ~10.2 |
| HF-HCFO-1233xf-HFC-245cb-HFO-1234zeE-HFO-1234yf | 0 to 40 | ~1.0 to ~11.4 |
| HF-HCFO-1233xf-HFC-245cb-HFO-1234zeZ-HFO-1243zf | 0 to 40 | ~1.1 to ~10.1 |
| HF-HCFO-1233xf-HFC-245cb-HFO-1234zeZ-HFO-1234yf | 0 to 40 | ~1.1 to ~11.2 |
| HF-HCFO-1233xf-HFO-1234yf-HFO-1234zeE-HFO-1234zeZ | 0 to 40 | ~1.1 to ~11.2 |
| HF-HCFO-1233xf-HFO-1234yf-HFO-1234zeE-HFO-1243zf | 0 to 40 | ~1.2 to ~11.4 |
| HF-HCFO-1233xf-HFO-1234yf-HFO-1234zeE-HCFO-1233zdE | 0 to 40 | ~1.0 to ~11.2 |
| HF-HCFO-1233xf-HFO-1234yf-HFO-1234zeZ-HFO-1243zf | 0 to 40 | ~1.2 to ~11.2 |
| HF-HCFO-1233xf-HFO-1234yf-HFO-1234zeZ-HCFO-1233zdE | 0 to 40 | ~1.0 ~ 11.1 |
| HF-HCFO-1233xf-HCFO-1233zdE-HFO-1234zeE-HFO-1234zeZ | 0 to 40 | ~0.9 to ~8.6 |
| HF-HCFO-1233xf-HCFO-1233zdE-HFO-1234zeE-HFO-1243zf | 0 to 40 | ~1.0 to ~10.1 |
| HF-HCFO-1233xf-HCFO-1233zdE-HFO-1234zeZ-HFO-1243zf | 0 to 40 | ~1.0 to ~9.9 |
| HF-HCFO-1233xf-HFO-1234zeE-HFO-1234zeZ-HFO-1243zf | 0 to 40 | ~1.0 to ~10.1 |
| HF-HFO-1234yf-HFO-1234zeE-HFO-1234zeZ-HCFO-1233zdE | 0 to 40 | ~1.0 to ~11.2 |
| HF-HFO-1234yf-HFO-1234zeE-HFO-1234zeZ-HFO-1243zf | 0 to 40 | ~1.3 to ~11.4 |
| HF-HFO-1234yf-HFO-1234zeE-HCFO-1233zdE-HFO-1243zf | 0 to 40 | ~1.0 to ~11.4 |
| HF-HFO-1234yf-HFO-1234zeZ-HCFO-1233zdE-HFO-1243zf | 0 to 40 | ~1.1 to ~11.2 |
| HF-HFO-1234yf-HFC-245cb-HFO-1234zeE-HCFO-1233zdE | 0 to 40 | ~1.1 to ~11.4 |
| HF-HFO-1234yf-HFC-245cb-HFO-1234zeE-HFO-1234zeZ | 0 to 40 | ~1.3 to ~9.1 |
| HF-HFO-1234yf-HFC-245cb-HFO-1234zeE-HFO-1243zf | 0 to 40 | ~2.5 to ~11.6 |
| HF-HFO-1234yf-HFC-245cb-HFO-1234zeZ-HCFO-1233zdE | 0 to 40 | ~1.0 to ~11.2 |
| HF-HFO-1234yf-HFC-245cb-HFO-1234zeZ-HFO-1243zf | 0 to 40 | ~1.3 to ~10.3 |
| HF-HFC-245cb-HCFO-1233zdE-HFO-1234zeE-HFO-1234zeZ | 0 to 40 | ~1.0 to ~8.9 |
| HF-HFC-245cb-HCFO-1233zdE-F 1234zeE-HFO-1243zf | 0 to 40 | ~1.1 to ~10.2 |
| HF-HFC-245cb-HCFO-1233zdE-F 1234zeZ-HFO-1243zf | 0 to 40 | ~1.0 to ~10.1 |
| HF-HFC-245cb-HFO-1234zeE-F 1234zeZ-HFO-1243zf | 0 to 40 | ~1.2 to ~10.2 |
| HF-HCFO-1233zdE-HFO-1234zeE-HFO-1234zeZ-HFO-1243zF | 0 to 40 | ~1.0 to ~10.1 |

EXAMPLE 9

Decantation Range Of Penternary Mixtures

| System with 5 compounds | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HCFO-1233zdE-HFO-1234zeE | 5-75 | 5-70 | 10-60 |
| HF-HCFO-1233xf-HFC-245cb-HCFO-1233zdE-HFO-1234zeZ | 5-80 | 5-75 | 5-70 |
| HF-HCFO-1233xf-HFC-245cb-HFO-1234zeE-HFO-1234zeZ | 5-75 | 5-70 | 10-60 |
| HF-HCFO-1233xf-HFC-245cb-HFO-1234zeE-HFO-1243zf | 10-75 | 10-65 | * |
| HF-HCFO-1233xf-HFC-245cb-HFO-1234zeE-HFO-1234yf | 5-75 | 10-70 | * |
| HF-HCFO-1233xf-HFC-245cb-HFO-1234zeZ-HFO-1243zf | 5-75 | 5-70 | 10-60 |
| HF-HCFO-1233xf-HFC-245cb-HFO-1234zeZ-HFO-1234yf | 5-75 | 5-75 | 10-65 |
| HF-HCFO-1233xf-HFO-1234yf-HFO-1234zeE-HFO-1234zeZ | 5-75 | 5-65 | 15-45 |
| HF-HCFO-1233xf-HFO-1234yf-HFO-1234zeE-HFO-1243zf | 5-70 | 10-60 | * |
| HF-HCFO-1233xf-HFO-1234yf-HFO-1234zeE-HCFO-1233zdE | 5-75 | 5-65 | 10-50 |
| HF-HCFO-1233xf-HFO-1234yf-HFO-1234zeZ-HFO-1243zf | 5-75 | 10-65 | 20-40 |
| HF-HCFO-1233xf-HFO-1234yf-HFO-1234zeZ-HCFO-1233zdE | 5-75 | 5-70 | 10-60 |
| HF-HCFO-1233xf-HCFO-1233zdE-HFO-1234zeE-HFO-1234zeZ | 5-75 | 5-70 | 5-60 |
| HF-HCFO-1233xf-HCFO-1233zdE-HFO-1234zeE-HFO-1243zf | 5-75 | 5-65 | 15-45 |
| HF-HCFO-1233xf-HCFO-1233zdE-HFO-1234zeZ-HFO-1243zf | 5-75 | 5-70 | 10-60 |
| HF-HCFO-1233xf-HFO-1234zeE-HFO-1234zeZ-HFO-1243zf | 5-75 | 10-65 | 15-40 |
| HF-HFO-1234yf-HFO-1234zeE-HFO-1234zeZ-HCFO-1233zdE | 5-75 | 5-65 | 15-45 |
| HF-HFO-1234yf-HFO-1234zeE-HFO-1234zeZ-HFO-1243zf | 5-70 | 10-60 | * |
| HF-HFO-1234yf-HFO-1234zeE-HCFO-1233zdE-HFO-1243zf | 5-70 | 10-60 | * |
| HF-HFO-1234yf-HFO-1234zeZ-HCFO-1233zdE-HFO-1243zf | 5-75 | 10-65 | 15-45 |
| HF-HFO-1234yf-HFC-245cb-HFO-1234zeE-HCFO-1233zdE | 5-75 | 10-70 | * |
| HF-HFO-1234yf-HFC-245cb-HFO-1234zeE-HFO-1234zeZ | 5-75 | 10-70 | * |
| HF-HFO-1234yf-HFC-245cb-HFO-1234zeE-HFO-1243zf | 5-75 | 15-65 | * |

|  | Decantation ranges Mass percentage of HF | | |
|---|---|---|---|
| System with 5 compounds | Isotherm 0° C. | Isotherm 25° C. | Isotherm 40° C. |
| HF-HFO-1234yf-HFC-245cb-HFO-1234zeZ-HCFO-1233zdE | 5-75 | 5-75 | 10-65 |
| HF-HFO-1234yf-HFC-245cb-HFO-1234zeZ-HFO-1243zf | 5-75 | 10-70 | * |
| HF-HFC-245cb-HCFO-1233zdE-HFO-1234zeE-HFO-1234zeZ | 5-75 | 5-70 | 10-60 |
| HF-HFC-245cb-HCFO-1233zdE-F 1234zeE-HFO-1243zf | 5-75 | 10-65 | * |
| HF-HFC-245cb-HCFO-1233zdE-F 1234zeZ-HFO-1243zf | 5-75 | 5-70 | 10-60 |
| HF-HFC-245cb-HFO-1234zeE-F 1234zeZ-HFO-1243zf | 5-75 | 10-65 | * |
| HF-HCFO-1233zdE-HFO-1234zeE-HFO-1234zeZ-HFO-1243zf | 5-75 | 5-65 | 15-50 |

EXAMPLE 10

Systems with Six Compounds, Isotherm at 25° C.

HF-HCFO-1233xf-HFO-1234yf-HFC-245cb-HFO-1234zeE-HFO-1234zeZ

| Organics 0.2 F1233xf + 0.2 F1234yf + 0.2 F245cb + 0.2 F1234zeE + 0.2 F1234zeZ | | Organics 0.96 F1233xf + 0.01 F1234yf + 0.01 F245cb + 0.01 F1234zeE + 0.01 F1234zeZ | | Organics 0.01 F1233xf + 0.96 F1234yf + 0.01 F245cb + 0.01 F1234zeE + 0.01 F1234zeZ | | Organics 0.01 F1233xf + 0.01 F1234yf + 0.96 F245cb + 0.01 F1234zeE + 0.01 F1234zeZ | | Organics 0.01 F1233xf + 0.01 F1234yf + 0.01 F245cb + 0.96 F1234zeE + 0.01 F1234zeZ | | Organics 0.01 F1233xf + 0.01 F1234yf + 0.01 F245cb + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.0 | 0 | 1.7 | 0 | 6.7 | 0 | 4.6 | 0 | 4.8 | 0 | 1.9 |
| 0.05 | 5.1 | 0.05 | 2.8 | 0.05 | 7.6 | 0.05 | 5.8 | 0.05 | 5.8 | 0.05 | 3.0 |
| 0.1 | 5.1 | 0.1 | 2.8 | 0.1 | 7.6 | 0.1 | 5.8 | 0.1 | 5.8 | 0.1 | 3.0 |
| 0.15 | 5.1 | 0.15 | 2.8 | 0.15 | 7.6 | 0.15 | 5.8 | 0.15 | 5.8 | 0.15 | 3.0 |
| 0.2 | 5.1 | 0.2 | 2.8 | 0.2 | 7.6 | 0.2 | 5.8 | 0.2 | 5.8 | 0.2 | 3.0 |
| 0.25 | 5.1 | 0.25 | 2.8 | 0.25 | 7.6 | 0.25 | 5.8 | 0.25 | 5.8 | 0.25 | 3.0 |
| 0.3 | 5.1 | 0.3 | 2.8 | 0.3 | 7.6 | 0.3 | 5.8 | 0.3 | 5.8 | 0.3 | 3.0 |
| 0.35 | 5.1 | 0.35 | 2.8 | 0.35 | 7.6 | 0.35 | 5.8 | 0.35 | 5.8 | 0.35 | 3.0 |
| 0.4 | 5.1 | 0.4 | 2.8 | 0.4 | 7.6 | 0.4 | 5.8 | 0.4 | 5.8 | 0.4 | 3.0 |
| 0.45 | 5.1 | 0.45 | 2.8 | 0.45 | 7.6 | 0.45 | 5.8 | 0.45 | 5.8 | 0.45 | 3.0 |
| 0.5 | 5.1 | 0.5 | 2.8 | 0.5 | 7.6 | 0.5 | 5.8 | 0.5 | 5.7 | 0.5 | 3.0 |
| 0.55 | 5.1 | 0.55 | 2.8 | 0.55 | 7.6 | 0.55 | 5.8 | 0.55 | 5.7 | 0.55 | 3.0 |
| 0.6 | 5.1 | 0.6 | 2.8 | 0.6 | 7.6 | 0.6 | 5.8 | 0.6 | 5.6 | 0.6 | 3.0 |
| 0.65 | 5.1 | 0.65 | 2.8 | 0.65 | 7.6 | 0.65 | 5.8 | 0.65 | 5.5 | 0.65 | 3.0 |
| 0.7 | 5.1 | 0.7 | 2.8 | 0.7 | 7.6 | 0.7 | 5.8 | 0.7 | 5.4 | 0.7 | 3.0 |
| 0.75 | 5.0 | 0.75 | 2.8 | 0.75 | 7.5 | 0.75 | 5.8 | 0.75 | 5.1 | 0.75 | 3.0 |
| 0.8 | 4.8 | 0.8 | 2.6 | 0.8 | 7.1 | 0.8 | 5.8 | 0.8 | 4.8 | 0.8 | 2.9 |
| 0.85 | 4.4 | 0.85 | 2.5 | 0.85 | 6.5 | 0.85 | 5.8 | 0.85 | 4.3 | 0.85 | 2.7 |
| 0.9 | 3.7 | 0.9 | 2.2 | 0.9 | 5.5 | 0.9 | 5.0 | 0.9 | 3.6 | 0.9 | 2.4 |
| 0.95 | 2.7 | 0.95 | 1.8 | 0.95 | 3.8 | 0.95 | 3.5 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-1234zeE-HCFO-1233zdE

| Organics 0.2 F1233xf + 0.2 F1234yf + 0.2 F245cb + 0.2 F1234zeE + 0.2 F1233zdE | | Organics 0.96 F1233xf + 0.01 F1234yf + 0.01 F245cb + 0.01 F1234zeE + 0.01 F1233zdE | | Organics 0.01 F1233xf + 0.96 F1234yf + 0.01 F245cb + 0.01 F1234zeE + 0.01 F1233zdE | | Organics 0.01 F1233xf + 0.01 F1234yf + 0.96 F245cb + 0.01 F1234zeE + 0.01 F1233zdE | | Organics 0.01 F1233xf + 0.01 F1234yf + 0.01 F245cb + 0.96 F1234zeE + 0.01 F1233zdE | | Organics 0.01 F1233xf + 0.01 F1234yf + 0.01 F245cb + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 1.7 | 0 | 6.7 | 0 | 4.6 | 0 | 4.8 | 0 | 1.5 |
| 0.05 | 5.0 | 0.05 | 2.8 | 0.05 | 7.6 | 0.05 | 5.8 | 0.05 | 5.8 | 0.05 | 2.6 |
| 0.1 | 5.0 | 0.1 | 2.8 | 0.1 | 7.6 | 0.1 | 5.8 | 0.1 | 5.8 | 0.1 | 2.6 |
| 0.15 | 5.0 | 0.15 | 2.8 | 0.15 | 7.6 | 0.15 | 5.8 | 0.15 | 5.8 | 0.15 | 2.6 |
| 0.2 | 5.0 | 0.2 | 2.8 | 0.2 | 7.6 | 0.2 | 5.8 | 0.2 | 5.8 | 0.2 | 2.6 |
| 0.25 | 5.0 | 0.25 | 2.8 | 0.25 | 7.6 | 0.25 | 5.8 | 0.25 | 5.8 | 0.25 | 2.6 |
| 0.3 | 5.0 | 0.3 | 2.8 | 0.3 | 7.6 | 0.3 | 5.8 | 0.3 | 5.8 | 0.3 | 2.6 |

-continued

| | | | | | | | | | | |
|---|---|---|---|---|---|---|---|---|---|---|
| 0.35 | 5.0 | 0.35 | 2.8 | 0.35 | 7.6 | 0.35 | 5.8 | 0.35 | 5.8 | 0.35 | 2.6 |
| 0.4 | 5.0 | 0.4 | 2.8 | 0.4 | 7.6 | 0.4 | 5.8 | 0.4 | 5.8 | 0.4 | 2.6 |
| 0.45 | 5.0 | 0.45 | 2.8 | 0.45 | 7.6 | 0.45 | 5.8 | 0.45 | 5.8 | 0.45 | 2.6 |
| 0.5 | 5.0 | 0.5 | 2.8 | 0.5 | 7.6 | 0.5 | 5.8 | 0.5 | 5.7 | 0.5 | 2.6 |
| 0.55 | 5.0 | 0.55 | 2.8 | 0.55 | 7.6 | 0.55 | 5.8 | 0.55 | 5.7 | 0.55 | 2.6 |
| 0.6 | 5.0 | 0.6 | 2.8 | 0.6 | 7.6 | 0.6 | 5.8 | 0.6 | 5.6 | 0.6 | 2.6 |
| 0.65 | 5.0 | 0.65 | 2.8 | 0.65 | 7.6 | 0.65 | 5.8 | 0.65 | 5.5 | 0.65 | 2.6 |
| 0.7 | 5.1 | 0.7 | 2.8 | 0.7 | 7.6 | 0.7 | 5.8 | 0.7 | 5.4 | 0.7 | 2.6 |
| 0.75 | 5.0 | 0.75 | 2.8 | 0.75 | 7.5 | 0.75 | 5.8 | 0.75 | 5.1 | 0.75 | 2.6 |
| 0.8 | 4.7 | 0.8 | 2.6 | 0.8 | 7.1 | 0.8 | 5.8 | 0.8 | 4.8 | 0.8 | 2.4 |
| 0.85 | 4.3 | 0.85 | 2.5 | 0.85 | 6.5 | 0.85 | 5.8 | 0.85 | 4.3 | 0.85 | 2.3 |
| 0.9 | 3.7 | 0.9 | 2.2 | 0.9 | 5.5 | 0.9 | 5.0 | 0.9 | 3.6 | 0.9 | 2.0 |
| 0.95 | 2.7 | 0.95 | 1.8 | 0.95 | 3.8 | 0.95 | 3.5 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-1234zeE-HFO-1243zf

| Organics | Organics | Organics | Organics | Organics | Organics |
|---|---|---|---|---|---|
| 0.2 F1233xf + 0.2 F1234yf + 0.2 F245cb + 0.2 F1234zeE + 0.2 F1243zF | 0.96 F1233xf + 0.01 F1234yf + 0.01 F245cb + 0.01 F1234zeE + 0.01 F1234zF | 0.01 F1233xf + 0.96 F1234yf + 0.01 F245cb + 0.01 F1234zeE + 0.01 F1234zF | 0.01 F1233xf + 0.01 F1234yf + 0.96 F245cb + 0.01 F1234zeE + 0.01 F1234zF | 0.01 F1233xf + 0.01 F1234yf + 0.01 F245cb + 0.96 F1234zeE + 0.01 F1234zF | 0.01 F1233xf + 0.01 F1234yf + 0.01 F245cb + 0.01 F1234zeE + 0.96 F1234zF |

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 4.9 | 0 | 1.7 | 0 | 6.7 | 0 | 4.7 | 0 | 4.9 | 0 | 5.8 |
| 0.05 | 5.9 | 0.05 | 2.8 | 0.05 | 7.7 | 0.05 | 5.8 | 0.05 | 5.8 | 0.05 | 6.7 |
| 0.1 | 5.9 | 0.1 | 2.8 | 0.1 | 7.7 | 0.1 | 5.8 | 0.1 | 5.9 | 0.1 | 6.8 |
| 0.15 | 5.9 | 0.15 | 2.8 | 0.15 | 7.7 | 0.15 | 5.8 | 0.15 | 5.8 | 0.15 | 6.8 |
| 0.2 | 5.9 | 0.2 | 2.8 | 0.2 | 7.7 | 0.2 | 5.8 | 0.2 | 5.8 | 0.2 | 6.8 |
| 0.25 | 5.9 | 0.25 | 2.8 | 0.25 | 7.7 | 0.25 | 5.8 | 0.25 | 5.8 | 0.25 | 6.8 |
| 0.3 | 5.9 | 0.3 | 2.8 | 0.3 | 7.7 | 0.3 | 5.8 | 0.3 | 5.8 | 0.3 | 6.8 |
| 0.35 | 5.9 | 0.35 | 2.8 | 0.35 | 7.7 | 0.35 | 5.8 | 0.35 | 5.8 | 0.35 | 6.8 |
| 0.4 | 5.9 | 0.4 | 2.8 | 0.4 | 7.7 | 0.4 | 5.8 | 0.4 | 5.8 | 0.4 | 6.8 |
| 0.45 | 5.9 | 0.45 | 2.8 | 0.45 | 7.7 | 0.45 | 5.8 | 0.45 | 5.8 | 0.45 | 6.7 |
| 0.5 | 5.9 | 0.5 | 2.8 | 0.5 | 7.7 | 0.5 | 5.8 | 0.5 | 5.8 | 0.5 | 6.7 |
| 0.55 | 5.9 | 0.55 | 2.8 | 0.55 | 7.7 | 0.55 | 5.8 | 0.55 | 5.7 | 0.55 | 6.7 |
| 0.6 | 5.9 | 0.6 | 2.8 | 0.6 | 7.7 | 0.6 | 5.8 | 0.6 | 5.7 | 0.6 | 6.7 |
| 0.65 | 5.9 | 0.65 | 2.8 | 0.65 | 7.7 | 0.65 | 5.8 | 0.65 | 5.6 | 0.65 | 6.6 |
| 0.7 | 5.9 | 0.7 | 2.8 | 0.7 | 7.6 | 0.7 | 5.8 | 0.7 | 5.4 | 0.7 | 6.5 |
| 0.75 | 5.7 | 0.75 | 2.8 | 0.75 | 7.5 | 0.75 | 5.8 | 0.75 | 5.2 | 0.75 | 6.4 |
| 0.8 | 5.5 | 0.8 | 2.7 | 0.8 | 7.2 | 0.8 | 5.8 | 0.8 | 4.8 | 0.8 | 6.1 |
| 0.85 | 5.0 | 0.85 | 2.5 | 0.85 | 6.6 | 0.85 | 5.8 | 0.85 | 4.3 | 0.85 | 5.6 |
| 0.9 | 4.2 | 0.9 | 2.2 | 0.9 | 5.5 | 0.9 | 5.0 | 0.9 | 3.6 | 0.9 | 4.8 |
| 0.95 | 3.0 | 0.95 | 1.8 | 0.95 | 3.8 | 0.95 | 3.5 | 0.95 | 2.6 | 0.95 | 3.4 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-1234zeZ-HCFO-1233zdE

| Organics | Organics | Organics | Organics | Organics | Organics |
|---|---|---|---|---|---|
| 0.2 F1233xf + 0.2 F1234yf + 0.2 F245cb 0.2 F1234zeZ + 0.2 F1233zdE | 0.96 F1233xf + 0.01 F1234yf + 0.01 F245cb + 0.01 F1234zeZ + 0.01 F1233zdE | 0.01 F1233xf + 0.96 F1234yf + 0.01 F245cb + 0.01 F1234zeZ + 0.01 F1233zdE | 0.01 F1233xf + 0.01 F1234yf + 0.96 F245cb + 0.01 F1234zeZ + 0.01 F1233zdE | 0.01 F1233xf + 0.01 F1234yf + 0.01 F245cb + 0.96 F1234zeZ + 0.01 F1233zdE | 0.01 F1233xf + 0.01 F1234yf + 0.01 F245cb + 0.01 F1234zeZ + 0.96 F1233zdE |

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 3.3 | 0 | 1.6 | 0 | 6.6 | 0 | 4.6 | 0 | 1.9 | 0 | 1.4 |
| 0.05 | 4.4 | 0.05 | 2.8 | 0.05 | 7.6 | 0.05 | 5.8 | 0.05 | 3.0 | 0.05 | 2.5 |
| 0.1 | 4.4 | 0.1 | 2.8 | 0.1 | 7.6 | 0.1 | 5.8 | 0.1 | 3.0 | 0.1 | 2.5 |
| 0.15 | 4.4 | 0.15 | 2.8 | 0.15 | 7.6 | 0.15 | 5.8 | 0.15 | 3.0 | 0.15 | 2.5 |
| 0.2 | 4.4 | 0.2 | 2.8 | 0.2 | 7.6 | 0.2 | 5.8 | 0.2 | 3.0 | 0.2 | 2.5 |
| 0.25 | 4.4 | 0.25 | 2.8 | 0.25 | 7.6 | 0.25 | 5.8 | 0.25 | 3.0 | 0.25 | 2.5 |
| 0.3 | 4.4 | 0.3 | 2.8 | 0.3 | 7.6 | 0.3 | 5.8 | 0.3 | 3.0 | 0.3 | 2.5 |
| 0.35 | 4.4 | 0.35 | 2.8 | 0.35 | 7.6 | 0.35 | 5.8 | 0.35 | 3.0 | 0.35 | 2.5 |
| 0.4 | 4.4 | 0.4 | 2.8 | 0.4 | 7.6 | 0.4 | 5.8 | 0.4 | 3.0 | 0.4 | 2.5 |
| 0.45 | 4.4 | 0.45 | 2.8 | 0.45 | 7.6 | 0.45 | 5.8 | 0.45 | 3.0 | 0.45 | 2.5 |
| 0.5 | 4.4 | 0.5 | 2.8 | 0.5 | 7.6 | 0.5 | 5.8 | 0.5 | 3.0 | 0.5 | 2.5 |
| 0.55 | 4.4 | 0.55 | 2.8 | 0.55 | 7.6 | 0.55 | 5.8 | 0.55 | 3.0 | 0.55 | 2.5 |
| 0.6 | 4.4 | 0.6 | 2.8 | 0.6 | 7.6 | 0.6 | 5.8 | 0.6 | 3.0 | 0.6 | 2.5 |
| 0.65 | 4.5 | 0.65 | 2.8 | 0.65 | 7.6 | 0.65 | 5.8 | 0.65 | 3.0 | 0.65 | 2.5 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0.7 | 4.5 | 0.7 | 2.8 | 0.7 | 7.6 | 0.7 | 5.8 | 0.7 | 3.0 | 0.7 | 2.5 |
| 0.75 | 4.5 | 0.75 | 2.8 | 0.75 | 7.4 | 0.75 | 5.8 | 0.75 | 3.0 | 0.75 | 2.5 |
| 0.8 | 4.3 | 0.8 | 2.6 | 0.8 | 7.1 | 0.8 | 5.8 | 0.8 | 2.9 | 0.8 | 2.4 |
| 0.85 | 4.0 | 0.85 | 2.4 | 0.85 | 6.5 | 0.85 | 5.8 | 0.85 | 2.7 | 0.85 | 2.3 |
| 0.9 | 3.4 | 0.9 | 2.2 | 0.9 | 5.5 | 0.9 | 5.0 | 0.9 | 2.3 | 0.9 | 2.0 |
| 0.95 | 2.5 | 0.95 | 1.7 | 0.95 | 3.8 | 0.95 | 3.5 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-1234zeZ-HFO-1243zf

| Organics 0.2 F1233xf + 0.2 F1234yf + 0.2 F245cb + 0.2 F1234zeZ + 0.2 F1243zf | | Organics 0.96 F1233xf + 0.01 F1234yf + 0.01 F245cb + 0.01 F1234zeZ + 0.01 F1243zf | | Organics 0.01 F1233xf + 0.96 F1234yf + 0.01 F245cb + 0.01 F1234zeZ + 0.01 F1243zf | | Organics 0.01 F1233xf + 0.01 F1234yf + 0.96 F245cb + 0.01 F1234zeZ + 0.01 F1243zf | | Organics 0.01 F1233xf + 0.01 F1234yf + 0.01 F245cb + 0.96 F1234zeZ + 0.01 F1243zf | | Organics 0.01 F1233xf + 0.01 F1234yf + 0.01 F245cb + 0.01 F1234zeZ + 0.96 F1243zf | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 1.7 | 0 | 6.7 | 0 | 4.6 | 0 | 1.9 | 0 | 5.8 |
| 0.05 | 5.3 | 0.05 | 2.8 | 0.05 | 7.6 | 0.05 | 5.8 | 0.05 | 3.0 | 0.05 | 6.7 |
| 0.1 | 5.3 | 0.1 | 2.8 | 0.1 | 7.7 | 0.1 | 5.8 | 0.1 | 3.0 | 0.1 | 6.8 |
| 0.15 | 5.3 | 0.15 | 2.8 | 0.15 | 7.6 | 0.15 | 5.8 | 0.15 | 3.0 | 0.15 | 6.7 |
| 0.2 | 5.3 | 0.2 | 2.8 | 0.2 | 7.6 | 0.2 | 5.8 | 0.2 | 3.0 | 0.2 | 6.7 |
| 0.25 | 5.3 | 0.25 | 2.8 | 0.25 | 7.6 | 0.25 | 5.8 | 0.25 | 3.0 | 0.25 | 6.7 |
| 0.3 | 5.3 | 0.3 | 2.8 | 0.3 | 7.6 | 0.3 | 5.8 | 0.3 | 3.0 | 0.3 | 6.7 |
| 0.35 | 5.3 | 0.35 | 2.8 | 0.35 | 7.6 | 0.35 | 5.8 | 0.35 | 3.0 | 0.35 | 6.7 |
| 0.4 | 5.3 | 0.4 | 2.8 | 0.4 | 7.6 | 0.4 | 5.8 | 0.4 | 3.0 | 0.4 | 6.7 |
| 0.45 | 5.3 | 0.45 | 2.8 | 0.45 | 7.6 | 0.45 | 5.8 | 0.45 | 3.0 | 0.45 | 6.7 |
| 0.5 | 5.3 | 0.5 | 2.8 | 0.5 | 7.6 | 0.5 | 5.8 | 0.5 | 3.0 | 0.5 | 6.7 |
| 0.55 | 5.3 | 0.55 | 2.8 | 0.55 | 7.6 | 0.55 | 5.8 | 0.55 | 3.0 | 0.55 | 6.7 |
| 0.6 | 5.3 | 0.6 | 2.8 | 0.6 | 7.6 | 0.6 | 5.8 | 0.6 | 3.0 | 0.6 | 6.7 |
| 0.65 | 5.3 | 0.65 | 2.8 | 0.65 | 7.6 | 0.65 | 5.8 | 0.65 | 3.0 | 0.65 | 6.6 |
| 0.7 | 5.3 | 0.7 | 2.8 | 0.7 | 7.6 | 0.7 | 5.8 | 0.7 | 3.0 | 0.7 | 6.5 |
| 0.75 | 5.3 | 0.75 | 2.8 | 0.75 | 7.5 | 0.75 | 5.8 | 0.75 | 3.0 | 0.75 | 6.4 |
| 0.8 | 5.1 | 0.8 | 2.7 | 0.8 | 7.2 | 0.8 | 5.8 | 0.8 | 2.9 | 0.8 | 6.1 |
| 0.85 | 4.7 | 0.85 | 2.5 | 0.85 | 6.6 | 0.85 | 5.8 | 0.85 | 2.7 | 0.85 | 5.6 |
| 0.9 | 4.0 | 0.9 | 2.2 | 0.9 | 5.5 | 0.9 | 5.0 | 0.9 | 2.4 | 0.9 | 4.7 |
| 0.95 | 2.9 | 0.95 | 1.8 | 0.95 | 3.8 | 0.95 | 3.5 | 0.95 | 1.9 | 0.95 | 3.4 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeE-HFO-1234zeZ-HCFO-1233zdE

| Organics 0.2 F1233xf + 0.2 F1234yf + 0.2 F1233zdE + 0.2 F1234zeE + 0.2 F1234zeZ | | Organics 0.96 F1233xf + 0.01 F1234yf + 0.01 F1233zdE + 0.01 F1234zeE + 0.01 F1234zeZ | | Organics 0.01 F1233xf + 0.96 F1234yf + 0.01 F1233zdE + 0.01 F1234zeE + 0.01 F1234zeZ | | Organics 0.01 F1233xf + 0.01 F1234yf + 0.96 F1233zdE + 0.01 F1234zeE + 0.01 F1234zeZ | | Organics 0.01 F1233xf + 0.01 F1234yf + 0.01 F1233zdE + 0.96 F1234zeE + 0.01 F1234zeZ | | Organics 0.01 F1233xf + 0.01 F1234yf + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.4 | 0 | 1.6 | 0 | 6.6 | 0 | 1.4 | 0 | 4.8 | 0 | 1.9 |
| 0.05 | 4.4 | 0.05 | 2.8 | 0.05 | 7.6 | 0.05 | 2.5 | 0.05 | 5.8 | 0.05 | 3.0 |
| 0.1 | 4.4 | 0.1 | 2.8 | 0.1 | 7.6 | 0.1 | 2.5 | 0.1 | 5.8 | 0.1 | 3.0 |
| 0.15 | 4.4 | 0.15 | 2.8 | 0.15 | 7.6 | 0.15 | 2.5 | 0.15 | 5.8 | 0.15 | 3.0 |
| 0.2 | 4.4 | 0.2 | 2.8 | 0.2 | 7.6 | 0.2 | 2.5 | 0.2 | 5.8 | 0.2 | 3.0 |
| 0.25 | 4.4 | 0.25 | 2.8 | 0.25 | 7.6 | 0.25 | 2.5 | 0.25 | 5.8 | 0.25 | 3.0 |
| 0.3 | 4.4 | 0.3 | 2.8 | 0.3 | 7.6 | 0.3 | 2.5 | 0.3 | 5.8 | 0.3 | 3.0 |
| 0.35 | 4.4 | 0.35 | 2.8 | 0.35 | 7.6 | 0.35 | 2.5 | 0.35 | 5.8 | 0.35 | 3.0 |
| 0.4 | 4.4 | 0.4 | 2.8 | 0.4 | 7.6 | 0.4 | 2.5 | 0.4 | 5.8 | 0.4 | 3.0 |
| 0.45 | 4.4 | 0.45 | 2.7 | 0.45 | 7.6 | 0.45 | 2.5 | 0.45 | 5.7 | 0.45 | 3.0 |
| 0.5 | 4.4 | 0.5 | 2.7 | 0.5 | 7.6 | 0.5 | 2.5 | 0.5 | 5.7 | 0.5 | 3.0 |
| 0.55 | 4.4 | 0.55 | 2.7 | 0.55 | 7.6 | 0.55 | 2.5 | 0.55 | 5.7 | 0.55 | 3.0 |
| 0.6 | 4.4 | 0.6 | 2.7 | 0.6 | 7.6 | 0.6 | 2.5 | 0.6 | 5.6 | 0.6 | 3.0 |
| 0.65 | 4.4 | 0.65 | 2.7 | 0.65 | 7.6 | 0.65 | 2.5 | 0.65 | 5.5 | 0.65 | 3.0 |
| 0.7 | 4.4 | 0.7 | 2.7 | 0.7 | 7.6 | 0.7 | 2.5 | 0.7 | 5.3 | 0.7 | 3.0 |
| 0.75 | 4.2 | 0.75 | 2.7 | 0.75 | 7.4 | 0.75 | 2.5 | 0.75 | 5.1 | 0.75 | 3.0 |
| 0.8 | 4.0 | 0.8 | 2.6 | 0.8 | 7.1 | 0.8 | 2.4 | 0.8 | 4.8 | 0.8 | 2.8 |
| 0.85 | 3.6 | 0.85 | 2.4 | 0.85 | 6.5 | 0.85 | 2.2 | 0.85 | 4.3 | 0.85 | 2.6 |
| 0.9 | 3.1 | 0.9 | 2.1 | 0.9 | 5.5 | 0.9 | 2.0 | 0.9 | 3.6 | 0.9 | 2.3 |

| MASSFRAC | bar | MASSFRAC | bar | MASSFRAC | bar | MASSFRAC | bar | MASSFRAC | bar | MASSFRAC | bar |
|---|---|---|---|---|---|---|---|---|---|---|---|
| 0.95 | 2.3 | 0.95 | 1.7 | 0.95 | 3.8 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeE-HFO-1234zeZ-HFO-1243zf

| Organics | Organics | Organics | Organics | Organics | Organics |
|---|---|---|---|---|---|
| 0.2 F1233xf + 0.2 F1234yf + 0.2 F1243zf + 0.2 F1234zeE + 0.2 F1234zeZ | 0.96 F1233xf + 0.01 F1234yf + 0.01 F1243zf + 0.01 F1234zeE + 0.01 F1234zeZ | 0.01 F1233xf + 0.96 F1234yf + 0.01 F1243zf + 0.01 F1234zeE + 0.01 F1234zeZ | 0.01 F1233xf + 0.01 F1234yf + 0.96 F1243zf + 0.01 F1234zeE + 0.01 F1234zeZ | 0.01 F1233xf + 0.01 F1234yf + 0.01 F1243zf + 0.96 F1234zeE + 0.01 F1234zeZ | 0.01 F1233xf + 0.01 F1234yf + 0.01 F1243zf + 0.01 F1234zeE + 0.96 F1234zeZ |

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 4.3 | 0 | 1.7 | 0 | 6.7 | 0 | 5.8 | 0 | 4.8 | 0 | 1.9 |
| 0.05 | 5.3 | 0.05 | 2.8 | 0.05 | 7.6 | 0.05 | 6.7 | 0.05 | 5.8 | 0.05 | 3.0 |
| 0.1 | 5.3 | 0.1 | 2.8 | 0.1 | 7.6 | 0.1 | 6.7 | 0.1 | 5.8 | 0.1 | 3.0 |
| 0.15 | 5.3 | 0.15 | 2.8 | 0.15 | 7.6 | 0.15 | 6.7 | 0.15 | 5.8 | 0.15 | 3.0 |
| 0.2 | 5.3 | 0.2 | 2.8 | 0.2 | 7.6 | 0.2 | 6.7 | 0.2 | 5.8 | 0.2 | 3.0 |
| 0.25 | 5.3 | 0.25 | 2.8 | 0.25 | 7.6 | 0.25 | 6.7 | 0.25 | 5.8 | 0.25 | 3.0 |
| 0.3 | 5.3 | 0.3 | 2.8 | 0.3 | 7.6 | 0.3 | 6.7 | 0.3 | 5.8 | 0.3 | 3.0 |
| 0.35 | 5.3 | 0.35 | 2.8 | 0.35 | 7.6 | 0.35 | 6.7 | 0.35 | 5.8 | 0.35 | 3.0 |
| 0.4 | 5.3 | 0.4 | 2.8 | 0.4 | 7.6 | 0.4 | 6.7 | 0.4 | 5.8 | 0.4 | 3.0 |
| 0.45 | 5.3 | 0.45 | 2.8 | 0.45 | 7.6 | 0.45 | 6.7 | 0.45 | 5.8 | 0.45 | 3.0 |
| 0.5 | 5.3 | 0.5 | 2.8 | 0.5 | 7.6 | 0.5 | 6.7 | 0.5 | 5.8 | 0.5 | 3.0 |
| 0.55 | 5.3 | 0.55 | 2.8 | 0.55 | 7.6 | 0.55 | 6.7 | 0.55 | 5.7 | 0.55 | 3.0 |
| 0.6 | 5.3 | 0.6 | 2.8 | 0.6 | 7.6 | 0.6 | 6.7 | 0.6 | 5.6 | 0.6 | 3.0 |
| 0.65 | 5.3 | 0.65 | 2.8 | 0.65 | 7.6 | 0.65 | 6.6 | 0.65 | 5.5 | 0.65 | 3.0 |
| 0.7 | 5.2 | 0.7 | 2.8 | 0.7 | 7.6 | 0.7 | 6.5 | 0.7 | 5.4 | 0.7 | 3.0 |
| 0.75 | 5.0 | 0.75 | 2.8 | 0.75 | 7.5 | 0.75 | 6.3 | 0.75 | 5.1 | 0.75 | 3.0 |
| 0.8 | 4.8 | 0.8 | 2.7 | 0.8 | 7.1 | 0.8 | 6.1 | 0.8 | 4.8 | 0.8 | 2.9 |
| 0.85 | 4.3 | 0.85 | 2.5 | 0.85 | 6.5 | 0.85 | 5.6 | 0.85 | 4.3 | 0.85 | 2.7 |
| 0.9 | 3.7 | 0.9 | 2.2 | 0.9 | 5.5 | 0.9 | 4.7 | 0.9 | 3.6 | 0.9 | 2.4 |
| 0.95 | 2.7 | 0.95 | 1.8 | 0.95 | 3.8 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeE-HCFO-1233zdE-HFO-1243zf

| Organics | Organics | Organics | Organics | Organics | Organics |
|---|---|---|---|---|---|
| 0.2 F1233xf + 0.2 F1234yf + 0.2 F1243zf + 0.2 F1234zeE + 0.2 F1233zdE | 0.96 F1233xf + 0.01 F1234yf + 0.01 F1243zf + 0.01 F1234zeE + 0.01 F1233zdE | 0.01 F1233xf + 0.96 F1234yf + 0.01 F1243zf + 0.01 F1234zeE + 0.01 F1233zdE | 0.01 F1233xf + 0.01 F1234yf + 0.96 F1243zf + 0.01 F1234zeE + 0.01 F1233zdE | 0.01 F1233xf + 0.01 F1234yf + 0.01 F1243zf + 0.96 F1234zeE + 0.01 F1233zdE | 0.01 F1233xf + 0.01 F1234yf + 0.01 F1243zf + 0.01 F1234zeE + 0.96 F1233zdE |

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 4.3 | 0 | 1.7 | 0 | 6.7 | 0 | 5.8 | 0 | 4.8 | 0 | 1.5 |
| 0.05 | 5.3 | 0.05 | 2.8 | 0.05 | 7.6 | 0.05 | 6.7 | 0.05 | 5.8 | 0.05 | 2.6 |
| 0.1 | 5.3 | 0.1 | 2.8 | 0.1 | 7.6 | 0.1 | 6.7 | 0.1 | 5.8 | 0.1 | 2.6 |
| 0.15 | 5.3 | 0.15 | 2.8 | 0.15 | 7.6 | 0.15 | 6.7 | 0.15 | 5.8 | 0.15 | 2.6 |
| 0.2 | 5.3 | 0.2 | 2.8 | 0.2 | 7.6 | 0.2 | 6.7 | 0.2 | 5.8 | 0.2 | 2.6 |
| 0.25 | 5.3 | 0.25 | 2.8 | 0.25 | 7.6 | 0.25 | 6.7 | 0.25 | 5.8 | 0.25 | 2.6 |
| 0.3 | 5.3 | 0.3 | 2.8 | 0.3 | 7.6 | 0.3 | 6.7 | 0.3 | 5.8 | 0.3 | 2.6 |
| 0.35 | 5.3 | 0.35 | 2.8 | 0.35 | 7.6 | 0.35 | 6.7 | 0.35 | 5.8 | 0.35 | 2.6 |
| 0.4 | 5.3 | 0.4 | 2.8 | 0.4 | 7.6 | 0.4 | 6.7 | 0.4 | 5.8 | 0.4 | 2.6 |
| 0.45 | 5.3 | 0.45 | 2.8 | 0.45 | 7.6 | 0.45 | 6.7 | 0.45 | 5.8 | 0.45 | 2.6 |
| 0.5 | 5.3 | 0.5 | 2.8 | 0.5 | 7.6 | 0.5 | 6.7 | 0.5 | 5.8 | 0.5 | 2.6 |
| 0.55 | 5.3 | 0.55 | 2.8 | 0.55 | 7.6 | 0.55 | 6.7 | 0.55 | 5.7 | 0.55 | 2.6 |
| 0.6 | 5.3 | 0.6 | 2.8 | 0.6 | 7.6 | 0.6 | 6.7 | 0.6 | 5.6 | 0.6 | 2.6 |
| 0.65 | 5.2 | 0.65 | 2.8 | 0.65 | 7.6 | 0.65 | 6.6 | 0.65 | 5.5 | 0.65 | 2.6 |
| 0.7 | 5.1 | 0.7 | 2.8 | 0.7 | 7.6 | 0.7 | 6.5 | 0.7 | 5.4 | 0.7 | 2.6 |
| 0.75 | 5.0 | 0.75 | 2.8 | 0.75 | 7.5 | 0.75 | 6.3 | 0.75 | 5.1 | 0.75 | 2.6 |
| 0.8 | 4.7 | 0.8 | 2.6 | 0.8 | 7.1 | 0.8 | 6.1 | 0.8 | 4.8 | 0.8 | 2.4 |
| 0.85 | 4.3 | 0.85 | 2.5 | 0.85 | 6.5 | 0.85 | 5.6 | 0.85 | 4.3 | 0.85 | 2.3 |
| 0.9 | 3.6 | 0.9 | 2.2 | 0.9 | 5.5 | 0.9 | 4.7 | 0.9 | 3.6 | 0.9 | 2.0 |
| 0.95 | 2.6 | 0.95 | 1.8 | 0.95 | 3.8 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

-continued

| HF-HCFO-1233xf-HFO-1234yf-HFO-1234zeZ-HCFO-1233zdE-HFO-1243zf ||||||||||||
| Organics 0.2 F1233xf + 0.2 F1234yf + 0.2 F1243zf + 0.2 F1234zeZ + 0.2 F1233zdE ||  Organics 0.96 F1233xf + 0.01 F1234yf + 0.01 F1243zf + 0.01 F1234zeZ + 0.01 F1233zdE ||  Organics 0.01 F1233xf + 0.96 F1234yf + 0.01 F1243zf + 0.01 F1234zeZ + 0.01 F1233zdE ||  Organics 0.01 F1233xf + 0.01 F1234yf + 0.96 F1243zf + 0.01 F1234zeZ + 0.01 F1233zdE ||  Organics 0.01 F1233xf + 0.01 F1234yf + 0.01 F1243zf + 0.96 F1234zeZ + 0.01 F1233zdE ||  Organics 0.01 F1233xf + 0.01 F1234yf + 0.01 F1243zf + 0.01 F1234zeZ + 0.96 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- | --- | --- | --- | --- |
| 0 | 3.6 | 0 | 1.7 | 0 | 6.6 | 0 | 5.7 | 0 | 1.9 | 0 | 1.4 |
| 0.05 | 4.7 | 0.05 | 2.8 | 0.05 | 7.6 | 0.05 | 6.7 | 0.05 | 3.0 | 0.05 | 2.6 |
| 0.1 | 4.7 | 0.1 | 2.8 | 0.1 | 7.6 | 0.1 | 6.7 | 0.1 | 3.0 | 0.1 | 2.6 |
| 0.15 | 4.7 | 0.15 | 2.8 | 0.15 | 7.6 | 0.15 | 6.7 | 0.15 | 3.0 | 0.15 | 2.6 |
| 0.2 | 4.7 | 0.2 | 2.8 | 0.2 | 7.6 | 0.2 | 6.7 | 0.2 | 3.0 | 0.2 | 2.6 |
| 0.25 | 4.7 | 0.25 | 2.8 | 0.25 | 7.6 | 0.25 | 6.7 | 0.25 | 3.0 | 0.25 | 2.6 |
| 0.3 | 4.7 | 0.3 | 2.8 | 0.3 | 7.6 | 0.3 | 6.7 | 0.3 | 3.0 | 0.3 | 2.6 |
| 0.35 | 4.7 | 0.35 | 2.8 | 0.35 | 7.6 | 0.35 | 6.7 | 0.35 | 3.0 | 0.35 | 2.5 |
| 0.4 | 4.7 | 0.4 | 2.8 | 0.4 | 7.6 | 0.4 | 6.7 | 0.4 | 3.0 | 0.4 | 2.5 |
| 0.45 | 4.7 | 0.45 | 2.8 | 0.45 | 7.6 | 0.45 | 6.7 | 0.45 | 3.0 | 0.45 | 2.5 |
| 0.5 | 4.7 | 0.5 | 2.8 | 0.5 | 7.6 | 0.5 | 6.7 | 0.5 | 3.0 | 0.5 | 2.5 |
| 0.55 | 4.7 | 0.55 | 2.8 | 0.55 | 7.6 | 0.55 | 6.7 | 0.55 | 3.0 | 0.55 | 2.5 |
| 0.6 | 4.7 | 0.6 | 2.8 | 0.6 | 7.6 | 0.6 | 6.6 | 0.6 | 3.0 | 0.6 | 2.5 |
| 0.65 | 4.7 | 0.65 | 2.8 | 0.65 | 7.6 | 0.65 | 6.6 | 0.65 | 3.0 | 0.65 | 2.5 |
| 0.7 | 4.7 | 0.7 | 2.8 | 0.7 | 7.6 | 0.7 | 6.5 | 0.7 | 3.0 | 0.7 | 2.5 |
| 0.75 | 4.5 | 0.75 | 2.8 | 0.75 | 7.4 | 0.75 | 6.3 | 0.75 | 3.0 | 0.75 | 2.5 |
| 0.8 | 4.3 | 0.8 | 2.6 | 0.8 | 7.1 | 0.8 | 6.0 | 0.8 | 2.9 | 0.8 | 2.4 |
| 0.85 | 3.9 | 0.85 | 2.4 | 0.85 | 6.5 | 0.85 | 5.5 | 0.85 | 2.7 | 0.85 | 2.3 |
| 0.9 | 3.4 | 0.9 | 2.2 | 0.9 | 5.5 | 0.9 | 4.7 | 0.9 | 2.3 | 0.9 | 2.0 |
| 0.95 | 2.5 | 0.95 | 1.7 | 0.95 | 3.8 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF-HCFO-1233xf-HFC-245cb-HFO-1234zeE-HFO-1234zeZ-HCFO-1233zdE ||||||||||||
| Organics 0.2 F1233xf + 0.2 F245cb + 0.2 F1233zdE + 0.2 F1234zeE + 0.2 F1234zeZ ||  Organics 0.96 F1233xf + 0.01 F245cb + 0.01 F1233zdE + 0.01 F1234zeE + 0.01 F1234zeZ ||  Organics 0.01 F1233xf + 0.96 F245cb + 0.01 F1233zdE + 0.01 F1234zeE + 0.01 F1234zeZ ||  Organics 0.01 F1233xf + 0.01 F245cb + 0.96 F1233zdE + 0.01 F1234zeE + 0.01 F1234zeZ ||  Organics 0.01 F1233xf + 0.01 F245cb + 0.01 F1233zdE + 0.96 F1234zeE + 0.01 F1234zeZ ||  Organics 0.01 F1233xf + 0.01 F245cb + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- | --- | --- | --- | --- |
| 0 | 2.9 | 0 | 1.6 | 0 | 4.6 | 0 | 1.4 | 0 | 4.8 | 0 | 1.9 |
| 0.05 | 4.0 | 0.05 | 2.7 | 0.05 | 5.7 | 0.05 | 2.5 | 0.05 | 5.7 | 0.05 | 3.0 |
| 0.1 | 4.0 | 0.1 | 2.7 | 0.1 | 5.7 | 0.1 | 2.5 | 0.1 | 5.8 | 0.1 | 3.0 |
| 0.15 | 4.0 | 0.15 | 2.7 | 0.15 | 5.7 | 0.15 | 2.5 | 0.15 | 5.8 | 0.15 | 3.0 |
| 0.2 | 4.0 | 0.2 | 2.7 | 0.2 | 5.7 | 0.2 | 2.5 | 0.2 | 5.8 | 0.2 | 3.0 |
| 0.25 | 4.0 | 0.25 | 2.7 | 0.25 | 5.7 | 0.25 | 2.5 | 0.25 | 5.8 | 0.25 | 3.0 |
| 0.3 | 4.0 | 0.3 | 2.7 | 0.3 | 5.7 | 0.3 | 2.5 | 0.3 | 5.8 | 0.3 | 3.0 |
| 0.35 | 4.0 | 0.35 | 2.7 | 0.35 | 5.7 | 0.35 | 2.5 | 0.35 | 5.7 | 0.35 | 3.0 |
| 0.4 | 4.0 | 0.4 | 2.7 | 0.4 | 5.7 | 0.4 | 2.5 | 0.4 | 5.7 | 0.4 | 3.0 |
| 0.45 | 4.0 | 0.45 | 2.7 | 0.45 | 5.7 | 0.45 | 2.5 | 0.45 | 5.7 | 0.45 | 3.0 |
| 0.5 | 4.0 | 0.5 | 2.7 | 0.5 | 5.7 | 0.5 | 2.5 | 0.5 | 5.7 | 0.5 | 3.0 |
| 0.55 | 4.0 | 0.55 | 2.7 | 0.55 | 5.7 | 0.55 | 2.5 | 0.55 | 5.6 | 0.55 | 3.0 |
| 0.6 | 4.0 | 0.6 | 2.7 | 0.6 | 5.7 | 0.6 | 2.5 | 0.6 | 5.6 | 0.6 | 3.0 |
| 0.65 | 4.0 | 0.65 | 2.7 | 0.65 | 5.7 | 0.65 | 2.5 | 0.65 | 5.5 | 0.65 | 3.0 |
| 0.7 | 4.0 | 0.7 | 2.7 | 0.7 | 5.8 | 0.7 | 2.5 | 0.7 | 5.3 | 0.7 | 3.0 |
| 0.75 | 4.0 | 0.75 | 2.7 | 0.75 | 5.8 | 0.75 | 2.5 | 0.75 | 5.1 | 0.75 | 3.0 |
| 0.8 | 3.8 | 0.8 | 2.6 | 0.8 | 5.8 | 0.8 | 2.4 | 0.8 | 4.7 | 0.8 | 2.8 |
| 0.85 | 3.5 | 0.85 | 2.4 | 0.85 | 5.8 | 0.85 | 2.2 | 0.85 | 4.3 | 0.85 | 2.6 |
| 0.9 | 3.0 | 0.9 | 2.1 | 0.9 | 5.0 | 0.9 | 2.0 | 0.9 | 3.6 | 0.9 | 2.3 |
| 0.95 | 2.3 | 0.95 | 1.7 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

-continued

HF-HCFO-1233xf-HFC-245cb-HFO-1234zeE-HFO-1234zeZ-HFO-1243zf

| Organics<br>0.2 F1233xf +<br>0.2 F245cb +<br>0.2 F1243zf +<br>0.2 F1234zeE +<br>0.2 F1234zeZ | | Organics<br>0.96 F1233xf +<br>0.01 F245cb +<br>0.01 F1243zf +<br>0.01 F1234zeE +<br>0.01 F1234zeZ | | Organics<br>0.01 F1233xf +<br>0.96 F245cb +<br>0.01 F1243zf +<br>0.01 F1234zeE +<br>0.01 F1234zeZ | | Organics<br>0.01 F1233xf +<br>0.01 F245cb +<br>0.96 F1243zf +<br>0.01 F1234zeE +<br>0.01 F1234zeZ | | Organics<br>0.01 F1233xf +<br>0.01 F245cb +<br>0.01 F1243zf +<br>0.96 F1234zeE +<br>0.01 F1234zeZ | | Organics<br>0.01 F1233xf +<br>0.01 F245cb +<br>0.01 F1243zf +<br>0.01 F1234zeE +<br>0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 | 0 | 5.8 | 0 | 4.8 | 0 | 1.9 |
| 0.05 | 4.9 | 0.05 | 2.8 | 0.05 | 5.8 | 0.05 | 6.7 | 0.05 | 5.8 | 0.05 | 3.0 |
| 0.1 | 4.9 | 0.1 | 2.8 | 0.1 | 5.8 | 0.1 | 6.7 | 0.1 | 5.8 | 0.1 | 3.0 |
| 0.15 | 4.9 | 0.15 | 2.8 | 0.15 | 5.8 | 0.15 | 6.7 | 0.15 | 5.8 | 0.15 | 3.0 |
| 0.2 | 4.9 | 0.2 | 2.8 | 0.2 | 5.8 | 0.2 | 6.7 | 0.2 | 5.8 | 0.2 | 3.0 |
| 0.25 | 4.9 | 0.25 | 2.8 | 0.25 | 5.8 | 0.25 | 6.7 | 0.25 | 5.8 | 0.25 | 3.0 |
| 0.3 | 4.9 | 0.3 | 2.8 | 0.3 | 5.8 | 0.3 | 6.7 | 0.3 | 5.8 | 0.3 | 3.0 |
| 0.35 | 4.9 | 0.35 | 2.8 | 0.35 | 5.8 | 0.35 | 6.7 | 0.35 | 5.8 | 0.35 | 3.0 |
| 0.4 | 4.9 | 0.4 | 2.8 | 0.4 | 5.8 | 0.4 | 6.7 | 0.4 | 5.8 | 0.4 | 3.0 |
| 0.45 | 4.9 | 0.45 | 2.8 | 0.45 | 5.8 | 0.45 | 6.7 | 0.45 | 5.8 | 0.45 | 3.0 |
| 0.5 | 4.9 | 0.5 | 2.8 | 0.5 | 5.8 | 0.5 | 6.7 | 0.5 | 5.7 | 0.5 | 3.0 |
| 0.55 | 4.9 | 0.55 | 2.8 | 0.55 | 5.8 | 0.55 | 6.7 | 0.55 | 5.7 | 0.55 | 3.0 |
| 0.6 | 4.9 | 0.6 | 2.8 | 0.6 | 5.8 | 0.6 | 6.6 | 0.6 | 5.6 | 0.6 | 3.0 |
| 0.65 | 4.9 | 0.65 | 2.8 | 0.65 | 5.8 | 0.65 | 6.6 | 0.65 | 5.5 | 0.65 | 3.0 |
| 0.7 | 4.9 | 0.7 | 2.8 | 0.7 | 5.8 | 0.7 | 6.5 | 0.7 | 5.4 | 0.7 | 3.0 |
| 0.75 | 4.8 | 0.75 | 2.8 | 0.75 | 5.8 | 0.75 | 6.3 | 0.75 | 5.1 | 0.75 | 3.0 |
| 0.8 | 4.6 | 0.8 | 2.6 | 0.8 | 5.8 | 0.8 | 6.0 | 0.8 | 4.8 | 0.8 | 2.9 |
| 0.85 | 4.2 | 0.85 | 2.4 | 0.85 | 5.8 | 0.85 | 5.6 | 0.85 | 4.3 | 0.85 | 2.7 |
| 0.9 | 3.6 | 0.9 | 2.2 | 0.9 | 5.0 | 0.9 | 4.7 | 0.9 | 3.6 | 0.9 | 2.4 |
| 0.95 | 2.6 | 0.95 | 1.8 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFC-245cb-HFO-1234zeE-HCFO-1233zdE-HFO-1243zf

| Organics<br>0.2 F1233xf +<br>0.2 F245cb +<br>0.2 F1243zf +<br>0.2 F1234zeE +<br>0.2 F1233zdE | | Organics<br>0.96 F1233xf +<br>0.01 F245cb +<br>0.01 F1243zf +<br>0.01 F1234zeE +<br>0.01 F1233zdE | | Organics<br>0.01 F1233xf +<br>0.96 F245cb +<br>0.01 F1243zf +<br>0.01 F1234zeE +<br>0.01 F1233zdE | | Organics<br>0.01 F1233xf +<br>0.01 F245cb +<br>0.96 F1243zf +<br>0.01 F1234zeE +<br>0.01 F1233zdE | | Organics<br>0.01 F1233xf +<br>0.01 F245cb +<br>0.01 F1243zf +<br>0.96 F1234zeE +<br>0.01 F1233zdE | | Organics<br>0.01 F1233xf +<br>0.01 F245cb +<br>0.01 F1243zf +<br>0.01 F1234zeE +<br>0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 | 0 | 5.8 | 0 | 4.8 | 0 | 1.5 |
| 0.05 | 4.9 | 0.05 | 2.8 | 0.05 | 5.8 | 0.05 | 6.7 | 0.05 | 5.8 | 0.05 | 2.6 |
| 0.1 | 4.9 | 0.1 | 2.8 | 0.1 | 5.8 | 0.1 | 6.7 | 0.1 | 5.8 | 0.1 | 2.6 |
| 0.15 | 4.9 | 0.15 | 2.8 | 0.15 | 5.8 | 0.15 | 6.7 | 0.15 | 5.8 | 0.15 | 2.6 |
| 0.2 | 4.9 | 0.2 | 2.8 | 0.2 | 5.8 | 0.2 | 6.7 | 0.2 | 5.8 | 0.2 | 2.6 |
| 0.25 | 4.9 | 0.25 | 2.8 | 0.25 | 5.8 | 0.25 | 6.7 | 0.25 | 5.8 | 0.25 | 2.6 |
| 0.3 | 4.9 | 0.3 | 2.8 | 0.3 | 5.8 | 0.3 | 6.7 | 0.3 | 5.8 | 0.3 | 2.6 |
| 0.35 | 4.9 | 0.35 | 2.8 | 0.35 | 5.8 | 0.35 | 6.7 | 0.35 | 5.8 | 0.35 | 2.6 |
| 0.4 | 4.9 | 0.4 | 2.8 | 0.4 | 5.8 | 0.4 | 6.7 | 0.4 | 5.8 | 0.4 | 2.6 |
| 0.45 | 4.9 | 0.45 | 2.8 | 0.45 | 5.8 | 0.45 | 6.7 | 0.45 | 5.8 | 0.45 | 2.6 |
| 0.5 | 4.9 | 0.5 | 2.8 | 0.5 | 5.8 | 0.5 | 6.7 | 0.5 | 5.7 | 0.5 | 2.6 |
| 0.55 | 4.9 | 0.55 | 2.8 | 0.55 | 5.8 | 0.55 | 6.7 | 0.55 | 5.7 | 0.55 | 2.6 |
| 0.6 | 4.9 | 0.6 | 2.8 | 0.6 | 5.8 | 0.6 | 6.6 | 0.6 | 5.6 | 0.6 | 2.6 |
| 0.65 | 4.9 | 0.65 | 2.8 | 0.65 | 5.8 | 0.65 | 6.6 | 0.65 | 5.5 | 0.65 | 2.5 |
| 0.7 | 4.9 | 0.7 | 2.8 | 0.7 | 5.8 | 0.7 | 6.5 | 0.7 | 5.4 | 0.7 | 2.5 |
| 0.75 | 4.7 | 0.75 | 2.8 | 0.75 | 5.8 | 0.75 | 6.3 | 0.75 | 5.1 | 0.75 | 2.5 |
| 0.8 | 4.5 | 0.8 | 2.6 | 0.8 | 5.8 | 0.8 | 6.0 | 0.8 | 4.8 | 0.8 | 2.4 |
| 0.85 | 4.1 | 0.85 | 2.4 | 0.85 | 5.8 | 0.85 | 5.6 | 0.85 | 4.3 | 0.85 | 2.3 |
| 0.9 | 3.5 | 0.9 | 2.2 | 0.9 | 5.0 | 0.9 | 4.7 | 0.9 | 3.6 | 0.9 | 2.0 |
| 0.95 | 2.6 | 0.95 | 1.7 | 0.95 | 3.5 | 0.95 | 3.3 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF-HCFO-1233xf-HFC-245cb-HFO-1234zeZ-HCFO-1233zdE-HFO-1243zf ||||||||||||
| Organics 0.2 F1233xf + 0.2 F245cb + 0.2 F1243zf + 0.2 F1234zeZ + 0.2 F1233zdE ||  Organics 0.96 F1233xf + 0.01 F245cb + 0.01 F1243zf + 0.01 F1234zeZ + 0.01 F1233zdE || Organics 0.01 F1233xf + 0.96 F245cb + 0.01 F1243zf + 0.01 F1234zeZ + 0.01 F1233zdE || Organics 0.01 F1233xf + 0.01 F245cb + 0.96 F1243zf + 0.01 F1234zeZ + 0.01 F1233zdE || Organics 0.01 F1233xf + 0.01 F245cb + 0.01 F1243zf + 0.96 F1234zeZ + 0.01 F1233zdE || Organics 0.01 F1233xf + 0.01 F245cb + 0.01 F1243zf + 0.01 F1234zeZ + 0.96 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 3.2 | 0 | 1.6 | 0 | 4.6 | 0 | 5.7 | 0 | 1.9 | 0 | 1.4 |
| 0.05 | 4.3 | 0.05 | 2.7 | 0.05 | 5.7 | 0.05 | 6.7 | 0.05 | 3.0 | 0.05 | 2.5 |
| 0.1 | 4.3 | 0.1 | 2.7 | 0.1 | 5.7 | 0.1 | 6.7 | 0.1 | 3.0 | 0.1 | 2.5 |
| 0.15 | 4.3 | 0.15 | 2.7 | 0.15 | 5.7 | 0.15 | 6.7 | 0.15 | 3.0 | 0.15 | 2.5 |
| 0.2 | 4.3 | 0.2 | 2.7 | 0.2 | 5.7 | 0.2 | 6.7 | 0.2 | 3.0 | 0.2 | 2.5 |
| 0.25 | 4.3 | 0.25 | 2.7 | 0.25 | 5.7 | 0.25 | 6.7 | 0.25 | 3.0 | 0.25 | 2.5 |
| 0.3 | 4.3 | 0.3 | 2.7 | 0.3 | 5.7 | 0.3 | 6.7 | 0.3 | 3.0 | 0.3 | 2.5 |
| 0.35 | 4.3 | 0.35 | 2.7 | 0.35 | 5.7 | 0.35 | 6.7 | 0.35 | 3.0 | 0.35 | 2.5 |
| 0.4 | 4.3 | 0.4 | 2.7 | 0.4 | 5.8 | 0.4 | 6.7 | 0.4 | 3.0 | 0.4 | 2.5 |
| 0.45 | 4.3 | 0.45 | 2.7 | 0.45 | 5.8 | 0.45 | 6.7 | 0.45 | 3.0 | 0.45 | 2.5 |
| 0.5 | 4.3 | 0.5 | 2.7 | 0.5 | 5.8 | 0.5 | 6.7 | 0.5 | 3.0 | 0.5 | 2.5 |
| 0.55 | 4.3 | 0.55 | 2.7 | 0.55 | 5.8 | 0.55 | 6.7 | 0.55 | 3.0 | 0.55 | 2.5 |
| 0.6 | 4.3 | 0.6 | 2.7 | 0.6 | 5.8 | 0.6 | 6.6 | 0.6 | 3.0 | 0.6 | 2.5 |
| 0.65 | 4.3 | 0.65 | 2.7 | 0.65 | 5.8 | 0.65 | 6.6 | 0.65 | 3.0 | 0.65 | 2.5 |
| 0.7 | 4.3 | 0.7 | 2.7 | 0.7 | 5.8 | 0.7 | 6.5 | 0.7 | 3.0 | 0.7 | 2.5 |
| 0.75 | 4.3 | 0.75 | 2.7 | 0.75 | 5.8 | 0.75 | 6.3 | 0.75 | 3.0 | 0.75 | 2.5 |
| 0.8 | 4.1 | 0.8 | 2.6 | 0.8 | 5.8 | 0.8 | 6.0 | 0.8 | 2.9 | 0.8 | 2.4 |
| 0.85 | 3.8 | 0.85 | 2.4 | 0.85 | 5.8 | 0.85 | 5.5 | 0.85 | 2.7 | 0.85 | 2.3 |
| 0.9 | 3.3 | 0.9 | 2.1 | 0.9 | 5.0 | 0.9 | 4.7 | 0.9 | 2.3 | 0.9 | 2.0 |
| 0.95 | 2.4 | 0.95 | 1.7 | 0.95 | 3.5 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF-HCFO-1233xf-HFO-1234zeE-HFO-1234zeZ-HCFO-1233zdE-HFO-1243zf ||||||||||||
| Organics 0.2 F1233xf + 0.2 F1243zf + 0.2 F1233zdE + 0.2 F1234zeE + 0.2 F1234zeZ || Organics 0.96 F1233xf + 0.01 F1243zf + 0.01 F1233zdE + 0.01 F1234zeE + 0.01 F1234zeZ || Organics 0.01 F1233xf + 0.96 F1243zf + 0.01 F1233zdE + 0.01 F1234zeE + 0.01 F1234zeZ || Organics 0.01 F1233xf + 0.01 F1243zf + 0.96 F1233zdE + 0.01 F1234zeE + 0.01 F1234zeZ || Organics 0.01 F1233xf + 0.01 F1243zf + 0.01 F1233zdE + 0.96 F1234zeE + 0.01 F1234zeZ || Organics 0.01 F1233xf + 0.01 F1243zf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 3.2 | 0 | 1.6 | 0 | 5.7 | 0 | 1.4 | 0 | 4.8 | 0 | 1.9 |
| 0.05 | 4.3 | 0.05 | 2.7 | 0.05 | 6.7 | 0.05 | 2.5 | 0.05 | 5.7 | 0.05 | 3.0 |
| 0.1 | 4.3 | 0.1 | 2.7 | 0.1 | 6.7 | 0.1 | 2.5 | 0.1 | 5.8 | 0.1 | 3.0 |
| 0.15 | 4.3 | 0.15 | 2.7 | 0.15 | 6.7 | 0.15 | 2.5 | 0.15 | 5.8 | 0.15 | 3.0 |
| 0.2 | 4.3 | 0.2 | 2.7 | 0.2 | 6.7 | 0.2 | 2.5 | 0.2 | 5.8 | 0.2 | 3.0 |
| 0.25 | 4.3 | 0.25 | 2.7 | 0.25 | 6.7 | 0.25 | 2.5 | 0.25 | 5.8 | 0.25 | 3.0 |
| 0.3 | 4.3 | 0.3 | 2.7 | 0.3 | 6.7 | 0.3 | 2.5 | 0.3 | 5.8 | 0.3 | 3.0 |
| 0.35 | 4.3 | 0.35 | 2.7 | 0.35 | 6.7 | 0.35 | 2.5 | 0.35 | 5.8 | 0.35 | 3.0 |
| 0.4 | 4.3 | 0.4 | 2.7 | 0.4 | 6.7 | 0.4 | 2.5 | 0.4 | 5.8 | 0.4 | 3.0 |
| 0.45 | 4.3 | 0.45 | 2.7 | 0.45 | 6.7 | 0.45 | 2.5 | 0.45 | 5.7 | 0.45 | 3.0 |
| 0.5 | 4.3 | 0.5 | 2.7 | 0.5 | 6.7 | 0.5 | 2.5 | 0.5 | 5.7 | 0.5 | 3.0 |
| 0.55 | 4.2 | 0.55 | 2.7 | 0.55 | 6.6 | 0.55 | 2.5 | 0.55 | 5.7 | 0.55 | 3.0 |
| 0.6 | 4.2 | 0.6 | 2.7 | 0.6 | 6.6 | 0.6 | 2.5 | 0.6 | 5.6 | 0.6 | 3.0 |
| 0.65 | 4.2 | 0.65 | 2.7 | 0.65 | 6.6 | 0.65 | 2.5 | 0.65 | 5.5 | 0.65 | 3.0 |
| 0.7 | 4.2 | 0.7 | 2.7 | 0.7 | 6.5 | 0.7 | 2.5 | 0.7 | 5.3 | 0.7 | 3.0 |
| 0.75 | 4.0 | 0.75 | 2.7 | 0.75 | 6.3 | 0.75 | 2.5 | 0.75 | 5.1 | 0.75 | 3.0 |
| 0.8 | 3.8 | 0.8 | 2.6 | 0.8 | 6.0 | 0.8 | 2.4 | 0.8 | 4.7 | 0.8 | 2.8 |
| 0.85 | 3.5 | 0.85 | 2.4 | 0.85 | 5.5 | 0.85 | 2.2 | 0.85 | 4.3 | 0.85 | 2.6 |
| 0.9 | 3.0 | 0.9 | 2.1 | 0.9 | 4.7 | 0.9 | 2.0 | 0.9 | 3.6 | 0.9 | 2.3 |
| 0.95 | 2.2 | 0.95 | 1.7 | 0.95 | 3.3 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeE-HFO-1234zeZ-HCFO-1233zdE

| Organics 0.2 F1234yf + 0.2 F245cb + 0.2 F1233zdE + 0.2 F1234zeE + 0.2 F1234zeZ | | Organics 0.96 F1234yf + 0.01 F245cb + 0.01 F1233zdE + 0.01 F1234zeE + 0.01 F1234zeZ | | Organics 0.01 F1234yf + 0.96 F245cb + 0.01 F1233zdE + 0.01 F1234zeE + 0.01 F1234zeZ | | Organics 0.01 F1234yf + 0.01 F245cb + 0.96 F1233zdE + 0.01 F1234zeE + 0.01 F1234zeZ | | Organics 0.01 F1234yf + 0.01 F245cb + 0.01 F1233zdE + 0.96 F1234zeE + 0.01 F1234zeZ | | Organics 0.01 F1234yf + 0.01 F245cb + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 6.7 | 0 | 4.6 | 0 | 1.5 | 0 | 4.8 | 0 | 1.9 |
| 0.05 | 5.0 | 0.05 | 7.6 | 0.05 | 5.8 | 0.05 | 2.6 | 0.05 | 5.8 | 0.05 | 3.0 |
| 0.1 | 5.0 | 0.1 | 7.6 | 0.1 | 5.8 | 0.1 | 2.6 | 0.1 | 5.8 | 0.1 | 3.0 |
| 0.15 | 5.0 | 0.15 | 7.6 | 0.15 | 5.8 | 0.15 | 2.6 | 0.15 | 5.8 | 0.15 | 3.0 |
| 0.2 | 5.0 | 0.2 | 7.6 | 0.2 | 5.8 | 0.2 | 2.6 | 0.2 | 5.8 | 0.2 | 3.0 |
| 0.25 | 5.0 | 0.25 | 7.6 | 0.25 | 5.8 | 0.25 | 2.6 | 0.25 | 5.8 | 0.25 | 3.0 |
| 0.3 | 5.0 | 0.3 | 7.6 | 0.3 | 5.8 | 0.3 | 2.6 | 0.3 | 5.8 | 0.3 | 3.0 |
| 0.35 | 5.0 | 0.35 | 7.6 | 0.35 | 5.8 | 0.35 | 2.6 | 0.35 | 5.8 | 0.35 | 3.0 |
| 0.4 | 5.0 | 0.4 | 7.6 | 0.4 | 5.8 | 0.4 | 2.6 | 0.4 | 5.8 | 0.4 | 3.0 |
| 0.45 | 5.0 | 0.45 | 7.6 | 0.45 | 5.8 | 0.45 | 2.6 | 0.45 | 5.8 | 0.45 | 3.0 |
| 0.5 | 5.0 | 0.5 | 7.6 | 0.5 | 5.8 | 0.5 | 2.6 | 0.5 | 5.7 | 0.5 | 3.0 |
| 0.55 | 5.0 | 0.55 | 7.6 | 0.55 | 5.8 | 0.55 | 2.6 | 0.55 | 5.7 | 0.55 | 3.0 |
| 0.6 | 5.0 | 0.6 | 7.6 | 0.6 | 5.8 | 0.6 | 2.6 | 0.6 | 5.6 | 0.6 | 3.0 |
| 0.65 | 5.0 | 0.65 | 7.6 | 0.65 | 5.8 | 0.65 | 2.6 | 0.65 | 5.5 | 0.65 | 3.0 |
| 0.7 | 5.1 | 0.7 | 7.6 | 0.7 | 5.8 | 0.7 | 2.6 | 0.7 | 5.4 | 0.7 | 3.0 |
| 0.75 | 5.0 | 0.75 | 7.5 | 0.75 | 5.8 | 0.75 | 2.6 | 0.75 | 5.1 | 0.75 | 3.0 |
| 0.8 | 4.7 | 0.8 | 7.1 | 0.8 | 5.8 | 0.8 | 2.5 | 0.8 | 4.8 | 0.8 | 2.9 |
| 0.85 | 4.3 | 0.85 | 6.5 | 0.85 | 5.8 | 0.85 | 2.3 | 0.85 | 4.3 | 0.85 | 2.7 |
| 0.9 | 3.7 | 0.9 | 5.5 | 0.9 | 5.0 | 0.9 | 2.0 | 0.9 | 3.6 | 0.9 | 2.4 |
| 0.95 | 2.7 | 0.95 | 3.8 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeE-HFO-1234zeZ-HFO-1243zf

| Organics 0.2 F1234yf + 0.2 F245cb + 0.2 F1243zf + 0.2 F1234zeE + 0.2 F1234zeZ | | Organics 0.96 F1234yf + 0.01 F245cb + 0.01 F1243zf + 0.01 F1234zeE + 0.01 F1234zeZ | | Organics 0.01 F1234yf + 0.96 F245cb + 0.01 F1243zf + 0.01 F1234zeE + 0.01 F1234zeZ | | Organics 0.01 F1234yf + 0.01 F245cb + 0.96 F1243zf + 0.01 F1234zeE + 0.01 F1234zeZ | | Organics 0.01 F1234yf + 0.01 F245cb + 0.01 F1243zf + 0.96 F1234zeE + 0.01 F1234zeZ | | Organics 0.01 F1234yf + 0.01 F245cb + 0.01 F1243zf + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 6.7 | 0 | 4.7 | 0 | 5.8 | 0 | 4.9 | 0 | 2.0 |
| 0.05 | 5.9 | 0.05 | 7.7 | 0.05 | 5.8 | 0.05 | 6.7 | 0.05 | 5.8 | 0.05 | 3.1 |
| 0.1 | 5.9 | 0.1 | 7.7 | 0.1 | 5.8 | 0.1 | 6.8 | 0.1 | 5.9 | 0.1 | 3.1 |
| 0.15 | 5.9 | 0.15 | 7.7 | 0.15 | 5.8 | 0.15 | 6.8 | 0.15 | 5.8 | 0.15 | 3.1 |
| 0.2 | 5.9 | 0.2 | 7.7 | 0.2 | 5.8 | 0.2 | 6.8 | 0.2 | 5.8 | 0.2 | 3.1 |
| 0.25 | 5.9 | 0.25 | 7.6 | 0.25 | 5.8 | 0.25 | 6.8 | 0.25 | 5.8 | 0.25 | 3.1 |
| 0.3 | 5.9 | 0.3 | 7.6 | 0.3 | 5.8 | 0.3 | 6.8 | 0.3 | 5.8 | 0.3 | 3.1 |
| 0.35 | 5.9 | 0.35 | 7.6 | 0.35 | 5.8 | 0.35 | 6.8 | 0.35 | 5.8 | 0.35 | 3.1 |
| 0.4 | 5.9 | 0.4 | 7.6 | 0.4 | 5.8 | 0.4 | 6.7 | 0.4 | 5.8 | 0.4 | 3.1 |
| 0.45 | 5.9 | 0.45 | 7.6 | 0.45 | 5.8 | 0.45 | 6.7 | 0.45 | 5.8 | 0.45 | 3.1 |
| 0.5 | 5.9 | 0.5 | 7.7 | 0.5 | 5.8 | 0.5 | 6.7 | 0.5 | 5.8 | 0.5 | 3.1 |
| 0.55 | 5.9 | 0.55 | 7.7 | 0.55 | 5.8 | 0.55 | 6.7 | 0.55 | 5.7 | 0.55 | 3.1 |
| 0.6 | 5.9 | 0.6 | 7.7 | 0.6 | 5.8 | 0.6 | 6.7 | 0.6 | 5.7 | 0.6 | 3.1 |
| 0.65 | 5.9 | 0.65 | 7.7 | 0.65 | 5.8 | 0.65 | 6.6 | 0.65 | 5.6 | 0.65 | 3.1 |
| 0.7 | 5.9 | 0.7 | 7.6 | 0.7 | 5.8 | 0.7 | 6.5 | 0.7 | 5.4 | 0.7 | 3.1 |
| 0.75 | 5.7 | 0.75 | 7.5 | 0.75 | 5.8 | 0.75 | 6.4 | 0.75 | 5.2 | 0.75 | 3.1 |
| 0.8 | 5.5 | 0.8 | 7.2 | 0.8 | 5.8 | 0.8 | 6.1 | 0.8 | 4.8 | 0.8 | 2.9 |
| 0.85 | 5.0 | 0.85 | 6.6 | 0.85 | 5.8 | 0.85 | 5.6 | 0.85 | 4.3 | 0.85 | 2.7 |
| 0.9 | 4.3 | 0.9 | 5.5 | 0.9 | 5.0 | 0.9 | 4.8 | 0.9 | 3.6 | 0.9 | 2.4 |
| 0.95 | 3.0 | 0.95 | 3.8 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeE-HCFO-1233zdE-HFO-1243zf

| Organics 0.2 F1234yf + 0.2 F245cb + 0.2 F1243zf + 0.2 F1234zeE + 0.2 F1233zdE | | Organics 0.96 F1234yf + 0.01 F245cb + 0.01 F1243zf + 0.01 F1234zeE + 0.01 F1233zdE | | Organics 0.01 F1234yf + 0.96 F245cb + 0.01 F1243zf + 0.01 F1234zeE + 0.01 F1233zdE | | Organics 0.01 F1234yf + 0.01 F245cb + 0.96 F1243zf + 0.01 F1234zeE + 0.01 F1233zdE | | Organics 0.01 F1234yf + 0.01 F245cb + 0.01 F1243zf + 0.96 F1234zeE + 0.01 F1233zdE | | Organics 0.01 F1234yf + 0.01 F245cb + 0.01 F1243zf + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 6.7 | 0 | 4.7 | 0 | 5.8 | 0 | 4.9 | 0 | 1.5 |
| 0.05 | 5.9 | 0.05 | 7.7 | 0.05 | 5.8 | 0.05 | 6.7 | 0.05 | 5.8 | 0.05 | 2.6 |
| 0.1 | 5.9 | 0.1 | 7.7 | 0.1 | 5.8 | 0.1 | 6.8 | 0.1 | 5.8 | 0.1 | 2.6 |
| 0.15 | 5.9 | 0.15 | 7.7 | 0.15 | 5.8 | 0.15 | 6.8 | 0.15 | 5.8 | 0.15 | 2.6 |
| 0.2 | 5.9 | 0.2 | 7.7 | 0.2 | 5.8 | 0.2 | 6.8 | 0.2 | 5.8 | 0.2 | 2.6 |
| 0.25 | 5.9 | 0.25 | 7.6 | 0.25 | 5.8 | 0.25 | 6.8 | 0.25 | 5.8 | 0.25 | 2.6 |
| 0.3 | 5.9 | 0.3 | 7.6 | 0.3 | 5.8 | 0.3 | 6.8 | 0.3 | 5.8 | 0.3 | 2.6 |
| 0.35 | 5.9 | 0.35 | 7.6 | 0.35 | 5.8 | 0.35 | 6.8 | 0.35 | 5.8 | 0.35 | 2.6 |
| 0.4 | 5.9 | 0.4 | 7.7 | 0.4 | 5.8 | 0.4 | 6.7 | 0.4 | 5.8 | 0.4 | 2.6 |
| 0.45 | 5.9 | 0.45 | 7.7 | 0.45 | 5.8 | 0.45 | 6.7 | 0.45 | 5.8 | 0.45 | 2.6 |
| 0.5 | 5.9 | 0.5 | 7.7 | 0.5 | 5.8 | 0.5 | 6.7 | 0.5 | 5.8 | 0.5 | 2.6 |
| 0.55 | 5.9 | 0.55 | 7.7 | 0.55 | 5.8 | 0.55 | 6.7 | 0.55 | 5.7 | 0.55 | 2.6 |
| 0.6 | 5.9 | 0.6 | 7.7 | 0.6 | 5.8 | 0.6 | 6.7 | 0.6 | 5.7 | 0.6 | 2.6 |
| 0.65 | 5.9 | 0.65 | 7.7 | 0.65 | 5.8 | 0.65 | 6.6 | 0.65 | 5.6 | 0.65 | 2.6 |
| 0.7 | 5.9 | 0.7 | 7.6 | 0.7 | 5.8 | 0.7 | 6.5 | 0.7 | 5.4 | 0.7 | 2.6 |
| 0.75 | 5.7 | 0.75 | 7.5 | 0.75 | 5.8 | 0.75 | 6.4 | 0.75 | 5.2 | 0.75 | 2.6 |
| 0.8 | 5.4 | 0.8 | 7.2 | 0.8 | 5.8 | 0.8 | 6.1 | 0.8 | 4.8 | 0.8 | 2.5 |
| 0.85 | 5.0 | 0.85 | 6.6 | 0.85 | 5.8 | 0.85 | 5.6 | 0.85 | 4.3 | 0.85 | 2.3 |
| 0.9 | 4.2 | 0.9 | 5.5 | 0.9 | 5.0 | 0.9 | 4.8 | 0.9 | 3.6 | 0.9 | 2.1 |
| 0.95 | 3.0 | 0.95 | 3.8 | 0.95 | 3.5 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeZ-HCFO-1233zdE-HFO-1243zf

| Organics 0.2 F1234yf + 0.2 F245cb + 0.2 F1243zf + 0.2 F1234zeZ + 0.2 F1233zdE | | Organics 0.96 F1234yf + 0.01 F245cb + 0.01 F1243zf + 0.01 F1234zeZ + 0.01 F1233zdE | | Organics 0.01 F1234yf + 0.96 F245cb + 0.01 F1243zf + 0.01 F1234zeZ + 0.01 F1233zdE | | Organics 0.01 F1234yf + 0.01 F245cb + 0.96 F1243zf + 0.01 F1234zeZ + 0.01 F1233zdE | | Organics 0.01 F1234yf + 0.01 F245cb + 0.01 F1243zf + 0.96 F1234zeZ + 0.01 F1233zdE | | Organics 0.01 F1234yf + 0.01 F245cb + 0.01 F1243zf + 0.01 F1234zeZ + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 6.7 | 0 | 4.6 | 0 | 5.8 | 0 | 1.9 | 0 | 1.5 |
| 0.05 | 5.3 | 0.05 | 7.6 | 0.05 | 5.8 | 0.05 | 6.7 | 0.05 | 3.0 | 0.05 | 2.6 |
| 0.1 | 5.3 | 0.1 | 7.6 | 0.1 | 5.8 | 0.1 | 6.7 | 0.1 | 3.0 | 0.1 | 2.6 |
| 0.15 | 5.3 | 0.15 | 7.6 | 0.15 | 5.8 | 0.15 | 6.7 | 0.15 | 3.0 | 0.15 | 2.6 |
| 0.2 | 5.3 | 0.2 | 7.6 | 0.2 | 5.8 | 0.2 | 6.7 | 0.2 | 3.0 | 0.2 | 2.6 |
| 0.25 | 5.3 | 0.25 | 7.6 | 0.25 | 5.8 | 0.25 | 6.7 | 0.25 | 3.0 | 0.25 | 2.6 |
| 0.3 | 5.3 | 0.3 | 7.6 | 0.3 | 5.8 | 0.3 | 6.7 | 0.3 | 3.0 | 0.3 | 2.6 |
| 0.35 | 5.3 | 0.35 | 7.6 | 0.35 | 5.8 | 0.35 | 6.7 | 0.35 | 3.0 | 0.35 | 2.6 |
| 0.4 | 5.3 | 0.4 | 7.6 | 0.4 | 5.8 | 0.4 | 6.7 | 0.4 | 3.0 | 0.4 | 2.6 |
| 0.45 | 5.3 | 0.45 | 7.6 | 0.45 | 5.8 | 0.45 | 6.7 | 0.45 | 3.0 | 0.45 | 2.6 |
| 0.5 | 5.3 | 0.5 | 7.6 | 0.5 | 5.8 | 0.5 | 6.7 | 0.5 | 3.0 | 0.5 | 2.6 |
| 0.55 | 5.3 | 0.55 | 7.6 | 0.55 | 5.8 | 0.55 | 6.7 | 0.55 | 3.0 | 0.55 | 2.6 |
| 0.6 | 5.3 | 0.6 | 7.6 | 0.6 | 5.8 | 0.6 | 6.7 | 0.6 | 3.0 | 0.6 | 2.6 |
| 0.65 | 5.3 | 0.65 | 7.6 | 0.65 | 5.8 | 0.65 | 6.6 | 0.65 | 3.0 | 0.65 | 2.6 |
| 0.7 | 5.3 | 0.7 | 7.6 | 0.7 | 5.8 | 0.7 | 6.5 | 0.7 | 3.0 | 0.7 | 2.6 |
| 0.75 | 5.2 | 0.75 | 7.5 | 0.75 | 5.8 | 0.75 | 6.4 | 0.75 | 3.0 | 0.75 | 2.6 |
| 0.8 | 5.0 | 0.8 | 7.2 | 0.8 | 5.8 | 0.8 | 6.1 | 0.8 | 2.9 | 0.8 | 2.5 |
| 0.85 | 4.6 | 0.85 | 6.6 | 0.85 | 5.8 | 0.85 | 5.6 | 0.85 | 2.7 | 0.85 | 2.3 |
| 0.9 | 3.9 | 0.9 | 5.5 | 0.9 | 5.0 | 0.9 | 4.7 | 0.9 | 2.4 | 0.9 | 2.0 |
| 0.95 | 2.9 | 0.95 | 3.8 | 0.95 | 3.5 | 0.95 | 3.4 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF-HFO-1234yf-HFO-1234zeE-HFO-1234zeZ-HCFO-1233zdE-HFO-1243zf ||||||||||||
|---|---|---|---|---|---|---|---|---|---|---|---|
| Organics 0.2 F1234yf + 0.2 F1243zf + 0.2 F1233zdE + 0.2 F1234zeE + 0.2 F1234zeZ || Organics 0.96 F1234yf + 0.01 F1243zf + 0.01 F1233zdE + 0.01 F1234zeE + 0.01 F1234zeZ || Organics 0.01 F1234yf + 0.96 F1243zf + 0.01 F1233zdE + 0.01 F1234zeE + 0.01 F1234zeZ || Organics 0.01 F1234yf + 0.01 F1243zf + 0.96 F1233zdE + 0.01 F1234zeE + 0.01 F1234zeZ || Organics 0.01 F1234yf + 0.01 F1243zf + 0.01 F1233zdE + 0.96 F1234zeE + 0.01 F1234zeZ || Organics 0.01 F1234yf + 0.01 F1243zf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 6.7 | 0 | 5.8 | 0 | 1.5 | 0 | 4.8 | 0 | 1.9 |
| 0.05 | 5.3 | 0.05 | 7.6 | 0.05 | 6.7 | 0.05 | 2.6 | 0.05 | 5.8 | 0.05 | 3.0 |
| 0.1 | 5.3 | 0.1 | 7.6 | 0.1 | 6.7 | 0.1 | 2.6 | 0.1 | 5.8 | 0.1 | 3.0 |
| 0.15 | 5.3 | 0.15 | 7.6 | 0.15 | 6.7 | 0.15 | 2.6 | 0.15 | 5.8 | 0.15 | 3.0 |
| 0.2 | 5.3 | 0.2 | 7.6 | 0.2 | 6.7 | 0.2 | 2.6 | 0.2 | 5.8 | 0.2 | 3.0 |
| 0.25 | 5.3 | 0.25 | 7.6 | 0.25 | 6.7 | 0.25 | 2.6 | 0.25 | 5.8 | 0.25 | 3.0 |
| 0.3 | 5.3 | 0.3 | 7.6 | 0.3 | 6.7 | 0.3 | 2.6 | 0.3 | 5.8 | 0.3 | 3.0 |
| 0.35 | 5.3 | 0.35 | 7.6 | 0.35 | 6.7 | 0.35 | 2.6 | 0.35 | 5.8 | 0.35 | 3.0 |
| 0.4 | 5.3 | 0.4 | 7.6 | 0.4 | 6.7 | 0.4 | 2.6 | 0.4 | 5.8 | 0.4 | 3.0 |
| 0.45 | 5.3 | 0.45 | 7.6 | 0.45 | 6.7 | 0.45 | 2.6 | 0.45 | 5.8 | 0.45 | 3.0 |
| 0.5 | 5.3 | 0.5 | 7.6 | 0.5 | 6.7 | 0.5 | 2.6 | 0.5 | 5.8 | 0.5 | 3.0 |
| 0.55 | 5.3 | 0.55 | 7.6 | 0.55 | 6.7 | 0.55 | 2.6 | 0.55 | 5.7 | 0.55 | 3.0 |
| 0.6 | 5.2 | 0.6 | 7.6 | 0.6 | 6.7 | 0.6 | 2.6 | 0.6 | 5.6 | 0.6 | 3.0 |
| 0.65 | 5.2 | 0.65 | 7.6 | 0.65 | 6.6 | 0.65 | 2.6 | 0.65 | 5.5 | 0.65 | 3.0 |
| 0.7 | 5.2 | 0.7 | 7.6 | 0.7 | 6.5 | 0.7 | 2.6 | 0.7 | 5.4 | 0.7 | 3.0 |
| 0.75 | 5.0 | 0.75 | 7.5 | 0.75 | 6.3 | 0.75 | 2.6 | 0.75 | 5.1 | 0.75 | 3.0 |
| 0.8 | 4.7 | 0.8 | 7.1 | 0.8 | 6.1 | 0.8 | 2.5 | 0.8 | 4.8 | 0.8 | 2.9 |
| 0.85 | 4.3 | 0.85 | 6.5 | 0.85 | 5.6 | 0.85 | 2.3 | 0.85 | 4.3 | 0.85 | 2.7 |
| 0.9 | 3.7 | 0.9 | 5.5 | 0.9 | 4.7 | 0.9 | 2.0 | 0.9 | 3.6 | 0.9 | 2.4 |
| 0.95 | 2.7 | 0.95 | 3.8 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF-HFC-245cb-HFO-1234zeE-HFO-1234zeZ-HCFO-1233zdE-HFO-1243zf ||||||||||||
|---|---|---|---|---|---|---|---|---|---|---|---|
| Organics 0.2 F245cb + 0.2 F1243zf + 0.2 F1233zdE + 0.2 F1234zeE + 0.2 F1234zeZ || Organics 0.96 F245cb + 0.01 F1243zf + 0.01 F1233zdE + 0.01 F1234zeE + 0.01 F1234zeZ || Organics 0.01 F245cb + 0.96 F1243zf + 0.01 F1233zdE + 0.01 F1234zeE + 0.01 F1234zeZ || Organics 0.01 F245cb + 0.01 F1243zf + 0.96 F1233zdE + 0.01 F1234zeE + 0.01 F1234zeZ || Organics 0.01 F245cb + 0.01 F1243zf + 0.01 F1233zdE + 0.96 F1234zeE + 0.01 F1234zeZ || Organics 0.01 F245cb + 0.01 F1243zf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 4.6 | 0 | 5.8 | 0 | 1.5 | 0 | 4.8 | 0 | 1.9 |
| 0.05 | 4.9 | 0.05 | 5.8 | 0.05 | 6.7 | 0.05 | 2.6 | 0.05 | 5.8 | 0.05 | 3.0 |
| 0.1 | 4.9 | 0.1 | 5.8 | 0.1 | 6.7 | 0.1 | 2.6 | 0.1 | 5.8 | 0.1 | 3.0 |
| 0.15 | 4.9 | 0.15 | 5.8 | 0.15 | 6.7 | 0.15 | 2.6 | 0.15 | 5.8 | 0.15 | 3.0 |
| 0.2 | 4.9 | 0.2 | 5.8 | 0.2 | 6.7 | 0.2 | 2.6 | 0.2 | 5.8 | 0.2 | 3.0 |
| 0.25 | 4.9 | 0.25 | 5.8 | 0.25 | 6.7 | 0.25 | 2.6 | 0.25 | 5.8 | 0.25 | 3.0 |
| 0.3 | 4.9 | 0.3 | 5.8 | 0.3 | 6.7 | 0.3 | 2.6 | 0.3 | 5.8 | 0.3 | 3.0 |
| 0.35 | 4.9 | 0.35 | 5.8 | 0.35 | 6.7 | 0.35 | 2.6 | 0.35 | 5.8 | 0.35 | 3.0 |
| 0.4 | 4.9 | 0.4 | 5.8 | 0.4 | 6.7 | 0.4 | 2.6 | 0.4 | 5.8 | 0.4 | 3.0 |
| 0.45 | 4.9 | 0.45 | 5.8 | 0.45 | 6.7 | 0.45 | 2.6 | 0.45 | 5.8 | 0.45 | 3.0 |
| 0.5 | 4.9 | 0.5 | 5.8 | 0.5 | 6.7 | 0.5 | 2.6 | 0.5 | 5.7 | 0.5 | 3.0 |
| 0.55 | 4.9 | 0.55 | 5.8 | 0.55 | 6.7 | 0.55 | 2.6 | 0.55 | 5.7 | 0.55 | 3.0 |
| 0.6 | 4.9 | 0.6 | 5.8 | 0.6 | 6.6 | 0.6 | 2.6 | 0.6 | 5.6 | 0.6 | 3.0 |
| 0.65 | 4.9 | 0.65 | 5.8 | 0.65 | 6.6 | 0.65 | 2.6 | 0.65 | 5.5 | 0.65 | 3.0 |
| 0.7 | 4.9 | 0.7 | 5.8 | 0.7 | 6.5 | 0.7 | 2.6 | 0.7 | 5.4 | 0.7 | 3.0 |
| 0.75 | 4.8 | 0.75 | 5.8 | 0.75 | 6.3 | 0.75 | 2.5 | 0.75 | 5.1 | 0.75 | 3.0 |
| 0.8 | 4.5 | 0.8 | 5.8 | 0.8 | 6.0 | 0.8 | 2.4 | 0.8 | 4.8 | 0.8 | 2.9 |
| 0.85 | 4.2 | 0.85 | 5.8 | 0.85 | 5.6 | 0.85 | 2.3 | 0.85 | 4.3 | 0.85 | 2.7 |
| 0.9 | 3.5 | 0.9 | 5.0 | 0.9 | 4.7 | 0.9 | 2.0 | 0.9 | 3.6 | 0.9 | 2.4 |
| 0.95 | 2.6 | 0.95 | 3.5 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

EXAMPLE 11

Temperature and Pressure Range of Systems with 6 Compounds

|  | Boiling point range | |
|---|---|---|
| System with 6 compounds | Temperature ° C. | Pressure bar abs |
| HF-HCFO-1233xf-HFO-1234yf-HFC-245cb-HFO-1234zeE-HFO-1234zeZ | 0 to 40 | ~1.0 ~ 11.6 |
| HF-HCFO-1233xf-HFO-1234yf-HFC-245cb-HFO-1234zeE-HCFO-1233zdE | 0 to 40 | ~0.9 to ~11.6 |
| HF-HCFO-1233xf-HFO-1234yf-HFC-245cb-HFO-1234zeE-HFO-1243zf | 0 to 40 | ~1.0 to ~11.6 |
| HF-HCFO-1233xf-HFO-1234yf-HFC-245cb-HFO-1234zeZ-HCFO-1233zdE | 0 to 40 | ~0.9 to ~11.5 |
| HF-HCFO-1233xf-HFO-1234yf-HFC-245cb-HFO-1234zeZ-HFO-1243zf | 0 to 40 | ~1.0 to ~11.6 |
| HF-HCFO-1233xf-HFO-1234yf-HFO-1234zeE-HFO-1234zeZ-HCFO-1233zdE | 0 to 40 | ~0.9 to ~11.5 |
| HF-HCFO-1233xf-HFO-1234yf-HFO-1234zeE-HFO-1234zeZ-HFO-1243zf | 0 to 40 | ~1.0 to ~11.6 |
| HF-HCFO-1233xf-HFO-1234yf-HFO-1234zeE-HCFO-1233zdE-HFO-1243zf | 0 to 40 | ~0.9 to ~11.6 |
| HF-HCFO-1233xf-HFO-1234yf-HFO-1234zeZ-HCFO-1233zdE-HFO-1243zf | 0 to 40 | ~0.9 to ~11.6 |
| HF-HCFO-1233xf-HFC-245cb-HFO-1234zeE-HFO-1234zeZ-HCFO-1233zdE | 0 to 40 | ~0.9 to ~9.0 |
| HF-HCFO-1233xf-HFC-245cb-HFO-1234zeE-HFO-1234zeZ-HFO-1243zf | 0 to 40 | ~1.0 to ~10.3 |
| HF-HCFO-1233xf-HFC-245cb-HFO-1234zeE-HCFO-1233zdE-HFO-1243zf | 0 to 40 | ~0.9 to ~10.3 |
| HF-HCFO-1233xf-HFC-245cb-HFO-1234zeZ-HCFO-1233zdE-HFO-1243zf | 0 to 40 | ~1.0 to ~10.3 |
| HF-HCFO-1233xf-HFO-1234zeE-HFO-1234zeZ-HCFO-1233zdE-HFO-1243zf | 0 to 40 | ~0.9 ~ 10.3 |
| HF-HFO-1234yf-HFC-245cb-HFO-1234zeE-HFO-1234zeZ-HCFO-1233zdE | 0 to 40 | ~0.9 ~ 11.6 |
| HF-HFO-1234yf-HFC-245cb-HFO-1234zeE-HFO-1234zeZ-HFO-1243zf | 0 to 40 | ~1.2 to ~11.6 |
| HF-HFO-1234yf-HFC-245cb-HFO-1234zeE-HCFO-1233zdE-HFO-1243zf | 0 to 40 | ~1.0 to ~11.7 |
| HF-HFO-1234yf-HFC-245cb-HFO-1234zeZ-HCFO-1233zdE-HFO-1243zf | 0 to 40 | ~0.9 to ~11.6 |
| HF-HFO-1234yf-HFO-1234zeE-HFO-1234zeZ-HCFO-1233zdE-HFO-1243zf | 0 to 40 | ~0.9 to ~11.6 |
| HF-HFC-245cb-HFO-1234zeE-HFO-1234zeZ-HCFO-1233zdE-HFO-1243zf | 0 to 40 | ~0.9 to ~10.3 |

EXAMPLE 12

Decantation Range of Systems with 6 Compounds

|  | Decantation ranges Mass percentage of HF Isotherm | | |
|---|---|---|---|
| System with 6 compounds | 0° C. | 25° C. | 40° C. |
| HF-HCFO-1233xf-HFO-1234yf-HFC-245cb-HFO-1234zeE-HFO-1234zeZ | 5-75 | 5-70 | 15-55 |
| HF-HCFO-1233xf-HFO-1234yf-HFC-245cb-HFO-1234zeE-HCFO-1233zdE | 5-75 | 5-70 | 15-55 |
| HF-HCFO-1233xf-HFO-1234yf-HFC-245cb-HFO-1234zeE-HFO-1243zf | 5-75 | 10-65 | * |
| HF-HCFO-1233xf-HFO-1234yf-HFC-245cb-HFO-1234zeZ-HCFO-1233zdE | 5-75 | 5-75 | 10-65 |
| HF-HCFO-1233xf-HFO-1234yf-HFC-245cb-HFO-1234zeZ-HFO-1243zf | 5-75 | 10-70 | 15-50 |
| HF-HCFO-1233xf-HFO-1234yf-HFO-1234zeE-HFO-1234zeZ-HCFO-1233zdE | 5-75 | 5-65 | 10-55 |
| HF-HCFO-1233xf-HFO-1234yf-HFO-1234zeE-HFO-1234zeZ-HFO-1243zf | 5-70 | 10-65 | * |
| HF-HCFO-1233xf-HFO-1234yf-HFO-1234zeE-HCFO-1233zdE-HFO-1243zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HCFO-1233xf-HFC-245cb-HFO-1234zeE-HFO-1234zeZ-HCFO-1233zdE | 5-75 | 5-70 | 10-65 |
| HF-HCFO-1233xf-HFC-245cb-HFO-1234zeE-HFO-1234zeZ-HFO-1243zf | 5-75 | 10-70 | 15-45 |
| HF-HCFO-1233xf-HFC-245cb-HFO-1234zeE-HCFO-1233zdE-HFO-1243zf | 5-75 | 5-70 | 15-50 |
| HF-HCFO-1233xf-HFC-245cb-HFO-1234zeZ-HCFO-1233zdE-HFO-1243zf | 5-75 | 5-70 | 10-65 |
| HF-HCFO-1233xf-HFO-1234zeE-HFO-1234zeZ-HCFO-1233zdE-HFO-1243zf | 5-75 | 5-65 | 10-55 |
| HF-HFO-1234yf-HFC-245cb-HFO-1234zeE-HFO-1234zeZ-HCFO-1233zdE | 5-75 | 5-70 | 15-55 |
| HF-HFO-1234yf-HFC-245cb-HFO-1234zeE-HFO-1234zeZ-HFO-1243zf | 5-75 | 10-65 | * |
| HF-HFO-1234yf-HFC-245cb-HFO-1234zeE-HCFO-1233zdE-HFO-1243zf | 5-75 | 10-65 | * |
| HF-HFO-1234yf-HFC-245cb-HFO-1234zeZ-HCFO-1233zdE-HFO-1243zf | 5-75 | 10-70 | 15-55 |
| HF-HFO-1234yf-HFO-1234zeE-HFO-1234zeZ-HCFO-1233zdE-HFO-1243zf | 5-70 | 10-65 | * |
| HF-HFC-245cb-HFO-1234zeE-HFO-1234zeZ-HCFO-1233zdE-HFO-1243zf | 5-75 | 5-70 | 15-50 |

EXAMPLE 13

Systems with Seven Compounds, Isotherm at 25° C.

HF-HCFO-1233xf-HFC-245cb-HCFO-1233zdE-HFO-1234zeE-HFO-1234zeZ-HFO-1243zf

| MASSFRAC HF | Organics 0.15 F1233xf + 0.17 F245cb + 0.17 F1233zdE + 0.17 F1234zeE + 0.17 F1234zeZ + 0.17 F1243zf TOTAL PRESSURE bar | Organics 0.95 F1233xf + 0.01 F245cb + 0.01 F1233zdE + 0.01 F1234zeE + 0.01 F1234zeZ + 0.01 F1243zf TOTAL PRESSURE bar | Organics 0.01 F1233xf + 0.95 F245cb + 0.01 F1233zdE + 0.01 F1234zeE + 0.01 F1234zeZ + 0.01 F1243zf TOTAL PRESSURE bar | Organics 0.01 F1233xf + 0.01 F245cb + 0.95 F1233zdE + 0.01 F1234zeE + 0.01 F1234zeZ + 0.01 F1243zf TOTAL PRESSURE bar | Organics 0.01 F1233xf + 0.01 F245cb + 0.01 F1233zdE + 0.95 F1234zeE + 0.01 F1234zeZ + 0.01 F1243zf TOTAL PRESSURE bar | Organics 0.01 F1233xf + 0.01 F245cb + 0.01 F1233zdE + 0.01 F1234zeE + 0.95 F1234zeZ + 0.01 F1243zf TOTAL PRESSURE bar | Organics 0.01 F1233xf + 0.01 F245cb + 0.01 F1233zdE + 0.01 F1234zeE + 0.01 F1234zeZ + 0.95 F1243zf TOTAL PRESSURE bar |
|---|---|---|---|---|---|---|---|
| 0 | 3.5 | 1.7 | 4.6 | 1.5 | 4.8 | 5.7 | 1.9 |
| 0.05 | 4.6 | 2.8 | 5.7 | 2.6 | 5.7 | 6.7 | 3.0 |
| 0.1 | 4.6 | 2.8 | 5.7 | 2.6 | 5.8 | 6.7 | 3.0 |
| 0.15 | 4.6 | 2.8 | 5.7 | 2.6 | 5.8 | 6.7 | 3.0 |
| 0.2 | 4.6 | 2.8 | 5.7 | 2.6 | 5.8 | 6.7 | 3.0 |
| 0.25 | 4.6 | 2.8 | 5.8 | 2.6 | 5.8 | 6.7 | 3.0 |
| 0.3 | 4.6 | 2.8 | 5.8 | 2.6 | 5.8 | 6.7 | 3.0 |
| 0.35 | 4.6 | 2.8 | 5.8 | 2.6 | 5.8 | 6.7 | 3.0 |
| 0.4 | 4.6 | 2.8 | 5.8 | 2.6 | 5.8 | 6.7 | 3.0 |
| 0.45 | 4.6 | 2.8 | 5.8 | 2.6 | 5.8 | 6.7 | 3.0 |
| 0.5 | 4.6 | 2.8 | 5.8 | 2.6 | 5.8 | 6.7 | 3.0 |
| 0.55 | 4.6 | 2.8 | 5.8 | 2.6 | 5.7 | 6.6 | 3.0 |
| 0.6 | 4.6 | 2.8 | 5.8 | 2.6 | 5.6 | 6.6 | 3.0 |
| 0.65 | 4.6 | 2.8 | 5.8 | 2.6 | 5.5 | 6.6 | 3.0 |
| 0.7 | 4.6 | 2.8 | 5.8 | 2.6 | 5.3 | 6.5 | 3.0 |
| 0.75 | 4.5 | 2.8 | 5.8 | 2.6 | 5.1 | 6.3 | 3.0 |
| 0.8 | 4.2 | 2.6 | 5.8 | 2.6 | 4.8 | 6.0 | 2.9 |
| 0.85 | 3.9 | 2.4 | 5.8 | 2.4 | 4.3 | 5.5 | 2.7 |
| 0.9 | 3.3 | 2.2 | 4.9 | 2.3 | 3.6 | 4.7 | 2.4 |
| 0.95 | 2.5 | 1.8 | 3.5 | 2.0 | 2.6 | 3.3 | 1.9 |
| 1 | 1.2 | 1.2 | 1.2 | 1.7 | 1.2 | 1.2 | 1.2 |

HF-HCFO-1233xf-HFO-1234yf-HFC-245cb-HCFO-1233zdE-HFO-1234zeE-HFO-1234zeZ

| MASSFRAC HF | Organics 0.01 F1233xf + 0.95 F1234yf + 0.01 F245cb + 0.01 F1233zdE + 0.01 F1234zeE + 0.01 F1234zeZ TOTAL PRESSURE bar | Organics 0.01 F1233xf + 0.01 F1234yf + 0.95 F245cb + 0.01 F1233zdE + 0.01 F1234zeE + 0.01 F1234zeZ TOTAL PRESSURE bar | Organics 0.01 F1233xf + 0.01 F1234yf + 0.01 F245cb + 0.95 F1233zdE + 0.01 F1234zeE + 0.01 F1234zeZ TOTAL PRESSURE bar | Organics 0.01 F1233xf + 0.01 F1234yf + 0.01 F245cb + 0.01 F1233zdE + 0.95 F1234zeE + 0.01 F1234zeZ TOTAL PRESSURE bar | Organics 0.95 F1233xf + 0.01 F1234yf + 0.01 F245cb + 0.01 F1233zdE + 0.01 F1234zeE + 0.01 F1234zeZ TOTAL PRESSURE bar | Organics 0.01 F1233xf + 0.01 F1234yf + 0.01 F245cb + 0.01 F1233zdE + 0.01 F1234zeE + 0.95 F1234zeZ TOTAL PRESSURE bar |
|---|---|---|---|---|---|---|
| 0 | 6.6 | 4.6 | 1.5 | 4.8 | 1.9 | 1.7 |
| 0.05 | 7.6 | 5.8 | 2.6 | 5.8 | 3.0 | 2.8 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|---|---|
| 0.1 | 4.7 | 0.1 | 7.6 | 0.1 | 5.8 | 0.1 | 2.6 | 0.1 | 5.8 | 0.1 | 3.0 | 0.1 | 2.8 |
| 0.15 | 4.7 | 0.15 | 7.6 | 0.15 | 5.8 | 0.15 | 2.6 | 0.15 | 5.8 | 0.15 | 3.0 | 0.15 | 2.8 |
| 0.2 | 4.7 | 0.2 | 7.6 | 0.2 | 5.8 | 0.2 | 2.6 | 0.2 | 5.8 | 0.2 | 3.0 | 0.2 | 2.8 |
| 0.25 | 4.7 | 0.25 | 7.6 | 0.25 | 5.8 | 0.25 | 2.6 | 0.25 | 5.8 | 0.25 | 3.0 | 0.25 | 2.8 |
| 0.3 | 4.7 | 0.3 | 7.6 | 0.3 | 5.8 | 0.3 | 2.6 | 0.3 | 5.8 | 0.3 | 3.0 | 0.3 | 2.8 |
| 0.35 | 4.7 | 0.35 | 7.6 | 0.35 | 5.8 | 0.35 | 2.6 | 0.35 | 5.8 | 0.35 | 3.0 | 0.35 | 2.8 |
| 0.4 | 4.7 | 0.4 | 7.6 | 0.4 | 5.8 | 0.4 | 2.6 | 0.4 | 5.8 | 0.4 | 3.0 | 0.4 | 2.8 |
| 0.45 | 4.7 | 0.45 | 7.6 | 0.45 | 5.8 | 0.45 | 2.6 | 0.45 | 5.8 | 0.45 | 3.0 | 0.45 | 2.8 |
| 0.5 | 4.7 | 0.5 | 7.6 | 0.5 | 5.8 | 0.5 | 2.6 | 0.5 | 5.7 | 0.5 | 3.0 | 0.5 | 2.8 |
| 0.55 | 4.7 | 0.55 | 7.6 | 0.55 | 5.8 | 0.55 | 2.6 | 0.55 | 5.7 | 0.55 | 3.0 | 0.55 | 2.8 |
| 0.6 | 4.7 | 0.6 | 7.6 | 0.6 | 5.8 | 0.6 | 2.6 | 0.6 | 5.6 | 0.6 | 3.0 | 0.6 | 2.8 |
| 0.65 | 4.7 | 0.65 | 7.6 | 0.65 | 5.8 | 0.65 | 2.6 | 0.65 | 5.5 | 0.65 | 3.0 | 0.65 | 2.8 |
| 0.7 | 4.7 | 0.7 | 7.6 | 0.7 | 5.8 | 0.7 | 2.6 | 0.7 | 5.3 | 0.7 | 3.0 | 0.7 | 2.8 |
| 0.75 | 4.6 | 0.75 | 7.4 | 0.75 | 5.8 | 0.75 | 2.6 | 0.75 | 5.1 | 0.75 | 3.0 | 0.75 | 2.8 |
| 0.8 | 4.4 | 0.8 | 7.1 | 0.8 | 5.8 | 0.8 | 2.5 | 0.8 | 4.8 | 0.8 | 3.0 | 0.8 | 2.8 |
| 0.85 | 4.1 | 0.85 | 6.5 | 0.85 | 5.8 | 0.85 | 2.3 | 0.85 | 4.3 | 0.85 | 2.9 | 0.85 | 2.6 |
| 0.9 | 3.5 | 0.9 | 5.5 | 0.9 | 5.0 | 0.9 | 2.0 | 0.9 | 3.6 | 0.9 | 2.7 | 0.9 | 2.5 |
| 0.95 | 2.5 | 0.95 | 3.8 | 0.95 | 3.5 | 0.95 | 1.7 | 0.95 | 2.6 | 0.95 | 2.4 | 0.95 | 2.2 |
| 1 | 1.2 | 1 | 1.2 | 1 | 1.2 | 1 | 1.2 | 1 | 1.2 | 1 | 1.9 | 1 | 1.8 |

Organics (by column):
- Col 1: 0.15 F1233xf + 0.17 F1234yf + 0.17 F245cb + 0.17 F1233zdE + 0.17 F1234zeE + 0.17 F1243zf
- Col 2: 0.01 F1233xf + 0.95 F1234yf + 0.01 F245cb + 0.01 F1233zdE + 0.01 F1234zeE + 0.01 F1243zf
- Col 3: 0.01 F1233xf + 0.01 F1234yf + 0.95 F245cb + 0.01 F1233zdE + 0.01 F1234zeE + 0.01 F1243zf
- Col 4: 0.01 F1233xf + 0.01 F1234yf + 0.01 F245cb + 0.95 F1233zdE + 0.01 F1234zeE + 0.01 F1243zf
- Col 5: 0.01 F1233xf + 0.01 F1234yf + 0.01 F245cb + 0.01 F1233zdE + 0.95 F1234zeE + 0.01 F1243zf
- Col 6: 0.01 F1233xf + 0.01 F1234yf + 0.01 F245cb + 0.01 F1233zdE + 0.01 F1234zeE + 0.01 F1243zf
- Col 7: 0.01 F1233xf + 0.01 F1234yf + 0.01 F245cb + 0.01 F1233zdE + 0.01 F1234zeE + 0.01 F1243zf HF-HCFO-1233xf-HFO-1234yf-HFC-245cb-HCFO-1233zdE-HFO-1234zeE-HFO-1243zf Organics (by column):
- Col 1: 0.01 F1233xf + 0.95 F1234yf + 0.01 F245cb + 0.01 F1233zdE + 0.01 F1234zeE + 0.01 F1243zf
- Col 2: 0.01 F1233xf + 0.01 F1234yf + 0.95 F245cb + 0.01 F1233zdE + 0.01 F1234zeE + 0.01 F1243zf
- Col 3: 0.01 F1233xf + 0.01 F1234yf + 0.01 F245cb + 0.95 F1233zdE + 0.01 F1234zeE + 0.01 F1243zf
- Col 4: 0.01 F1233xf + 0.01 F1234yf + 0.01 F245cb + 0.01 F1233zdE + 0.95 F1234zeE + 0.01 F1243zf
- Col 5: 0.01 F1233xf + 0.01 F1234yf + 0.01 F245cb + 0.01 F1233zdE + 0.01 F1234zeE + 0.95 F1243zf

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|
| 0 | 6.6 | 0 | 4.6 | 0 | 1.5 | 0 | 4.8 | 0 | 1.7 |
| 0.05 | 7.6 | 0.05 | 5.8 | 0.05 | 2.6 | 0.05 | 5.8 | 0.05 | 2.8 |
| 0.1 | 7.6 | 0.1 | 5.8 | 0.1 | 2.6 | 0.1 | 5.8 | 0.1 | 2.8 |
| 0.15 | 7.6 | 0.15 | 5.8 | 0.15 | 2.6 | 0.15 | 5.8 | 0.15 | 2.8 |
| 0.2 | 7.6 | 0.2 | 5.8 | 0.2 | 2.6 | 0.2 | 5.8 | 0.2 | 2.8 |
| 0.25 | 7.6 | 0.25 | 5.8 | 0.25 | 2.6 | 0.25 | 5.8 | 0.25 | 2.8 |
| 0.3 | 7.6 | 0.3 | 5.8 | 0.3 | 2.6 | 0.3 | 5.8 | 0.3 | 2.8 |
| 0.35 | 7.6 | 0.35 | 5.8 | 0.35 | 2.6 | 0.35 | 5.8 | 0.35 | 2.8 |
| 0.4 | 7.6 | 0.4 | 5.8 | 0.4 | 2.6 | 0.4 | 5.8 | 0.4 | 2.8 |
| 0.45 | 7.6 | 0.45 | 5.8 | 0.45 | 2.6 | 0.45 | 5.8 | 0.45 | 2.8 |
| 0.5 | 7.6 | 0.5 | 5.8 | 0.5 | 2.6 | 0.5 | 5.8 | 0.5 | 2.8 |
| 0.55 | 7.6 | 0.55 | 5.8 | 0.55 | 2.6 | 0.55 | 5.7 | 0.55 | 2.8 |
| 0.6 | 7.6 | 0.6 | 5.8 | 0.6 | 2.6 | 0.6 | 5.6 | 0.6 | 2.8 |
| 0.65 | 7.6 | 0.65 | 5.8 | 0.65 | 2.6 | 0.65 | 5.5 | 0.65 | 2.8 |
| 0.7 | 7.6 | 0.7 | 5.8 | 0.7 | 2.6 | 0.7 | 5.4 | 0.7 | 2.8 |
| 0.75 | 7.4 | 0.75 | 5.8 | 0.75 | 2.6 | 0.75 | 5.1 | 0.75 | 2.8 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|---|---|
| 0.8 | 5.0 | 0.8 | 7.1 | 0.8 | 5.8 | 0.8 | 2.5 | 0.8 | 4.8 | 0.8 | 6.1 | 0.8 | 2.7 |
| 0.85 | 4.6 | 0.85 | 6.5 | 0.85 | 5.8 | 0.85 | 2.3 | 0.85 | 4.3 | 0.85 | 5.6 | 0.85 | 2.5 |
| 0.9 | 3.9 | 0.9 | 5.5 | 0.9 | 5.0 | 0.9 | 2.1 | 0.9 | 3.6 | 0.9 | 4.7 | 0.9 | 2.2 |
| 0.95 | 2.8 | 0.95 | 3.8 | 0.95 | 3.5 | 0.95 | 1.7 | 0.95 | 2.6 | 0.95 | 3.4 | 0.95 | 1.8 |
| 1 | 1.2 | 1 | 1.2 | 1 | 1.2 | 1 | 1.2 | 1 | 1.2 | 1 | 1.2 | 1 | 1.2 |

Organics
0.15 F1233xf + 0.17 F1234yf + 0.17 F245cb + 0.17 F1243zf + 0.17 F1233zdE + 0.17 F1234zeZ Organics
0.01 F1233xf + 0.95 F1234yf + 0.01 F245cb + 0.01 F1243zf + 0.01 F1233zdE + 0.01 F1234zeZ Organics
0.01 F1233xf + 0.01 F1234yf + 0.95 F245cb + 0.01 F1243zf + 0.01 F1233zdE + 0.01 F1234zeZ Organics
0.01 F1233xf + 0.01 F1234yf + 0.01 F245cb + 0.95 F1243zf + 0.01 F1233zdE + 0.01 F1234zeZ Organics
0.01 F1233xf + 0.01 F1234yf + 0.01 F245cb + 0.01 F1243zf + 0.95 F1233zdE + 0.01 F1234zeZ Organics
0.01 F1233xf + 0.01 F1234yf + 0.01 F245cb + 0.01 F1243zf + 0.01 F1233zdE + 0.95 F1234zeZ Organics
0.95 F1233xf + 0.01 F1234yf + 0.01 F245cb + 0.01 F1243zf + 0.01 F1233zdE + 0.01 F1234zeZ HF-HCFO-1233xf-HFO-1234yf-HFC-245cb-HCFO-1233zdE-HFO-1234zeZ

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|---|---|
| 0 | 3.8 | 0 | 6.6 | 0 | 4.6 | 0 | 5.7 | 0 | 1.5 | 0 | 1.9 | 0 | 1.7 |
| 0.05 | 4.9 | 0.05 | 7.6 | 0.05 | 5.8 | 0.05 | 6.7 | 0.05 | 2.6 | 0.05 | 3.0 | 0.05 | 2.8 |
| 0.1 | 4.9 | 0.1 | 7.6 | 0.1 | 5.8 | 0.1 | 6.7 | 0.1 | 2.6 | 0.1 | 3.0 | 0.1 | 2.8 |
| 0.15 | 4.9 | 0.15 | 7.6 | 0.15 | 5.8 | 0.15 | 6.7 | 0.15 | 2.6 | 0.15 | 3.0 | 0.15 | 2.8 |
| 0.2 | 4.9 | 0.2 | 7.6 | 0.2 | 5.8 | 0.2 | 6.7 | 0.2 | 2.6 | 0.2 | 3.0 | 0.2 | 2.8 |
| 0.25 | 4.9 | 0.25 | 7.6 | 0.25 | 5.8 | 0.25 | 6.7 | 0.25 | 2.6 | 0.25 | 3.0 | 0.25 | 2.8 |
| 0.3 | 4.9 | 0.3 | 7.6 | 0.3 | 5.8 | 0.3 | 6.7 | 0.3 | 2.6 | 0.3 | 3.0 | 0.3 | 2.8 |
| 0.35 | 4.9 | 0.35 | 7.6 | 0.35 | 5.8 | 0.35 | 6.7 | 0.35 | 2.6 | 0.35 | 3.0 | 0.35 | 2.8 |
| 0.4 | 4.9 | 0.4 | 7.6 | 0.4 | 5.8 | 0.4 | 6.7 | 0.4 | 2.6 | 0.4 | 3.0 | 0.4 | 2.8 |
| 0.45 | 4.9 | 0.45 | 7.6 | 0.45 | 5.8 | 0.45 | 6.7 | 0.45 | 2.6 | 0.45 | 3.0 | 0.45 | 2.8 |
| 0.5 | 4.9 | 0.5 | 7.6 | 0.5 | 5.8 | 0.5 | 6.7 | 0.5 | 2.6 | 0.5 | 3.0 | 0.5 | 2.8 |
| 0.55 | 4.9 | 0.55 | 7.6 | 0.55 | 5.8 | 0.55 | 6.7 | 0.55 | 2.6 | 0.55 | 3.0 | 0.55 | 2.8 |
| 0.6 | 4.9 | 0.6 | 7.6 | 0.6 | 5.8 | 0.6 | 6.6 | 0.6 | 2.6 | 0.6 | 3.0 | 0.6 | 2.8 |
| 0.65 | 4.9 | 0.65 | 7.6 | 0.65 | 5.8 | 0.65 | 6.6 | 0.65 | 2.6 | 0.65 | 3.0 | 0.65 | 2.8 |
| 0.7 | 4.9 | 0.7 | 7.6 | 0.7 | 5.8 | 0.7 | 6.5 | 0.7 | 2.6 | 0.7 | 3.0 | 0.7 | 2.8 |
| 0.75 | 4.9 | 0.75 | 7.4 | 0.75 | 5.8 | 0.75 | 6.3 | 0.75 | 2.6 | 0.75 | 3.0 | 0.75 | 2.8 |
| 0.8 | 4.7 | 0.8 | 7.1 | 0.8 | 5.8 | 0.8 | 6.0 | 0.8 | 2.5 | 0.8 | 2.9 | 0.8 | 2.7 |
| 0.85 | 4.3 | 0.85 | 6.5 | 0.85 | 5.8 | 0.85 | 5.5 | 0.85 | 2.3 | 0.85 | 2.7 | 0.85 | 2.5 |
| 0.9 | 3.7 | 0.9 | 5.5 | 0.9 | 5.0 | 0.9 | 4.7 | 0.9 | 2.0 | 0.9 | 2.4 | 0.9 | 2.2 |
| 0.95 | 2.7 | 0.95 | 3.8 | 0.95 | 3.5 | 0.95 | 3.3 | 0.95 | 1.7 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

-continued

| MASSFRAC HF | Organics 0.15 F1233xf + 0.17 F1234yf + 0.17 F245cb + 0.17 F1243zf + 0.17 F1234zeE + 0.17 F1234zeZ | TOTAL PRESSURE bar | MASSFRAC HF | Organics 0.01 F1233xf + 0.95 F1234yf + 0.01 F1233zdE + 0.01 F1243zf + 0.01 F1234zeE + 0.01 F1234zeZ | TOTAL PRESSURE bar | MASSFRAC HF | Organics 0.15 F1233xf + 0.17 F1234yf + 0.17 F245cb + 0.17 F1243zf + 0.17 F1234zeE + 0.17 F1233zfZ | TOTAL PRESSURE bar | MASSFRAC HF | Organics 0.01 F1233xf + 0.01 F1234yf + 0.95 F245cb + 0.01 F1243zf + 0.01 F1234zeE + 0.01 F1234zeZ | TOTAL PRESSURE bar | MASSFRAC HF | Organics 0.01 F1233xf + 0.01 F1234yf + 0.01 F245cb + 0.95 F1243zf + 0.01 F1234zeE + 0.01 F1234zeZ | TOTAL PRESSURE bar | MASSFRAC HF | Organics 0.95 F1233xf + 0.01 F1234yf + 0.01 F245cb + 0.01 F1243zf + 0.01 F1234zeE + 0.01 F1234zeZ | TOTAL PRESSURE bar |
|---|---|---|---|---|---|---|---|---|---|---|---|---|---|---|---|---|---|
| 0 | | 4.4 | 0 | | 6.6 | 0 | | 4.6 | 0 | | 5.8 | 0 | | 4.8 | 0 | | 1.7 |
| 0.05 | | 5.5 | 0.05 | | 7.6 | 0.05 | | 5.8 | 0.05 | | 6.7 | 0.05 | | 5.8 | 0.05 | | 2.8 |
| 0.1 | | 5.5 | 0.1 | | 7.6 | 0.1 | | 5.8 | 0.1 | | 6.7 | 0.1 | | 5.8 | 0.1 | | 2.8 |
| 0.15 | | 5.5 | 0.15 | | 7.6 | 0.15 | | 5.8 | 0.15 | | 6.7 | 0.15 | | 5.8 | 0.15 | | 2.8 |
| 0.2 | | 5.5 | 0.2 | | 7.6 | 0.2 | | 5.8 | 0.2 | | 6.7 | 0.2 | | 5.8 | 0.2 | | 2.8 |
| 0.25 | | 5.5 | 0.25 | | 7.6 | 0.25 | | 5.8 | 0.25 | | 6.7 | 0.25 | | 5.8 | 0.25 | | 2.8 |
| 0.3 | | 5.5 | 0.3 | | 7.6 | 0.3 | | 5.8 | 0.3 | | 6.7 | 0.3 | | 5.8 | 0.3 | | 2.8 |
| 0.35 | | 5.5 | 0.35 | | 7.6 | 0.35 | | 5.8 | 0.35 | | 6.7 | 0.35 | | 5.8 | 0.35 | | 2.8 |
| 0.4 | | 5.5 | 0.4 | | 7.6 | 0.4 | | 5.8 | 0.4 | | 6.7 | 0.4 | | 5.8 | 0.4 | | 2.8 |
| 0.45 | | 5.5 | 0.45 | | 7.6 | 0.45 | | 5.8 | 0.45 | | 6.7 | 0.45 | | 5.8 | 0.45 | | 2.8 |
| 0.5 | | 5.5 | 0.5 | | 7.6 | 0.5 | | 5.8 | 0.5 | | 6.7 | 0.5 | | 5.8 | 0.5 | | 2.8 |
| 0.55 | | 5.5 | 0.55 | | 7.6 | 0.55 | | 5.8 | 0.55 | | 6.7 | 0.55 | | 5.7 | 0.55 | | 2.8 |
| 0.6 | | 5.5 | 0.6 | | 7.6 | 0.6 | | 5.8 | 0.6 | | 6.7 | 0.6 | | 5.6 | 0.6 | | 2.8 |
| 0.65 | | 5.5 | 0.65 | | 7.6 | 0.65 | | 5.8 | 0.65 | | 6.6 | 0.65 | | 5.5 | 0.65 | | 2.8 |
| 0.7 | | 5.5 | 0.7 | | 7.6 | 0.7 | | 5.8 | 0.7 | | 6.5 | 0.7 | | 5.4 | 0.7 | | 2.8 |
| 0.75 | | 5.3 | 0.75 | | 7.4 | 0.75 | | 5.8 | 0.75 | | 6.3 | 0.75 | | 5.1 | 0.75 | | 2.8 |
| 0.8 | | 5.1 | 0.8 | | 7.1 | 0.8 | | 5.8 | 0.8 | | 6.1 | 0.8 | | 4.8 | 0.8 | | 2.8 |
| 0.85 | | 4.6 | 0.85 | | 6.5 | 0.85 | | 5.8 | 0.85 | | 5.6 | 0.85 | | 4.3 | 0.85 | | 2.7 |
| 0.9 | | 3.9 | 0.9 | | 5.5 | 0.9 | | 5.0 | 0.9 | | 4.7 | 0.9 | | 3.6 | 0.9 | | 2.5 |
| 0.95 | | 2.8 | 0.95 | | 3.8 | 0.95 | | 3.5 | 0.95 | | 3.4 | 0.95 | | 2.6 | 0.95 | | 1.8 |
| 1 | | 1.2 | 1 | | 1.2 | 1 | | 1.2 | 1 | | 1.2 | 1 | | 1.2 | 1 | | 1.2 |

| MASSFRAC HF | Organics 0.15 F1233xf + 0.95 F1234yf + 0.01 F1233zdE + 0.01 F1243zf + 0.01 F1234zeE + 0.01 F1234zeZ | TOTAL PRESSURE bar | MASSFRAC HF | Organics 0.01 F1233xf + 0.01 F1234yf + 0.95 F1233zdE + 0.01 F1243zf + 0.01 F1234zeE + 0.01 F1234zeZ | TOTAL PRESSURE bar | MASSFRAC HF | Organics 0.01 F1233xf + 0.01 F1234yf + 0.01 F1233zdE + 0.95 F1243zf + 0.01 F1234zeE + 0.01 F1234zeZ | TOTAL PRESSURE bar | MASSFRAC HF | Organics 0.01 F1233xf + 0.01 F1234yf + 0.01 F1233zdE + 0.01 F1243zf + 0.95 F1234zeE + 0.01 F1234zeZ-HFO-1243zf | TOTAL PRESSURE bar | MASSFRAC HF | Organics 0.95 F1233xf + 0.01 F1234yf + 0.01 F1233zdE + 0.01 F1243zf + 0.01 F1234zeE + 0.01 F1234zeZ | TOTAL PRESSURE bar |
|---|---|---|---|---|---|---|---|---|---|---|---|---|---|---|
| 0 | | 3.9 | 0 | | 1.5 | 0 | | 5.7 | 0 | | 4.8 | 0 | | 1.7 |
| 0.05 | | 5.0 | 0.05 | | 2.6 | 0.05 | | 6.7 | 0.05 | | 5.8 | 0.05 | | 2.8 |
| 0.1 | | 4.9 | 0.1 | | 2.6 | 0.1 | | 6.7 | 0.1 | | 5.8 | 0.1 | | 2.8 |

-continued

Organics: 0.15 F1234yf + 0.17 F245cb + 0.17 F1233zdE + 0.17 F1234zeE + 0.17 F1234zeZ + 0.17 F1243zf

| MASSFRAC HF | TOTAL PRESSURE bar |
|---|---|
| 0.15 | 4.9 |
| 0.2 | 4.9 |
| 0.25 | 4.9 |
| 0.3 | 4.9 |
| 0.35 | 4.9 |
| 0.4 | 4.9 |
| 0.45 | 4.9 |
| 0.5 | 4.9 |
| 0.55 | 4.9 |
| 0.6 | 4.9 |
| 0.65 | 4.9 |
| 0.7 | 4.8 |
| 0.75 | 4.7 |
| 0.8 | 4.4 |
| 0.85 | 4.0 |
| 0.9 | 3.4 |
| 0.95 | 2.5 |
| 1 | 1.2 |

Organics: 0.95 F1234yf + 0.01 F245cb + 0.01 F1233zdE + 0.01 F1234zeE + 0.01 F1234zeZ + 0.01 F1243zf

| MASSFRAC HF | TOTAL PRESSURE bar |
|---|---|
| 0.15 | 7.6 |
| 0.2 | 7.6 |
| 0.25 | 7.6 |
| 0.3 | 7.6 |
| 0.35 | 7.6 |
| 0.4 | 7.6 |
| 0.45 | 7.6 |
| 0.5 | 7.6 |
| 0.55 | 7.6 |
| 0.6 | 7.6 |
| 0.65 | 7.6 |
| 0.7 | 7.6 |
| 0.75 | 7.4 |
| 0.8 | 7.1 |
| 0.85 | 6.5 |
| 0.9 | 5.5 |
| 0.95 | 3.8 |
| 1 | 1.2 |

Organics: 0.01 F1234yf + 0.95 F245cb + 0.01 F1233zdE + 0.01 F1234zeE + 0.01 F1234zeZ + 0.01 F1243zf

| MASSFRAC HF | TOTAL PRESSURE bar |
|---|---|
| 0.15 | 2.6 |
| 0.2 | 2.6 |
| 0.25 | 2.6 |
| 0.3 | 2.6 |
| 0.35 | 2.6 |
| 0.4 | 2.6 |
| 0.45 | 2.6 |
| 0.5 | 2.6 |
| 0.55 | 2.6 |
| 0.6 | 2.6 |
| 0.65 | 2.6 |
| 0.7 | 2.6 |
| 0.75 | 2.6 |
| 0.8 | 2.5 |
| 0.85 | 2.3 |
| 0.9 | 2.0 |
| 0.95 | 1.7 |
| 1 | 1.2 |

Organics: 0.01 F1234yf + 0.01 F245cb + 0.01 F1233zdE + 0.01 F1234zeE + 0.01 F1234zeZ + 0.95 F1243zf

| MASSFRAC HF | TOTAL PRESSURE bar |
|---|---|
| 0.15 | 2.8 |
| 0.2 | 2.8 |
| 0.25 | 2.8 |
| 0.3 | 2.8 |
| 0.35 | 2.8 |
| 0.4 | 2.8 |
| 0.45 | 2.8 |
| 0.5 | 2.8 |
| 0.55 | 2.8 |
| 0.6 | 2.8 |
| 0.65 | 2.8 |
| 0.7 | 2.8 |
| 0.75 | 2.8 |
| 0.8 | 2.6 |
| 0.85 | 2.5 |
| 0.9 | 2.2 |
| 0.95 | 1.8 |
| 1 | 1.2 |

HF-HFO-1234yf-HFC-245cb-HCFO-1233zdE-HFO-1234zeE-HFO-1234zeZ-HFO-1243zf

Organics: 0.01 F1234yf + 0.95 F245cb + 0.01 F1233zdE + 0.01 F1234zeE + 0.01 F1234zeZ + 0.01 F1243zf

| MASSFRAC HF | TOTAL PRESSURE bar |
|---|---|
| 0 | 4.6 |
| 0.05 | 5.8 |
| 0.1 | 5.8 |
| 0.15 | 5.8 |
| 0.2 | 5.8 |
| 0.25 | 5.8 |
| 0.3 | 5.8 |
| 0.35 | 5.8 |
| 0.4 | 5.8 |
| 0.45 | 5.8 |
| 0.5 | 5.8 |
| 0.55 | 5.8 |
| 0.6 | 5.8 |
| 0.65 | 5.8 |
| 0.7 | 5.8 |
| 0.75 | 5.8 |
| 0.8 | 5.8 |
| 0.85 | 5.8 |
| 0.9 | 5.0 |

Organics: 0.01 F1234yf + 0.01 F245cb + 0.95 F1233zdE + 0.01 F1234zeE + 0.01 F1234zeZ + 0.01 F1243zf

| MASSFRAC HF | TOTAL PRESSURE bar |
|---|---|
| 0 | 1.5 |
| 0.05 | 2.6 |
| 0.1 | 2.6 |
| 0.15 | 2.6 |
| 0.2 | 2.6 |
| 0.25 | 2.6 |
| 0.3 | 2.6 |
| 0.35 | 2.6 |
| 0.4 | 2.6 |
| 0.45 | 2.6 |
| 0.5 | 2.6 |
| 0.55 | 2.6 |
| 0.6 | 2.6 |
| 0.65 | 2.6 |
| 0.7 | 2.6 |
| 0.75 | 2.6 |
| 0.8 | 2.5 |
| 0.85 | 2.3 |
| 0.9 | 2.1 |

Organics: 0.01 F1234yf + 0.01 F245cb + 0.01 F1233zdE + 0.95 F1234zeE + 0.01 F1234zeZ + 0.01 F1243zf

| MASSFRAC HF | TOTAL PRESSURE bar |
|---|---|
| 0 | 4.8 |
| 0.05 | 5.8 |
| 0.1 | 5.8 |
| 0.15 | 5.8 |
| 0.2 | 5.8 |
| 0.25 | 5.8 |
| 0.3 | 5.8 |
| 0.35 | 5.8 |
| 0.4 | 5.8 |
| 0.45 | 5.8 |
| 0.5 | 5.8 |
| 0.55 | 5.8 |
| 0.6 | 5.7 |
| 0.65 | 5.6 |
| 0.7 | 5.5 |
| 0.75 | 5.4 |
| 0.8 | 5.1 |
| 0.85 | 4.8 |
| 0.9 | 4.3 |
| | 3.6 |

Organics: 0.01 F1234yf + 0.01 F245cb + 0.01 F1233zdE + 0.01 F1234zeE + 0.95 F1234zeZ + 0.01 F1243zf

| MASSFRAC HF | TOTAL PRESSURE bar |
|---|---|
| 0 | 5.8 |
| 0.05 | 6.7 |
| 0.1 | 6.7 |
| 0.15 | 6.7 |
| 0.2 | 6.7 |
| 0.25 | 6.7 |
| 0.3 | 6.7 |
| 0.35 | 6.7 |
| 0.4 | 6.7 |
| 0.45 | 6.7 |
| 0.5 | 6.7 |
| 0.55 | 6.7 |
| 0.6 | 6.6 |
| 0.65 | 6.5 |
| 0.7 | 6.3 |
| 0.75 | 6.1 |
| 0.8 | 5.6 |
| 0.85 | 4.7 |
| 0.9 | |

Organics: 0.01 F1234yf + 0.01 F245cb + 0.01 F1233zdE + 0.01 F1234zeE + 0.01 F1234zeZ + 0.95 F1243zf

| MASSFRAC HF | TOTAL PRESSURE bar |
|---|---|
| 0 | 2.0 |
| 0.05 | 3.1 |
| 0.1 | 3.1 |
| 0.15 | 3.1 |
| 0.2 | 3.1 |
| 0.25 | 3.1 |
| 0.3 | 3.1 |
| 0.35 | 3.1 |
| 0.4 | 3.1 |
| 0.45 | 3.1 |
| 0.5 | 3.1 |
| 0.55 | 3.1 |
| 0.6 | 3.1 |
| 0.65 | 3.1 |
| 0.7 | 3.1 |
| 0.75 | 3.1 |
| 0.8 | 2.9 |
| 0.85 | 2.7 |
| 0.9 | 2.4 |

| MASSFRAC HF | Organics 0.15 F1234zeE + 0.17 F244bb + 0.17 F245fa + 0.17TFP + 0.17 F1225yeZ + 0.17 F1225ac TOTAL PRESSURE bar | 0.95 1 | Organics 0.95 F1234zeZ + 0.01 F244bb + 0.01 F245fa + 0.01 TFP + 0.01 F1225yeZ + 0.01 F1225ac TOTAL PRESSURE bar | 0.95 1 | Organics 0.01 F1234zeE + 0.95 F244bb + 0.01 F245fa + 0.01 TFP + 0.01 F1225yeZ + 0.01 F1225zc TOTAL PRESSURE bar | 0.95 1 | Organics 0.01 F1234zeE + 0.01 F244bb + 0.95 F245fa + 0.01 TFP + 0.01 F1225yeZ + 0.01 F1225zc TOTAL PRESSURE bar | 0.95 1 | Organics 0.01 F1234zeE + 0.01 F244bb + 0.01 F245fa + 0.95 TFP + 0.01 F1225yeZ + 0.01 F1225zc TOTAL PRESSURE bar | 0.95 1 | Organics 0.01 F1234zeE + 0.01 F244bb + 0.01 F245fa + 0.01 TFP + 0.95 F1225yeZ + 0.01 F1225zc TOTAL PRESSURE bar |
|---|---|---|---|---|---|---|---|---|---|---|---|
| | 2.8 1.2 | 0.95 1 | 3.8 1.2 | 0.95 1 | 3.5 1.2 | 0.95 1 | 1.7 1.2 | 0.95 1 | 2.6 1.2 | 0.95 1 | 3.4 1.2 | 0.95 1 | 1.9 1.2 |

HF-HFO-1234zeE-HCFC-244bb-HFC-245fa-Trifluoropropyne-HFO-1225yeZ-HFO-1225zc

| MASSFRAC HF | PRESSURE bar | PRESSURE bar | PRESSURE bar | PRESSURE bar | PRESSURE bar | PRESSURE bar |
|---|---|---|---|---|---|---|
| 0 | 5.3 | 4.9 | 1.0 | 1.8 | 5.2 | 5.3 |
| 0.05 | 6.3 | 5.8 | 2.1 | 2.9 | 6.2 | 6.3 |
| 0.1 | 6.3 | 5.9 | 2.1 | 2.9 | 6.2 | 6.3 |
| 0.15 | 6.3 | 5.9 | 2.1 | 2.9 | 6.2 | 6.3 |
| 0.2 | 6.3 | 5.9 | 2.1 | 2.9 | 6.2 | 6.3 |
| 0.25 | 6.3 | 5.9 | 2.1 | 2.9 | 6.2 | 6.3 |
| 0.3 | 6.3 | 5.9 | 2.1 | 2.9 | 6.2 | 6.3 |
| 0.35 | 6.3 | 5.9 | 2.1 | 2.9 | 6.2 | 6.3 |
| 0.4 | 6.2 | 5.9 | 2.1 | 2.9 | 6.2 | 6.3 |
| 0.45 | 6.2 | 5.8 | 2.1 | 2.9 | 6.2 | 6.3 |
| 0.5 | 6.2 | 5.8 | 2.1 | 2.9 | 6.2 | 6.3 |
| 0.55 | 6.2 | 5.8 | 2.1 | 2.9 | 6.2 | 6.2 |
| 0.6 | 6.1 | 5.7 | 2.1 | 2.9 | 6.2 | 6.2 |
| 0.65 | 6.1 | 5.6 | 2.1 | 2.8 | 6.2 | 6.1 |
| 0.7 | 6.0 | 5.4 | 2.1 | 2.8 | 6.1 | 6.0 |
| 0.75 | 5.8 | 5.2 | 2.0 | 2.8 | 5.9 | 5.9 |
| 0.8 | 5.5 | 4.8 | 2.0 | 2.7 | 5.6 | 5.6 |
| 0.85 | 5.0 | 4.3 | 2.0 | 2.5 | 5.1 | 5.2 |
| 0.9 | 4.2 | 3.6 | 1.9 | 2.2 | 4.2 | 4.7 |
| 0.95 | 3.0 | 2.6 | 1.6 | 1.8 | 3.0 | 3.8 |
| 1 | 1.2 | 1.2 | 1.2 | 1.2 | 1.2 | 2.7 |
| | | | | | | 1.2 |

HF-HFO-1234zeZ-HCFC-244bb-HFC-245fa-Trifluoropropyne-HFO-1225yeZ-HFO-1225zc

| MASSFRAC HF | PRESSURE bar | PRESSURE bar | PRESSURE bar | PRESSURE bar | PRESSURE bar | PRESSURE bar |
|---|---|---|---|---|---|---|
| 0 | 4.8 | 2.0 | 0.9 | 1.7 | 5.1 | 5.3 |
| 0.05 | 5.9 | 3.1 | 2.1 | 2.8 | 6.2 | 6.2 |

-continued

| | | | | | | |
|---|---|---|---|---|---|---|
| 0.1 | 5.9 | 3.1 | 2.1 | 2.8 | 12.0 | 6.2 | 6.3 |
| 0.15 | 5.9 | 3.1 | 2.1 | 2.8 | 11.9 | 6.2 | 6.3 |
| 0.2 | 5.8 | 3.1 | 2.1 | 2.8 | 11.8 | 6.2 | 6.3 |
| 0.25 | 5.8 | 3.1 | 2.1 | 2.8 | 11.7 | 6.2 | 6.2 |
| 0.3 | 5.8 | 3.1 | 2.1 | 2.8 | 11.6 | 6.2 | 6.2 |
| 0.35 | 5.8 | 3.1 | 2.1 | 2.8 | 11.5 | 6.2 | 6.2 |
| 0.4 | 5.8 | 3.1 | 2.1 | 2.8 | 11.4 | 6.2 | 6.2 |
| 0.45 | 5.8 | 3.1 | 2.1 | 2.8 | 11.4 | 6.2 | 6.2 |
| 0.5 | 5.8 | 3.1 | 2.0 | 2.8 | 11.5 | 6.2 | 6.2 |
| 0.55 | 5.7 | 3.1 | 2.0 | 2.8 | 11.5 | 6.2 | 6.2 |
| 0.6 | 5.7 | 3.1 | 2.0 | 2.8 | 11.5 | 6.2 | 6.1 |
| 0.65 | 5.6 | 3.1 | 2.0 | 2.8 | 11.5 | 6.2 | 6.0 |
| 0.7 | 5.6 | 3.1 | 2.0 | 2.8 | 11.5 | 6.1 | 5.8 |
| 0.75 | 5.5 | 3.1 | 2.0 | 2.8 | 11.5 | 5.9 | 5.6 |
| 0.8 | 5.2 | 2.9 | 2.0 | 2.7 | 11.3 | 5.6 | 5.2 |
| 0.85 | 4.7 | 2.7 | 2.0 | 2.5 | 10.5 | 5.0 | 4.6 |
| 0.9 | 4.0 | 2.4 | 1.9 | 2.2 | 8.9 | 4.2 | 3.8 |
| 0.95 | 2.8 | 1.9 | 1.6 | 1.8 | 6.0 | 3.0 | 2.7 |
| 1 | 1.2 | 1.2 | 1.2 | 1.2 | 1.2 | 1.2 | 1.2 |

EXAMPLE 14

Temperature and Pressure Range of System with 7 Compounds

| System with 7 compounds | Boiling point range | |
|---|---|---|
| | Temp. ° C. | Pressure bar abs |
| HF-HCFO-1233xf-HFO-1234yf-HFC-245cb-HCFO-1233zdE-HFO-1234zeE-HFO-1234zeZ | 0 to 40 | ~0.9 ~ 11.5 |
| HF-HCFO-1233xf-HFO-1234yf-HFC-245cb-HCFO-1233zdE-HFO-1234zeE-HFO-1243zf | 0 to 40 | ~1.0 to ~11.6 |
| HF-HCFO-1233xf-HFO-1234yf-HFC-245cb-HCFO-1233zdE-HFO-1234zeZ-HFO-1243zf | 0 to 40 | ~0.9 to ~11.5 |
| HF-HCFO-1233xf-HFO-1234yf-HFC-245cb-HFO-1234zeE-HFO-1234zeZ-HFO-1243zf | 0 to 40 | ~1.1 to ~11.6 |
| HF-HCFO-1233xf-HFO-1234yf-HCFO-1233zdE-HFO-1234zeE-HFO-1234zeZ-HFO-1243zf | 0 to 40 | ~0.9 to ~11.5 |
| HF-HCFO-1233xf-HFC-245cb-HCFO-1233zdE-HFO-1234zeE-HFO-1234zeZ-HFO-1243zf | 0 to 40 | ~0.9 to ~10.3 |
| HF-HFO-1234yf-HFC-245cb-HCFO-1233zdE-HFO-1234zeE-HFO-1234zeZ-HFO-1243zf | 0 to 40 | ~1.0 to ~11.6 |
| HF-HFO-1234zeE-HCFC-244bb-HFC-245fa-Trifluoropropyne-HFO-1225yeZ-HFO-1225zc | 0 to 40 | ~0.7 to ~17.5 |
| HF-HFO-1234zeZ-HCFC-244bb-HFC-245fa-Trifluoropropyne-HFO-1225yeZ-HFO-1225zc | 0 to 40 | ~0.7 to ~17.5 |

EXAMPLE 15

Decantation Range of System with 7 Compounds

| System with 7 compounds | Decantation ranges Mass percentage of HF | | |
|---|---|---|---|
| | Temp 0° C. | Temp 25° C. | Temp 40° C. |
| HF-HCFO-1233xf-HFO-1234yf-HFC-245cb-HCFO-1233zdE-HFO-1234zeE-HFO-1234zeZ | 5-75 | 5-70 | 10-60 |
| HF-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeZ-HFO-1243zf | 5-70 | 5-70 | 10-60 |
| HF-HCFO-1233xf-HFO-1234yf-HFC-245cb-HFO-1234zeE-HFO-1234zeZ-HFO-1243zf | 5-75 | 10-65 | * |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HCFO-1233xf-HFC-245cb-HCFO-1233zdE-HFO-1234zeE-HFO-1234zeZ-HFO-1243zf | 5-75 | 5-70 | 10-55 |
| HF-HFO-1234yf-HFC-245cb-HCFO-1233zdE-HFO-1234zeE-HFO-1234zeZ-HFO-1243zf | 5-75 | 10-65 | * |
| HF-HFO-1234zeE-HCFC-244bb-HFC-245fa-Trifluoropropyne-HFO-1225yeZ-HFO-1225zc | 5-75 | 10-70 | * |
| HF-HFO-1234zeZ-HCFC-244bb-HFC-245fa-Trifluoropropyne-HFO-1225yeZ-HFO-1225zc | 5-75 | 5-70 | 10-60 |

EXAMPLE 16

Systems with 8 Compounds

HF-HCFO-1233xf-HFO-1234yf-HFC-245cb-HCFO-1233zdE-HFO-1234zeE-HFO-1234zeZ-HFO-1243zf

| MASSFRAC HF | Organics: 0.01 F1233xf + 0.94 F1234yf + 0.01 F245cb + 0.01 F1233zdE + 0.01 F1234zeE + 0.01 F1234zeZ + 0.01 F1243zf — TOTAL PRESSURE bar | Organics: 0.01 F1233xf + 0.01 F1234yf + 0.94 F245cb + 0.01 F1233zdE + 0.01 F1234zeE + 0.01 F1234zeZ + 0.01 F1243zf — TOTAL PRESSURE bar | Organics: 0.01 F1233xf + 0.01 F1234yf + 0.01 F245cb + 0.94 F1233zdE + 0.01 F1234zeE + 0.01 F1234zeZ + 0.01 F1243zf — TOTAL PRESSURE bar | Organics: 0.01 F1233xf + 0.01 F1234yf + 0.01F 245cb + 0.01 F1233zdE + 0.01 F1234zeE + 0.94 F1234zeZ + 0.01 F1243zf — TOTAL PRESSURE bar | Organics: 0.01 F1233xf + 0.01 F1234yf + 0.01 F245cb + 0.01 F1233zdE + 0.01 F1234zeE + 0.01 F1234zeZ + 0.94 F1243zf — TOTAL PRESSURE bar | Organics: 0.16 F1233xf + 0.14 F1234yf + 0.14 F245cb + 0.14 F1233zdE + 0.14 F1234zeE + 0.14 F1234zeZ + 0.14 F1243zf — TOTAL PRESSURE bar |
|---|---|---|---|---|---|---|
| 0 | 6.6 | 1.5 | 4.8 | 2.0 | 5.7 | 3.9 |
| 0.05 | 7.6 | 2.6 | 5.8 | 3.1 | 6.7 | 5.0 |
| 0.1 | 7.6 | 2.6 | 5.8 | 3.1 | 6.7 | 5.0 |
| 0.15 | 7.6 | 2.6 | 5.8 | 3.1 | 6.7 | 5.0 |
| 0.2 | 7.6 | 2.6 | 5.8 | 3.1 | 6.7 | 5.0 |
| 0.25 | 7.6 | 2.6 | 5.8 | 3.1 | 6.7 | 5.0 |
| 0.3 | 7.6 | 2.6 | 5.8 | 3.1 | 6.7 | 5.0 |
| 0.35 | 7.6 | 2.6 | 5.8 | 3.1 | 6.7 | 5.0 |
| 0.4 | 7.6 | 2.6 | 5.8 | 3.1 | 6.7 | 5.0 |
| 0.45 | 7.6 | 2.6 | 5.8 | 3.1 | 6.7 | 5.0 |
| 0.5 | 7.6 | 2.6 | 5.8 | 3.1 | 6.7 | 5.0 |
| 0.55 | 7.6 | 2.6 | 5.7 | 3.1 | 6.7 | 5.0 |
| 0.6 | 7.6 | 2.6 | 5.7 | 3.1 | 6.7 | 5.0 |
| 0.65 | 7.6 | 2.6 | 5.6 | 3.1 | 6.6 | 5.0 |
| 0.7 | 7.6 | 2.6 | 5.5 | 3.1 | 6.6 | 5.0 |
| 0.75 | 7.5 | 2.6 | 5.4 | 3.1 | 6.5 | 5.0 |
| 0.8 | 7.4 | 2.6 | 5.1 | 3.1 | 6.3 | 4.9 |
| 0.85 | 7.1 | 2.5 | 4.8 | 2.9 | 6.0 | 4.6 |
| 0.9 | 6.5 | 2.3 | 4.3 | 2.7 | 5.5 | 4.2 |
| 0.95 | 5.5 | 2.1 | 3.6 | 2.4 | 4.7 | 3.6 |
| 1 | 3.8 | 1.7 | 2.6 | 1.9 | 3.3 | 2.6 |
|   | 1.2 | 1.2 | 1.2 | 1.2 | 1.2 | 1.2 |

-continued

HF-HFO-1234yf-HFC-245cb-HCFO-1233xf-HFO-1234zeE-HFO-1234zeZ-HCFO-1233zdE-HCFC-244bb

| MASSFRAC HF | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar | Organics 0.94 F1233xf + 0.01 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.94 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.94 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.94 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.94 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.94 F1234zeZ + 0.01 F244bb TOTAL PRESSURE bar | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar |
|---|---|---|---|---|---|---|---|---|
| 0 | 1.7 | 6.6 | 4.5 | 1.5 | 4.8 | 1.9 | 0.8 | 3.2 |
| 0.05 | 2.8 | 7.5 | 5.7 | 2.6 | 5.7 | 3.0 | 2.0 | 4.3 |
| 0.1 | 2.8 | 7.5 | 5.7 | 2.6 | 5.7 | 3.0 | 2.0 | 4.3 |
| 0.15 | 2.8 | 7.5 | 5.7 | 2.6 | 5.7 | 3.0 | 2.0 | 4.3 |
| 0.2 | 2.8 | 7.5 | 5.7 | 2.6 | 5.7 | 3.0 | 2.0 | 4.3 |
| 0.25 | 2.8 | 7.5 | 5.7 | 2.6 | 5.7 | 3.0 | 2.0 | 4.3 |
| 0.3 | 2.8 | 7.5 | 5.7 | 2.6 | 5.7 | 3.0 | 2.0 | 4.3 |
| 0.35 | 2.8 | 7.5 | 5.7 | 2.6 | 5.7 | 3.0 | 2.0 | 4.3 |
| 0.4 | 2.8 | 7.5 | 5.7 | 2.6 | 5.7 | 3.0 | 2.0 | 4.3 |
| 0.45 | 2.8 | 7.5 | 5.7 | 2.6 | 5.7 | 3.0 | 2.0 | 4.3 |
| 0.5 | 2.8 | 7.5 | 5.7 | 2.6 | 5.7 | 3.0 | 2.0 | 4.3 |
| 0.55 | 2.8 | 7.5 | 5.7 | 2.6 | 5.6 | 3.0 | 2.0 | 4.2 |
| 0.6 | 2.8 | 7.5 | 5.7 | 2.6 | 5.6 | 3.0 | 2.0 | 4.2 |
| 0.65 | 2.8 | 7.5 | 5.7 | 2.6 | 5.5 | 3.0 | 2.0 | 4.2 |
| 0.7 | 2.8 | 7.5 | 5.7 | 2.6 | 5.3 | 3.0 | 2.0 | 4.2 |
| 0.75 | 2.8 | 7.4 | 5.7 | 2.6 | 5.1 | 3.0 | 2.0 | 4.2 |
| 0.8 | 2.6 | 7.0 | 5.7 | 2.4 | 4.7 | 2.9 | 1.9 | 4.0 |
| 0.85 | 2.4 | 6.5 | 5.7 | 2.3 | 4.3 | 2.7 | 1.9 | 3.7 |
| 0.9 | 2.2 | 5.4 | 4.9 | 2.0 | 3.6 | 2.4 | 1.8 | 3.2 |
| 0.95 | 1.8 | 3.8 | 3.5 | 1.7 | 2.6 | 1.9 | 1.6 | 2.4 |
| 1 | 1.2 | 1.2 | 1.2 | 1.2 | 1.2 | 1.2 | 1.2 | 1.2 |

HF-HFO-1234yf-HFC-245cb-HCFO-1233xf-HFO-1234zeE-HFO-1234zeZ-HCFO-1233zdE-Trifluoropropyne

| MASSFRAC HF | Organics 0.16 F1234yf + 0.14 F245cb + 0.14 F1233xf + 0.14 F1234zeE + 0.14 F1234zeZ + 0.14 F1233zdE + 0.14 TPF TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 TPF TOTAL PRESSURE bar |
|---|---|---|---|---|---|---|---|---|
| 0 | 5.0 | 6.7 | 4.7 | 1.8 | 4.9 | 2.0 | 1.6 | 11.2 |
| 0.05 | 6.0 | 7.6 | 5.8 | 2.9 | 5.8 | 3.1 | 2.7 | 12.0 |

-continued

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F245fa TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F245fa TOTAL PRESSURE bar |
|---|---|---|---|---|---|---|---|
| 0.1  | 6.0 | 7.6 | 5.8 | 2.9 | 5.9 | 2.7 | 11.9 |
| 0.15 | 6.0 | 7.6 | 5.8 | 2.9 | 5.9 | 2.7 | 11.8 |
| 0.2  | 6.0 | 7.6 | 5.8 | 2.9 | 5.9 | 2.7 | 11.7 |
| 0.25 | 6.0 | 7.6 | 5.8 | 2.9 | 5.9 | 2.7 | 11.6 |
| 0.3  | 6.0 | 7.6 | 5.8 | 2.9 | 5.8 | 2.7 | 11.5 |
| 0.35 | 6.0 | 7.6 | 5.8 | 2.9 | 5.8 | 2.7 | 11.5 |
| 0.4  | 6.0 | 7.6 | 5.8 | 2.9 | 5.8 | 2.7 | 11.4 |
| 0.45 | 6.0 | 7.6 | 5.8 | 2.9 | 5.8 | 2.7 | 11.4 |
| 0.5  | 6.0 | 7.6 | 5.8 | 2.9 | 5.8 | 2.7 | 11.5 |
| 0.55 | 6.0 | 7.6 | 5.8 | 2.9 | 5.8 | 2.7 | 11.5 |
| 0.6  | 6.0 | 7.6 | 5.8 | 2.9 | 5.8 | 2.7 | 11.5 |
| 0.65 | 6.0 | 7.6 | 5.8 | 2.9 | 5.7 | 2.7 | 11.5 |
| 0.7  | 6.0 | 7.6 | 5.8 | 2.9 | 5.6 | 2.7 | 11.5 |
| 0.75 | 5.9 | 7.5 | 5.8 | 2.9 | 5.4 | 2.7 | 11.5 |
| 0.8  | 5.6 | 7.1 | 5.8 | 2.8 | 5.2 | 2.6 | 11.2 |
| 0.85 | 5.1 | 6.6 | 5.8 | 2.6 | 4.9 | 2.4 | 10.4 |
| 0.9  | 4.3 | 5.5 | 5.0 | 2.2 | 4.4 | 2.1 | 8.8 |
| 0.95 | 3.1 | 3.8 | 3.5 | 1.8 | 3.6 | 1.7 | 5.9 |
| 1    | 1.2 | 1.2 | 1.2 | 1.2 | 1.2 | 1.2 | 1.2 |

HF-HFO-1234yf-HFC-245cb-HCFO-1233xf-HFO-1234zeE-HFO-1234zeZ-HCFO-1233zdE-HFC-245fa

| MASSFRAC HF | Organics 0.01 F1234yf + 0.94 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F245fa TOTAL PRESSURE bar |
|---|---|---|---|---|---|---|
| 0    | 4.5 | 1.7 | 4.8 | 1.9 | 1.5 | 1.6 |
| 0.05 | 5.7 | 2.8 | 5.7 | 3.0 | 2.6 | 2.8 |
| 0.1  | 5.7 | 2.8 | 5.7 | 3.0 | 2.6 | 2.8 |
| 0.15 | 5.7 | 2.8 | 5.7 | 3.0 | 2.6 | 2.8 |
| 0.2  | 5.7 | 2.8 | 5.7 | 3.0 | 2.6 | 2.8 |
| 0.25 | 5.7 | 2.8 | 5.7 | 3.0 | 2.6 | 2.8 |
| 0.3  | 5.7 | 2.8 | 5.7 | 3.0 | 2.6 | 2.8 |
| 0.35 | 5.7 | 2.8 | 5.7 | 3.0 | 2.6 | 2.8 |
| 0.4  | 5.7 | 2.8 | 5.7 | 3.0 | 2.6 | 2.8 |
| 0.45 | 5.7 | 2.8 | 5.7 | 3.0 | 2.6 | 2.8 |
| 0.5  | 5.7 | 2.8 | 5.7 | 3.0 | 2.6 | 2.8 |
| 0.55 | 5.7 | 2.8 | 5.7 | 3.0 | 2.6 | 2.8 |
| 0.6  | 5.7 | 2.8 | 5.6 | 3.0 | 2.6 | 2.8 |
| 0.65 | 5.7 | 2.8 | 5.5 | 3.0 | 2.6 | 2.8 |
| 0.7  | 5.7 | 2.8 | 5.3 | 3.0 | 2.6 | 2.8 |
| 0.75 | 7.4 | 2.8 | 5.1 | 3.0 | 2.6 | 2.8 |
| 0.8  | 5.8 | 2.6 | 4.7 | 2.9 | 2.5 | 2.7 |
| 0.85 | 5.7 | 2.5 | 4.3 | 2.7 | 2.3 | 2.5 |
| 0.9  | 4.9 | 2.2 | 3.6 | 2.4 | 2.0 | 2.2 |

| | | | | | | | | |
|---|---|---|---|---|---|---|---|---|
| 0.95 | 2.4 | 3.8 | 3.5 | 1.8 | 2.6 | 1.9 | 1.7 | 1.8 |
| 1 | 1.2 | 1.2 | 1.2 | 1.2 | 1.2 | 1.2 | 1.2 | 1.2 |

HF-HFO-1234yf-HFC-245cb-HCFO-1233xf-HFO-1234zeE-HFO-1234zeZ-HCFO-1233zdE-HFO-1225yeZ

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225yeZ TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225yeZ TOTAL PRESSURE bar |
|---|---|---|---|---|---|---|---|---|
| 0 | 3.8 | 6.6 | 4.6 | 1.7 | 4.8 | 1.9 | 1.5 | 5.1 |
| 0.05 | 4.9 | 7.6 | 5.8 | 2.8 | 5.8 | 3.0 | 2.6 | 6.1 |
| 0.1 | 4.9 | 7.6 | 5.8 | 2.8 | 5.8 | 3.0 | 2.6 | 6.1 |
| 0.15 | 4.9 | 7.6 | 5.8 | 2.8 | 5.8 | 3.0 | 2.6 | 6.1 |
| 0.2 | 4.9 | 7.5 | 5.8 | 2.8 | 5.8 | 3.0 | 2.6 | 6.1 |
| 0.25 | 4.9 | 7.6 | 5.8 | 2.8 | 5.8 | 3.0 | 2.6 | 6.1 |
| 0.3 | 4.9 | 7.6 | 5.8 | 2.8 | 5.8 | 3.0 | 2.6 | 6.1 |
| 0.35 | 4.9 | 7.6 | 5.8 | 2.8 | 5.8 | 3.0 | 2.6 | 6.1 |
| 0.4 | 4.9 | 7.6 | 5.8 | 2.8 | 5.8 | 3.0 | 2.6 | 6.1 |
| 0.45 | 4.9 | 7.6 | 5.8 | 2.8 | 5.8 | 3.0 | 2.6 | 6.1 |
| 0.5 | 4.9 | 7.6 | 5.8 | 2.8 | 5.7 | 3.0 | 2.6 | 6.1 |
| 0.55 | 4.9 | 7.6 | 5.8 | 2.8 | 5.7 | 3.0 | 2.6 | 6.1 |
| 0.6 | 4.9 | 7.6 | 5.8 | 2.8 | 5.6 | 3.0 | 2.6 | 6.1 |
| 0.65 | 4.9 | 7.5 | 5.8 | 2.8 | 5.5 | 3.0 | 2.6 | 6.0 |
| 0.7 | 5.0 | 7.4 | 5.8 | 2.8 | 5.3 | 3.0 | 2.6 | 5.8 |
| 0.75 | 4.8 | 7.1 | 5.8 | 2.8 | 5.1 | 3.0 | 2.6 | 5.5 |
| 0.8 | 4.6 | 6.5 | 5.8 | 2.7 | 4.8 | 2.9 | 2.5 | 5.0 |
| 0.85 | 4.2 | 5.5 | 4.9 | 2.5 | 4.3 | 2.7 | 2.3 | 4.2 |
| 0.9 | 3.6 | 5.5 | 4.9 | 2.2 | 3.6 | 2.4 | 2.1 | 2.9 |
| 0.95 | 2.6 | 3.8 | 3.5 | 1.8 | 2.6 | 1.9 | 1.7 | 2.9 |
| 1 | 1.2 | 1.2 | 1.2 | 1.2 | 1.2 | 1.2 | 1.2 | 1.2 |

-continued

HF-HFO-1234yf-HFC-245cb-HCFO-1233xf-HFO-1234zeE-HFO-1234zeZ-HCFC-1233zdE-HFO-1225zc

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225zc TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225zc TOTAL PRESSURE bar |
|---|---|---|---|---|---|---|---|
| 0 | 3.9 | 6.6 | 4.6 | 1.7 | 4.8 | 1.9 | 1.5 | 5.2 |
| 0.05 | 4.9 | 7.6 | 5.8 | 2.8 | 5.8 | 3.0 | 2.6 | 6.2 |
| 0.1 | 4.9 | 7.6 | 5.8 | 2.8 | 5.8 | 3.0 | 2.6 | 6.2 |
| 0.15 | 4.9 | 7.6 | 5.8 | 2.8 | 5.8 | 3.0 | 2.6 | 6.2 |
| 0.2 | 4.9 | 7.6 | 5.8 | 2.8 | 5.8 | 3.0 | 2.6 | 6.2 |
| 0.25 | 4.9 | 7.6 | 5.8 | 2.8 | 5.8 | 3.0 | 2.6 | 6.2 |
| 0.3 | 4.9 | 7.6 | 5.8 | 2.8 | 5.8 | 3.0 | 2.6 | 6.2 |
| 0.35 | 4.9 | 7.6 | 5.8 | 2.8 | 5.8 | 3.0 | 2.6 | 6.2 |
| 0.4 | 4.9 | 7.6 | 5.8 | 2.8 | 5.8 | 3.0 | 2.6 | 6.2 |
| 0.45 | 4.9 | 7.6 | 5.8 | 2.8 | 5.8 | 3.0 | 2.6 | 6.2 |
| 0.5 | 4.9 | 7.6 | 5.8 | 2.8 | 5.7 | 3.0 | 2.6 | 6.1 |
| 0.55 | 4.9 | 7.6 | 5.8 | 2.8 | 5.7 | 3.0 | 2.6 | 6.1 |
| 0.6 | 4.9 | 7.6 | 5.8 | 2.8 | 5.6 | 3.0 | 2.6 | 6.0 |
| 0.65 | 4.9 | 7.6 | 5.8 | 2.8 | 5.5 | 3.0 | 2.6 | 5.9 |
| 0.7 | 4.9 | 7.5 | 5.8 | 2.8 | 5.3 | 3.0 | 2.6 | 5.8 |
| 0.75 | 4.8 | 7.4 | 5.8 | 2.8 | 5.1 | 3.0 | 2.6 | 5.5 |
| 0.8 | 4.6 | 7.1 | 5.8 | 2.7 | 4.8 | 2.9 | 2.5 | 5.1 |
| 0.85 | 4.2 | 6.5 | 5.8 | 2.5 | 4.3 | 2.7 | 2.3 | 4.6 |
| 0.9 | 3.5 | 5.5 | 4.9 | 2.2 | 3.6 | 2.4 | 2.1 | 3.8 |
| 0.95 | 2.6 | 3.8 | 3.5 | 1.8 | 2.6 | 1.9 | 1.7 | 2.7 |
| 1 | 1.2 | 1.2 | 1.2 | 1.2 | 1.2 | 1.2 | 1.2 | 1.2 |

EXAMPLE 17

Temperature and Pressure Range of System with 8 Compounds

| System with 8 compounds | Boiling point range | |
|---|---|---|
| | Temperature °C. | Pressure bar abs |
| HF-HCFO-1233xf-HFO-1234yf-HFC-245cb-HCFO-1233zdE-HFO-1234zeE-HFO-1234zeZ-HFO-1243zf | 0 to 40 | ~1.0 ~ 11.5 |
| HF-HFO-1234yf-HFC-245cb-HCFO-1233xf-HFO-1234zeE-HFO-1234zeZ-HCFO-1233zdE-HCFC-244bb | 0 to 40 | ~0.7 to ~11.5 |
| HF-HFO-1234yf-HFC-245cb-HCFO-1233xf-HFO-1234zeE-HFO-1234zeZ-HCFO-1233zdE-Trifluoropropyne | 0 to 40 | ~1.0 to ~17.4 |
| HF-HFO-1234yf-HFC-245cb-HCFO-1233xf-HFO-1234zeE-HFO-1234zeZ-HCFO-1233zdE-HFC-245fa | 0 to 40 | ~0.9 to ~11.5 |
| HF-HFO-1234yf-HFC-245cb-HCFO-1233xf-HFO-1234zeE-HFO-1234zeZ-HCFO-1233zdE-HFO-1225yeZ | 0 to 40 | ~1.0 to ~11.5 |
| HF-HFO-1234yf-HFC-245cb-HCFO-1233xf-HFO-1234zeE-HFO-1234zeZ-HCFC-1233zdE-HFO-1225zc | 0 to 40 | ~1.0 to ~11.5 |

EXAMPLE 18

Decantation Ranges of System with 8 Compounds

| System with 8 compounds | Decantation ranges Mass percentage of HF Temperature | | |
|---|---|---|---|
| | 0° C. | 25° C. | 40° C. |
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |
| HF-HFO-1234yf-HFC-245cb-HCFO-1233xf-HFO-1234zeE-HFO-1234zeZ-HCFO-1233zdE-HCFC-244bb | 5-80 | 5-75 | 5-70 |
| HF-HFO-1234yf-HFC-245cb-HCFO-1233xf-HFO-1234zeE-HFO-1234zeZ-HCFO-1233zdE-Trifluoropropyne | 5-75 | 10-65 | * |
| HF-HFO-1234yf-HFC-245cb-HCFO-1233xf-HFO-1234zeE-HFO-1234zeZ-HCFO-1233zdE-HFC-245fa | 5-75 | 5-70 | 10-60 |
| HF-HFO-1234yf-HFC-245cb-HCFO-1233xf-HFO-1234zeE-HFO-1234zeZ-HCFO-1233zdE-HFO-1225yeZ | 5-75 | 5-70 | 15-55 |
| HF-HFO-1234yf-HFC-245cb-HCFO-1233xf-HFO-1234zeE-HFO-1234zeZ-HCFC-1233zdE-HFO-1225zc | 5-75 | 5-65 | 15-50 |

EXAMPLE 19

Systems with 13 Compounds

HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc

| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
|---|---|---|---|---|---|
| 0 | 4.5 | 6.5 | 1.9 | 4.8 | 1.7 |
| 0.05 | 5.6 | 7.5 | 3.0 | 5.8 | 2.9 |
| 0.1 | 5.6 | 7.5 | 3.0 | 5.8 | 2.9 |
| 0.15 | 5.6 | 7.5 | 3.0 | 5.8 | 2.8 |
| 0.2 | 5.6 | 7.5 | 3.0 | 5.8 | 2.8 |
| 0.25 | 5.6 | 7.5 | 3.0 | 5.8 | 2.8 |
| 0.3 | 5.6 | 7.5 | 3.0 | 5.8 | 2.8 |

| | HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | | | | |
|---|---|---|---|---|---|
| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.6 | 4.3 | 2.5 |
| 0.9 | 3.9 | 5.4 | 2.3 | 3.6 | 2.2 |
| 0.95 | 2.8 | 3.7 | 1.8 | 2.6 | 1.8 |
| 1 | 1.2 | 1.2 | 1.2 | 1.2 | 1.2 |

EXAMPLE 20

Temperature and Pressure Range of System with 13 Compounds

| | Boiling point range | |
|---|---|---|
| System with 13 compounds | Temperature ° C. | Pressure bar abs |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 0 to 40 | ~0.7 ~ 18.0 |

EXAMPLE 21

Decantation Ranges of System with 13 Compounds

| | Decantation ranges Mass percentage of HF Temperature | | |
|---|---|---|---|
| System with 13 compounds | 0° C. | 25° C. | 40° C. |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 5-75% | 10-70% | 15-60% |

The invention claimed is:

1. An azeotropic or quasi-azeotropic composition comprising hydrogen fluoride, 1,3,3,3-tetrafluoropropene, and one or more compounds selected from the group consisting of 3,3,3-trifluoro-2-chloropropene, E-3,3,3-trifluoro-1-chloropropene, 2,3,3,3-tetrafluoropropene, 1,1,1,2,2-pentafluoropropane, and 3,3,3-trifluoropropene, in which the boiling point of said composition is between −20° C. and 80° C., and at a pressure of between 0.1 and 44 bar absolute.

2. An azeotropic or quasi-azeotropic composition comprising hydrogen fluoride, 1,3,3,3-tetrafluoropropene, and one or more compounds chosen from 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane, in which the boiling point of said composition is between −20° C. and 80° C., and at a pressure of between 0.1 and 44 bar absolute.

3. The composition as claimed in claim 1, in which the composition comprises hydrogen fluoride, 1,3,3,3-tetrafluoropropene and at least one or more organic compounds chosen from 3,3,3-trifluoro-2-chloropropene, E-3,3,3-trifluoro-1-chloropropene, 3,3,3-trifluoropropene, 1,1,1,2,2-pentafluoropropane and 2,3,3,3-tetrafluoropropene.

4. The composition as claimed in claim 1, in which the 1,3,3,3-tetrafluoropropene is E-1,3,3,3-tetrafluoropropene.

5. The composition as claimed in claim 1, in which the 1,3,3,3-tetrafluoropropene is Z-1,3,3,3-tetrafluoropropene.

6. The composition as claimed in claim 1, in which the composition is heteroazeotropic or quasi-heteroazeotropic.

7. The composition as claimed in claim 1, in which the composition comprises hydrogen fluoride, 1,3,3,3-tetrafluoropropene, 3,3,3-trifluoro-2-chloropropene and optionally one or more organic compounds chosen from E-3,3,3-trifluoro-1-chloropropene, 3,3,3-trifluoropropene, 1,1,1,2,2-pentafluoropropane and 2,3,3,3-tetrafluoropropene.

8. The composition as claimed in claim 1, in which the composition comprises hydrogen fluoride, 1,3,3,3-tetrafluoropropene, E-3,3,3-trifluoro-1-chloropropene and optionally one or more organic compounds chosen from 3,3,3-trifluoropropene, 1,1,1,2,2-pentafluoropropane and 2,3,3,3-tetrafluoropropene.

9. The composition as claimed in claim 1, in which the composition comprises hydrogen fluoride, 1,3,3,3-tetrafluoropropene, 3,3,3-trifluoropropene and optionally one or more organic compounds chosen from 1,1,1,2,2-pentafluoropropane and 2,3,3,3-tetrafluoropropene.

10. The composition as claimed in claim 1, in which the composition comprises hydrogen fluoride, 1,3,3,3-tetrafluoropropene, 1,1,1,2,2-pentafluoropropane and optionally 2,3,3,3-tetrafluoropropene.

11. The composition as claimed in claim 1, in which the composition comprises hydrogen fluoride, 1,3,3,3-tetrafluoropropene, and 2,3,3,3-tetrafluoropropene.

12. The composition as claimed in claim 1, in which the composition comprises from 1% to 95% by weight of hydrogen fluoride and from 99% to 5% by weight of the sum of the organic compounds.

13. The composition as claimed in claim 1, in which the composition comprises from 5% to 85% by weight of hydrogen fluoride and from 95% to 15% by weight of the sum of the organic compounds.

14. The composition as claimed in claim 1, in which the boiling point of said composition is between 0° C. and 40° C. and at a pressure of between 0.7 and 18 bar absolute.

15. The composition as claimed in claim 1, in which the boiling point of said composition is between 0° C. and 40° C. and at a pressure of between 0.9 and 12.5 bar absolute.

16. The composition as claimed in claim 1, comprising two or more compounds selected from the group consisting of 3,3,3-trifluoro-2-chloropropene, E-3,3,3-trifluoro-1-chloropropene, 2,3,3,3-tetrafluoropropene, 1,1,1,2,2-pentafluoropropane, and 3,3,3-trifluoropropene.

17. An azeotropic or quasi-azeotropic composition comprising hydrogen fluoride, 1,3,3,3-tetrafluoropropene and three or more compounds selected from the group consisting of 3,3,3-trifluoro-2-chloropropene, E-3,3,3-trifluoro-1-chloropropene, 2,3,3,3-tetrafluoropropene, 1,1,1,2,2-pentafluoropropane, and 3,3,3-trifluoropropene.

* * * * *